(12) United States Patent
Rodgers et al.

(10) Patent No.: US 9,193,733 B2
(45) Date of Patent: Nov. 24, 2015

(54) PIPERIDINYLCYCLOBUTYL SUBSTITUTED PYRROLOPYRIDINE AND PYRROLOPYRIMIDINE DERIVATIVES AS JAK INHIBITORS

(71) Applicants: Incyte Corporation, Wilmington, DE (US); Incyte Holdings Corporation, Wilmington, DE (US)

(72) Inventors: James D. Rodgers, Landenberg, PA (US); Stacey Shepard, Wilmington, DE (US); Wenyu Zhu, Media, PA (US); Lixin Shao, Newark, DE (US); Joseph Glenn, Mount Royal, NJ (US)

(73) Assignees: Incyte Holdings Corporation, Wilmington, DE (US); Incyte Corporation, Wilmington, DE (US)

( * ) Notice: Subject to any disclaimer, the term of this patent is extended or adjusted under 35 U.S.C. 154(b) by 0 days.

(21) Appl. No.: 13/896,802

(22) Filed: May 17, 2013

(65) Prior Publication Data

US 2014/0005166 A1    Jan. 2, 2014

Related U.S. Application Data

(60) Provisional application No. 61/648,869, filed on May 18, 2012.

(51) Int. Cl.
| | |
|---|---|
| *A01N 43/90* | (2006.01) |
| *A61K 31/519* | (2006.01) |
| *C07D 487/00* | (2006.01) |
| *C07D 487/04* | (2006.01) |
| *C07D 471/04* | (2006.01) |
| *C07D 491/107* | (2006.01) |

(52) U.S. Cl.
CPC ............ *C07D 487/04* (2013.01); *C07D 471/04* (2013.01); *C07D 491/107* (2013.01)

(58) Field of Classification Search
None
See application file for complete search history.

(56) References Cited

U.S. PATENT DOCUMENTS

| | | | |
|---|---|---|---|
| 2,985,589 | A | 5/1961 | Broughton et al. |
| 3,832,460 | A | 8/1974 | Kosti |
| 4,402,832 | A | 9/1983 | Gerhold |
| 4,498,991 | A | 2/1985 | Oroskar |
| 4,512,984 | A | 4/1985 | Seufert et al. |
| 4,548,990 | A | 10/1985 | Mueller et al. |
| 4,814,477 | A | 3/1989 | Wijnberg et al. |
| 5,378,700 | A | 1/1995 | Sakuma et al. |
| 5,510,101 | A | 4/1996 | Stroppolo |
| 5,521,184 | A | 5/1996 | Zimmermann |
| 5,630,943 | A | 5/1997 | Grill |
| 5,795,909 | A | 8/1998 | Shashoua et al. |
| 5,856,326 | A | 1/1999 | Anthony |
| 5,919,779 | A | 7/1999 | Proudfoot et al. |
| 6,060,038 | A | 5/2000 | Burns |
| 6,075,056 | A | 6/2000 | Quigley, Jr. et al. |
| 6,136,198 | A | 10/2000 | Adam et al. |
| 6,217,895 | B1 | 4/2001 | Guo |
| 6,335,342 | B1 | 1/2002 | Longo et al. |
| 6,375,839 | B1 | 4/2002 | Adam et al. |
| 6,413,419 | B1 | 7/2002 | Adam et al. |
| 6,486,322 | B1 | 11/2002 | Longo et al. |
| 6,548,078 | B2 | 4/2003 | Guo |
| 6,569,443 | B1 | 5/2003 | Dawson |
| 6,579,882 | B2 | 6/2003 | Bhatia et al. |
| 6,624,138 | B1 | 9/2003 | Sung et al. |
| 6,635,762 | B1 | 10/2003 | Blumenkopf et al. |
| 6,712,973 | B2 | 3/2004 | Adam et al. |
| 6,713,089 | B1 | 3/2004 | Bertelsen et al. |
| 6,852,727 | B2 | 2/2005 | Goulet et al. |
| 6,953,776 | B2 | 10/2005 | Di Napoli |
| 7,005,436 | B2 | 2/2006 | Lloyd et al. |
| 7,167,750 | B2 | 1/2007 | Knudson et al. |
| 7,265,108 | B2 | 9/2007 | Ozaki |
| 7,335,667 | B2 | 2/2008 | Rodgers et al. |
| 7,358,255 | B2 | 4/2008 | Nakamura |
| 7,517,870 | B2 | 4/2009 | Auricchio |
| 7,598,257 | B2 | 10/2009 | Rodgers et al. |
| 7,745,437 | B2 | 6/2010 | Ren et al. |
| 7,750,007 | B2 | 7/2010 | Bearss et al. |
| 7,834,022 | B2 | 11/2010 | Rodgers et al. |
| 8,053,433 | B2 | 11/2011 | Rodgers et al. |
| 8,158,616 | B2 | 4/2012 | Rodgers et al. |
| 8,309,718 | B2 | 11/2012 | Li et al. |
| 8,410,265 | B2 | 4/2013 | Zhou et al. |
| 8,415,362 | B2 | 4/2013 | Rodgers et al. |

(Continued)

FOREIGN PATENT DOCUMENTS

| | | |
|---|---|---|
| DE | 30 36 390 | 5/1982 |
| EP | 0223420 | 5/1987 |

(Continued)

OTHER PUBLICATIONS

26th Annual JPMorgan Healthcare Conference presentation dated Jan. 8, 2008 (28 pages).
Abe, et al., Heterocycles, "Effective Methods for Introducing Some Aryl and Heteroaryl Substituent onto 1-Azaazulene Nuclei", 66, 229-240 (2005).
Abelson et al., "Alternate reference values for tear film break-up time in normal and dry eye populations, Lacrimal Gland, Tear Film, and Dry Eye Syndromes 3 Part B", Adv Exp Med Biol, 2002; 506:1121-1125.
Abelson et al., "Dry eye syndrome: diagnosis, clinical trials, and pharmaceutical treatment—'improving clinical trials'. Lacrimal Gland, Tear Film, and Dry Eye Syndromes 3 Part B", Adv Exp Med Biol, 2002; 506:1079-86).
Abstract of Chilean patent application No. 3496-06 published in Official Gazette of the Republic of Chile (Jun. 1, 2007) and publication (2 pages).

(Continued)

*Primary Examiner* — Jeffrey H Murray
(74) *Attorney, Agent, or Firm* — Fish & Richardson P.C.

(57) ABSTRACT

The present invention provides piperidinylcyclobutyl substituted pyrrolopyrimidines and pyrrolopyridines of Formula I, as defined herein, as well as their compositions and methods of use, that modulate the activity of Janus kinases (JAKs) and are useful in the treatment of diseases related to the activity of JAKs including, for example, inflammatory disorders, autoimmune disorders, cancer, and other diseases.

48 Claims, No Drawings

(56) References Cited

U.S. PATENT DOCUMENTS

| | | |
|---|---|---|
| 8,420,629 B2 | 4/2013 | Rodgers et al. |
| 8,445,488 B2 | 5/2013 | Rodgers et al. |
| 8,486,902 B2 | 7/2013 | Rodgers et al. |
| 8,513,270 B2 | 8/2013 | Arvanitis et al. |
| 8,530,485 B2 | 9/2013 | Rodgers et al. |
| 8,541,425 B2 | 9/2013 | Rodgers et al. |
| 8,563,541 B2 | 10/2013 | Arvanitis et al. |
| 8,604,043 B2 | 12/2013 | Li et al. |
| 8,691,807 B2 | 4/2014 | Yao et al. |
| 8,716,303 B2 | 5/2014 | Rodgers et al. |
| 8,722,693 B2 | 5/2014 | Rodgers et al. |
| 8,741,895 B2 | 6/2014 | Rodgers et al. |
| 8,748,401 B2 | 6/2014 | Rodgers et al. |
| 8,765,734 B2 | 7/2014 | Huang et al. |
| 8,822,481 B1 | 9/2014 | Rodgers et al. |
| 8,829,013 B1 | 9/2014 | Rodgers et al. |
| 8,835,423 B2 | 9/2014 | Arvanitis et al. |
| 8,841,318 B2 | 9/2014 | Arvanitis et al. |
| 8,883,806 B2 | 11/2014 | Zhou et al. |
| 8,889,697 B2 | 11/2014 | Rodgers et al. |
| 8,933,085 B2 | 1/2015 | Rodgers et al. |
| 8,933,086 B2 | 1/2015 | Rodgers et al. |
| 8,946,245 B2 | 2/2015 | Rodgers et al. |
| 2002/0111353 A1 | 8/2002 | Ledeboer et al. |
| 2003/0064969 A1 | 4/2003 | Bhagwat et al. |
| 2003/0100756 A1 | 5/2003 | Adams et al. |
| 2003/0144309 A1 | 7/2003 | Choon-Moon |
| 2003/0165576 A1 | 9/2003 | Fujii et al. |
| 2004/0009222 A1 | 1/2004 | Chou et al. |
| 2004/0009983 A1 | 1/2004 | Cox et al. |
| 2004/0029857 A1 | 2/2004 | Hale et al. |
| 2004/0077654 A1 | 4/2004 | Bouillot |
| 2004/0198737 A1 | 10/2004 | Cox et al. |
| 2004/0204404 A1 | 10/2004 | Zelle |
| 2004/0214928 A1 | 10/2004 | Aronov |
| 2004/0235862 A1 | 11/2004 | Burns |
| 2005/0014966 A1 | 1/2005 | Tabe |
| 2005/0054568 A1 | 3/2005 | Ling |
| 2005/0153989 A1 | 7/2005 | Grotzfeld et al. |
| 2006/0004010 A1 | 1/2006 | Habashita et al. |
| 2006/0020011 A1 | 1/2006 | Wu et al. |
| 2006/0079511 A1 | 4/2006 | Liu et al. |
| 2006/0106020 A1 | 5/2006 | Rodgers et al. |
| 2006/0106027 A1 | 5/2006 | Furet et al. |
| 2006/0128803 A1 | 6/2006 | Klimko |
| 2006/0135537 A1 | 6/2006 | Knegtel et al. |
| 2006/0178393 A1 | 8/2006 | Pitts |
| 2006/0183761 A1 | 8/2006 | Ledeboer et al. |
| 2006/0183906 A1 | 8/2006 | Rodgers et al. |
| 2006/0223864 A1 | 10/2006 | Biju |
| 2006/0293311 A1 | 12/2006 | Li et al. |
| 2007/0135461 A1 | 6/2007 | Rodgers et al. |
| 2007/0135466 A1 | 6/2007 | Ledeboer et al. |
| 2007/0149506 A1 | 6/2007 | Arvanitis et al. |
| 2007/0149561 A1 | 6/2007 | Dhanak et al. |
| 2007/0191364 A1 | 8/2007 | Braun et al. |
| 2007/0191405 A1 | 8/2007 | Noronha |
| 2007/0208053 A1 | 9/2007 | Wang et al. |
| 2007/0259904 A1 | 11/2007 | Noronha |
| 2008/0021026 A1 | 1/2008 | Kahraman et al. |
| 2008/0085898 A1 | 4/2008 | Lu |
| 2008/0096852 A1 | 4/2008 | Yanni |
| 2008/0119496 A1 | 5/2008 | Ohlmeyer |
| 2008/0161346 A1 | 7/2008 | Cheng |
| 2008/0188500 A1 | 8/2008 | Arvanitis et al. |
| 2008/0194468 A1 | 8/2008 | Bodor |
| 2008/0207570 A1 | 8/2008 | Segura-Orsoni |
| 2008/0207584 A1 | 8/2008 | Habashita et al. |
| 2008/0280876 A1 | 11/2008 | Hobson et al. |
| 2008/0312258 A1 | 12/2008 | Rodgers et al. |
| 2008/0312259 A1 | 12/2008 | Rodgers et al. |
| 2009/0018156 A1 | 1/2009 | Tang et al. |
| 2009/0076070 A1 | 3/2009 | Harada et al. |
| 2009/0088445 A1 | 4/2009 | Ledeboer et al. |
| 2009/0131403 A1 | 5/2009 | Kusuda |
| 2009/0181959 A1 | 7/2009 | Rodgers et al. |
| 2009/0197869 A1 | 8/2009 | Arvanitis et al. |
| 2009/0203637 A1 | 8/2009 | Hocek et al. |
| 2009/0215766 A1 | 8/2009 | Rodgers et al. |
| 2009/0221608 A1 | 9/2009 | Cui et al. |
| 2009/0233903 A1 | 9/2009 | Rodgers et al. |
| 2009/0318405 A1 | 12/2009 | Li et al. |
| 2010/0022522 A1 | 1/2010 | Rodgers et al. |
| 2010/0069381 A1 | 3/2010 | Itoh et al. |
| 2010/0113416 A1 | 5/2010 | Friedman et al. |
| 2010/0190981 A1 | 7/2010 | Zhou et al. |
| 2010/0210627 A1 | 8/2010 | Mao et al. |
| 2010/0298334 A1 | 11/2010 | Rodgers et al. |
| 2010/0298355 A1 | 11/2010 | Li et al. |
| 2011/0059951 A1 | 3/2011 | Rodgers et al. |
| 2011/0082159 A1 | 4/2011 | Rodgers et al. |
| 2011/0086810 A1 | 4/2011 | Rodgers et al. |
| 2011/0086835 A1 | 4/2011 | Rodgers et al. |
| 2011/0201593 A1 | 8/2011 | Babu et al. |
| 2011/0207754 A1 | 8/2011 | Li et al. |
| 2011/0223210 A1 | 9/2011 | Rodgers et al. |
| 2011/0224157 A1 | 9/2011 | Rodgers et al. |
| 2011/0224190 A1 | 9/2011 | Huang et al. |
| 2011/0288107 A1 | 11/2011 | Parikh et al. |
| 2012/0014989 A1 | 1/2012 | Rodgers |
| 2012/0077798 A1 | 3/2012 | Rodgers et al. |
| 2012/0149681 A1 | 6/2012 | Rodgers |
| 2012/0149682 A1 | 6/2012 | Rodgers et al. |
| 2012/0214825 A1 | 8/2012 | Vannucchi et al. |
| 2012/0301464 A1 | 11/2012 | Friedman et al. |
| 2012/0329782 A1 | 12/2012 | Arvanitis et al. |
| 2013/0018034 A1 | 1/2013 | Yao et al. |
| 2013/0040973 A1 | 2/2013 | Vannucchi et al. |
| 2013/0045963 A1 | 2/2013 | Rodgers et al. |
| 2013/0060026 A1 | 3/2013 | Zhou et al. |
| 2013/0137681 A1 | 5/2013 | Rodgers et al. |
| 2013/0225556 A1 | 8/2013 | Rodgers et al. |
| 2013/0253190 A1 | 9/2013 | Zhou et al. |
| 2013/0253191 A1 | 9/2013 | Zhou et al. |
| 2013/0253193 A1 | 9/2013 | Zhou et al. |
| 2013/0274257 A1 | 10/2013 | Arvanitis et al. |
| 2013/0296299 A1 | 11/2013 | Rodgers et al. |
| 2014/0005210 A1 | 1/2014 | Rodgers et al. |
| 2014/0018374 A1 | 1/2014 | Rodgers et al. |
| 2014/0031344 A1 | 1/2014 | Arvanitis et al. |
| 2014/0073657 A1 | 3/2014 | Li et al. |
| 2014/0094477 A1 | 4/2014 | Rodgers et al. |
| 2014/0121198 A1 | 5/2014 | Li et al. |
| 2014/0171409 A1 | 6/2014 | Yao et al. |
| 2014/0221379 A1 | 8/2014 | Rodgers et al. |
| 2014/0228346 A1 | 8/2014 | Rodgers et al. |
| 2014/0243360 A1 | 8/2014 | Rodgers et al. |
| 2014/0256941 A1 | 9/2014 | Liu et al. |
| 2014/0275031 A1 | 9/2014 | Huang et al. |
| 2014/0303196 A1 | 10/2014 | Rodgers et al. |
| 2014/0343030 A1 | 11/2014 | Li et al. |
| 2015/0087632 A1 | 3/2015 | Rodgers et al. |

FOREIGN PATENT DOCUMENTS

| | | |
|---|---|---|
| EP | 0587473 | 3/1994 |
| EP | 0727217 | 8/1996 |
| EP | 0795556 | 9/1997 |
| EP | 1104764 | 6/2001 |
| JP | 07-010876 | 1/1995 |
| JP | 2003/155285 | 5/2003 |
| JP | 2006/518341 | 8/2006 |
| WO | WO 96/30343 | 10/1996 |
| WO | WO 97/02262 | 1/1997 |
| WO | WO 97/02266 | 1/1997 |
| WO | WO 97/36587 | 10/1997 |
| WO | WO 97/38664 | 10/1997 |
| WO | WO 97/45412 | 12/1997 |
| WO | WO 98/44797 | 10/1998 |
| WO | WO 98/51391 | 11/1998 |
| WO | WO 99/00654 | 1/1999 |
| WO | WO 99/62908 | 12/1999 |
| WO | WO 99/65908 | 12/1999 |
| WO | WO 99/65909 | 12/1999 |

(56) References Cited

FOREIGN PATENT DOCUMENTS

| | | |
|---|---|---|
| WO | WO 00/09495 | 2/2000 |
| WO | WO 00/51614 | 9/2000 |
| WO | WO 00/53595 | 9/2000 |
| WO | WO 00/63168 | 10/2000 |
| WO | WO 01/14402 | 3/2001 |
| WO | WO 01/27104 | 4/2001 |
| WO | WO 01/42246 | 6/2001 |
| WO | WO 01/64655 | 9/2001 |
| WO | WO 01/81345 | 11/2001 |
| WO | WO 01/98344 | 12/2001 |
| WO | WO 02/00196 | 1/2002 |
| WO | WO 02/00661 | 1/2002 |
| WO | WO 02/16370 | 2/2002 |
| WO | WO 02/46184 | 6/2002 |
| WO | WO 02/055084 | 7/2002 |
| WO | WO 02/055496 | 7/2002 |
| WO | WO 02/060492 | 8/2002 |
| WO | WO 02/080926 | 10/2002 |
| WO | WO 02/092573 | 11/2002 |
| WO | WO 02/096909 | 12/2002 |
| WO | WO 03/000695 | 1/2003 |
| WO | WO 03/011285 | 2/2003 |
| WO | WO 03/024967 | 3/2003 |
| WO | WO 03/037347 | 5/2003 |
| WO | WO 03/048162 | 6/2003 |
| WO | WO 03/092595 | 11/2003 |
| WO | WO 03/099771 | 12/2003 |
| WO | WO 03/099796 | 12/2003 |
| WO | WO 2004/003026 | 1/2004 |
| WO | WO 2004/005281 | 1/2004 |
| WO | WO 2004/005282 | 1/2004 |
| WO | WO 2004/026406 | 4/2004 |
| WO | WO 2004/041814 | 5/2004 |
| WO | WO 2004/046120 | 6/2004 |
| WO | WO 2004/047843 | 6/2004 |
| WO | WO 2004/056786 | 7/2004 |
| WO | WO 2004/072063 | 8/2004 |
| WO | WO 2004/080980 | 9/2004 |
| WO | WO 2004/092154 | 10/2004 |
| WO | WO 2004/099204 | 11/2004 |
| WO | WO 2004/099205 | 11/2004 |
| WO | WO 2005/005988 | 1/2005 |
| WO | WO 2005/013986 | 2/2005 |
| WO | WO 2005/020921 | 3/2005 |
| WO | WO 2005/026129 | 3/2005 |
| WO | WO 2005/028444 | 3/2005 |
| WO | WO 2005/049033 | 6/2005 |
| WO | WO 2005/051393 | 6/2005 |
| WO | WO 2005/060972 | 7/2005 |
| WO | WO 2005/061463 | 7/2005 |
| WO | WO 2005/062795 | 7/2005 |
| WO | WO 2005/089502 | 9/2005 |
| WO | WO 2005/095400 | 10/2005 |
| WO | WO 2005/105146 | 11/2005 |
| WO | WO 2005/105814 | 11/2005 |
| WO | WO 2005/105988 | 11/2005 |
| WO | WO 2005/110410 | 11/2005 |
| WO | WO 2005/117909 | 12/2005 |
| WO | WO 2005/121130 | 12/2005 |
| WO | WO 2005/123719 | 12/2005 |
| WO | WO 2006/004984 | 1/2006 |
| WO | WO 2006/013114 | 2/2006 |
| WO | WO 2006/022459 | 3/2006 |
| WO | WO 2006/039718 | 4/2006 |
| WO | WO 2006/046023 | 5/2006 |
| WO | WO 2006/046024 | 5/2006 |
| WO | WO 2006/052913 | 5/2006 |
| WO | WO 2006/056399 | 6/2006 |
| WO | WO 2006/067445 | 6/2006 |
| WO | WO 2006/069080 | 6/2006 |
| WO | WO 2006/077499 | 7/2006 |
| WO | WO 2006/096270 | 9/2006 |
| WO | WO 2006/101783 | 9/2006 |
| WO | WO 2006/108103 | 10/2006 |
| WO | WO 2006/122806 | 11/2006 |
| WO | WO 2006/127587 | 11/2006 |
| WO | WO 2006/129199 | 12/2006 |
| WO | WO 2006/136823 | 12/2006 |
| WO | WO 2007/002433 | 1/2007 |
| WO | WO 2007/025090 | 3/2007 |
| WO | WO 2007/041130 | 4/2007 |
| WO | WO 2007/043677 | 4/2007 |
| WO | WO 2007/044894 | 4/2007 |
| WO | WO 2007/049041 | 5/2007 |
| WO | WO 2007/062459 | 6/2007 |
| WO | WO 2007/070514 | 6/2007 |
| WO | WO 2007/076423 | 7/2007 |
| WO | WO 2007/077949 | 7/2007 |
| WO | WO 2007/084557 | 7/2007 |
| WO | WO 2007/090141 | 8/2007 |
| WO | WO 2007/090748 | 8/2007 |
| WO | WO 2007/17494 | 10/2007 |
| WO | WO 2007/116313 | 10/2007 |
| WO | WO 2007/129195 | 11/2007 |
| WO | WO 2007/135461 | 11/2007 |
| WO | WO 2007/140222 | 12/2007 |
| WO | WO 2008/013925 | 1/2008 |
| WO | WO 2008/028937 | 3/2008 |
| WO | WO 2008/035376 | 3/2008 |
| WO | WO 2008/043031 | 4/2008 |
| WO | WO 2008/058126 | 5/2008 |
| WO | WO 2008/064157 | 5/2008 |
| WO | WO 2008/067119 | 6/2008 |
| WO | WO 2008/077712 | 7/2008 |
| WO | WO 2008/079291 | 7/2008 |
| WO | WO 2008/079292 | 7/2008 |
| WO | WO 2008/082198 | 7/2008 |
| WO | WO 2008/082839 | 7/2008 |
| WO | WO 2008/082840 | 7/2008 |
| WO | WO 2008/106692 | 9/2008 |
| WO | WO 2008/124323 | 10/2008 |
| WO | WO 2008/139161 | 11/2008 |
| WO | WO 2008/145681 | 12/2008 |
| WO | WO 2008/145688 | 12/2008 |
| WO | WO 2008/157207 | 12/2008 |
| WO | WO 2008/157208 | 12/2008 |
| WO | WO 2009/016460 | 2/2009 |
| WO | WO 2009/049028 | 4/2009 |
| WO | WO 2009/064486 | 5/2009 |
| WO | WO 2009/064835 | 5/2009 |
| WO | WO 2009/071577 | 6/2009 |
| WO | WO 2009/100130 | 8/2009 |
| WO | WO 2009/109576 | 9/2009 |
| WO | WO 2009/114512 | 9/2009 |
| WO | WO 2009/115572 | 9/2009 |
| WO | WO 2009/155156 | 12/2009 |
| WO | WO 2009/158687 | 12/2009 |
| WO | WO 2010/000978 | 1/2010 |
| WO | WO 2010/001169 | 1/2010 |
| WO | WO 2010/020905 | 2/2010 |
| WO | WO 2010/022076 | 2/2010 |
| WO | WO 2010/022081 | 2/2010 |
| WO | WO 2010/026121 | 3/2010 |
| WO | WO 2010/026122 | 3/2010 |
| WO | WO 2010/026124 | 3/2010 |
| WO | WO 2010/039939 | 4/2010 |
| WO | WO 2010/081692 | 7/2010 |
| WO | WO 2010/083283 | 7/2010 |
| WO | WO 2010/135621 | 11/2010 |
| WO | WO 2010/135650 | 11/2010 |
| WO | WO 2011/003418 | 1/2011 |
| WO | WO 2011/025685 | 3/2011 |
| WO | WO 2011/028685 | 3/2011 |
| WO | WO 2011/029802 | 3/2011 |
| WO | WO 2011/031554 | 3/2011 |
| WO | WO 2011/035900 | 3/2011 |
| WO | WO 2011/044481 | 4/2011 |
| WO | WO 2011/057784 | 5/2011 |
| WO | WO 2011/069141 | 6/2011 |
| WO | WO 2011/112662 | 9/2011 |
| WO | WO 2011/130146 | 10/2011 |
| WO | WO 2011/144338 | 11/2011 |
| WO | WO 2011/146808 | 11/2011 |
| WO | WO 2012/003457 | 1/2012 |

(56) References Cited

FOREIGN PATENT DOCUMENTS

| | | |
|---|---|---|
| WO | WO 2012/068440 | 5/2012 |
| WO | WO 2012/068450 | 5/2012 |
| WO | WO 2012/177606 | 12/2012 |
| WO | WO 2013/007765 | 1/2013 |
| WO | WO 2013/007768 | 1/2013 |
| WO | WO 2013/023119 | 2/2013 |
| WO | WO 2013/026025 | 2/2013 |
| WO | WO 2013/036611 | 3/2013 |
| WO | WO 2014/071031 | 5/2014 |
| WO | WO 2014/138168 | 9/2014 |

OTHER PUBLICATIONS

Aho, T. et al., Expression of human pim family genes is selectively up-regulated by cytokines promoting T helper type 1, but not T helper type 2, cell differentiation, Immunology 116: 82-88, 2005.

Albach et al., "Diagnosis of keratoconjunctivitis sicca in rheumatoid arthritis. The value of various tests", Ophthalmologe, Apr. 1994; 91(2):229-34—in German (with English abstract/summary contained therein).

Anderson et al., "Biochemical characterization of GSK1070916, a potent and selective inhibitor of Aurora B and Aurora C kinases with an extremely long residence time", Biochem. J., 420(2), 259-265 (2009).

Bachmann, et al., "The serine/threonine kinease Pim-1," The International Journal of Biochechemistry and Cell Biology 37: 726-730 (2005).

Banker, et al., "Modern Pharmaceuticals" p. 596 (1996).

Barabino et al., "Tear film and ocular surface tests in animal models of dry eye; uses and limitations", Experimental Eye Research, 2004, 79, 613-621.

Barr et al., "Corneal scarring in the Collaborative Longitudinal Evaluation of Keratoconus (CLEK) Study: baseline prevalence and repeatability of detection", Cornea, 1999; 18(1):34-46.

Baudouin et al., "Flow cytometry in impression cytology specimens. A new method for evaluation of conjunctival Inflammation", Invest Ophthalmol Vis Sci, 1997; 38:1458-1464.

Baytel et al., "The human Pim-2 proto-oncogene and its testicular expression" Biochimica et Biophysica Acta 1442: 274-285, (1998).

Begley, et al., "Use of the dry eye questionnaire to measure symptoms of ocular irritation in patients with aqueous tear deficient dry eye", Cornea, 2002:21:664-70.

Bell, Malcolm, and Zalay, Andrew, "Synthesis of Substituted 3-Amino[6, 5-b] triazinoindoles." Journal of Heterocyclic Chemistry, 12(5):1001-1004, Oct. 1975.

Berge, et al., "Pharmaceutical salts", J. Pharma. Science (1977) vol. 66(1) pp. 1-19.

Beyer, "Uber die Synthese von 2-Methylmercapto-1.3.4-thiodiazinen und deren Umlagerung in Pyrazolderivate (The synthesis of 2-methylthio-1,3,4-thiadiazines and their rearrangement to pyrazole derivatives)", Chem. Berichte Jahrg., 92:2593-2599 (1959) (abstract provided).

Bhattacharya et al., "Brittain, ed. Polymorphism in Pharmaceutical Solids," 2009, p. 327-345.

Bhovi, et al., "1 ,3-Dipolar Cycloaddition Reaction: Synthesis and Antimicrobial, Activity of Some New 3-Ethoxycarbonyl-s-Methoxy-6-Bromo-2-Triazolylmethylindoles", Indian Journal of Heterocyclic Chemistry, vol. 14, (Jul.-Sep. 2004), pp. 15-18.

Bioreversible Carriers in Drug Design, ed. Edward B. Roche, American Pharmaceutical Association and Pergamon Press, 1987* too voluminous to provide.

Blume-Jensen, et al, "Oncogenic kinase signaling", Nature 2001, 411(6835):355-365.

Bock, C., et al. "Managing drug resistance in cancer: lessons from HIV therapy." Nature. (Jul. 2012), vol. 12, pp. 494-501.

Bolen, "Nonreceptor tyrosine protein kinases", Oncogene, 1993, 8(8):2025-31.

Bollrath et al., "gp130-Mediated Stat3 Activation in Enterocytes Regulates Cell Survival and Cell-Cycle Progression during Colitis-Associated Tumorigenesis," Cancer Cell, 15:91-102 (2009).

Borie, et al., "Combined Use of the Jak3 Inhibitor CP-690, 550 with Mycophenolate Mofetil to Prevent Kidney Allograft Rejection in Nonhuman Primates", Transplantation, Dec. 27, 2005;80(12):1756-64.

Bosworth, JAK1/JAK2 Inhibitor Ruxolitinib Is a Rising Start, Clinical Oncology, vol. 06:04 (Apr. 2011) 3 pages.

Boudny, et al., "JAK/STAT signaling pathways and cancer", Neoplasm, 49:349-355, 2002.

Bourcier et al., "Expression of CD40 and CD40 ligand in the human conjunctival epithelium", Invest Ophthalmol Vis Sci, 2000;41:120-126.

Bowman, et al. "STATs in oncogenesis", Oncogene, 19:2474-2488, 2000.

Brignole et al., "Expression of Fas-Fas Ligand Antigens and Apoptotic Marker AP02-7 by the Human Conjunctival Epithelium. Positive correlation with class II HLA DR expression in inflammatory Ocular Surface Disorders", Exp Eye Res, 1998;67:687-697.

Brignole et al., "Flow cytometric analysis of inflammatory markers in conjunctival epithelial cells of patients with dry eyes", Invest Ophthalmol Vis Sci, 2000; 41:1356-1363.

Brignole et al., "Flow cytometric analysis of inflammatory markers in KCS: 6-month treatment with topical cyclosporin A", Invest Ophthalmol Vis Sci, 2001; 42:90-95.

Brignole et al., "Flow cytometry in conjunctival impression cytology: a new tool for exploring ocular surface pathologies", Exp Eye Res, 2004;78:473-481.

Bromberg et al., "Inflammation and Cancer: IL-6 and STAT3 Complete the Link," Cancer Cell, 15:79-80 (2009).

Bron, et al., "Grading of corneal and conjunctival staining in the context of other dry eye tests", Cornea, 2003;22(7):640-50.

Bron, et al., "Methodologies to Diagnose and Monitor Dry Eye Disease: Report of the Diagnostic Methodology Subcommittee of the International Dry Eye Workshop (2007)", The Ocular Surface, 5(2), 108-152 (Apr. 2007).

Burger et al., "Janus kinase inhibitor INCB20 has antiproliferative and apoptotic effects on human myeloma cells in vitro and in vivo", Mol. Cancer Ther. 2009:8(1), Jan. 2009 pp. 26-35.

Burger, et al., "Gp130 and ras mediated signaling in human plasma cell line IN/a-6: a cytokine-regulated tumor model for plasmacytoma", Hematol J., 2:42-53, 2001.

Campas-Moya, C., "Ruxolitinib. Tyrosine-protein kinase JAK1/2 inhibitor, treatment of myelofibrosis, treatment of myeloproliferative neoplasms, treatment of psoriasis", Drugs of the Future, (Jun. 2010) vol. 35, No. 6, pp. 457-465.

Candotti, et al. (2002). "Molecular aspects of primary immunodeficiencies: lessons from cytokine and other signaling pathways.", J Clin Invest, 109(10): 1261-9.

Candotti, F., et al. (1997). "Structural and functional basis for JAK3-deficient severe combined immunodeficiency.", Blood, 90(10): 3996-4003.

Carey and Sundberg, Advanced Organic Chemistry, Part B: Reactions and Synthesis, 4th ed., Kluwer Academic/Plenum Publishers:New York, pp. 111-119 (2001).

Carey and Sundberg, Advanced Organic Chemistry, Part B: Reactions and Synthesis, Oxidations, 4th ed., Kluwer Academic/Plenum Publishers:New York, pp. 747-757 (2001).

Cermak, et al, "Is complete androgen insensitivity syndrome associated with alterations in the meibomium gland and ocular surface", Cornea, 2003;22:516-521.

Cetkovic-Cvrlje, et al. (2003). "Targeting JAK3 with JANEX-1 for prevention of autoimmune type 1 diabetes in NOD mice.", Clin Immunol, 106(3): 213-25.

Chalandon, "Targeting mutated protein tyrosine kinases and their signaling pathways in hematologic malignancies", Haematologica, 90 (7):949-68 (2005).

Changelian, et al., "Prevention of Organ Allograft Rejection by a Specific Janus Kinase 3 Inhibitor", Science, 2003, 302, 875-878.

Chauhan, et al, "Autoimmunity in Dry Eye due to resistance of Th17 to Treg Suppression", J. Immunology, 182(3):1247-52 (2009).

Chemical encyclopedia, vol. 1, pp. 242-243, publication "Soviet Encyclopedia," Moscow, 1988.

Chen, et al., "Stat3 Activation in Human Endometrial and Cervical Cancer", British Journal of Cancer, 96, 591-599, 2007.

(56) References Cited

OTHER PUBLICATIONS

Chew, et al., "An instrument for quantifying meibomian lipid on the lid margin: the Meibometer", Curr Eye Res, 1993a;12:247-254.
Chew, et al., "The casual level of meibomian lipids in humans", Current Eye Research, 1993b;12:255-259.
Cho, et al, "Review of the tear break-up time and a closer look at the tear break-up time of Hong Kong Chinese", Optom Vis Sci, 1993;70(1):30-8.
Choi Ha-Soon, et al, "Design and synthesis of 7H-pyrrolo[2,3-d]pyrimidines as focal adhesion kinase inhibitors. Part 1", Bioorg. & Med. Chem. Lett., 16(8):2173-2176 (2006).
Chu-Moyer, et al., "Preparation of the Four Regioisomeric 2-(Methylthio)oxazolopyridines: Useful Synthons for Elaboration to 2-(Amino substituted)oxazolopyridines", J. Org. Chem. 60(17): 5721-5725 (1995).
Cilloni et al., "Emerging drugs for chronic myeloid leukemia", Expert Opinion on Emerging Drugs, (Jun. 2010) vol. 15, No. 2, pp. 175-184.
Clark et al., "Discovery and Development of Janus Kinase (JAK) inhibitors for Inflammatory Diseases," J Med Chem., 2014, pp. A-P.
Coligan, J.E. et al, Wiley Press; Methods in Molecular Biology: vol. 225, Inflammation Protocols., Winyard, P.G. and Willoughby, D.A., Humana Press (2003)* too voluminous to provide.
Communication dated Jan. 22, 2009 for European Appln. No. 06839328.9 (5 pages).
Conklyn, M. et al., "The JAK3 inhibitor CP0690550 selectively reduces NK and CD8+ cell numbers in cynomolgus monkey blood following chronic oral dosing", Journal of Leukocyte Biology, 2004, 76, 1248-1255.
Costa Rican Office Action in CR Application No. 10065, dated Jul. 16, 2013, 8 pages.
Cottet and Schlosser, "Three Chloro(trifluoromethyl)pyridines as Model Substrates for Regioexhaustive Functionalization," Eur J Org Chem, 2004, 18:3793-3798.
Craig et al. "Tear lipid layer structure and stability following expression of the meibomian glands.", Ophthalmic Physiol Opt, 1995, 15(6):569-74.
Current Protocols in Immunology, vol. 3., Coligan, J.E. et al, Wiley Press (1988)* too voluminous to provide.
Daniels et al., "Imatinib mesylate inhibits the profibrogenic activity of TGF-? and prevents bleomycinmediated lung fibrosis." J. Clin. Invest., 114(9):1308-1316, Nov. 2004.
Danjo et al., "Observation of precorneal tear film in patients with Sjogren's syndrome", Acta Ophthalmol Scand, 73:501-505 (1995).
De Paiva, et al, "IL-17 disrupts corneal barrier following desiccating stress", Mucosal Immunol. 2(3):243-53 (2009).
De Vos, J., et al. (2000). "JAK2 tyrosine kinase inhibitor tyrphostin AG490 downregulates the mitogen-activated protein kinase (MAPK) and signal transducer and activator of transcription (STAT) pathways and induces apoptosis in myeloma cells.", Br J Haematol, 109(4): 823-8.
Deng Jun, et al, "Rh-catalyzed asymmetric hydrogenation of gamma-phthalimido-substituted esters: an efficient enantioselective synthesis of beta-aryl-gamma-amino acids", Org. Lett. 9(23):4825-4827 (2007).
Deuse, T. et al., "Novel Immunosuppression: R348, a JAK3- and Syk-Inhibitor Attenuates Acute Cardiac Allograft Rejection", Transplantation, 2008, 85(6) 885-892.
Doane, "An instrument for in vivo tear film interferometry", Optom Vis Sci, 1989; 66: 383-8.
Doleschall G., et al., "Thermal and Acid Catalysed Degradations of 3-alkylthio-6,7-dihydro[1.2.4]triazino[1,6-c]quinazolin-5-ium-1-olates", Tetrahedron, 30:3997-4012, 1974.
Dudley, A.C., et al. "AVEGF/JAK2/STAT5 axis may partially mediate endothelial cell tolerance to hypoxia", Biochem. J. 2005, 390(Pt 2):427-36.
Eghtedar, "Phase II Study of the JAK2 Inhibitor, INCB018424, in Patients with Refractory Leukemias Including Post-Myeloproliferative Disorder Acute Myeloid Leukemia", American Society of Hematology (ASH) annual meeting in Orlando, FL (Dec. 6, 2010), Abstract/poster 509.
Einmahl, et al., "Therapeutic applications of viscous and injectable poly(ortho esters)", Adv. Drug. Deliv. Rev. 53:45-73 (2001).
Eliason, et al., "Staining of the conjunctiva and conjunctival tear film", Br J Ophthalmol, 1990;74:519-22.
Expert Scientific Group on Phase One Clinical Trials Final Report, Nov. 30, 2006, pp. C1, C35-C38.
Fabrizio Saettone, "Ocular inserts for topical delivery", Advanced Drug Delivery Reviews 16:95-106 (1998).
Farrell et al., "A classification for dry eyes following comparison of tear thinning time with Schirmer tear test", Acta Ophthalmol (Copenh), 1992; 70(3):357-60.
Farrell et al., "A clinical procedure to predict the value of temporary occlusion therapy in keratoconjunctivitis sicca" Ophthal Physiol Opt, 2003;23:1-8.
Farris, "Tear osmolarity—a new gold standard?" Adv Exp Med Biol, 350:495-503, 1994.
Fiskus, W. et al., "Synergistic Activity of Combinations of JAK2 Kinase Inhibitor with PI3K/mTOR, MEK or PIM Kinase Inhibitor Against Human Myeloproliferative Neoplasm Cells Expressing JAK2V617F" J. American Chem. Soc., 52nd Annual Meeting of the American-Society-of-Hematology (ASH); Orlando, FL, USA; Dec. 4-7, 2010, ACS Publications; vol. 116, No. 21 Nov. 1, 2010 p. 349, XP002667216, ISSN: 0002-7863 (1 page).
Flex E., et al., "Somatically acquired JAK1 mutations in adult acute lymphoblastic leukemia", J. Exp Med. 205:751-8, (2008).
Fonseca, J.E. et al., "Interleukin-6 as a key player in systemic inflammation and joint destruction", Autoimmunity Reviews, 8:538-42, (2009).
Fridman, et al., "Preclinical evaluation of local JAK1 and JAK2 inhibition in cutaneous inflammation", Journal of Investigative Dermatology, (Sep. 2011) vol. 131, No. 9, pp. 1838-1844.
Fridman, J. et al. "Selective JAK Inhibition is Efficacious against Multiple Myeloma Cells and Reverses the Protective Effects of Cytokine and Stromal Cell Support" Abstract #0956, presented Sunday, Jun. 15, 2008 at the European Hematology Association, 13th Congress, Jun. 12-15, Copenhagen, Denmark (1 page).
Fridman, Jordan et al. "Discovery and Preclinical Characterization of INCB018424, a Selective JAK2 Inhibitor for the Treatment of Myeloproliferative Disorders" poster presented at the American Society of Hematology, 49th Annual Meeting and Exposition, GA. Abstract #3538, poster #757, Dec. 10, 2007 (1 page).
Fridman, Jordan et al. "Efficacy and Tolerability of Novel JAK Inhibitors in Animal Models of Rheumatoid Arthritis" poster presented at the ACR/ARHP (American College of Rheumatology/Association of Rheumatology Health Professionals) Scientific Meeting 2007, Boston, MA. Nov. 10, 2007. Abstract 1771, poster 285 (1 page).
Fridman, Jordan, et al. "Discovery and Preclinical Development of Selective JAK Inhibitors for the Treatment of Hematological Malignancies" poster presented at European Hematology Association, 12th Congress, Vienna, Austria. Abstract 0324, Jun. 8, 2007 (1 page).
Fridman, Jordan, et al. "Discovery and Preclinical Development of Selective JAK Inhibitors for the Treatment of Myeloproliferative Disorders" poster presented at the 4th International Congress on Myeloproliferative Diseases and Myelodysplastic Syndromes, New York, NY. Nov 8-10, 2007. Poster 0009 (1 page).
Fujihara et al., "Evaluation of human conjunctival epithelium by a combination of brush cytology and flow cytometry: an approach to the quantitative technique", Diagn Cytopathol, 1997;17:456-60.
Fujii, C. et al., "Aberrant expression of serine.thereonine kinase Pim-3 in hepatocellular carcinoma development and its role in the proliferation of human hepatoma cell lines" International Journal of Cancer 114: 209-218, (2005).
Fukagawa et al., "Histological evaluation of brush cytology of rabbit conjunctiva", Nippon Ganka Gakkai Zasshi, 1993;97:1173-8 (contains English abstract within the article).
Gaertner, "Cyclization ofl-Alkylamino-3-halo-2-alkanolst o 1-Alkyl-3-azetidinols," J. Org. Chem., 1967, 32, 2972-76.
Ghelardi, et al., "A Mucoadhesive Polymer Extracted from Tamarind Seed Improves the Intraocular Penetration and Efficacy of

(56) References Cited

OTHER PUBLICATIONS

Rufloxacin in Topical Treatment of Experimental Bacterial Keratitis", Antimicrob. Agents Chemother. 48:3396-3401 (2004).
Glasson et al., "Differences in clinical parameters and tear film of tolerant and intolerant contact lens wearers", Invest Ophthalmol Vis Sci, 2003;44:5116-5124.
Glattfeld, "Improvements in the Preparation of DL-Threonic and DL-Erythronic Acids", J. Am. Chem. Soc. 62:974-977 (1940).
Gobbels et al., Tear secretion in dry eyes as assessed by objective fluorophotometry. Ger J Ophthalmol, 1992; 1:350-353.
Golding et al., "X-ray and scanning electron microscopic analysis of the structural composition of tear ferns", Cornea Jan. 1994;13(1):58-66.
Gomtsyan, et al, "Design, synthesis, and structure-activity relationship of 6-alkynylpyrimidines as potent adenosine kinase inhibitors", J. Med. Chem. 45(17):3639-3648 (2002).
Gooseman, et al., "The intramolecular b-fluorine . . . ammonium interaction in 4- and 8-membered rings", Chem. Commun, vol. 30, pp. 3190-3192 (2006).
Gorre, M.E. et al., "Clinical Resistance to STI-571 Cancer Therapy Caused by BCR-ABL Gene Mutation or Amplification." Science, 293:876, 2001.
Gotlieb, Alice, Presentation at the 2008 American Academy of Dermatology, 66th Annual Meeting, San Antonio, TX. Feb. 1, 2008, symposium-303 (12 pp.).
Goto et al., Color mapping of tear lipid layer thickness distribution from the image analysis in DR-1 tear lipid layer interference images (ARVO abstract). ARVO 2004.
Goto et al., "Computer-synthesis of an interference color chart of human tear lipid layer by a colorimetric approach",Invest Ophthalmol Vis Sci, 2003;44:4693-7.
Goto et al., "Differentiation of lipid tear deficiency dry eye by kinetic analysis of tear interference images", Arch Ophthalmol, 2003;121:173-80.
Goto et al., "Evaluation of the tear film stability after laser in situ keratomileusis using the tear film stability analysis system", Am J Ophthalmol, 2004b Jan.;137(1):116-20.
Goto et al., "Tear Film Stability Analysis System: Introducing a new application for videokeratography", Cornea, 2004a; Nov.;23(8):S65-S70.
Goto, et al., Kinetic analysis of tear interference images in aqueous tear deficiency dry eye before and after punctal occlusion. Invest Ophthalmol Vis Sci, 2003;44:1897-905.
Gottlieb, A.B., et al, "Psoriasis: Emerging Therapeutic Strategies", Nat Rev Drug Disc., 4:19-34 (2005).
Grabbe, et al., "Immunoregulatory mechanisms involved in elicitation of allergic—contact hypersensitivity", Immunol Today, Jan.; 19(1):37-44 (1998) (only 1 page provide and marked "best available copy").
Green, T.W. and Wuts, P.G.M.. Protective Groups in Organic Synthesis, 3rd. Ed., Wiley & Sons, Inc., New York (1999)* too voluminous to provide.
Gregory, et al., "Clinical and laboratory features of myelofibrosis and limitations of current therapies", Clinical Advances in Hematology and Oncology, (Sep. 2011) vol. 9, No. 9, pp. 1-3.
Grivennikov, et al., "IL-6 and STAT3 are required for survival of intestinal epithelial cells and the development of colitis-associated cancer", Cancer Cell, 15:103-111 (2009).
Groneberg et al., "Animal models of allergic and inflammatory conjunctivitis," Allergy, 2003, 58, 1101-1113.
Guillon, Jean-Pierre, "Tear film photography and contact lens wear", J Br Contact Lens Assoc, 1982;5:84-7.
Gura, Science, vol. 278, No. 5340, pp. 1041-1042 (1997).
Guschin, et al, "A major role for the protein tyrosine kinase JAK1 in the JAKSTAT signal transduction pathway in response to interleukin-6", Embo J 14:1421-1429 (1995).
Hamze et al., "Synthesis of Various 3-Substituted 1,2,4-Oxadiazole-Containing Chiral β3- and r-Amino Acids from Fmoc-Protected Aspartic Acid," J. Org. Chem., 2003, 68(19), pp. 7316-7321.
Hardwicke, et al., "GSK1070916, a potent Aurora B/C kinase inhibitor with broad antitumor activity in tissue culture cells and human tumor xenograft models", Molecular Cancer Therapeutics 8(7), 1808-1817 (2009).
Helal et al., "Stereoselective Synthesis of cis-1,3-Disubstituted Cyclobutyl Kinase Inhibitors," Organic Letters, (2004), 6(11), pp. 1853-1856.
Hickenbottom "Reactions of organic compounds," State Scientific-Technical Publishing Association, Chemical Literature Section, Moscow, 1939, pp. 360-362.
Higuchi, et al., "Pro-drugs as Novel Delivery Systems," vol. 14 of the A.C.S. Symposium Series (1975)* too voluminous to provide.
Holly et al., "Lacrimation kinetics in Humans as determined by a novel technique", in Holly FJ (ed). The preocular tear film. Lubbock TX, Lubbock Dry Eye Institute, 1986, pp. 76-88).
Hong, et al., "Total Synthesis of Onnamide A", J. Am. Chem. Soc., 113:9693-94 (1991).
Huang, "Inhibition of STAT3 activity with AG490 decreases the invasion of human pancreatic cancer cells in vitro", Cancer Sci. 97(12):1417-23 (2006).
Huttel, et al., "Lithium pyrazole compounds", Liebigs Ann. Chem. Bd., 625:55-65 (1959) (abstract provided).
International Preliminary Report on Patentability (with Written Opinion) dated Jun. 18, 2008 for International Appln. No. PCT/US2006/047369 (10 pgs.).
International Preliminary Report on Patentability (with Written Opinion) dated Mar. 6, 2012 for International Appln. No. PCT/US2010/047252 (7 pgs.).
International Preliminary Report on Patentability (with Written Opinion) dated Nov. 22, 2011 for International Appln. No. PCT/US2010/035728 (8 pgs.).
International Preliminary Report on Patentability (with Written Opinion) dated Nov. 22, 2011 for International Appln. No. PCT/US2010/035783 (5 pgs.).
International Preliminary Report on Patentability for International Appln. No. PCT/US2008/066662 dated Dec. 17, 2009 (7 pgs.).
International Preliminary Report on Patentability for PCT/US2008/66658 mailed Dec. 17, 2009 (7 pages).
International Preliminary Report on Patentability for PCT/US2009/036635 mailed Sep. 14, 2010 (6 pages).
International Preliminary Report on Patentability for PCT/US2009/059203 mailed Apr. 5, 2011 (6 pages).
International Preliminary Report on Patentability for PCT/US2010/021003 mailed Jul. 19, 2011(11 pages).
International Preliminary Report on Patentability for PCT/US2010/052011 mailed Apr. 11, 2012 (4 pages).
International Preliminary Report on Patentability for PCT/US2011/025433 mailed Aug. 21, 2012 (7 pages).
International Preliminary Report on Patentability for PCT/US2011/027665 mailed Sep. 11, 2012 (7 pages).
International Preliminary Report on Patentability for PCT/US2011/037291 mailed Nov. 27, 2012 (7 pages).
International Preliminary Report on Patentability for PCT/US2011/061351 mailed May 30, 2013 (7 pages).
International Preliminary Report on Patentability for PCT/US2011/061374 mailed May 30, 2013 (5 pages).
International Preliminary Report on Patentability for PCT/US2012/043099 mailed Dec. 23, 2013, 6 pages.
International Preliminary Report on Patentability for PCT/US2012/050210 mailed Feb. 11, 2014, 8 pages.
International Preliminary Report on Patentability for PCT/US2012/051439 mailed Feb. 27, 2014, 7 pages.
International Preliminary Report on Patentability for PCT/US2012/053921 mailed Mar. 20, 2014, 8 pages.
International Search Report and the Written Opinion, PCT/US2012/051439, mailed Nov. 30, 2012 (15 pages).
International Search Report and the Written Opinion, PCT/US2012/053921, mailed Nov. 7, 2012 (19 pages).
International Search Report and Written Opinion dated Feb. 9, 2010 for International Appln. No. PCT/US2009/059203 (10 pages).
International Search Report and Written Opinion for International Appln. No. PCT/US2005/046207 dated May 15, 2007 (6 pages).

(56) References Cited

OTHER PUBLICATIONS

International Search Report and Written Opinion for International Appln. No. PCT/US2008/066662 dated Dec. 23, 2008 (11 pgs.).
International Search Report and Written Opinion for International Appln. No. PCT/US2009/036635 dated Jun. 3, 2009 14 pages.
International Search Report and Written Opinion for PCT/US2006/047369, 16 pages (Apr. 24, 2007).
International Search Report and Written Opinion for PCT/US2008/083319, 29 pages mailed Mar. 13, 2009.
International Search Report and Written Opinion for PCT/US2011/025433, 12 pages (mailed Jul. 20, 2011).
International Search Report and Written Opinion for PCT/US2011/027665 mailed Jun. 27, 2011 (14 pages).
International Search Report and Written Opinion for PCT/US2011/037291, 11 pages (Apr. 19, 2012).
International Search Report and Written Opinion for PCT/US2011/061351 mailed Feb. 17, 2012 (12 pages).
International Search Report and Written Opinion for PCT/US2011/061374 mailed Mar. 27, 2012 (10 pages).
International Search Report and Written Opinion for PCT/US2012/025581, 16 pages (mailed Apr. 26, 2011).
International Search Report and Written Opinion for PCT/US2012/043099, 11 pages (Sep. 13, 2012).
International Search Report and Written Opinion for PCT/US2012/050252 mailed Jan. 2, 2013, 17 pages.
International Search Report for PCT/US2008/66658 mailed Dec. 23, 2008 (4 pages).
International Search Report for PCT/US2010/021003 mailed Aug. 16, 2010 (8 pages).
International Search Report for PCT/US2010/035728 mailed Jul. 8, 2010 (3 pages).
International Search Report for PCT/US2010/035783 mailed Aug. 23, 2010 (4 pages).
International Search Report for PCT/US2010/047252 mailed Nov. 17, 2010 (4 pages).
International Search Report for PCT/US2010/052011 mailed Nov. 30, 2010 (3 pages).
International Search Report and Written Opinion in International Application No. PCT/US2014/020554, dated Jul. 16, 2014, 17 pages.
International Search Report in International Application No. PCT/US2013/041601, mailed Sep. 3, 2013, 3 pages.
Iranpoor, N.; Firouzabadi, H.; Aghapour, "A Rapid and Facile Conversion of Primary Amides and Aldoximes to Nitriles and Ketoximes to Amides with Triphenylphosphine and N-Chlorosuccinimide", G Syn. Commun 32:2535-41 (2002).
Ishizaki, et al., "Pharmacological Properties of Y-27632, a Specific Inhibitor of Rho-Associated Kinases", Molecular Pharmacology, 2000, 57, 976-983.
Itagaki, et al, "Expedient Synthesis of Potent Cannabinoid Receptor Agonist (−)-CP55,940", Organic Letters, 2005; 7(19); 4181-4183.
James, et al., "A unique clonal JAK2 mutation leading to constitutive signalling causes polycythaemia vera", Nature, 434 (7037):1144-8 (2005).
Janes, M. et al., "Effective and selective targeting of leukemia cells using a TORC1/2 kinase inhibitor.", Nature Medicine (2010) LNKD-PUBMED:20072130, vol. 16, No. 2, pp. 205-213 XP002673719.
Jee, et al., "Overview: animal models of osteopenia and osteoporosis", J Musculoskel. Neuron. Interact., 1(3):193-207 (2001).
Jester, et al., "In vivo biomcroscopy and photography of meibomian glands in a rabbit model of meibomian gland dysfunction", Invest Ophthalmol Vis Sci, 1982;22:660-7.
Johnson, et al., "The effect of instilled fluorescein solution vol. On the values and repeatability of TBUT measurements", Cornea, 2005;24:811-7.
Kaercher, T., "Ocular symptoms and signs in patients with ectodermal dysplasia symdromes", Grafes Arch Clin Exp Ophthalmol, 2004;495-500.
Kamb, Nature Reviews Drug Discovery 4, pp. 161-165 (2005).

Kaushansky, K., "Lineage-Specific Hematopoietic Growth Factors", NEJM 354:2034-45 (2006).
Kawamura, et al. (1994). "Molecular cloning of L-JAK, a Janus family protein-tyrosine kinase expressed in natural killer cells and activated leukocytes.", Proc Natl Acad Sci U S A, 91(14): 6374-8).
Kharas, et al., "ABL Oncogenes and Phosphoinositide 3-Kinase: Mechanism of Activation and Downstream Effectors.", Cancer Res., 65(6):2047-2053, Mar. 15, 2005.
Kim, et al., "Zinc-Modified Cyanoborohydride as a Selective Reducing Agent", J. Org. Chem. 50: 1927-1932 (1985).
King-Smith et al., "Three interferometric methods for measuring the thickness of layers of the tear film", Optom Vis Sci, 1999; 76:19-32.
Kiss, Robert, "Recent developments on JAK2 inhibitors: A patent review", Expert Opinion on Therapeutic Patents, (Apr. 2010) vol. 20, No. 4, pp. 471-495.
Kojima et al., "A new noninvasive tear stability analysis system for the assessment of dry eyes", Invest Ophthalmol Vis Sci, 2004; May;45(5):1369-74).
Kola, Nature Reviews Drug Discovery 3, pp. 711-715 (2004).
Komuro et al., "Assessment of meibomian gland function by a newly developed laser meibometer", Adv Exp Med Biol, 2002; 506:517-520.
Korb et al., "The effect of two novel lubricant eye drops on tear film lipid layer thickness in subjects with dry eye symptoms", Optom Vis Sci, 2005; 82: 594-601.
Korb, et al., "Increase in tear film lipid layer thickness following treatment of meibomian gland dysfunction", Adv Exp Med Biol, 1994;350:293-8.
Korolev, et al., "Pd-EDTA as an efficient catalyst for Suzuki-Miyaura reactions in water", Tet. Lett. 46: 5751-5754 (2005).
Kortylewski, et al., "Regulation of the IL-23 and IL-12 balance by Stat3 signaling in the tumor microenvironment", Cancer Cell, 15:114-123 (2009).
Kruh et al., "The complete coding sequence of arg defines the Abelson subfamily of cytoplasmic tyrosine kinases.", Proc. Natl. Acad. Sci., 87:5802-5806, Aug. 1990.
Kubinyi, H. "QSAR: Hansch Analysis and Related Approaches," Methods and Principles in Medicinal Chemistry, Manhold, R. ed. Weinhein, NY, 1993.
Kudelacz, et al. "The JAK-3 inhibitor CP-690550 is a potent anti-inflammatory agent in a murine model of pulmonary eosinophilia", European Journal of Pharmacology 582 (2008) 154-161.
Kumar, C., "Kinase drug discovery approaches in chronic myeloproliferative disorders", Oncogene, (Jun. 18, 2009) vol. 28, No. 24, pp. 2305-2323.
Kuo, et al., "Pd-EDTA as an efficient catalyst for Suzuki-Miyaura reactions in water", Chem Commun 301-3 (2007).
Kuppens et al., "Basal tear turnover and topical timolol in glaucoma patients and healthy controls by Fluorophotometry", Invest Ophthalmol Vis Sci, 1992; 33:3442-3448.
Lai, et al., "Mechanistic Study on the Inactivation of General Acyl-CoA Dehydrogenase by a Metabolite of Hypoglycin A", J. Am. Chem. Soc. 113: 7388-7397 (1991).
Lam, et al, "Tear Cytokine Profiles in Dysfunctional Tear Syndrome", Am J Ophthalmol., 147(2):198-205 (2009).
Larock, R., "Comprehensive Organic Transformations", Wiley-VCH, 2nd Ed. (1999) pp. 1949-1950, 1958-1959, 1976, and 1983-1985.
Leaf, Clifton, Health Administrator vol. XVII, No. 1:172-183 (2005).
Lemp "Report of National Eye Institute/Industry Workshop on clinical trials in dry eyes", CLAO J, 1995;21:221-232.
Lemp et al., "Corneal desiccation despite normal tear volume", Ann Ophthalmol, 1970 (2) pages:258-261 & 284.
Lemp et al., "The Definition and Classification of Dry Eye Disease: Report of the Definition and Classification Subcommittee of the International Dry Eye WorkShop", The Ocular Surface, 5(2), 75-92 Apr. 2007.
Letter translation of Office Action, Chilean Application No. 3496-2006 as received from the foreign associate (Jul. 5, 2010) (4 pages).
Levine, et al., "Activating mutation in the tyrosine kinase JAK2 in polycythemia vera, essential thrombocythemia, and myeloid metaplasia with myelofibrosis", Cancer Cell, vol. 7, 2005: 387-397.

(56) References Cited

OTHER PUBLICATIONS

Levitzki, "Tyrosine kinases as targets for cancer therapy", Eur. J. Cancer 38(suppl. 5):S11-S18 (2002).
Levy, et al. "INCB018424 A Selective Janus Kinase 1/2 Inhibitor" Presentation at the 50th American Society of Hematology Annual Meeting (ASH), Dec. 8, 2008.
Levy, et al., INCB18424 Discussion presentation at the American Society of Hematology, 49th Annual Meeting and Exposition, Atlanta, GA. Abstract #558, Dec. 10, 2007 (25 pages).
Li, et al., "Pim-3, a proto-oncogene with serine/threonine kinase activity, is aberrantly expressed in human pancreatic cancer and phosphorylates Bad-mediated apoptosis in human pancreatic cell lines" Cancer Research 66(13): 6741-7 (2006).
Lin, "Constitutive Activation of JAK3/STAT3 in Colon Carcinoma Tumors and Cell Lines", Am J Pathol. 167(4):969-80 (2005).
Lin, et al., "Enantioselective synthesis of Janus kinase inhibitor INCB018424 via an organocatalytic aza-Michael reaction," Organic Letters, (2009), 11(9), 1999-2002.
Liu, et al., "Combined Inhibition of Janus Kinase 1/2 for the Treatment of JAK2V617F-Driven Neoplasms: Selective Effects on Mutant Cells and Improvements in Measures of Disease Severity", Clin Cancer Res 2009;15(22) pp. 6891-6900; Nov. 15, 2009; Published Online First on Nov. 3, 2009 as 10.1158/1078-0432.CCR-09-1298.
Lucet et al., "The structural basis of Janus kinas 2 inhibition by a potent and specific pan-Janus kinase inhibitor," Blood, 2006, 107(1):176-183.
Macchi, et al., "Mutations of Jak-3 gene in patients with autosomal severe combined immune deficiency (SCID)", Nature 377:65-8 (1995).
Madden et al. Comparative study of two non-invasive tear film stability techniques. Curr Eye Res, 1994; 13(4):263-9.
Madhusudan et al., "Tyrosine kinase inhibitors in cancer therapy", Clin Biochem., 2004, 37(7):618-35.
Maffioli, et al., "Mild and Reversible Dehydration of Primary Amides with PdC12 in Aqueous Acetonitrile", Organic Letters vol. 7 No. 23, 5237-39 (2005).
Main et al, "High throughput synthesis of diverse 2,5-disubstituted indoles using titanium carbenoids bearing boronate functionality", Tetrahedron, 64(5):901-914 (2007).
Mainstone et al., "Tear meniscus measurement in the diagnosis of dry eye", Curr Eye Res, 1996; 15:653-661.
Mancini, M. et al., "RAD 001 (everolimus) prevents mTOR and Akt late re-activation in response to imatinib in chronic myeloid leukemia.", J. Cellular Biochemistry (2010) LNKD-PUBMED:20014066, XP-002673720 vol. 109, No. 2 (2010) pp. 320-328.
Mandal, "Cancer Classification," 2014. Available from: <http://www.news-medical.net/health/Cancer-Classification.aspx, 6 pages.
Manjula, et al., "Rapid Method of Converting Primary Amides to Nitriles and Nitriles to Primary Amides by ZnC12 using Microwaves under Different Reaction Conditions", Syn. Commun 37:1545-50 (2007).
Manning, et al., "The Protein Kinase Complement of the Human Genome", Science. 2002, 298(5600):1912-16 and 1933-34.
March, Jerry, Advanced Organic Chemistry: Reactions, Mechanisms, and Structure, 3rd ed., John Wiley & Sons:New York, pp. 845-855 (1985).
Marquardt et al., "Modification of tear film break-up time test for increased reliability" in Holly ed. The Preocular Tear Film inHealth, Disease and Contact Lens Wear. Lubbock, Texas: Dry Eye Institute, 1986:57-63.
Maruyama et al., "Effect of environmental conditions on tear dynamics in soft contact lens wearers", Invest Ophthalmol Vis Sci, 2004;45(8):2563-8.
Mathers et al., "Assessment of the tear film with tandem scanning confocal microscopy", Cornea, 1997;16:162-8.
Mathers et al., "Tear film changes associated with normal aging", Cornea, 1996; 15:229-334.
Mathers et al., "Tear flow and evaporation in patients with and without dry eye", Ophthalmology, 1996; 103:664-669.
Mathers et al., "Video imaging of the meibomian gland", Arch Ophthalmol, 1994;112:448-9.
Mathers, "Evaporation from the ocular surface", Exp Eye Res, 2004; 78:389-394.
Mayo Clinic. Available at: <http://www.mayoclinic.com/health/pancreatic-cancer/DS00357>. 2 pages, retrieved from the Internet Apr. 3, 2013.
Mayo Clinic. Available at: <http://www.mayoclinic.com/health/prostate-cancer-prevention/MC00027>. 3 pages, retrieved from the Internet Apr. 3, 2013.
Mayo Clinic. Available at: <http://www.mayoclinic.com/health/crohns-disease/DS00104/DSECTION=treatments-and-drugs> 6 pages, retrieved from the Internet May 27, 2013.
Mayo Clinic. Available at: <http://www.mayoclinic.com/health/multiple-sclerosis/DS00188/DSECTION=treatments-and-drugs>. 3 pages, retrieved from the Internet May 27, 2013.
Mayo Clinic. Available at: <http://www.mayoclinic.com/health/myasthenia-gravis/DS00375> 2 pages, retrieved from the Internet May 27, 2013.
Mayo Clinic. Available at: <http://www.mayoclinic.com/health/rheumatoid-arthritis/DS00020/DSECTION=treatments-and-drugs> 3 pages, retrieved from the Internet Jun. 26, 2013.
Mayo Clinic. Available at: <http://www.mayoclinic.org/diseases-conditions/type-1-diabetes/basics/prevention> 2014, 19 pages.
McNamara et al., "Fluorometry in contact lens research: The next step", Optom Vis Sci, 1998; 75:316-322.
MD Anderson Cancer Center. "Leukemia Prevention and Screening," 2014, 2 pages.
MD Anderson Cancer Center. "Myeloproliferative Disease Prevention and Screening," 2014, 2 pages.
Mengher et al., "Non-invasive tear film break-up time: sensitivity and specificity", Acta Ophthalmol (Copenh), 1986; 64(4):441-4.
Mesa, et al. "INCB018424, A Selective JAK 1/2 Inhibitor, Significantly Improves the Compromised Nutritional Status and Frank Cachexia in Patients with Myelofibrosis (MF)" Poster #1760 at the American Society of Hematology Annual Meeting (ASH), Dec. 6, 2008 (19 pages).
Mesa, et al., "Evaluating the serial use of the myelofibrosis symptom assessment form for measuring symptomatic improvement: Performance in 87 myelofibrosis patients on a JAK1 and JAK2 inhibitor (INCB018424) clinical trial", Cancer, (Nov. 1, 2011) vol. 117, No. 21, pp. 4869-4877.
Mesa, R. et al., "Emerging drugs for the therapy of primary and post essential thrombocythemia, post polycythemia vera myelofibrosis", Expert Opinion on Emerging Drugs England, vol. 14, No. 3 (2009) pp. 471-479.
Methods in Molecular Biology: vol. 225, Inflammation Protocols., Winyard, P.G. And Willoughby, D.A., Humana Press, 2003* too voluminous to provide.
Meydan et al., "Inhibition of acute lymphoblastic leukaemia by a Jak-2 inhibitor", Nature. Feb. 15, 1996;379(6566):645-8.
Miethchen, "Micelle-activated reactions. I. Micelle-activated iodination and partial dehalogenation of pyrazoles and 1,2,4-triazoles", Journal F. prakt. Chemie, Band 331, Heft 5, S. 799-805 (1989) (1 page abstract also provided).
Milici, A.J., et al., "Cartilage preservation by inhibition of Janus kinase 3 in two rodent models of rheumatoid arthritis", Arthritis Research & Therapy, 2008, 10:R14 (http://arthritis-research.com/content/10/1/R14) (9 pages).
Minegishi, et al., "Human Tyrosine Kinase 2 Deficiency Reveals Its Requisite Roles in Multiple Cytokine Signals Involved in Innate and Acquired Immunity", Immunity 25:745-55 (2006).
Mishchenko et al., "Treatment options for hydroxyurea-refractory disease complications in myeloproliferative neoplasms: JAK2 inhibitors, radiotherapy, splenectomy and transjugular intrahepatic portosystemic shunt", Eur J Haematol. Sep. 2010;85(3):192-9. Epub Jun. 2, 2010.
Mishima, et al., "Determination of tear volume and tear flow", Invest Ophthalmol, 1966; 5:264-276.
Mishima, S., "Some physiological aspects of the precorneal tear film", Arch Ophthalmol, 1965;73:233-241.

(56) References Cited

OTHER PUBLICATIONS

Mitsunobu, O., "The Use of Diethyl Axodicarboxylate and Triphenylphosphine in Synthesis and Transformation of Natural Products." Synthesis (1): 1-28 (1981).
Miyata, et al., "Stereospecific nucleophilic addition reactions to olefins.", J. Org. Chem. 56:6556-6564 (1991).
Miyaura et al., "Palladium-Catalyzed Cross-Coupling Reactions of Organoboron Compounds," Chem. Rev., 1995, 95, 2457-2483.
Miyoshi et al., "Interleukin-8 concentrations in conjunctival epithelium brush cytology samples correlate with neutrophil, eosinophil infiltration, and corneal damage", Cornea, 2001;20:743-7.
Moreland, et al. "A Randomized Placebo-Controlled Study of INCB018424, a Selective Janus Kinase 1&2 (JAK 1&2) Inhibitor in Rheumatoid Arthritis (RA)" Presentation at the American College of Rheumatology meeting, Oct. 26, 2008. (20 pages).
Moriarty, et al., "The synthesis and SAR of 2-amino-pyrrolo[2,3-d]pyrimidines: A new class of Aurora-A kinase inhibitors", Bioorganic and Medicinal Chemistry Letters, 16(22), 5778-5783 (2006).
Mosby's Dictionary of Medicine, Nursing, & Health Professions, sicca complex, 2009, Elsevier, printed from http://www.credoreference.com/entry/ehsmosbymed/sicca_complex, 2 pages.
Mullighan, et al, "JAK mutations in high-risk childhood acute lymphoblastic leukemia", Proc Natl Acad Sci USA. 106:9414-8 (2009).
Naka T., "The paradigm of IL-6: from basic science to medicine", Arthritis Res. 2002;4 Suppl 3:S233-42. Epub May 9, 2002.
Nakagawara, Akira, "Trk receptor tyrosine kinases: A bridge between cancer and neural development." Cancer Letters, 169:107-114, 2001.
Nally et al., "Ocular discomfort and tear film break-up time in dry eye patients: A correlation", Invest Ophthalmol Vis Sci, 2000;41:4:1436 (Poster Presentation).
Naqvi, et al., "A potential role of ruxolitinib in leukemia", Expert Opinion on Investigational Drugs, (Aug. 2011) vol. 20, No. 8, pp. 1159-1166.
National Cancer Institute, "FDA Approval for Ruxolitinib Phosphate", http://www.cancer.gov/cancertopics/druginfo/fda-ruxolitinibphosphate posted Nov. 18, 2011 (3 pages).
Naus, et al., "6-(Het)aryl-7-Deazapurine Ribonucleosides as Novel Potent Cytostatic Agents", J. Med. Chem., 53(1):460-470 (2010).
Neidle, Stephen, Cancer Drug Design and Discovery, (Elsevier/Academic Press, 2008) pp. 427-431.
Nelson et al., "Tear film osmolality determination: an evaluation of potential errors in measurement" Curr Eye Res, Sep.;5(9):677-81, 1986.
Neubauer, H., et al., "Jak2 Deficiency Defines an Essential Developmental Checkpoint in Definitive Hematopoiesis", Cell, 93(3): 397-409 (1998).
Nicholoff et al., "Recent Insights into the immunopathogenesis of psoriasis provide new therapeutic opportunities", J. Clin. Invest., 113; 1664-1675 (2004).
Nichols et al., "The lack of association between signs and symptoms in patients with dry eye disease", Cornea, vol. 23(8):762-770 (2004).
Nichols et al., "The repeatability of clinical measurements of dry eye", Cornea, vol. 23(3):272-85 (2004).
Nishio, et al., "Tyrosine kinase-dependent modulation by interferon-α of the ATP-sensitive K+ current in rabbit ventricular myocytes", FEBS Letters, (1999), 445, 87-91.
Nitta, et al., "Peptide-Titanium Complex as Catalyst for Asymmetric Addition of Hydrogen Cyanide to Aldehyde", J. Am. Chem. Soc., 1992, 114, 7969-75 (1992).
Norman, "Selective JAK1 inhibitor and selective Tyk2 inhibitor patents," *Expert Opinion*, Informa Healthcare. 2012, available at: <http://informahealthcare.com/dol/pdfplus/10.1517/13543776.2012.723693>.
Norn, M., "Quantitative tear ferning. Clinical investigations", Acta Ophthalmol (Copenh), Jun. 1994;72(3):369-72.
Notice of Allowance and Fee(s) Due dated Sep. 21, 2007 in connection with U.S. Appl. No. 11/313,394 (6 pages).

Notice of Hearing and Preliminary Report for EP Patent 1966202, dated Mar. 18, 2013 (7 pages).
Office Action (Non-final) dated Aug. 22, 2007 in connection with U.S. Appl. No. 11/115,702 (9 pages).
Office Action (Non-final) dated Dec. 3, 2007 in connection with U.S. Appl. No. 11/524,641 (13 pages).
Office Action (Non-final) dated Feb. 25, 2009 for U.S. Appl. No. 12/137,892 (13 pgs.).
Office Action (Final) dated Feb. 7, 2008 for U.S. Appl. No. 11/115,702 (5 pages).
Office Action (Final) dated Jan. 29, 2014 in U.S. Appl. No. 13/043,986, 10 pages.
Office Action (Final) dated Nov. 30, 2009 for U.S. Appl. No. 12/137,892 (9 pgs.).
Office Action (Non-final) dated Apr. 20, 2007 in connection with U.S. Appl. No. 11/313,394 (16 pages).
Office Action in U.S. Appl. No. 14/186,338, mailed May 5, 2014, 18 pages.
Office Action received for European Application No. 06 839 328.9 (Jan. 22, 2009) (5 pages).
Office Action received for Japanese Application No. 2008-545733 dated Oct. 11, 2011 (5 pages).
Office Action received for New Zealand Application No. 569015 dated Feb. 24, 2010 (2 pages).
Office Action received for Singapore Application No. 2008-04386-1 (Aug. 24, 2010).
Office Action received for Vietnamese Patent Application No. 1-2011-03188 dated Mar. 8, 2012 as translated by foreign associate (10 pages).
Office Action, Canadian Patent Office, Application No. 2,632,466, dated May 8, 2012 (3 pages).
Office Action, China, Patent Application No. 201080033308.6 dated Aug. 2, 2013, 10 pages.
Office Action, Eurasian Patent Office, prepared Feb. 5, 2010.
Office Action, European Patent Office, Application No. 06 839 328.9 mailed Oct. 21, 2010.
Office Action, European Patent Office, mailed Nov. 6, 2009.
Office Action, Mexico, Patent Appl. No. MX/a/2008/007635 as received from foreign associate dated Jun. 15, 2010 (1 page).
Office Action, Mexico, Patent Appl. No. MX/a/2008/007635 as received from foreign associate dated Nov. 13, 2009 (4 pages).
Office Action/Examination Report received for Pakistan Application No. 211/2009 dated Jan. 18, 2010 (1 page).
Oguz, et al., "The height and radius of the tear meniscus and methods for examining these parameters", Cornea, 2000;19:497-500.
Opposition for EP Patent 1966202, filed on Jun. 21, 2012 (30 pages).
Opposition for India Patent Application No. 2365/KOLNP/2008 dated Nov. 12, 2012 (received by Applicants from Indian associate on Apr. 17, 2013) 37 pages.
Opposition, Costa Rica, translation from Foreign Associate Dated Jun. 13, 2012, 6 pages.
Opposition, Costa Rica, translation from Foreign Associate Dated Nov. 20, 2013, 9 pages.
Opposition, Ecuador Patent Office, mailed Nov. 18, 2008 1 page letter from Foreign Associate enclosing the translation (5 pages) of the Opposition.
Ortmann, et al., "Janus kinases and signal transducers and activators of transcription: their roles in cytokine signaling, development and immunoregulation." Arthritis Res, 2(1): 16-32 (2000).
Ostojic et al., "Ruxolitinib for the treatment of myelofibrosis", Drugs of Today, (Nov. 2011) vol. 47, No. 11, pp. 817-827.
Ousler, et al., "Factors that influence the inter-blink interval (IBI) as measured by the ocular protection index (OPI)", Invest Ophthalmol Vis Sci 2001; 43: E-abstract 56 (Poster presentation) ARVO (2002) 2 pages, downloaded from http://abstracts.iov.s.org/cgi/content/abstract/43/12/56?maxtoshow on Aug. 14, 2009.
Palmer, et al., "Multiple roles of ephrins in morphogenesis, neuronal networking, and brain function." Genes & Dev., 17:1429-1450, 2003.
Pardanani A., "JAK2 inhibitor therapy in myeloproliferative disorders: rationale, preclinical studies and ongoing clinical trialsJAK2 inhibitor therapy in MPD", Leukemia 22, 23-30 (Jan. 2008).
Parganas, E., D. Wang, et al., "Jak2 is Essential for Signaling through a Variety of Cytokine Receptors", (1998). Cell, 93(3): 385-95.

(56) References Cited

OTHER PUBLICATIONS

Park et al., "Homogeneous Proximity Tyrosine Kinase Assays: Scintillation Proximity Assay versus Homogeneous Time-Resolved Fluorescense", Analytical Biochemistry, 1999, 269, 94-104.
Parks, "Tofacitinib and Other Kinase Inhibitors Offer New Approach to Treating Rheumatoid Arthritis," Rheumatologist, Jun. 2013, pp. 1-12 Available from: <http://www.the-rheumatologist.org/details/article/487 1781/Tofacitinib_and_Other_Kinase_Inhibitors_Offer_New_Approach_to_Treating_Rheumatoi.html>, 12 pages.
Patani, et al., "Bioisosterism: A Rational Approach in Drug Design", Chem. Rev., 1996, 96, 3147-3176.
Patrick, Graham L., "An Introduction to medicinal chemistry" *Oxford University Press Inc.*, New York, 1995 (31 pages) (cited in Opposition from India dated Nov. 12, 2012.
Pearce et al., "Spatial location studies on the chemical composition of human tear ferns", Ophthalmic Physiol Opt, (2000) vol. 20(4):306-13.
Pearce, et al., "An improved fluorophotometric method for tear turnover assessment", Optom Vis Sci, (2001) 78(1):30-36).
Pensyl et al., "The repeatability of tear mucus ferning grading", Optom Vis Sci, Aug. 1998;75(8):600-4.
Pernis, et al., "JAK-STAT signaling in asthma." J Clin Invest, 109(10): 1279-83 (2002).
Peters, K. G. et al., "Functional Significance of Tie2 Signaling in the Adult Vasculature", 2004, © The Endocrine Society (21 pages).
Pflugfelder, et al., "Evaluation of subjective assessments and objective diagnostic tests for diagnosing tear-film disorders known to cause ocular irritation", Cornea, 1998;17(1):38-56.
Pillonel, Christian, "Evaluation of phenylaminopyrimidines as antifungal protein kinase inhibitors", Pest Management Science, Wiley & Sons, vol. 61, Jun. 13, 2005 pp. 1069-1076.
Pirard, B. et al., "Classification of Kinase Inhibitors Using BCUT Descriptors", J. Chem. Inf. Comput. Sci., 2000, 40, 1431-1440.
Pisella et al., Flow cytometric analysis of conjunctival epithelium in ocular rosacea and keratoconjunctivitis sicca. Ophthalmology, 2000;107:1841-1849.
Pisella, et al., Conjunctival proinflammatory and proapoptotic effects of latanoprost, preserved timolol and unpreserved timolol: an ex vivo and in vitro study. Invest Ophthalmol Vis Sci, 2004;45:1360-1368).
Portnaya, et. al., "Azomethine dyes. IV. Indoaniline dyes derived from heterocyclic N-substituted 1-hydroxy-2-naphthamid", Ts Vses Nauchn Issled Kinofotoinst, Issue 40, (1960) pp. 106-8 (with English abstract 20 pages total).
Press Release dated Sep. 18, 2008: "Incyte's Topical JAK Inhibitor Demonstrates Positive Proof-of-Concept Results in Patients with Mild to Moderate Psoriasis" (4 pages).
Prezent, et al., "Boron chelates as intermediates in the synthesis of new functionalized pyridines and pyrimidines from a, a-dioxoketene aminals", Proceedings of the International Conference on the Chemistry of Boron, vol. 11 (2003) (abstract only—1 page).
Punwani et al., Poster/presentation, "Initial Efficacy and Safety of Topical INCYB018424 Cream, a Selective Janus Kinase 1&2 (JAK 1&2) Inhibitor in Psoriasis" 17th Congress of the European Academy of Dermatology and Venereology, Paris, France, Sep. 17, 2008 (15 pages).
Quesada et al, "One-pot conversion of activated alcohols into 1,1-dibromoalkenes and terminal alkynes using tandem oxidation processes with manganese dioxide", Tetrahedron, 62 (2006) 6673-6680.
Quintas-Cardama et al., "Preclinical characterization of the selective JAK1/2 inhibitor INCB018424: therapeutic implications for the treatment of myeloproliferative neoplasms", Blood First Edition Paper, prepublished online Feb. 3, 2010, American Society of Hematology; DOI 10.1182/blood-2009-04-214957, 115(15):3109-3117.
Ravin, L., "Preformulation", Remington's Pharmaceutical Sciences, 17th ed., Mack Publishing Company, Easton, Pa., 1985, Chapter 76, pp. 1409-1423.
Ren et al., "Compounds and Compositions as Protein Kinase Inhibitors," U.S. Appl. No. 60/578,491, filed Jun. 10, 2004 (56 pages).
Response and Amendment dated Aug. 25, 2009 to non-final Office Action for U.S. Appl. No. 12/137,892 (34 pgs.).
Response and Amendment in Reply to Action of Apr. 20, 2007 filed Jul. 17, 2007 for U.S. Appl. No. 11/313,394 (39 pages).
Response to Action of Aug. 22, 2007 dated Nov. 19, 2007, U.S. Appl. No. 11/115,702 (7 pages).
Response to Restriction Requirement dated May 29, 2007, U.S. Appl. No. 11/115,702 (8 pages).
Restriction Requirement dated Mar. 6, 2007 in connection with U.S. Appl. No. 11/115,702 (8 pages).
Roberts, Jr., et al., JAMA 292(17):2130-2140 (2004).
Robin et al., In vivo transillumination biomicroscopy and photography of meibomian gland dysfunction. Ophthalmology, 1985;92:1423-6.
Rodig, et al., "Disruption of the Jak1 gene demonstrates obligatory and nonredundant roles of the Jaks in cytokine-induced biologic responses." Cell, 93(3): 373-83 (1998).
Rolando et al., "Tear mucus crystallization in children with cystic fibrosis", Ophthalmologica, 1988;197(4):202-6).
Rolando et al., "Tear mucus ferning test in keratoconjunctivitis sicca", Holly FJ, Lamberts DW, MacKeen DL (eds.): The preocular tear film in health, disease, and contact lens wear,. 1st Intern Tear Film Symposium. Lubbok (Texas, USA), Dry Eye Institute, 1986, 203-210.
Rolando et al., "The effect of hyperosmolarity on tear mucus ferning", Fortschr Ophthalmol, 1986;83:644-646.
Rolando et al., The Ocular Surface and Tear Film and Their Dysfuntion in Dry Eye Disease, Survey of Ophthalmology, Mar. 2001, vol. 45, Supplement 2, S203-S210.
Rolando, M. "Tear mucus ferning test in normal and keratoconjunctivitis sicca eyes." Chibret Int J Ophthalmol, 1984;2(4):32-41.
Roudebush et al., "Pharmacologic manipulation of a four day marine delayed type hyper sensitivity model", Agents Actions, 1993, 38(1-2):116-21.
Rousvoal, G. et al. "Janus kinase 3 inhibition with CP-690,550 prevents allograft vasculopathy", Transpl Int., 2006 19(12):1014-21.
Saemann, et al., "Prevention of CD40-triggered dendritic cell maturation and induction of T-cell hyporeactivity by targeting of Janus kinase 3." Am J Transplant, 3(11): 1341-9 (2003).
Saettone et al. "Ocular inserts for topical delivery," Advanced Drug Delivery Reviews, 16: 95-106, 1995.
Samanta et al., "Janus kinase 2: a critical target in chronic myelogenous leukemia", Cancer Res. Jul. 1, 2006;66(13):6468-72.
Sawada et al, "Increased Lipophilicity and Subsequent Cell Partitioning Decrease Passive Transcellular Diffusion of Novel, Highly Lipophilic Antioxidents", The Journal of Pharmacology and Experimental Therapeutics, 1999, No. 288, vol. 3, pp. 1317-1326, p. 1321, compound 26.
Schindler et al., "Hormones and Signaling: Cytokines and STAT Signaling", Adv Pharmacol. 2000; 47:113-74.
Schrader et al., "Animal Models of Dry Eye," Developmental Opthalmology, Karger 2008, 41, 298-312.
Scott, et al., "Jaks, STATs, Cytokines, and Sepsis." Clin Diagn Lab Immunol, 9(6): 1153-9 (2002).
Seefeld, et al, "Discovery of 5-pyrrolopyridinyl-2-thiophenecarboxamides as potent AKT kinase", Bioorganic & Medicinal Chemistry Letters, 19(8):2244-2248 (2009).
Seela, et al., "Synthesis of Pyrrolo[2,3-d]pyrimidine 2', 3'-Dideoxyribenucleosides Related to 2',3'- Dideoxyadenosine and 2',3'-Dideoxgtuanosine and Inhibitory Activity of 5'-Triphosphates on HIV-1 Reverse Transcriptase", Helvetica Chimica, Acta, 1991, 74(3), 554-64.
Seki, "STAT3 and MAPK in human lung cancer tissues and suppression of oncogenic growth by JAB and dominant negative STAT3", Int J Oncol. 24(4):931-4 (2004).
Seto, et al. (2003). "Enhanced Th2 cell-mediated allergic inflammation in Tyk2-deficient mice." J Immunol, 170(2): 1077-83.
Shah et al., "Multiple BCR-ABL kinase domain mutations confer polyclonal resistance to the tyrosine kinase inhibitor imatinib (STI571) in chronic phase and blast crisis chronic myeloid leukemia." Cancer Cell, 2:117-125, Aug. 2002.

(56) References Cited

OTHER PUBLICATIONS

Shi, et al., "The pharmacokinetics, pharmacodynamics, and safety of orally dosed INCB018424 phosphate in healthy volunteers", Journal of Clinical Pharmacology, (Dec. 2011) vol. 51, No. 12, pp. 1644-1654.
Shimazaki et al., "Meibomian gland dysfunction in patients with Sjogren syndrome", Ophthalmology, 1998;105(8):1485-8.
Smith et al, "Basic pathogenic mechanisms operating in experimental model acute anterior uveitis," Immunology and Cell Biology, 1998, 76, 497-512.
Smolen, et al, "Effect of interleukin-6 receptor inhibition with tocilizumab in patients with rheumatoid arthritis (Option study): a double-blind, placebo-controlled, randomized trial", Lancet 371:987, 2008.
Sriram, K. et al., "Induction of gp130-related Cytokines and Activation of JAK2/STAT3 Pathway in Astrocytes Precedes Up-regulation of Glial Fibrillary Acidic Protein in the 1-Methy1-4-phenyl-1,2,3,6-tetrahydropyridine Model of Neurodengeneration", J. Biol. Chem., 2004, 279(19):19936-47. Epub Mar. 2, 2004.
Staerk, J., et. al., "JAK1 and Tyk2 activation by the homologous polycythemia vera JAK2 V617F mutation: cross-talk with IGF1 receptor", J Biol Chem., 280:41893-41899 (2005).
State Intellectual Property Office, PR China, Office Action, dated Sep. 3, 2010 Pat. Appl. No. 200680052750.7 (8 pages).
Stirewalt et al., "Predictors of relapse and overall survival in Philadelphia chromosome-positive acute lymphoblastic leukemia after transplantation", Biol Blood Marrow Transplant. Mar. 2003;9(3):206-12.
STN Search conducted Aug. 30, 2010 (17 pages).
STN Search conducted Jun. 24, 2011 (24 pages).
STN Search conducted Nov. 5, 2010 (5 pages).
STN Search conducted Nov. 9, 2010 (43 pages).
STN Search, Nov. 12, 2009 (180 pages).
STN Search, Oct. 20, 2009 (601 pages).
STN Search, Sep. 20, 2009 (864 pages).
Sullivan et al., "4th International Conference on the Lacrimal Gland, Tear Film & Ocular Surface and Dry Eye Syndromes, Nov. 20, 2004" (2 pages).
Takahashi, et al., "Solvent-Free Reaction Using Pmospwonium Salts: Chlorination of Hydroxyheteroaromatics and dehydration of Primary Amides", Heterocycles 68: 1973-1979 (2006).
Takano et al., "Inflammatory cells in brush cytology samples correlate with the severity of corneal lesions in atopic keratoconjunctivitis", Br J Ophthalmol, 2004;88:1504-5.
Takemoto, et al. (1997). "Proliferation of adult T cell leukemia/lymphoma cells is associated with the constitutive activation of JAK/STAT proteins." Proc Natl Acad Sci U S A, 94(25): 13897-902.
Tan, et al, "Racemization processes at a quaternary carbon center in the context of the asymmetric Michael reaction", Tetrahedron Lett., 42(30):5021-5023 (2001).
Tang et al., "Knowledge-based design of 7-azaindoles as selective B-Raf inhibitors", Bioorganic & Medicinal Chemistry Letters (2008), 18(16):4610-4614.
Tasian et al., "Understanding the biology of CRLF2-overexpressing acute lymphoblastic leukemia", Critical Reviews in Oncogenesis, (2011) vol. 16, No. 1-2, pp. 13-24.
Tefferi, A. et al. "The Clinical Phenotype of Myelofibrosis Encompasses a Chronic Inflammatory State that is Favorably Altered by INCB018424, A Selective Inhibitor of JAK1/2" Poster #2804 at the American Society of Hematology Annual Meeting (ASH), Dec. 7, 2008, (18 pages).
Tefferi, Ayalew, "Primary myelofibrosis: 2012 update on diagnosis, risk stratification, and management", American Journal of Hematology, (Dec. 2011) vol. 86, No. 12, pp. 1017-1026.
Tefferi, et al., "Serious adverse events during ruxolitinib treatment discontinuation in patients with myelofibrosis", Mayo Clinic Proceedings, (Dec. 2011) vol. 86, No. 12, pp. 1188-1191.
Thompson, J., et al., "Photochemical Preparation of a Pyridone Containing Tetracycle: A Jak Protein Kinase Inhibitor", Bioorganic & Medicinal Chemistry Letters, 12 (2002) 1219-1223.
Tiffany et al., Meniscometry using the Tearscope-plus (ARVO abstract). Invest Ophthalmol Vis Sci, (2001);42, s37 (1 page).
Tiffany, J., "Refractive index of meibomian and other lipids", Curr Eye Res, (1986);5:887-9.
Ting, et al., "The Synthesis of substituted bipiperidine amide compounds as CCR3 antagonists", Bioorg. Med. Chem. Lett., vol. 15, No. 5, 1 (2005) pp. 1375-1378.
Toyonaga, "Blockade of constitutively activated Janus kinase/signal transducer and activator of transcription-3 pathway inhibits growth of human pancreatic cancer", Cancer Lett. 201(1):107-16 (2003).
Tsubota et al., "Brush cytology for the evaluation of dry-eye", Nippon Ganka Gakkai Zasshi, 1990a;94:224-30; in Japanese with English abstract.
Tsubota et al., "Conjunctival brush cytology", Acta Cytol, (1990) vol. 34(2):233-5.
Tsubota et al., "Detection by brush cytology of mast cells and eosinophils in allergic and vernal conjunctivitis"; Cornea, (1991) vol. 10(6):525-31.
Ueda et al., "1,2-Benzisoxazol-3-yl Diphenyl Phosphate: A New, Reactive Activating Agent for the Synthesis of Amides, Esters, and Peptides via Condensation", J. Org. Chem. 50:760-763 (1985).
van Best et al., "Measurement of basal tear turnover using a standardized protocol", Graefe's Arch Clin Exp Ophthalmol, 1995; 233:1-7.
van Bijsterveld, O., "Diagnostic tests in the sicca syndrome", Arch Ophthalmol, 1969;82:10-14.
Vannucchi A. et al., "The mTOR Inhibitor, RAD001, Inhibits the Growth of Cells From Patients with Myeloproliferative Neoplasms", Blood: ASH Annual Meeting Absracts, $51^{st}$ Annual Meeting of the American Society of Hematology, vol. 114, No. 22 (2009) 2 pages.
Vannucchi, A. et al, "Inhibitors of PI3K/Akt and/or mTOR Inhibit the Growth of Cells of Myeloproliferative Neoplasms and Synergize with JAK2 Inhibitor and Interferon", Blood, vol. 118, No. 21, pp. 1638-1639, XP008150742 ASH Annual Meeting Abstract 3835 American Society of Hematology (2011).
Vannucchi, A. et al., "RAD001, An Inhibitor of mTOR, Shows Clinical Activity in a Phase I/II Study in Patients with Primary Myelofibrosis (PMF) and Post Polycythemia Vera/Essential Thrombocythemia Myelofibrosis (PPV/PET MF)", Blood, ASH Annual Meeting Abstracts 307, vol. 114, No. 22 (2009) 2 pages.
Vasilevsky, et al., "Ethyl Vinyl Ether—an Agent for Protection of the Pyrazole NH-Fragment. A Convenient Method for the Preparation of N-Unsubstituted 6Alkynylpyrazoles", Heterocycles, 60(4):879-886 (2003).
Verma, et al., "Jak family of kinases in cancer", Cancer and Metastasis Reviews, vol. 22, No. 4, 423-434, DOI: 10.1023/A:1023805715476 (2003).
Verstovsek, "Therapeutic Potential of JAK2 Inhibitors", Hematology Am Soc Hematol Educ Program, 2009:636-42.
Verstovsek, S. et al. "The JAK Inhibitor INCB018424 Demonstrates Durable and Marked Clinical Responses in Primary Myelofibrosis (PMF) and Post-Polycythemia/Essential Thrombocythemia Myelofibrosis (Post-PV/ET-MF)" Poster #1762 at the American Society of Hematology Annual Meeting (ASH), Dec. 6, 2008 (19 pages).
Verstovsek, S. et al. "The selective Janus kinase (JAK) inhibitor, INCB018424, shows efficacy in phase I/II trial in patients with primary myelofibrosis (PMF) and post polycythemia vera/essential thrombocythemia myelofibrosis (Post-PV/ET MF)" Abstract #0444, presented Saturday, Jun. 14, 2008 at the European Hematology Association, 13th Congress, Jun. 12-15, Copenhagen, Denmark (2 pages).
Verstovsek, S. et al. INCB18424, an Oral, Selective JAK2 Inhibitor, Shows Significant Clinical Activity in a Phase I/II Study in Patient with Primary Myelofibrosis (PMF) and Post Polycythemia Vera/Essential Thrombocythemia Myelofibrosis (Post-PV/ET MF), presentation at the American Society of Hematology 49th Annual Meeting and Exposition, Dec. 10, 2007 (16 pages).
Verstovsek, Srdan et al. "Characterization of JAKS V617F Allele Burden in Advanced Myelofibrosis (MF) Patients: No Change in V617F:WT JAK2 Ratio in Patients with High Allele Burdens despite Profound Clinical Improvement Following Treatment with the JAKL Inhibitor, INCB018424, "50th ASH Annual Meeting and Exposition, Abstract No. 2802 (2008).

(56) References Cited

OTHER PUBLICATIONS

Vitali et al. "The European Community Study Group on diagnostic criteria for Sjogren's syndrome. Sensitivity and specificity of tests for ocular and oral involvement in Sjogren's syndrome." 1994; Ann Rheum Dis, 53(10): 637-47.
Wagh, et al., "Polymers used in ocular dosage form and drug delivery systems", Asian J. Pharm., pp. 12-17 (Jan. 2008).
WebMD. "Diabetes Health Center." Available at: <http://diabetes.webmd.com/guide/diabetestreatment_care >. 3 pages, retrieved from the Internet May 28, 2013.
Webster's New World Medical Dictionary, Sjogren's syndrome, 2003, Wiley Publishing, printed fro http://www.credoreference.com/entry/webstermed/sjogren_s_syndrome, 2 pages.
Weiss, et al., "Evaluation of a Series of Naphthamides as Potent, Orally Active Vascular Endothelial Growth Factor Receptor-2 Tyrosine Kinase Inhibitors", J. Med Chem., 51:1668-1680 (2008).
Welch et al., "An approach to a more standardized method of evaluating tear film break-up time", Invest Ophthalmol Vis Sci, 2003; 2485/B324 (abstract only—2 pages).
White et al., "Human basic tear fluid osmolality. I. Importance of sample collection strategy", Acta Ophthalmol (Copenh), Aug.;71(4):524-9, 1993.
Williams et al., "Carbohydrate Chemistry: Recent Advances", Chem. Rev. 81:589-636 (1981).
Williams, et al. "Initial Efficacy of INCB018424, a selective Janus Kinase1 & 2 (JAK1&2) Inhibitor in Rheumatoid Arthritis (RA)," European League Against Rheumatism (EULAR) meeting presentation and abstract (Jun. 11-14, 2008, Paris, France). Annals Rheum Dis 67SII:62, 2008.
Wolf, et al., "Burger's Medicinal Chemistry and Drug Discovery", 5th Ed. Part I, pp. 975-977 (1995).
Wu et al., One-Pot Two-Step Microwave-Assisted Reaction in Construction 4,5-Disubstituted Pyrazolopyrimidines Organic Letters, 2003, 5(20), 3587-3590.
Xiaoyang et al., "Knockdown of STAT3 Expression by RNA Interference Inhibits the Induction of Breast Tumors in Immunocompetent Mice", Cancer Res Apr. 1, 2005 65; 2532.
Yamaoka et al., "Janus kinase (JAK) inhibitors in rheumatoid arthritis", Current Rheumatology Reviews, (Nov. 2011) vol. 7, No. 4, pp. 306-312.
Yang et al., "Constitutive NF-kB activation confers interleukin 6 (IL6) independence and resistance to dexamethasone and Janus kinase inhibitor INCB018424 in murine plasmacytoma cells", Journal of Biological Chemistry, (Aug. 12, 2011) vol. 286, No. 32, pp. 27988-27997.
Yao, et al. "Glucocorticoid-Induced Bone Loss in Mice Can Be Reversed by the Actions of Parathyroid Hormone and Risedronate on Different Pathways for Bone Formation and Mineralization", Arthritis and Rheumatism, 58(11):3485-3497 (2008).
Yao, et al., "Glucocorticoid Excess in Mice Results in Early Activation of Osteoclastogenesis and Adipogenesis and Prolonged Suppression of Osteogenesis", Arthritis and Rheumatism, 58(6), 1674-1686 (2008).
Ye et al., "The synthesis and the antitumor activity of 5,7-disubstituted pyrazolo [1,5-a] pyrimidines," Chinese J Med Chem., Feb. 28, 2007, 17(1):18-22.
Yokoi et al., "A newly developed video-meibography system featuring a newly designed probe", Jpn J Ophthalmol, 2007; 51: 53-6).
Yokoi et al., "Assessment of meibomian gland function in dry eye using meibometry", Arch Ophthalmol, 1999;117:723-9).
Yokoi et al., "Correlation of tear lipid layer interference patterns with the diagnosis and severity of dry eye", Am J Ophthalmol, 1996;122:818-24.
Yokoi et al., "Non-invasive methods of assessing the tear film", Exp Eye Res, 2004;78:399-407).
Yongjun et al., "Advances in research of tyrosine kinases inhibitor of vascular endothelial growth factor receptor," Chinese J New Drugs, Dec. 31, 2008, 17(7):544-550.

Yu, et al., "Constitutive activation of the Janus kinase-STAT pathway in T lymphoma overexpressing the Lck protein tyrosine kinase", J Immunol 159(11):5206-10 (1997).
Zheng, et al., "Discovery of INCB108201PF-4178903, a potent, selective, and orally bioavailabledual CCR2 and CCR5 antagonist", Bioorganic & Medicinal Chemistry Letters 21 (2011) 1442-45.
Zoppellaro, et al., "A Multifunctional High-Spin Biradical Pyrazolylbipyridine-bisnitronylnitroxide", Org. Lett. 6(26):4929-4932 (2004).
Zou, et al., "Signaling Pathways Activated by Oncogenic Forms of Abl Tyrosine Kinase." Journal of Biological Chemistry, 274(26):18141-18144, 1999.
Beck et al., "Brief Report: Alleviation of Systemic Manifestations of Castleman's Disease by Monoclonal Anti-Interleukin-6 Antibody," N. Engl. J. Med., 1994, 330(9):602-605.
Brett et al., "Structural chemistry of polycyclic heteroaromatic compound. Part 4. Electronic structures of angular dithienopyridines," J Chem Soc, Perkin Trans 2, Jan. 1, 1994, 9:2045.
Chari et al., "Complete Remission Achieved with Single Agent CNTO328, an Anti-IL-6 Monoclonal Antibody, in Relapsed and Refractory Myeloma," Clinical Lymphoma, Myeloma & Leukemia, 2013, 13(3):333-337.
Choy et al., "Therapeutic Benefit of Blocking Interleukin-6 Activity With an Anti-Interleukin-6 Receptor Monoclonal Antibody in Rheumatoid Arthritis," Arthritis & Rheumatism, 2002, 46(12) 3143-3150.
Claridge et al., "Discovery of a novel and potent series of thieno[3,2-b]pyridine-based inhibitors of c-Met and VEGFR2 tyrosine kinases," Bioorganic and Medicinal Chemistry Letters, 2008, 18,2793-2798.
DeVos et al., "JAK2 tyrosine kinase inhibitor tyrphostin AG490 downregulates the mitogen-activated protein kinase (MAPK) and signal transducer and activator of transcription (STAT) pathways and induces apoptosis in myeloma cells," Br J. Hematol., 2000, 109:823-828.
Dorwald; "Side Reactions in Organic Synthesis: A Guide to Successful Synthesis Design" 2005 Wiley-VCH Verlag GmbH & Co. KGaA, Wienheim, chapter 1, 32 pages.
Fayad et al., "Interleukin-6 and interleukin-10 levels in chronic lymphocytic leukemia: correlation with phenotypic characteristics and outcome," Blood, Jan. 2001, 97(1): 256-263.
Forbes et al., "Synthesis and evaluation of a series of aryl [e] fused pyrazolo [4,3-c]pyridines with potential anxiolytic activity," J Medicinal Chem., Jan. 1, 1990, 33(9):2640-2645.
Gaestel et al., "Targeting innate immunity protein kinase signalling in inflammation," Nat Rev Drug Discov., Jun. 2009, 8(6):480-99.
Gilchrist et al., "5H-2-Pyrindines from 2-Bromocyclopentene-1-carboxaldehyde," Tetrahedron, Jan. 1, 1995, pp. 9119-9126.
Goodman, et al., "IL-6 Signaling in Psoriasis Prevents Immune Suppression by Regulatory T Cells," J. Immunol., Sep. 2009, 183: 3170-3176.
Grossman, et al., "Interleukin 6 is expressed in high levels in psoriatic skin and stimulates proliferation of cultured human keratinocytes," Proc. Natl. Acad., Sci. USA, Aug. 1989, 86: 6367-6371.
International Preliminary Report on Patentability for PCT/US2013/041601, issued Nov. 18, 2014, 7 pages.
International Search Report and Written Opinion in International Application No. PCT/US2013/067794, mailed Dec. 17, 2013, 14 pages.
Kurzrock et al., "A Phase I, Open-Label Study of Siltuximab, an Anti-IL-6 Monoclonal Antibody, in Patients with B-cell Non-Hodgkin Lymphoma, Multiple Myeloma, or Castleman Disease," Clin. Cancer Res., published online May 9, 2013, 39 pages.
Kurzrock et al., "Serum Interleukin 6 Levels Are Elevated in Lymphoma Patients and Correlate with Survival in Advanced Hodgkin's Disease and with B Symptoms," Cancer Res., May 1993, 52: 2118-2122.
Lima and Barreiro, "Bioisosterism: a useful strategy for molecular modification and drug design," Curr Med Chem. 2005;12(1):23-49.
Maxson et al., "Oncogenic CSF3R Mutations in Chronic Neutrophilic Leukemia and Atypical CML," N. Engl. J. Med., 2013, 368(19):1781-1790.
Neuner et al., "Increased IL-6 Production by Monocytes and Keratinocytes in Patients with Psoriasis," J. Invest. Dermatol. 1991, 97: 27-33.

(56) References Cited

OTHER PUBLICATIONS

Nishimoto et. al., "Improvement in Castleman's disease by humanized anti-interleukin-6 receptor antibody theraphy," Blood, 2000, 95(1):56-61.

Panteli et al., "Serum interleukin (IL)-1, IL-2, sIL-2Ra, IL-6 and thrombopoietin levels in patients with chronic myeloproliferative diseases," British Journal of Haematology, 2005, 130, 709-715.

Search Report in TW Application No. 100117866, dated Dec. 2014, 1 page.

Sonbol et al., "Comprehensive review of JAK inhibitors in myeloproliferative neoplasms," Therapeutic Advances in Hematology, 2013, 4(1): 15-35.

Song et al. "JAK1 Activates STAT3 Activity in Non-Small-Cell Lung Cancer cells and IL-6 Neutralizing Antibodies can Suppress JAK1-STAT3 Signaling," Mol Cancer Ther., Mar. 2011, 10(3): 481-94.

Strassmann et al., "Suramin Interferes with Interleukin-6 Receptor Binding in Vitro and Inhibits Colon-26-mediated Experimental Cancer Cachexia in Vivo," J. Clin. Invest., Nov. 1993, 92: 2152-2159.

Tamura et al., "Involvement of Human Interleukin 6 in Experimental Cachexia Induced by a Human Uterine Cervical Carcinoma Xenograft," Clin. Cancer Res., Nov. 1995, 1: 1353-1358.

Trikha et al., "Targeted anti-interleukin-6 monoclonal antibody therapy for cancer: a review of the rationale and clinical evidence," Clinical Cancer Research, 2003, 9: 4653-4665.

van Rhee et al., "Anti-Interleukin-6 Monoclonal man's Disease," J. Clin. Oncol., 2010, 28(23):3701-3708.

Vaillant et al., "Turbidity of pulpy fruit juice: A key factor for predicting cross-flow microfiltration performance," J Membrane Sci., 2008, 325:404-412.

Vanhoutte et al., "Selective JAK1 Inhibition in the Treatment of Rheumatoid Arthritis: Proof of Concept with GLPG0634," Arthritis Rheum 64.10 (2012): S1051-1.

Xiong, "Inhibition of JAK1, 2/STAT3 Signaling Induces Apoptosis, Cell Cycle Arrest, and Reduces Tumor Cell Invasion in Colorectal Cancer Cells," Neoplasia, Mar. 2008, 10(3): 287-297.

Yamamura et al., "Circulating interleukin-6 levels are elevated in adult T-cell leukaemia/lymphoma patients and correlate with adverse clinical features and survival," Br. J. Haematol., 1998, 100: 129-134.

PIPERIDINYLCYCLOBUTYL SUBSTITUTED PYRROLOPYRIDINE AND PYRROLOPYRIMIDINE DERIVATIVES AS JAK INHIBITORS

This application claims the benefit of priority of U.S. Provisional Application No. 61/648,869, filed May 18, 2012, which is incorporated herein by reference in its entirety.

TECHNICAL FIELD

The present invention provides piperidinylcyclobutyl substituted pyrrolopyrimidines and pyrrolopyridines, as well as their compositions and methods of use, that modulate the activity of Janus kinases (JAKs) and are useful in the treatment of diseases related to the activity of JAKs including, for example, inflammatory disorders, autoimmune disorders, cancer, and other diseases.

BACKGROUND OF THE INVENTION

Protein kinases (PKs) regulate diverse biological processes including cell growth, survival, differentiation, organ formation, morphogenesis, neovascularization, tissue repair, and regeneration, among others. Protein kinases also play specialized roles in a host of human diseases including cancer. Cytokines, low-molecular weight polypeptides or glycoproteins, regulate many pathways involved in the host inflammatory response to sepsis. Cytokines influence cell differentiation, proliferation and activation, and can modulate both pro-inflammatory and anti-inflammatory responses to allow the host to react appropriately to pathogens. Signaling of a wide range of cytokines involves the Janus kinase family (JAKs) of protein tyrosine kinases and Signal Transducers and Activators of Transcription (STATs). There are four known mammalian JAKs: JAK1 (Janus kinase-1), JAK2, JAK3 (also known as Janus kinase, leukocyte; JAKL; and L-JAK), and TYK2 (protein-tyrosine kinase 2).

Cytokine-stimulated immune and inflammatory responses contribute to pathogenesis of diseases: pathologies such as severe combined immunodeficiency (SCID) arise from suppression of the immune system, while a hyperactive or inappropriate immune/inflammatory response contributes to the pathology of autoimmune diseases (e.g., asthma, systemic lupus erythematosus, thyroiditis, myocarditis), and illnesses such as scleroderma and osteoarthritis (Ortmann, R. A., T. Cheng, et al. (2000) *Arthritis Res* 2(1): 16-32).

Deficiencies in expression of JAKs are associated with many disease states. For example, Jak1-/- mice are runted at birth, fail to nurse, and die perinatally (Rodig, S. J., M. A. Meraz, et al. (1998) *Cell* 93(3): 373-83). Jak2-/- mouse embryos are anemic and die around day 12.5 postcoitum due to the absence of definitive erythropoiesis.

The JAK/STAT pathway, and in particular all four JAKs, are believed to play a role in the pathogenesis of asthmatic response, chronic obstructive pulmonary disease, bronchitis, and other related inflammatory diseases of the lower respiratory tract. Multiple cytokines that signal through JAKs have been linked to inflammatory diseases/conditions of the upper respiratory tract, such as those affecting the nose and sinuses (e.g., rhinitis and sinusitis) whether classically allergic reactions or not. The JAK/STAT pathway has also been implicated in inflammatory diseases/conditions of the eye and chronic allergic responses.

Activation of JAK/STAT in cancers may occur by cytokine stimulation (e.g. IL-6 or GM-CSF) or by a reduction in the endogenous suppressors of JAK signaling such as SOCS (suppressor or cytokine signaling) or PIAS (protein inhibitor of activated STAT) (Boudny, V., and Kovarik, J., *Neoplasm.* 49:349-355, 2002). Activation of STAT signaling, as well as other pathways downstream of JAKs (e.g., Akt), has been correlated with poor prognosis in many cancer types (Bowman, T., et al. *Oncogene* 19:2474-2488, 2000). Elevated levels of circulating cytokines that signal through JAK/STAT play a causal role in cachexia and/or chronic fatigue. As such, JAK inhibition may be beneficial to cancer patients for reasons that extend beyond potential anti-tumor activity.

JAK2 tyrosine kinase can be beneficial for patients with myeloproliferative disorders, e.g., polycythemia vera (PV), essential thrombocythemia (ET), myeloid metaplasia with myelofibrosis (MMM) (Levin, et al., *Cancer Cell*, vol. 7, 2005: 387-397). Inhibition of the JAK2V617F kinase decreases proliferation of hematopoietic cells, suggesting JAK2 as a potential target for pharmacologic inhibition in patients with PV, ET, and MMM.

Inhibition of the JAKs may benefit patients suffering from skin immune disorders such as psoriasis, and skin sensitization. The maintenance of psoriasis is believed to depend on a number of inflammatory cytokines in addition to various chemokines and growth factors (JCI, 113:1664-1675), many of which signal through JAKs (*Adv Pharmacol.* 2000; 47:113-74).

Accordingly, inhibitors of Janus kinases or related kinases are widely sought. For example, certain JAK inhibitors, including pyrrolopyridine and pyrrolopyrimidines, are reported in U.S. Ser. No. 11/637,545, filed Dec. 12, 2006.

Thus, new or improved agents which inhibit kinases such as JAKs are continually needed for developing new and more effective pharmaceuticals that are aimed at augmentation or suppression of the immune and inflammatory pathways (such as immunosuppressive agents for organ transplants), as well as agents for the prevention and treatment of autoimmune diseases, diseases involving a hyperactive inflammatory response (e.g., eczema), allergies, cancer (e.g., prostate, leukemia, multiple myeloma), and some immune reactions (e.g., skin rash or contact dermatitis or diarrhea) caused by other therapeutics. The compounds of the invention, as well as its compositions and methods described herein are directed toward these needs and other ends.

SUMMARY OF THE INVENTION

The present invention provides, inter alia, compounds of Formula I:

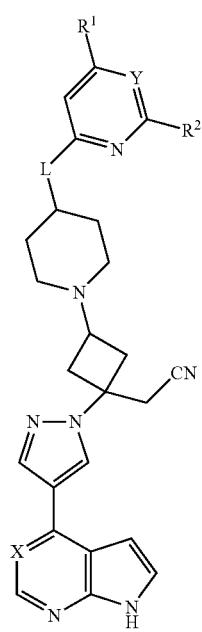

and pharmaceutically acceptable salts thereof; wherein X, Y, L, $R^1$ and $R^2$ are defined herein.

The present invention further provides pharmaceutical compositions comprising a compound of Formula I as described herein, or a pharmaceutically acceptable salt thereof, and at least one pharmaceutically acceptable carrier.

The present invention further provides methods of modulating an activity of JAK1 comprising contacting JAK1 with a compound of Formula I as described herein, or a pharmaceutically acceptable salt thereof.

The present invention further provides methods of treating a disease or a disorder associated with abnormal kinase expression or activity in a patient by administering to a patient a therapeutically effective amount of a compound of Formula I as described herein, or a pharmaceutically acceptable salt thereof.

The present invention further provides methods of treating an autoimmune disease, a cancer, a myeloproliferative disorder, an inflammatory disease, a bone resorption disease, or organ transplant rejection in a patient in need thereof, comprising administering to said patient a therapeutically effective amount of a compound of Formula I as described herein, or a pharmaceutically acceptable salt thereof.

The present invention also provides compounds of Formula I as described herein, or pharmaceutically acceptable salts thereof, as described herein for use in methods of treating autoimmune diseases, cancer, myeloproliferative disorders, inflammatory diseases, a bone resorption disease, or organ transplant rejection.

The present invention further provides compounds of Formula I as described herein, or pharmaceutically acceptable salts thereof, for use in methods of modulating a JAK1.

The present invention also provides uses of compounds of Formula I as described herein, or pharmaceutically acceptable salts thereof, for the preparation of medicaments for use in treating autoimmune diseases, cancer, myeloproliferative disorders, inflammatory diseases, a bone resorption disease, or organ transplant rejection.

The present invention further provides uses of compounds of Formula I as described herein, or pharmaceutically acceptable salts thereof, for the preparation of medicaments for use in methods of modulating a JAK1.

DETAILED DESCRIPTION

The present invention provides, inter alia, a compound of Formula I:

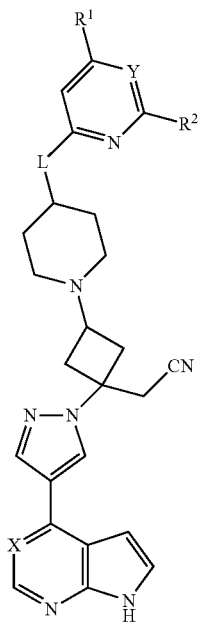

or a pharmaceutically acceptable salt thereof; wherein:
X is N or CH;
L is O or $NR^{2a}$;
(a) wherein when L is O, then:
Y is CH;
$R^1$ is —C(=O)$NR^3R^4$, —$CH_2CH_2OH$, —$CH_2NR^3R^4$, or an oxetane ring, wherein the oxetane ring is optionally substituted with $R^5$;
$R^2$ is $CF_3$;
$R^3$ is —[CH($R^{6a}$)]$_n$—$OR^{6b}$, cyclopropyl, cyclobutyl, tetrahydro-2H-pyran ring, tetrahydrofuran ring, or oxetane ring, wherein said cyclopropyl, cyclobutyl, tetrahydro-2H-pyran ring, tetrahydrofuran ring, and oxetane ring are each optionally substituted with 1 or 2 groups independently selected from CN, OH, methyl, ethyl, n-propyl, isopropyl, methoxy, ethoxy, and propoxy;
$R^4$ is H, $CH_3$, or —[CH($R^{6a}$)]$_n$—$OR^{6b}$;
or alternatively, $R^3$ and $R^4$, taken together with the nitrogen atom to which they are attached, form an azetidinyl, 1H-pyrazolyl, a 1H-imidazolyl, or a 1H-triazolyl group, wherein said azetidinyl group is optionally substituted with 1 or 2 independently selected $R^{3a}$ groups;
each $R^{3a}$ is independently CN, OH, methyl, ethyl, n-propyl, isopropyl, methoxy, ethoxy, propoxy, or —$CH_2$—OH;
or alternatively, two $R^{3a}$ groups, taken together with the carbon atom to which they are both attached, form an oxetane ring;
$R^5$ is OH or $NH_2$;
$R^{6a}$ and $R^{6b}$ are each independently H or $CH_3$; and
each n is independently 2 or 3;
provided that when X is N, then $NR^3R^4$ is not $NHCH_2CH_2$—OH, $NHCH_2CH_2CH_2$—OH,

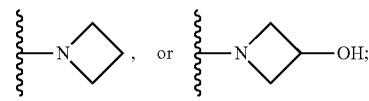 [SMILES: *N1CCC1 ; *N1CC(O)C1]

or alternatively, (b) wherein when L is NR$^{2a}$, then:

Y is CH or N;

R$^1$ is halo, cyano, nitro, C$_{1-6}$ alkyl, C$_{1-6}$ haloalkyl, C$_{2-6}$ alkenyl, C$_{2-6}$ alkynyl, C$_{3-10}$ cycloalkyl, C$_{3-10}$ cycloalkyl-C$_{1-4}$-alkyl, C$_{2-10}$ heterocycloalkyl, C$_{2-10}$ heterocycloalkyl-C$_{1-4}$-alkyl, C$_{6-10}$ aryl, C$_{6-10}$ aryl-C$_{1-4}$-alkyl, C$_{1-10}$ heteroaryl, C$_{1-10}$ heteroaryl-C$_{1-4}$-alkyl, —OR$^a$, —SR$^a$, —S(=O)R$^b$, —S(=O)$_2$R$^b$, —S(=O)$_2$NR$^e$R$^f$, —C(=O)R$^b$, —C(=O)OR$^a$, —C(=O)NR$^e$R$^f$, —OC(=O)R$^b$, —OC(=O)NR$^e$R$^f$, —NR$^e$R$^f$, —NR$^c$C(=O)R$^d$, —NR$^c$C(=O)OR$^d$, —NR$^c$C(=O)NR$^d$, —NR$^c$S(=O)$_2$R$^d$, or —NR$^c$S(=O)$_2$NR$^e$R$^f$; wherein said C$_{1-6}$ alkyl, C$_{2-6}$ alkenyl, C$_{2-6}$ alkynyl, C$_{3-10}$ cycloalkyl, C$_{3-10}$ cycloalkyl-C$_{1-4}$-alkyl, C$_{2-10}$ heterocycloalkyl, C$_{2-10}$ heterocycloalkyl-C$_{1-4}$-alkyl, C$_{6-10}$ aryl, C$_{6-10}$ aryl-C$_{1-4}$-alkyl, C$_{1-10}$ heteroaryl, and C$_{1-10}$ heteroaryl-C$_{1-4}$-alkyl are each optionally substituted by 1, 2, 3, or 4 independently selected R$^g$ groups;

R$^2$ is H, halo, cyano, nitro, C$_{1-4}$ alkyl, or C$_{1-4}$ haloalkyl;

R$^{2a}$ is H or CH$_3$;

each R$^a$, R$^c$, R$^d$, R$^e$, and R$^f$ is independently selected from H, C$_{1-6}$ alkyl, C$_{1-6}$ haloalkyl, C$_{2-6}$ alkenyl, C$_{2-6}$ alkynyl, C$_{3-10}$ cycloalkyl, C$_{3-10}$ cycloalkyl-C$_{1-4}$-alkyl, C$_{2-10}$ heterocycloalkyl, C$_{2-10}$ heterocycloalkyl-C$_{1-4}$-alkyl, C$_{6-10}$ aryl, C$_{6-10}$ aryl-C$_{1-4}$-alkyl, C$_{1-10}$ heteroaryl, and C$_{1-10}$ heteroaryl-C$_{1-4}$-alkyl; wherein said C$_{1-6}$ alkyl, C$_{2-6}$ alkenyl, C$_{2-6}$ alkynyl, C$_{3-10}$ cycloalkyl, C$_{3-10}$ cycloalkyl-C$_{1-4}$-alkyl, C$_{2-10}$ heterocycloalkyl, C$_{2-10}$ heterocycloalkyl-C$_{1-4}$-alkyl, C$_{6-10}$ aryl, C$_{6-10}$ aryl-C$_{1-4}$-alkyl, C$_{1-10}$ heteroaryl, and C$_{1-10}$ heteroaryl-C$_{1-4}$-alkyl are each optionally substituted by 1, 2, 3, or 4 independently selected R$^g$ groups;

each R$^b$ is independently selected from C$_{1-6}$ alkyl, C$_{1-6}$ haloalkyl, C$_{2-6}$ alkenyl, C$_{2-6}$ alkynyl, C$_{3-10}$ cycloalkyl, C$_{3-10}$ cycloalkyl-C$_{1-4}$-alkyl, C$_{2-10}$ heterocycloalkyl, C$_{2-10}$ heterocycloalkyl-C$_{1-4}$-alkyl, C$_{6-10}$ aryl, C$_{6-10}$ aryl-C$_{1-4}$-alkyl, C$_{1-10}$ heteroaryl, and C$_{1-10}$ heteroaryl-C$_{1-4}$-alkyl; wherein said C$_{1-6}$ alkyl, C$_{2-6}$ alkenyl, C$_{2-6}$ alkynyl, C$_{3-10}$ cycloalkyl, C$_{3-10}$ cycloalkyl-C$_{1-4}$-alkyl, C$_{2-10}$ heterocycloalkyl, C$_{2-10}$ heterocycloalkyl-C$_{1-4}$-alkyl, C$_{6-10}$ aryl, C$_{6-10}$ aryl-C$_{1-4}$-alkyl, C$_{1-10}$ heteroaryl, and C$_{1-10}$ heteroaryl-C$_{1-4}$-alkyl are each optionally substituted by 1, 2, 3, or 4 independently selected R$^g$ groups;

each R$^g$ is independently selected from halo, cyano, nitro, C$_{1-6}$ alkyl, C$_{1-6}$ haloalkyl, C$_{2-6}$ alkenyl, C$_{2-6}$ alkynyl, C$_{3-7}$ cycloalkyl, C$_{3-7}$ cycloalkyl-C$_{1-3}$-alkyl, C$_{2-7}$ heterocycloalkyl, C$_{2-7}$ heterocycloalkyl-C$_{1-3}$-alkyl, phenyl, phenyl-C$_{1-3}$-alkyl, C$_{1-7}$ heteroaryl, C$_{1-7}$ heteroaryl-C$_{1-3}$-alkyl, —OR$^{a1}$, —SR$^{a1}$, —S(=O)R$^{b1}$, —S(=O)$_2$R$^{b1}$, —S(=O)$_2$NR$^{e1}$R$^{f1}$, —C(=O)R$^{b1}$, —C(=O)OR$^{a1}$, —C(=O)NR$^{e1}$R$^{f1}$, —OC(=O)R$^{b1}$, —OC(=O)NR$^{e1}$R$^{f1}$, —NR$^{e1}$R$^{f1}$, —NR$^{c1}$C(=O)R$^{d1}$, —NR$^{c1}$C(=O)OR$^{d1}$, —NR$^{c1}$C(=O)NR$^{d1}$, —NR$^{c1}$S(=O)$_2$R$^{d1}$, and —NR$^{c1}$S(=O)$_2$NR$^{e1}$R$^{f1}$; wherein said C$_{1-6}$ alkyl, C$_{2-6}$ alkenyl, C$_{2-6}$ alkynyl, C$_{3-7}$ cycloalkyl, C$_{3-7}$ cycloalkyl-C$_{1-3}$-alkyl, C$_{2-7}$ heterocycloalkyl, C$_{2-7}$ heterocycloalkyl-C$_{1-3}$-alkyl, phenyl, phenyl-C$_{1-3}$-alkyl, C$_{1-7}$ heteroaryl, and C$_{1-7}$ heteroaryl-C$_{1-3}$-alkyl are each optionally substituted with 1, 2, 3, or 4 independently selected R$^h$ groups;

each R$^{a1}$, R$^{c1}$, R$^{d1}$, R$^{e1}$, and R$^{f1}$ is independently selected from H, C$_{1-6}$ alkyl, C$_{1-6}$ haloalkyl, C$_{2-6}$ alkenyl, C$_{2-6}$ alkynyl, C$_{3-7}$ cycloalkyl, C$_{3-7}$ cycloalkyl-C$_{1-3}$-alkyl, C$_{2-7}$ heterocycloalkyl, C$_{2-7}$ heterocycloalkyl-C$_{1-3}$-alkyl, phenyl, phenyl-C$_{1-3}$-alkyl, C$_{1-7}$ heteroaryl, and C$_{1-7}$ heteroaryl-C$_{1-3}$-alkyl; wherein said C$_{1-6}$ alkyl, C$_{2-6}$ alkenyl, C$_{2-6}$ alkynyl, C$_{3-7}$ cycloalkyl, C$_{3-7}$ cycloalkyl-C$_{1-3}$-alkyl, C$_{2-7}$ heterocycloalkyl, C$_{2-7}$ heterocycloalkyl-C$_{1-3}$-alkyl, phenyl, phenyl-C$_{1-3}$-alkyl, C$_{1-7}$ heteroaryl, and C$_{1-7}$ heteroaryl-C$_{1-3}$-alkyl are each optionally substituted by 1, 2, 3, or 4 independently selected R$^h$ groups;

each R$^{b1}$ is independently selected from C$_{1-6}$ alkyl, C$_{1-6}$ haloalkyl, C$_{2-6}$ alkenyl, C$_{2-6}$ alkynyl, C$_{3-7}$ cycloalkyl, C$_{3-7}$ cycloalkyl-C$_{1-3}$-alkyl, C$_{2-7}$ heterocycloalkyl, C$_{2-7}$ heterocycloalkyl-C$_{1-3}$-alkyl, phenyl, phenyl-C$_{1-3}$-alkyl, C$_{1-7}$ heteroaryl, and C$_{1-7}$ heteroaryl-C$_{1-3}$-alkyl; wherein said C$_{1-6}$ alkyl, C$_{2-6}$ alkenyl, C$_{2-6}$ alkynyl, C$_{3-7}$ cycloalkyl, C$_{3-7}$ cycloalkyl-C$_{1-3}$-alkyl, C$_{2-7}$ heterocycloalkyl, C$_{2-7}$ heterocycloalkyl-C$_{1-3}$-alkyl, phenyl, phenyl-C$_{1-3}$-alkyl, C$_{1-7}$ heteroaryl, and C$_{1-7}$ heteroaryl-C$_{1-3}$-alkyl are each optionally substituted by 1, 2, 3, or 4 independently selected R$^h$ groups; and each R$^h$ is independently selected from cyano, halo, hydroxy, C$_{1-4}$ alkyl, C$_{1-4}$ haloalkyl, C$_{1-4}$ alkoxy, C$_{1-4}$ haloalkoxy, amino, C$_{1-4}$ alkylamino, di-C$_{1-4}$-alkylamino, hydroxy-C$_{1-4}$ alkyl, C$_{1-4}$ alkoxy-C$_{1-4}$ alkyl, cyano-C$_{1-4}$ alkyl, thio, C$_{1-6}$ alkylthio, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, C$_{1-6}$ alkoxycarbonyl, C$_{1-6}$ alkylcarbonylamino, C$_{1-6}$ alkylsulfonylamino, aminosulfonyl, C$_{1-6}$ alkylaminosulfonyl, di(C$_{1-6}$ alkyl)aminosulfonyl, aminosulfonylamino, C$_{1-6}$ alkylaminosulfonylamino, di(C$_{1-6}$ alkyl)aminosulfonylamino, aminocarbonylamino, C$_{1-6}$ alkylaminocarbonylamino, and di(C$_{1-6}$ alkyl)aminocarbonylamino.

In some embodiments, X is N.

In some embodiments, X is CH.

In some embodiments, Y is N.

In some embodiments, Y is CH.

In some embodiments, the compound is a compound of Formula II:

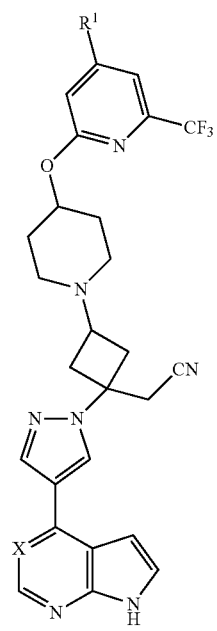

II or a pharmaceutically acceptable salt thereof.

In some embodiments, when L is O:

R$^3$ is —CH(R$^{6a}$)CH$_2$—OR$^{6b}$, —CH$_2$CH(R$^{6a}$)—OR$^{6b}$, cyclopropyl, cyclobutyl, tetrahydro-2H-pyran ring, tetrahydrofuran ring, or oxetane ring, wherein said cyclopropyl, cyclobutyl, tetrahydro-2H-pyran ring, tetrahydrofuran ring, and oxetane ring are each optionally substituted with 1 or 2 groups independently selected from CH$_3$, CN, OH, and OCH$_3$; and R$^4$ is H, CH$_3$, —CH(R$^{6a}$)CH$_2$—OR$^{6b}$, or —CH$_2$CH(R$^{6a}$)—OR$^{6b}$;

or alternatively, R$^3$ and R$^4$, taken together with the nitrogen atom to which they are attached, form an azetidinyl, 1H-pyrazolyl, a 1H-imidazolyl, a 1H-1,3,4-triazolyl, or a 1H-1,2,4-triazolyl group, wherein said azetidinyl group is optionally substituted with 1 or 2 independently selected R$^{3a}$ groups.

In some embodiments, when L is O:

R$^1$ is —C(=O)NR$^3$R$^4$, —CH$_2$CH$_2$OH, —CH$_2$NR$^3$R$^4$, or an oxetane ring, wherein the oxetane ring is optionally substituted with R$^5$;

R$^3$ is —CH$_2$CH$_2$—OR$^{6b}$, —CH(CH$_3$)CH$_2$—OR$^{6b}$, —CH$_2$CH(CH$_3$)—OR$^{6b}$, cyclopropyl, cyclobutyl, tetrahydro-2H-pyran ring, tetrahydrofuran ring, or oxetane ring, wherein said cyclopropyl, cyclobutyl, tetrahydro-2H-pyran ring, tetrahydrofuran ring, and oxetane ring are each optionally substituted with 1 or 2 groups independently selected from CH$_3$, CN, OH, and OCH$_3$;

R$^4$ is H, CH$_3$, —CH$_2$CH$_2$—OR$^{6b}$, —CH(CH$_3$)CH$_2$—OR$^{6b}$, or —CH$_2$CH(CH$_3$)—OR$^{6b}$;

or alternatively, R$^3$ and R$^4$, taken together with the nitrogen atom to which they are attached, form an azetidinyl, 1H-pyrazolyl, a 1H-imidazolyl, a 1H-1,3,4-triazolyl, or a 1H-1,2,4-triazolyl group, wherein said azetidinyl group is optionally substituted with 1 or 2 independently selected R$^{3a}$ groups;

each R$^{3a}$ is independently CN, OH, methyl, ethyl, n-propyl, isopropyl, methoxy, ethoxy, propoxy, or —CH$_2$—OH;

or alternatively, two R$^{3a}$ groups, taken together with the carbon atom to which they are both attached, form an oxetane ring;

R$^5$ is OH or NH$_2$; and

R$^{6b}$ is independently H or CH$_3$.

In some embodiments, when L is O, each R$^{3a}$ is independently CH$_3$, CN, OH, OCH$_3$, or —CH$_2$—OH; or alternatively, two R$^{3a}$ groups, taken together with the carbon atom to which they are both attached, form an oxetane ring.

In some embodiments:

L is O;

X is N or CH;

R$^1$ is —C(=O)NR$^3$R$^4$, —CH$_2$CH$_2$OH, —CH$_2$NR$^3$R$^4$, or an oxetane ring, wherein the oxetane ring is optionally substituted with R$^5$;

R$^2$ is CF$_3$;

R$^3$ is —CH(R$^{6a}$)CH$_2$—OR$^{6b}$, —CH$_2$CH(R$^{6a}$)—OR$^{6b}$, cyclopropyl, cyclobutyl, tetrahydro-2H-pyran ring, tetrahydrofuran ring, or oxetane ring, wherein said cyclopropyl, cyclobutyl, tetrahydro-2H-pyran ring, tetrahydrofuran ring, and oxetane ring are each optionally substituted with 1 or 2 groups independently selected from CH$_3$, CN, OH, and OCH$_3$;

R$^4$ is H, CH$_3$, —CH(R$^{6a}$)CH$_2$—OR$^{6b}$, or —CH$_2$CH(R$^{6a}$)—OR$^{6b}$;

or alternatively, R$^3$ and R$^4$, taken together with the nitrogen atom to which they are attached, form an azetidinyl, 1H-pyrazolyl, a 1H-imidazolyl, a 1H-1,3,4-triazolyl, or a 1H-1,2,4-triazolyl group, wherein said azetidinyl group is optionally substituted with 1 or 2 independently selected R$^{3a}$ groups;

each R$^{3a}$ is independently CH$_3$, CN, OH, OCH$_3$, or —CH$_2$—OH;

or alternatively, two R$^{3a}$ groups, taken together with the carbon atom to which they are both attached, form a oxetane ring;

R$^5$ is OH or NH$_2$; and

R$^{6a}$ and R$^{6b}$ are each independently H or CH$_3$;

provided that NR$^3$R$^4$ is not NHCH$_2$CH$_2$—OH,

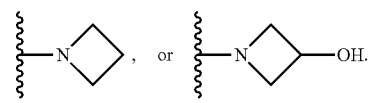

In some embodiments:

L is O;

X is N or CH;

R$^1$ is an oxetane ring, wherein the oxetane ring is optionally substituted with R$^5$;

R$^2$ is CF$_3$; and

R$^5$ is OH or NH$_2$.

In some embodiments, the compound is a compound of Formula IIa:

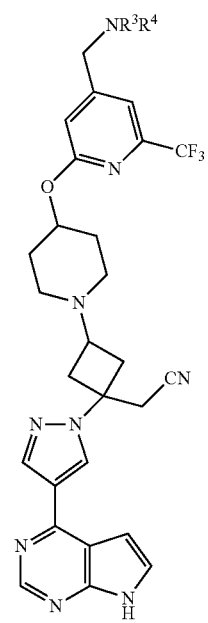

IIa or a pharmaceutically acceptable salt thereof.

In some embodiments, the compound is a compound of Formula IIa,

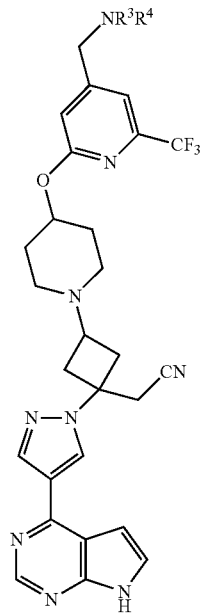

IIa

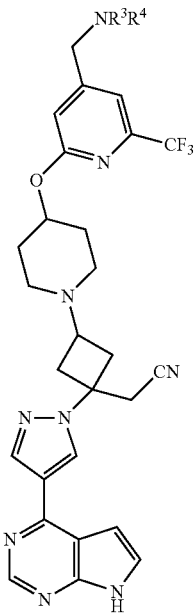

IIa or a pharmaceutically acceptable salt thereof, wherein:

R$^3$ is —CH(R$^{6a}$)CH$_2$—OR$^{6b}$, —CH$_2$CH(R$^{6a}$)—OR$^{6b}$, cyclopropyl, cyclobutyl, tetrahydro-2H-pyran ring, tetrahydrofuran ring, or oxetane ring, wherein said cyclopropyl, cyclobutyl, tetrahydro-2H-pyran ring, tetrahydrofuran ring, and oxetane ring are each optionally substituted with 1 or 2 groups independently selected from CH$_3$, CN, OH, and OCH$_3$;

R$^4$ is H, CH$_3$, —CH(R$^{6a}$)CH$_2$—OR$^{6b}$, or —CH$_2$CH(R$^{6a}$)—OR$^{6b}$;

or alternatively, R$^3$ and R$^4$, taken together with the nitrogen atom to which they are attached, form an azetidinyl, 1H-pyrazolyl, a 1H-imidazolyl, a 1H-1,3,4-triazolyl, or a 1H-1,2,4-triazolyl group, wherein said azetidinyl group is optionally substituted with 1 or 2 independently selected R$^{3a}$ groups;

each R$^{3a}$ is independently CH$_3$, CN, OH, OCH$_3$, or —CH$_2$—OH;

or alternatively, two R$^{3a}$ groups, taken together with the carbon atom to which they are both attached, form a oxetane ring;

R$^5$ is OH or NH$_2$; and

R$^{6a}$ and R$^{6b}$ are each independently H or CH$_3$;

provided that NR$^3$R$^4$ is not NHCH$_2$CH$_2$—OH,

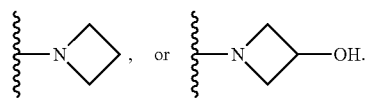 [SMILES: *N1CCC1 ; *N1CC(O)C1]

or a pharmaceutically acceptable salt thereof, wherein:

R$^3$ is —CH$_2$CH$_2$—OR$^{6b}$, —CH(CH$_3$)CH$_2$—OR$^{6b}$, —CH$_2$CH(CH$_3$)—OR$^{6b}$, cyclopropyl, cyclobutyl, tetrahydro-2H-pyran ring, tetrahydrofuran ring, or oxetane ring, wherein said cyclopropyl, cyclobutyl, tetrahydro-2H-pyran ring, tetrahydrofuran ring, and oxetane ring are each optionally substituted with 1 or 2 groups independently selected from CH$_3$, CN, OH, and OCH$_3$;

R$^4$ is H, CH$_3$, —CH$_2$CH$_2$—OR$^{6b}$, —CH(CH$_3$)CH$_2$—OR$^{6b}$, or —CH$_2$CH(CH$_3$)—OR$^{6b}$;

or alternatively, R$^3$ and R$^4$, taken together with the nitrogen atom to which they are attached, form an azetidinyl, 1H-pyrazolyl, a 1H-imidazolyl, a 1H-1,3,4-triazolyl, or a 1H-1,2,4-triazolyl group, wherein said azetidinyl group is optionally substituted with 1 or 2 independently selected R$^{3a}$ groups;

each R$^{3a}$ is independently CH$_3$, CN, OH, OCH$_3$, or —CH$_2$—OH;

or alternatively, two R$^{3a}$ groups, taken together with the carbon atom to which they are both attached, form a oxetane ring;

R$^5$ is OH or NH$_2$; and

R$^{6b}$ is independently H or CH$_3$;

provided that NR$^3$R$^4$ is not NHCH$_2$CH$_2$—OH,

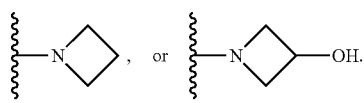 [SMILES: *N1CCC1 ; *N1CC(O)C1]

In some embodiments, the compound is a compound of Formula IIa,

In some embodiments, the compound is a compound of Formula IIa,

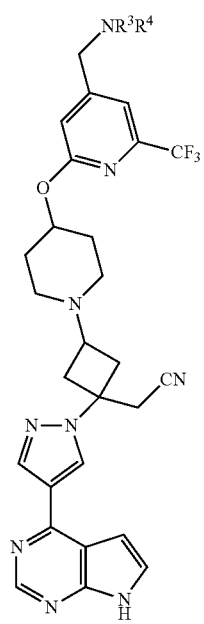

or a pharmaceutically acceptable salt thereof, wherein:
$R^3$ is —CH($R^{6a}$)CH$_2$—OR$^{6b}$ or —CH$_2$CH($R^{6a}$)—OR$^{6b}$;
$R^4$ is H, CH$_3$, —CH($R^{6a}$)CH$_2$—OR$^{6b}$, or —CH$_2$CH($R^{6a}$)—OR$^{6b}$; and
$R^{6a}$ and $R^{6b}$ are each independently H or CH$_3$;
provided that NR$^3$R$^4$ is not NHCH$_2$CH$_2$—OH.
In some embodiments, the compound is a compound of Formula IIa:

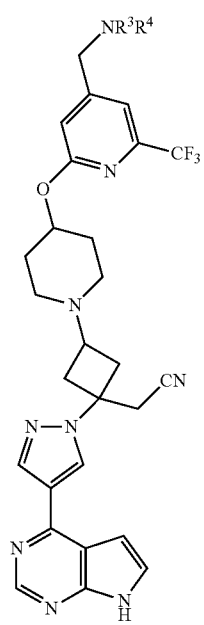

or a pharmaceutically acceptable salt thereof, wherein:
$R^3$ is —CH$_2$CH$_2$—OR$^{6b}$, —CH(CH$_3$)CH$_2$—OR$^{6b}$, or —CH$_2$CH(CH$_3$)—OR$^{6b}$;
$R^4$ is H, CH$_3$, —CH$_2$CH$_2$—OR$^{6b}$, —CH(CH$_3$)CH$_2$—OR$^{6b}$, or —CH$_2$CH(CH$_3$)—OR$^{6b}$; and $R^{6b}$ is independently H or CH$_3$;
provided that NR$^3$R$^4$ is not NHCH$_2$CH$_2$—OH.
In some embodiments, the compound is a compound of Formula IIa,

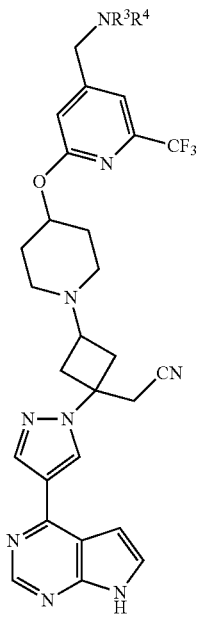

or a pharmaceutically acceptable salt thereof, wherein:
$R^3$ is cyclopropyl, cyclobutyl, tetrahydro-2H-pyran ring, tetrahydrofuran ring, or oxetane ring, wherein said cyclopropyl, cyclobutyl, tetrahydro-2H-pyran ring, tetrahydrofuran ring, and oxetane ring are each optionally substituted with 1 or 2 groups independently selected from CH$_3$, CN, OH, and OCH$_3$; and
$R^4$ is H.
In some embodiments, the compound is a compound of Formula IIa,

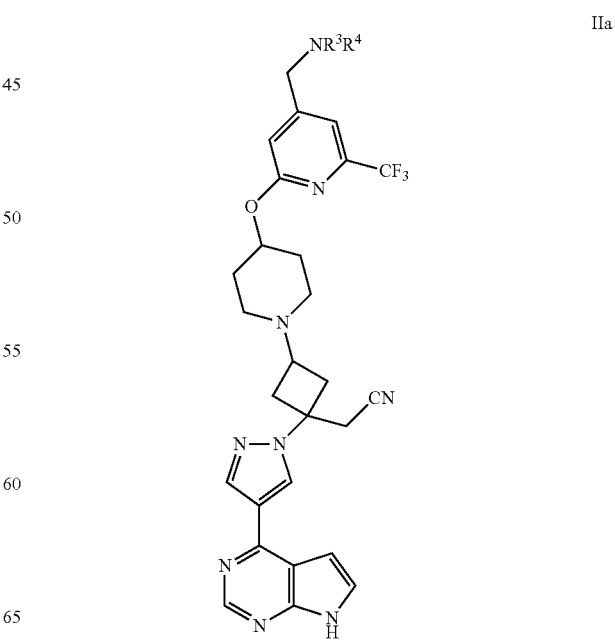

or a pharmaceutically acceptable salt thereof, wherein:

$R^3$ and $R^4$, taken together with the nitrogen atom to which they are attached, form an azetidinyl group, which is optionally substituted with 1 or 2 independently selected $R^{3a}$ groups;

each $R^{3a}$ is independently $CH_3$, CN, OH, $OCH_3$, or —$CH_2$—OH;

or alternatively, two $R^{3a}$ groups, taken together with the carbon atom to which they are both attached, form a oxetane ring; and provided that $NR^3R^4$ is not

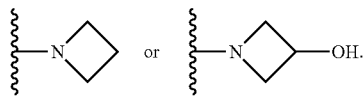 [SMILES: *N1CCC1 ; *N1CC(O)C1]

In some embodiments, the compound is a compound of Formula IIa,

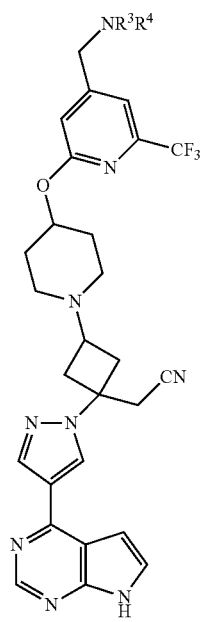

IIa or a pharmaceutically acceptable salt thereof, wherein:

$R^3$ and $R^4$, taken together with the nitrogen atom to which they are attached, form a 1H-pyrazolyl, a 1H-imidazolyl, a 1H-1,3,4-triazolyl, or a 1H-1,2,4-triazolyl group.

In some embodiments, the compound is a compound of Formula III:

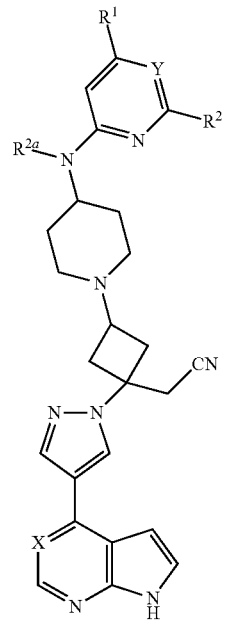

III or a pharmaceutically acceptable salt thereof.

In some embodiments, wherein L is $NR^{2a}$, $R^1$ is cyano, halo, $C_{1-6}$ alkyl, or $C_{1-6}$ haloalkyl, wherein said $C_{1-6}$ alkyl is optionally substituted by 1, 2, 3, or 4 independently selected $R^g$ groups.

In some embodiments, $R^g$ is $C_{2-7}$ heterocycloalkyl, $C_{1-7}$ heteroaryl, —$OR^{a1}$, —$SR^{a1}$, —$S(=O)R^{b1}$, —$S(=O)_2R^{b1}$, —$S(=O)_2NR^{e1}R^{f1}$, —$C(=O)R^{b1}$, —$C(=O)OR^{a1}$, —$C(=O)NR^{e1}R^{f1}$, —$OC(=O)R^{b1}$, —$OC(=O)NR^{e1}R^{f1}$, —$NR^{e1}R^{f1}$, —$NR^{c1}C(=O)R^{d1}$, —$NR^{c1}C(=O)OR^{d1}$, —$NR^{c1}C(=O)NR^{d1}$, —$NR^{c1}S(=O)_2R^{d1}$, or —$NR^{c1}S(=O)_2NR^{e1}R^{f1}$.

In some embodiments, $R^g$ is $C_{2-7}$ heterocycloalkyl, $C_{1-7}$ heteroaryl, —$OR^{a1}$, or —$NR^{e1}R^{f1}$.

In some embodiments:

each $R^{a1}$, $R^{c1}$, $R^{d1}$, $R^{e1}$, and $R^{f1}$ is independently selected from H, $C_{1-6}$ alkyl, $C_{1-6}$ haloalkyl, $C_{3-7}$ cycloalkyl, $C_{3-7}$ cycloalkyl-$C_{1-3}$-alkyl, $C_{2-7}$ heterocycloalkyl, $C_{2-7}$ heterocycloalkyl-$C_{1-3}$-alkyl, phenyl, phenyl-$C_{1-3}$-alkyl, $C_{1-7}$ heteroaryl, and $C_{1-7}$ heteroaryl-$C_{1-3}$-alkyl; wherein said $C_{1-6}$ alkyl, $C_{2-6}$ alkenyl, $C_{2-6}$ alkynyl, $C_{3-7}$ cycloalkyl, $C_{3-7}$ cycloalkyl-$C_{1-3}$-alkyl, $C_{2-7}$ heterocycloalkyl, $C_{2-7}$ heterocycloalkyl-$C_{1-3}$-alkyl, phenyl, phenyl-$C_{1-3}$-alkyl, $C_{1-7}$ heteroaryl, and $C_{1-7}$ heteroaryl-$C_{1-3}$-alkyl are each optionally substituted by 1 or 2 $R^h$ groups independently selected from cyano, halo, hydroxyl, $C_{1-4}$ alkoxy, $C_{1-4}$ haloalkoxy, amino, $C_{1-4}$ alkylamino, and di-$C_{1-4}$-alkylamino;

each $R^{b1}$ is independently selected from $C_{1-6}$ alkyl, $C_{1-6}$ haloalkyl, $C_{3-7}$ cycloalkyl, $C_{3-7}$ cycloalkyl-$C_{1-3}$-alkyl, $C_{2-7}$ heterocycloalkyl, $C_{2-7}$ heterocycloalkyl-$C_{1-3}$-alkyl, phenyl, phenyl-$C_{1-3}$-alkyl, $C_{1-7}$ heteroaryl, and $C_{1-7}$ heteroaryl-$C_{1-3}$-alkyl; wherein said $C_{1-6}$ alkyl, $C_{3-7}$ cycloalkyl, $C_{3-7}$ cycloalkyl-$C_{1-3}$-alkyl, $C_{2-7}$ heterocycloalkyl, $C_{2-7}$ heterocycloalkyl-$C_{1-3}$-alkyl, phenyl, phenyl-$C_{1-3}$-alkyl, $C_{1-7}$ heteroaryl, and $C_{1-7}$ heteroaryl-$C_{1-3}$-alkyl are each optionally substituted by 1 or 2 $R^h$ groups independently selected from cyano, halo, hydroxyl, $C_{1-4}$ alkoxy, $C_{1-4}$ haloalkoxy, amino, $C_{1-4}$ alkylamino, and di-$C_{1-4}$-alkylamino.

In some embodiments, wherein L is $NR^{2a}$, $R^1$ is $C_{1-3}$ alkyl substituted by $C_{2-7}$ heterocycloalkyl, $C_{1-7}$ heteroaryl, —$OR^{a1}$, or —$NR^{e1}R^{f1}$.

In some embodiments, wherein L is $NR^{2a}$, $R^1$ is $C_{1-3}$ alkyl substituted by $C_{2-7}$ heterocycloalkyl, $-OR^{a1}$, or $-NR^{e1}R^{f1}$.

In some embodiments, wherein L is $NR^{2a}$:

$R^1$ is $C_{1-3}$ alkyl substituted by $-OR^{a1}$, $-NR^{e1}R^{f1}$, or $C_{2-7}$ heterocycloalkyl;

$R^{a1}$ is H or $C_{1-4}$ alkyl;

$R^{e1}$ is H or $C_{1-4}$ alkyl; wherein $C_{1-4}$ alkyl is substituted by 1 or 2 independently selected $R^h$ groups;

$R^{f1}$ is H, $C_{1-4}$ alkyl, cyclopropyl, cyclobutyl, or cyclohexyl; wherein $C_{1-4}$ alkyl, cyclopropyl, cyclobutyl, or cyclohexyl are each substituted by 1 or 2 independently selected $R^h$ groups; and each $R^h$ is independently selected from hydroxy, halo, cyano, $C_{1-4}$ alkyl, and $C_{1-4}$ alkoxy.

In some embodiments, wherein L is $NR^{2a}$, $R^2$ is $CF_3$.
In some embodiments, wherein L is $NR^{2a}$, Y is N.
In some embodiments, wherein L is $NR^{2a}$, Y is CH.
In some embodiments, wherein L is $NR^{2a}$, X is N.
In some embodiments, wherein L is $NR^{2a}$, X is CH.

In some embodiments, the compound is a compound of Formula I, or a pharmaceutically acceptable salt thereof; wherein:

X is N or CH;

L is $NR^{2a}$;

Y is CH or N;

$R^1$ is $C_{1-3}$ alkyl substituted by $-OR^{a1}$, $-NR^{e1}R^{f1}$, or $C_{2-7}$ heterocycloalkyl;

$R^2$ is $CF_3$;

$R^{2a}$ is H or $CH_3$;

$R^{a1}$ is H or $C_{1-4}$ alkyl;

$R^{e1}$ is H or $C_{1-4}$ alkyl; wherein $C_{1-4}$ alkyl is substituted by 1 or 2 independently selected $R^h$ groups;

$R^{f1}$ is H, $C_{1-4}$ alkyl, cyclopropyl, cyclobutyl, or cyclohexyl; wherein $C_{1-4}$ alkyl, cyclopropyl, cyclobutyl, or cyclohexyl are each substituted by 1 or 2 independently selected $R^h$ groups; and each $R^h$ is independently selected from hydroxy, halo, cyano, $C_{1-4}$ alkyl, and $C_{1-4}$ alkoxy.

In some embodiments, the cyclobutyl ring in Formula I, II, IIa, or III is the cis form.

In some embodiments, the cyclobutyl ring in Formula I, II, IIa, or III is the trans form.

It is appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

As used herein, the phrase "optionally substituted" means unsubstituted or substituted. As used herein, the term "substituted" means that a hydrogen atom is removed and replaced by a substituent. It is to be understood that substitution at a given atom is limited by valency. Throughout the definitions, the term "$C_{n-m}$" indicates a range which includes the endpoints, wherein n and m are integers and indicate the number of carbons. Examples include $C_{1-4}$, $C_{1-6}$, and the like.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

As used herein, the term "$C_{n-m}$ alkyl", employed alone or in combination with other terms, refers to a saturated hydrocarbon group that may be straight-chain or branched, having n to m carbons. In some embodiments, the alkyl group contains from 1 to 3 carbon atoms. Examples of alkyl moieties include, but are not limited to, chemical groups such as methyl, ethyl, n-propyl, and isopropyl.

As used herein, the term "$C_{n-m}$ alkoxy", employed alone or in combination with other terms, refers to a group of formula —O-alkyl, wherein the alkyl group has n to m carbons. Example alkoxy groups include methoxy, ethoxy, and propoxy (e.g., n-propoxy and isopropoxy). In some embodiments, the alkyl group has 1 to 3 carbon atoms.

As used herein, the term "alkylene", employed alone or in combination with other terms, refers to a divalent alkyl linking group. Examples of alkylene groups include, but are not limited to, ethan-1,2-diyl, propan-1,3-diyl, propan-1,2-diyl, butan-1,4-diyl, butan-1,3-diyl, butan-1,2-diyl, 2-methyl-propan-1,3-diyl, and the like.

As used herein, "$C_{n-m}$ alkenyl" refers to an alkyl group having one or more double carbon-carbon bonds and having n to m carbons. In some embodiments, the alkenyl moiety contains 2 to 6 or to 2 to 4 carbon atoms. Example alkenyl groups include, but are not limited to, ethenyl, n-propenyl, isopropenyl, n-butenyl, sec-butenyl, and the like.

As used herein, "$C_{n-m}$ alkynyl" refers to an alkyl group having one or more triple carbon-carbon bonds and having n to m carbons. Example alkynyl groups include, but are not limited to, ethynyl, propyn-1-yl, propyn-2-yl, and the like. In some embodiments, the alkynyl moiety contains 2 to 6 or 2 to 4 carbon atoms.

As used herein, the term "$C_{n-m}$ alkylamino" refers to a group of formula —NH(alkyl), wherein the alkyl group has n to m carbon atoms. In some embodiments, the alkyl group has 1 to 6 or 1 to 4 carbon atoms.

As used herein, the term "di-$C_{n-m}$-alkylamino" refers to a group of formula —N(alkyl)$_2$, wherein the two alkyl groups each has, independently, n to m carbon atoms. In some embodiments, each alkyl group independently has 1 to 6 or 1 to 4 carbon atoms.

As used herein, the term "$C_{n-m}$ alkoxycarbonyl" refers to a group of formula —C(O)O-alkyl, wherein the alkyl group has n to m carbon atoms. In some embodiments, the alkyl group has 1 to 6 or 1 to 4 carbon atoms.

As used herein, the term "$C_{n-m}$ alkylcarbonyl" refers to a group of formula —C(O)-alkyl, wherein the alkyl group has n to m carbon atoms. In some embodiments, the alkyl group has 1 to 6 or 1 to 4 carbon atoms.

As used herein, the term "$C_{n-m}$ alkylcarbonylamino" refers to a group of formula —NHC(O)-alkyl, wherein the alkyl group has n to m carbon atoms. In some embodiments, the alkyl group has 1 to 6 or 1 to 4 carbon atoms.

As used herein, the term "$C_{n-m}$ alkylsulfonylamino" refers to a group of formula —NHS(O)$_2$-alkyl, wherein the alkyl group has n to m carbon atoms. In some embodiments, the alkyl group has 1 to 6 or 1 to 4 carbon atoms.

As used herein, the term "aminosulfonyl", employed alone or in combination with other terms, refers to a group of formula —S(O)$_2$NH$_2$.

As used herein, the term "$C_{n-m}$ alkylaminosulfonyl" refers to a group of formula —S(O)$_2$NH(alkyl), wherein the alkyl group has n to m carbon atoms. In some embodiments, the alkyl group has 1 to 6 or 1 to 4 carbon atoms.

As used herein, the term "di($C_{n-m}$ alkyl)aminosulfonyl" refers to a group of formula —S(O)$_2$N(alkyl)$_2$, wherein each alkyl group independently has n to m carbon atoms. In some embodiments, each alkyl group has, independently, 1 to 6 or 1 to 4 carbon atoms.

As used herein, the term "aminosulfonylamino" refers to a group of formula —NHS(O)$_2$NH$_2$.

As used herein, the term "$C_{n-m}$ alkylaminosulfonylamino" refers to a group of formula —NHS(O)$_2$NH(alkyl), wherein the alkyl group has n to m carbon atoms. In some embodiments, the alkyl group has 1 to 6 or 1 to 4 carbon atoms.

As used herein, the term "di($C_{n-m}$ alkyl)aminosulfonylamino" refers to a group of formula —NHS(O)$_2$N(alkyl)$_2$, wherein each alkyl group independently has n to m carbon atoms. In some embodiments, each alkyl group has, independently, 1 to 6 or 1 to 4 carbon atoms.

As used herein, the term "aminocarbonylamino" refers to a group of formula —NHC(O)NH$_2$.

As used herein, the term "$C_{n-m}$ alkylaminocarbonylamino" refers to a group of formula —NHC(O)NH(alkyl), wherein the alkyl group has n to m carbon atoms. In some embodiments, the alkyl group has 1 to 6 or 1 to 4 carbon atoms.

As used herein, the term "di($C_{n-m}$ alkyl)aminocarbonylamino" refers to a group of formula —NHC(O)N(alkyl)$_2$, wherein each alkyl group independently has n to m carbon atoms. In some embodiments, each alkyl group has, independently, 1 to 6 or 1 to 4 carbon atoms.

As used herein, the term "$C_{n-m}$ alkylcarbamyl" refers to a group of formula —C(O)—NH(alkyl), wherein the alkyl group has n to m carbon atoms. In some embodiments, the alkyl group has 1 to 6 or 1 to 4 carbon atoms.

As used herein, the term "di($C_{n-m}$-alkyl)carbamyl" refers to a group of formula —C(O)N(alkyl)$_2$, wherein the two alkyl groups each has, independently, n to m carbon atoms. In some embodiments, each alkyl group independently has 1 to 6 or 1 to 4 carbon atoms.

As used herein, the term "thio" refers to a group of formula —SH.

As used herein, the term "$C_{n-m}$ alkylthio" refers to a group of formula —S-alkyl, wherein the alkyl group has n to m carbon atoms. In some embodiments, the alkyl group has 1 to 6 or 1 to 4 carbon atoms.

As used herein, the term "$C_{n-m}$ alkylsulfinyl" refers to a group of formula —S(O)-alkyl, wherein the alkyl group has n to m carbon atoms. In some embodiments, the alkyl group has 1 to 6 or 1 to 4 carbon atoms.

As used herein, the term "$C_{n-m}$ alkylsulfonyl" refers to a group of formula —S(O)$_2$-alkyl, wherein the alkyl group has n to m carbon atoms. In some embodiments, the alkyl group has 1 to 6 or 1 to 4 carbon atoms.

As used herein, the term "amino" refers to a group of formula —NH$_2$.

As used herein, the term "hydroxy-$C_{n-m}$-alkyl" refers to a group of formula -alkylene-OH, wherein said alkylene group has n to m carbon atoms. In some embodiments, the alkylene group has 1 to 4 carbon atoms.

As used herein, the term "$C_{o-p}$ alkoxy-$C_{n-m}$-alkyl" refers to a group of formula -alkylene-O-alkyl, wherein said alkylene group has n to m carbon atoms and said alkyl group has o to p carbon atoms. In some embodiments, the alkyl and alkylene groups each independently have 1 to 4 carbon atoms.

As used herein, the term "cyano-$C_{n-m}$-alkyl" refers to a group of formula -alkylene-CN, wherein said alkylene group has n to m carbon atoms. In some embodiments, the alkylene group has 1 to 4 carbon atoms.

As used herein, the term "aryl", employed alone or in combination with other terms, refers to a monocyclic or polycyclic (e.g., having 2, 3 or 4 fused rings) aromatic hydrocarbon, such as, but not limited to, phenyl, 1-naphthyl, 2-naphthyl, anthracenyl, phenanthrenyl, and the like. In some embodiments, aryl is $C_{6-10}$ aryl. In some embodiments, the aryl group is a naphthalene ring or phenyl ring. In some embodiments, the aryl group is phenyl.

As used herein, the term "arylalkyl" refers to a group of formula -alkylene-aryl. In some embodiments, arylalkyl is $C_{6-10}$ aryl-$C_{1-3}$ alkyl. In some embodiments, arylalkyl is $C_{6-10}$ aryl-$C_{1-4}$ alkyl. In some embodiments, arylalkyl is benzyl.

As used herein, the term "carbamyl" refers to a group of formula —C(O)NH$_2$.

As used herein, the term "carbonyl", employed alone or in combination with other terms, refers to a —C(O)— group.

As used herein, the term "carboxy" refers to a group of formula —C(O)OH.

As used herein, the term "cycloalkyl", employed alone or in combination with other terms, refers to a non-aromatic cyclic hydrocarbon moiety, which may optionally contain one or more alkenylene groups as part of the ring structure. Cycloalkyl groups can include mono- or polycyclic (e.g., having 2, 3 or 4 fused rings) ring systems. Also included in the definition of cycloalkyl are moieties that have one or more aromatic rings fused (i.e., having a bond in common with) to the cycloalkyl ring, for example, benzo derivatives of cyclopentane, cyclopentene, cyclohexane, and the like. One or more ring-forming carbon atoms of a cycloalkyl group can be oxidized to form carbonyl linkages. In some embodiments, cycloalkyl is $C_{3-12}$ cycloalkyl, which is monocyclic or bicyclic. Exemplary cycloalkyl groups include 1,2,3,4-tetrahydro-naphthalene, cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like. In some embodiments, the cycloalkyl group is cyclopropyl, cyclobutyl, cyclopentyl, or cyclohexyl.

As used herein, the term "cycloalkylalkyl" refers to a group of formula -alkylene-cycloalkyl. In some embodiments, cycloalkylalkyl is $C_{3-12}$ cycloalkyl-$C_{1-3}$ alkyl, wherein the cycloalkyl portion is monocyclic or bicyclic. In some embodiments, cycloalkylalkyl is $C_{3-12}$ cycloalkyl-$C_{1-4}$ alkyl, wherein the cycloalkyl portion is monocyclic or bicyclic.

As used herein, "$C_{n-m}$ haloalkoxy" refers to a group of formula —O-haloalkyl having n to m carbon atoms. An example haloalkoxy group is OCF$_3$. In some embodiments, the haloalkoxy group is fluorinated only. In some embodiments, the alkyl group has 1 to 6 or 1 to 4 carbon atoms.

As used herein, the term "halo" refers to a halogen atom selected from F, Cl, I or Br.

As used herein, the term "$C_{n-m}$ haloalkyl", employed alone or in combination with other terms, refers to an alkyl group having from one halogen atom to 2s+1 halogen atoms which may be the same or different, where "s" is the number of carbon atoms in the alkyl group, wherein the alkyl group has n to m carbon atoms. In some embodiments, the haloalkyl group is fluorinated only. In some embodiments, the haloalkyl group is fluoromethyl, difluoromethyl, or trifluoromethyl. In some embodiments, the haloalkyl group is trifluoromethyl. In some embodiments, the alkyl group has 1 to 6 or 1 to 4 carbon atoms.

As used herein, the term "heteroaryl", employed alone or in combination with other terms, refers to a monocyclic or polycyclic (e.g., having 2, 3 or 4 fused rings) aromatic hydrocarbon moiety, having one or more heteroatom ring members selected from nitrogen, sulfur and oxygen. In some embodiments, heteroaryl is 5- to 10-membered $C_{1-9}$ heteroaryl, which is monocyclic or bicyclic and which has 1, 2, 3, or 4 heteroatom ring members independently selected from nitrogen, sulfur and oxygen. When the heteroaryl group contains more than one heteroatom ring member, the heteroatoms may be the same or different. Example heteroaryl groups include, but are not limited to, pyridine, pyrimidine, pyrazine, pyridazine, pyrrole, pyrazole, azolyl, oxazole, thiazole, imidazole, furan, thiophene, quinoline, isoquinoline, indole, benzothiophene, benzofuran, benzisoxazole, imidazo[1,2-b]thiazole, purine, or the like.

A five-membered ring heteroaryl is a heteroaryl with a ring having five ring atoms wherein one or more (e.g., 1, 2, or 3) ring atoms are independently selected from N, O, and S. Exemplary five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl.

A six-membered ring heteroaryl is a heteroaryl with a ring having six ring atoms wherein one or more (e.g., 1, 2, or 3) ring atoms are independently selected from N, O, and S. Exemplary six-membered ring heteroaryls are pyridyl, pyrazinyl, pyrimidinyl, triazinyl and pyridazinyl.

As used herein, the term "heteroarylalkyl" refers to a group of formula -alkylene-heteroaryl. In some embodiments, heteroarylalkyl is $C_{1-9}$ heteroaryl-$C_{1-3}$ alkyl, wherein the heteroaryl portion is monocyclic or bicyclic and has 1, 2, 3, or 4 heteroatom ring members independently selected from nitrogen, sulfur and oxygen. In some embodiments, heteroarylalkyl is $C_{1-9}$ heteroaryl-$C_{1-4}$ alkyl, wherein the heteroaryl portion is monocyclic or bicyclic and has 1, 2, 3, or 4 heteroatom ring members independently selected from nitrogen, sulfur and oxygen.

As used herein, the term "heterocycloalkyl", employed alone or in combination with other terms, refers to non-aromatic ring system, which may optionally contain one or more alkenylene or alkynylene groups as part of the ring structure, and which has at least one heteroatom ring member independently selected from nitrogen, sulfur and oxygen. When the heterocycloalkyl groups contains more than one heteroatom, the heteroatoms may be the same or different. Heterocycloalkyl groups can include mono- or polycyclic (e.g., having 2, 3 or 4 fused rings) ring systems, including spiro systems. Also included in the definition of heterocycloalkyl are moieties that have one or more aromatic rings fused (i.e., having a bond in common with) to the non-aromatic ring, for example, 1,2,3,4-tetrahydro-quinoline and the like. The carbon atoms or heteroatoms in the ring(s) of the heterocycloalkyl group can be oxidized to form a carbonyl, or sulfonyl group (or other oxidized linkage) or a nitrogen atom can be quaternized. In some embodiments, heterocycloalkyl is 5- to 10-membered $C_{2-9}$ heterocycloalkyl, which is monocyclic or bicyclic and which has 1, 2, 3, or 4 heteroatom ring members independently selected from nitrogen, sulfur and oxygen. Examples of heterocycloalkyl groups include 1,2,3,4-tetrahydro-quinoline, azetidine, azepane, pyrrolidine, piperidine, piperazine, morpholine, thiomorpholine, pyran, and a 2-oxo-1,3-oxazolidine ring.

As used herein, the term "heterocycloalkylalkyl" refers to a group of formula -alkylene-heterocycloalkyl. In some embodiments, heterocycloalkylalkyl is $C_{2-9}$ heterocycloalkyl-$C_{1-3}$ alkyl, wherein the heterocycloalkyl portion is monocyclic or bicyclic and has 1, 2, 3, or 4 heteroatom ring members independently selected from nitrogen, sulfur and oxygen. In some embodiments, heterocycloalkylalkyl is $C_{2-9}$ heterocycloalkyl-$C_{1-4}$ alkyl, wherein the heterocycloalkyl portion is monocyclic or bicyclic and has 1, 2, 3, or 4 heteroatom ring members independently selected from nitrogen, sulfur and oxygen.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

Resolution of racemic mixtures of compounds can be carried out by any of numerous methods known in the art. An example method includes fractional recrystallization using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, amide-imidic acid pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the invention can also include all isotopes of atoms occurring in the intermediates or final compounds. Isotopes include those atoms having the same atomic number but different mass numbers. For example, isotopes of hydrogen include tritium and deuterium. In some embodiments, 1, 2, or 3 $CH_2$ or CH groups in the cyclobutyl ring of Formula I are replaced by a CHD or $CD_2$ group. In some embodiments, 1, 2, or 3 $CH_2$ or CH groups in the moiety

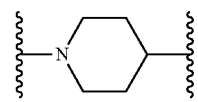

of Formula I are replaced by a CHD, $CD_2$ or CD group, respectively.

For example, some embodiments of the compounds of Formula I may have a deuterium atom attached to one atom of the cyclobutyl ring:

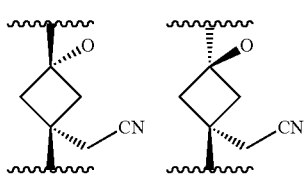 [SMILES: *[C@]1(O)C[C@@](*)(CC#N)C1 ; *[C@]1(O)C[C@](*)(CC#N)C1]

The term, "compound," as used herein is meant to include all stereoisomers, geometric iosomers, tautomers, and isotopes of the structures depicted. Compounds herein identified by name or structure as one particular tautomeric form are intended to include other tautomeric forms unless otherwise specified (e.g., in the case of purine rings, unless otherwise indicated, when the compound name or structure has the 9H tautomer, it is understood that the 7H tautomer is also encompassed).

All compounds, and pharmaceutically acceptable salts thereof, can be found together with other substances such as water and solvents (e.g. hydrates and solvates) or can be isolated.

In some embodiments, the compounds of the invention, or salts thereof, are substantially isolated. By "substantially isolated" is meant that the compound is at least partially or substantially separated from the environment in which it was formed or detected. Partial separation can include, for example, a composition enriched in the compounds of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof. Methods for isolating compounds and their salts are routine in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions, "ambient temperature" and "room temperature," as used herein, are understood in the art, and refer generally to a temperature, e.g. a reaction temperature, that is about the temperature of the room in which the reaction is carried out, for example, a temperature from about 20° C. to about 30° C.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (ACN) are preferred. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

Synthesis

Compounds of the invention, including salts and N-oxides thereof, can be prepared using known organic synthesis techniques and can be synthesized according to any of numerous possible synthetic routes.

The reactions for preparing compounds of the invention can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in Wuts and Greene, Protective Groups in Organic Synthesis, 4th ed., John Wiley & Sons: New Jersey, (2007), which is incorporated herein by reference in its entirety.

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC) or thin layer chromatography (TLC).

Useful intermediates 3-4 can be made according to the methods outlined in Scheme I. The heterocycloalkyl ring compound 3-1 (such as tert-butyl 4-hydroxypiperidine-1-carboxylate) can be reacted with phenol 3-2 under Mitsunobu coupling reaction condition to afford ether 3-3. [See, Mitsunobu, O. (1981). "The Use of Diethyl Azodicarboxylate and Triphenylphosphine in Synthesis and Transformation of Natural Products". Synthesis 1982 (1): 1-28.] The amino protecting group $Pg^1$ can be removed to afford intermediate 3-4.

Scheme I

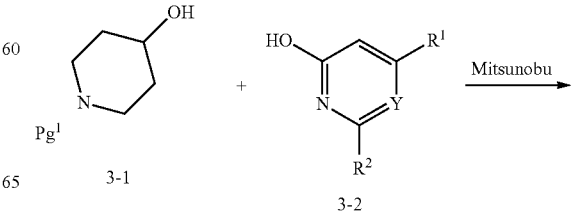

-continued

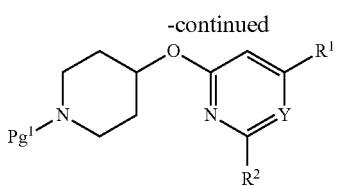

3-3

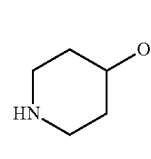

Pg¹ is an amine protecting group such as Boc    3-4

Compound of Formula I can be made by the methods shown in Scheme II. Accordingly formula 4-2 can be formed by reaction of the cyclobutanone of formula 4-1 with a Horner-Wadsworth-Emmons reagent. A protected pyrazol-4-yl-pyrrolo[2,3-d]pyrimidine or pyrrolo[2,3-b]pyridine of formula 4-3 is reacted with a protected alkene of formula 4-2 in a Michael addition in the presence of a coupling agent to give the compound of formula 4-4. Removal of ether protecting group of formula 4-4 gives an alcohol derivative of formula 4-5, which can be oxidized to give the compound of formula 4-6. The compound of formula 4-6 can be converted to compound of formula 4-7 and 4-8 via reductive amination, which can be deprotected to remove $P_1$ to give compounds of the invention.

Scheme II

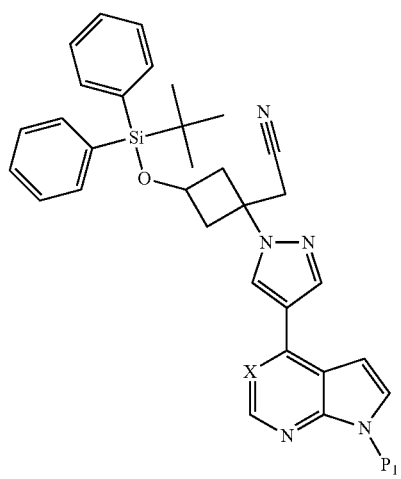

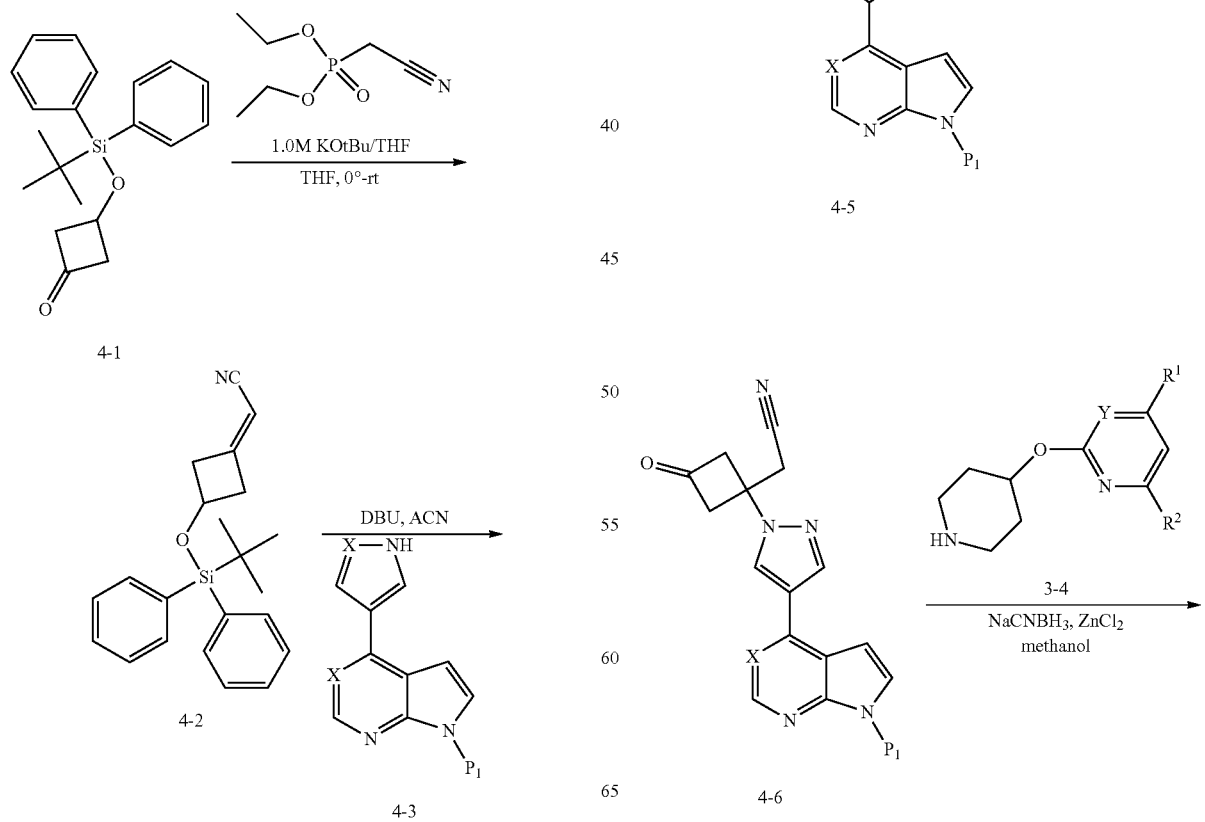

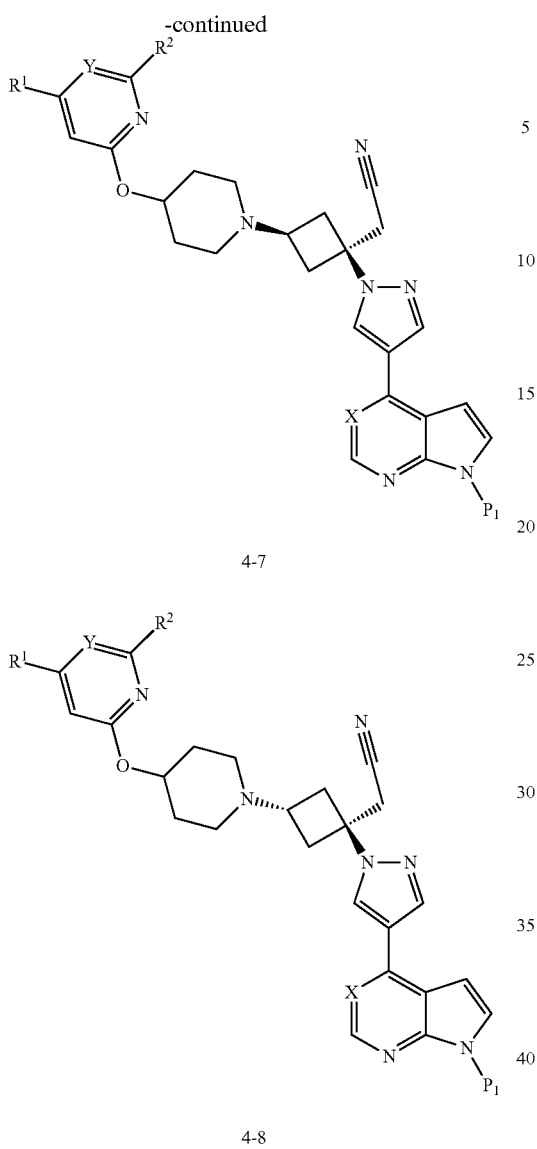

4-7

4-8

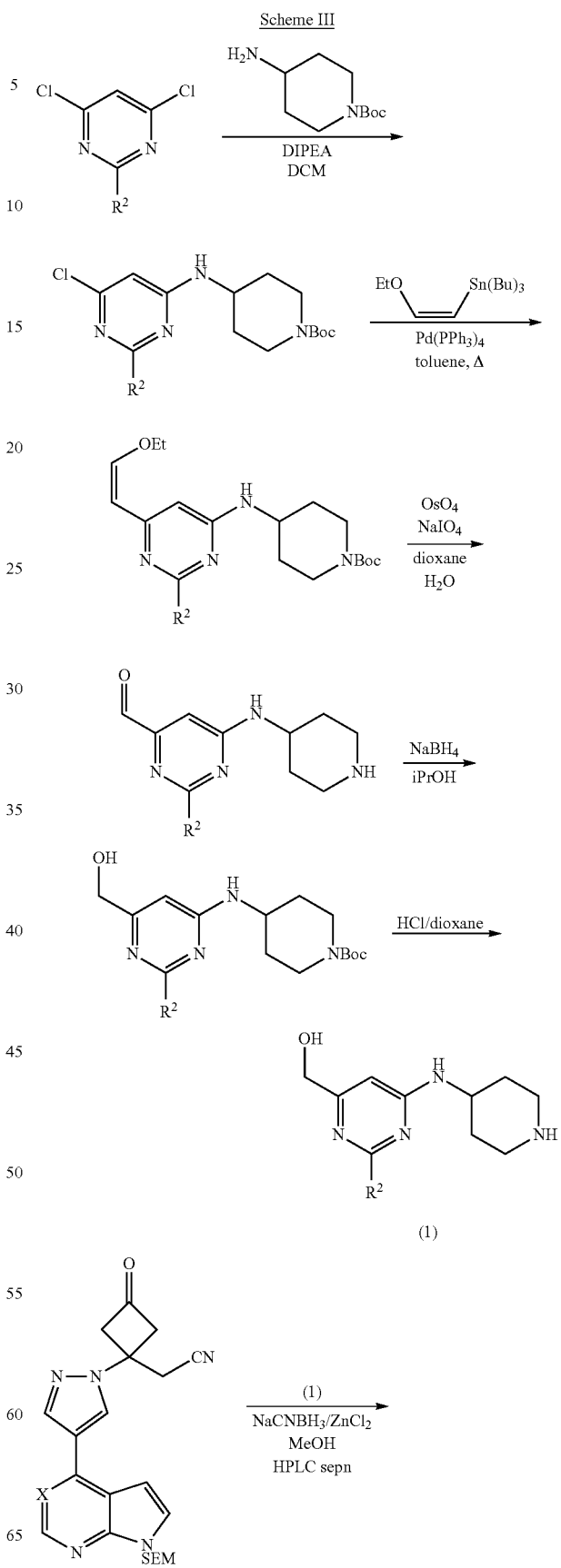

Specific compounds of Formula III can by made by the processes in Schemes III-X. For example, in Scheme III, a 4,6-dichloropyrimidine derivative can be treated with tert-butyl 4-aminopiperidine-1-carboxylate in a nucleophilic aromatic substitution reaction to provide the adduct. The resulting 6-chloropyrimidine is then used in a Stille coupling to afford the enol ether intermediate which can undergo oxidative cleavage to afford the aldehyde. The aldehyde can be reduced to the alcohol using sodium borohydride, and the resulting compound is then Boc-deprotected to provide piperidine for the reductive amination. Reductive amination between the piperidine and the cyclobutanone, employing a mixture of sodium cyanoborohydride and zinc dichloride in methanol, affords a mixture of cis and trans isomers which are separable by HPLC. Direct deprotection affords the hydroxymethylpyrimidine (Scheme III). Alternatively, as shown in Scheme IV, the SEM-protected hydroxymethyl intermediate could be converted to the mesylate and the mesylate could be displaced with amines in a mixture of THF/MeOH at temperatures between ambient and 40° C. The aminomethyl compounds are deprotected the same way.

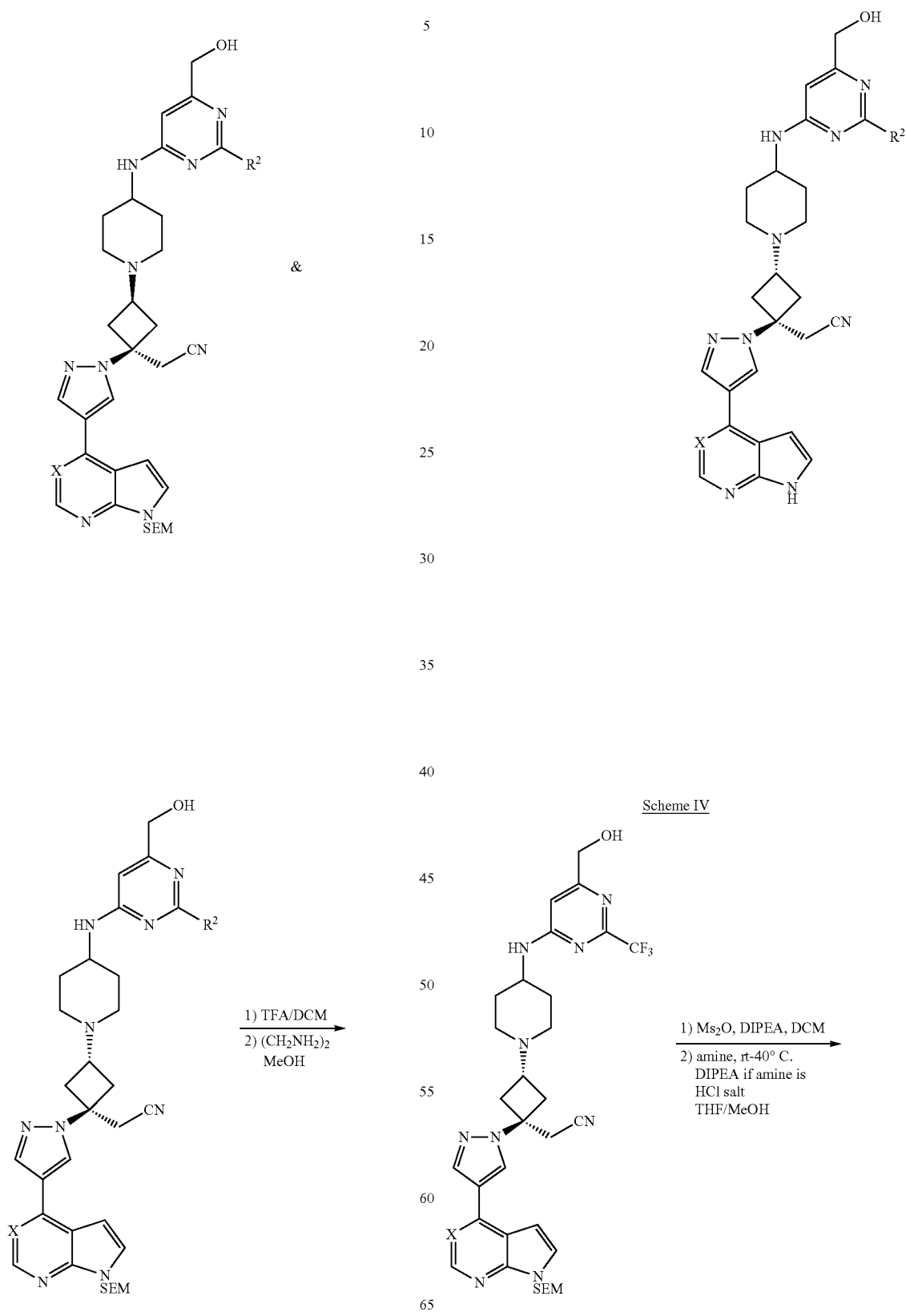

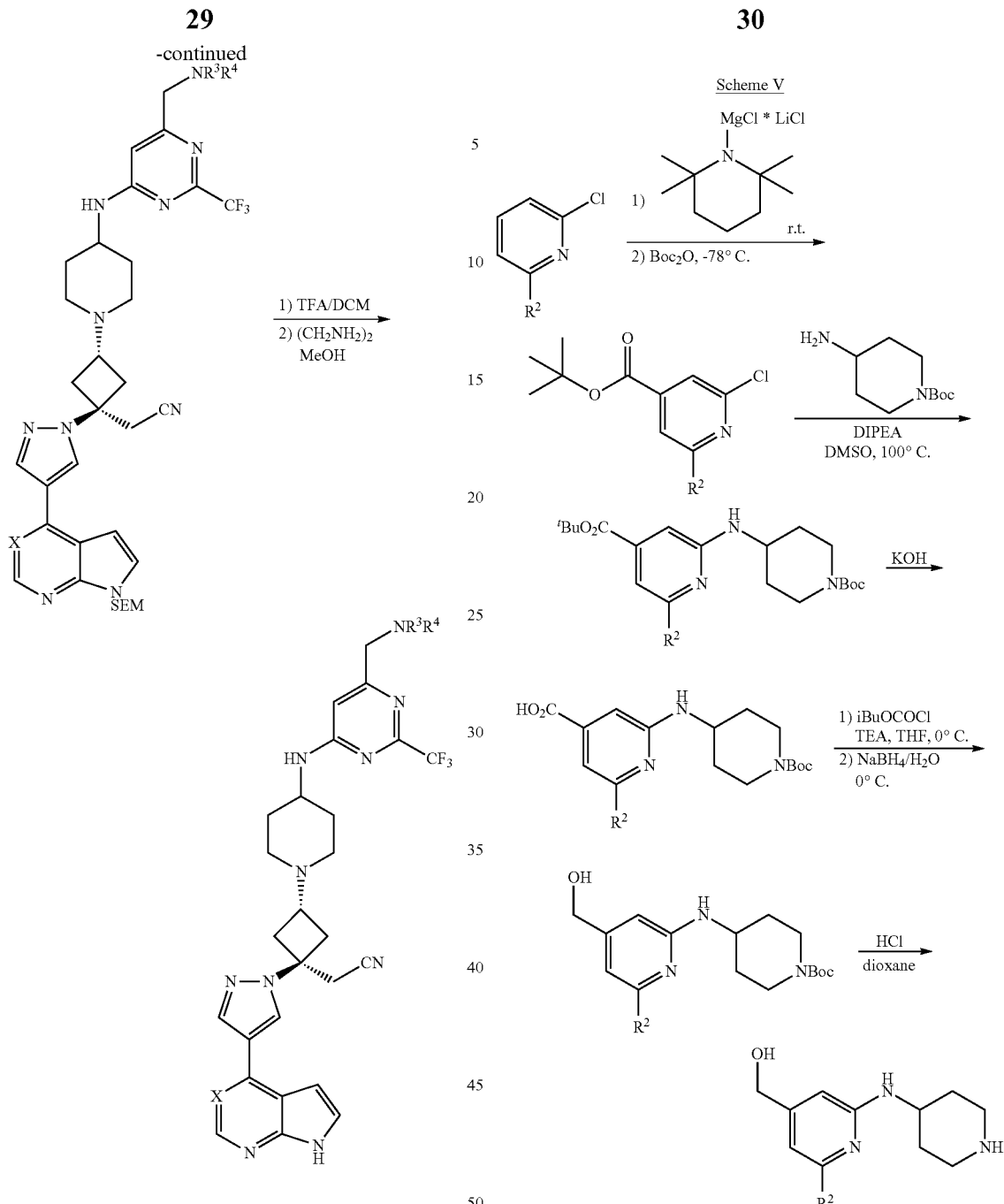

In Scheme V, to prepare the pyridine congeners, tert-butyl 2-chloro-6-(trifluoromethyl)isonicotinate is produced by metalation of a 2-chloropyridine followed by reaction with di-tert-butyl dicarbonate. Heating this chloropyridine with tert-butyl 4-aminopiperidine-1-carboxylate in DMSO affords the adduct. After hydrolysis of the ester, reduction to the alcohol is effected via reacting the mixed anhydride with sodium borohydride. Boc-deprotection of the piperidine with HCl/dioxane is followed by reductive amination with the cyclobutanone under the same conditions as in Scheme III. HPLC separation of the isomers allowed for deprotection of the trans isomer, or conversion to the mesylate and formation of amines by displacement (Scheme VI). SEM-deprotection can be carried out after the displacement to form the amines. Alternatively, as shown in Scheme VII, the SEM-protected hydroxymethylpyridine adduct can be used to form the ether (via the same mesylate intermediate) by reacting with methanol at 85° C.

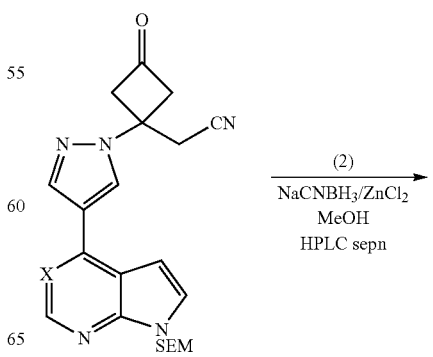

Scheme VI
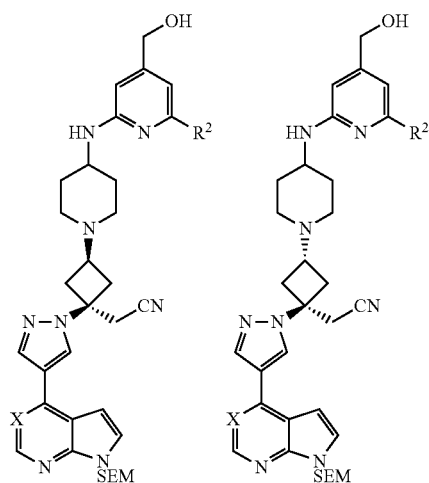
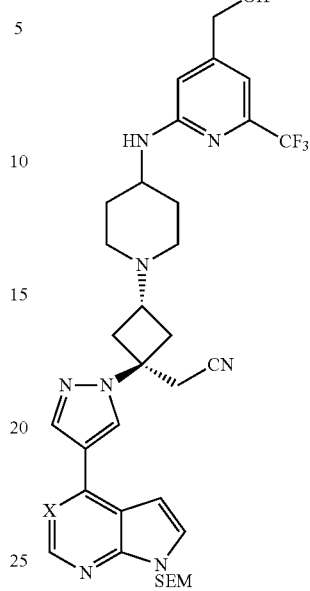
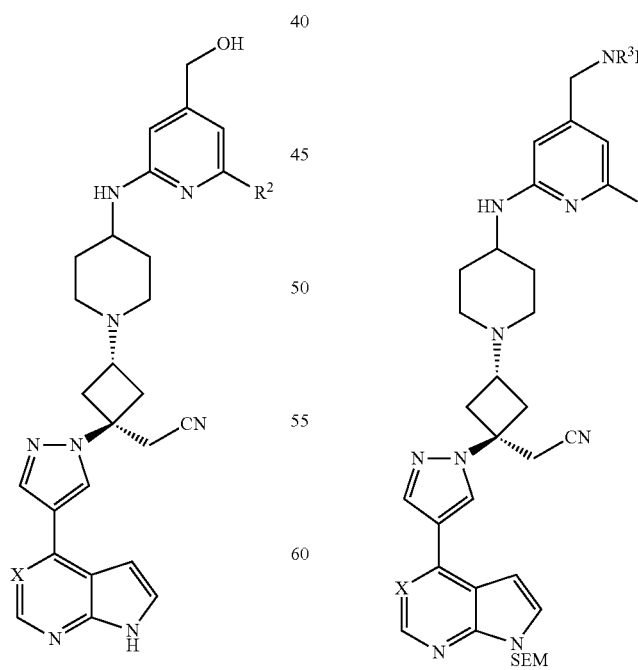
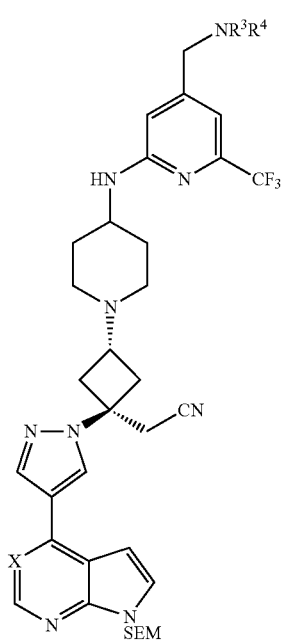

33
-continued

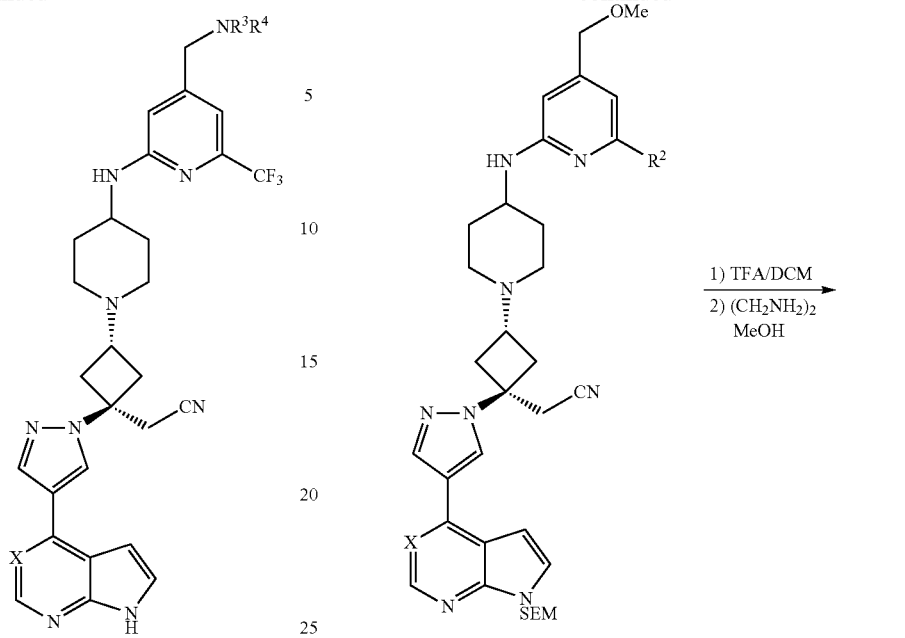

Scheme VII

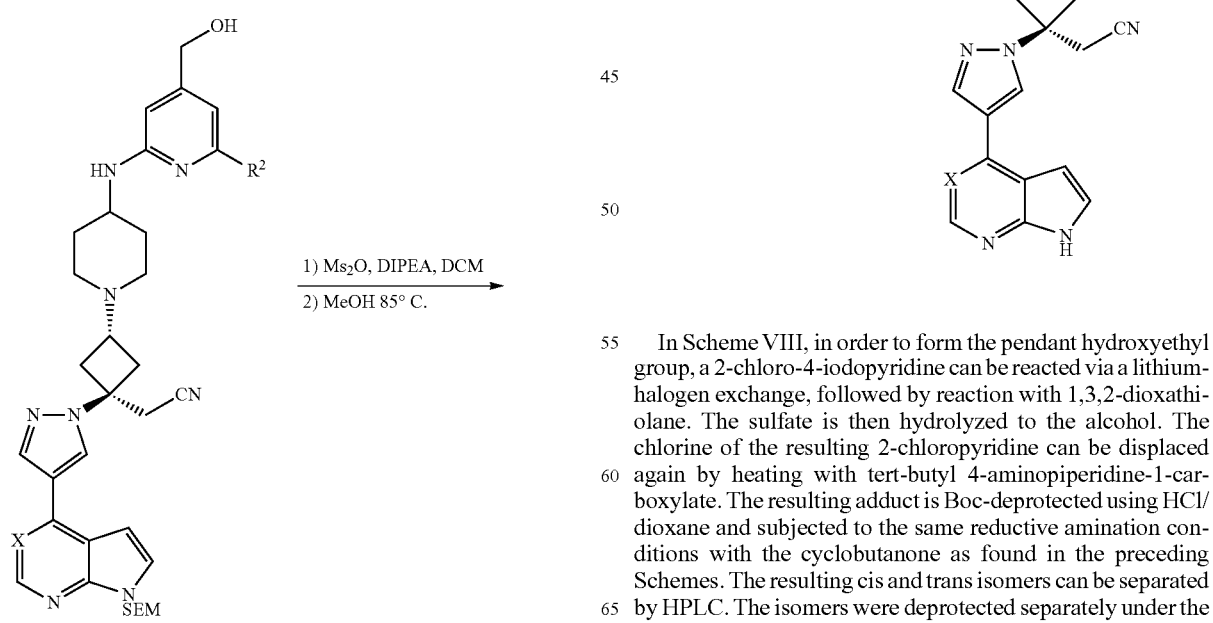

34
-continued

In Scheme VIII, in order to form the pendant hydroxyethyl group, a 2-chloro-4-iodopyridine can be reacted via a lithium-halogen exchange, followed by reaction with 1,3,2-dioxathiolane. The sulfate is then hydrolyzed to the alcohol. The chlorine of the resulting 2-chloropyridine can be displaced again by heating with tert-butyl 4-aminopiperidine-1-carboxylate. The resulting adduct is Boc-deprotected using HCl/dioxane and subjected to the same reductive amination conditions with the cyclobutanone as found in the preceding Schemes. The resulting cis and trans isomers can be separated by HPLC. The isomers were deprotected separately under the usual conditions of TFA/DCM followed by ethylenediamine in methanol.

Scheme VIII

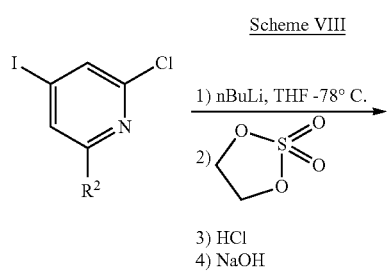

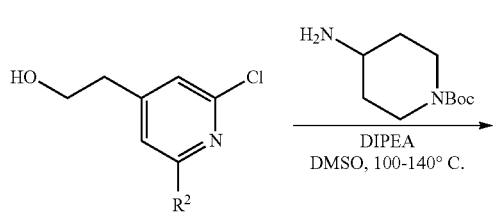

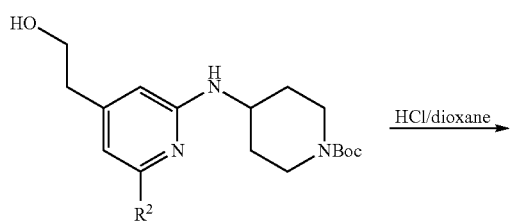

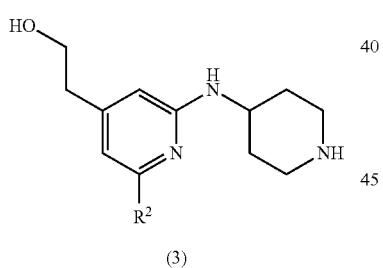

(3)

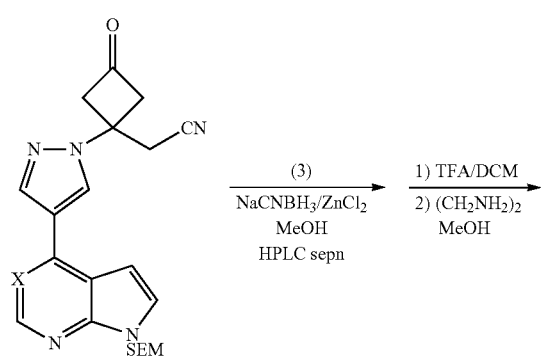

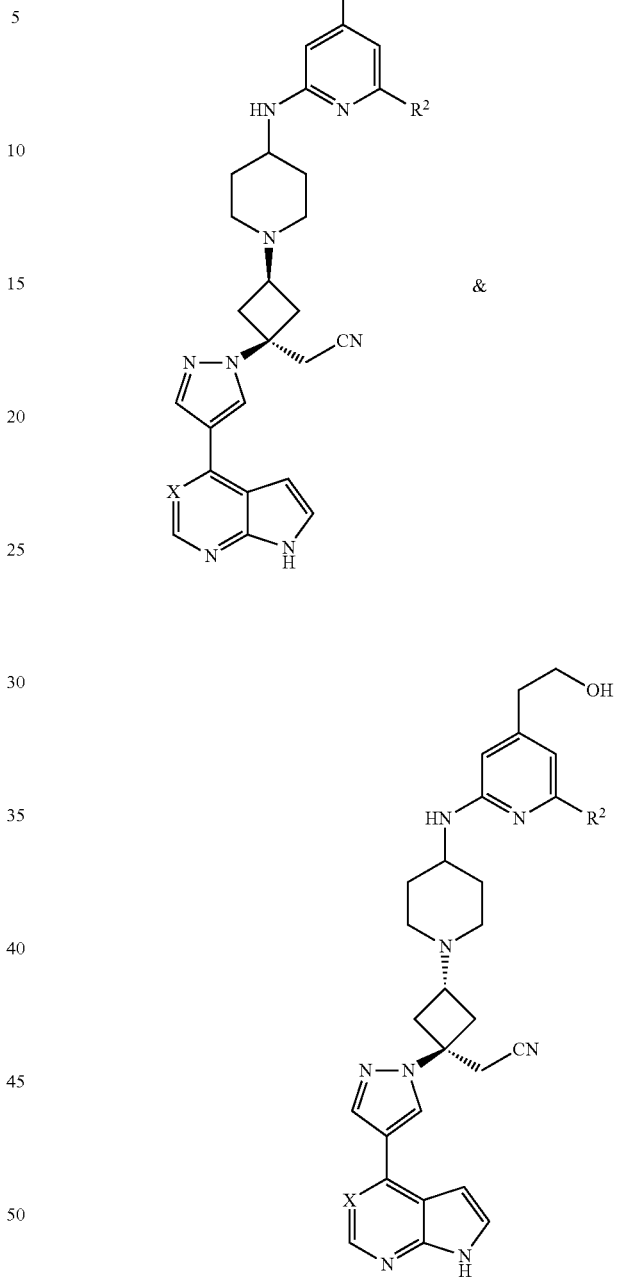

In Scheme IX, to form the methylated N-linked analogs, first tert-butyl 4-(methylamino)piperidine-1-carboxylate is formed by reductive amination between the piperidinone and methylamine. Displacement of the chloro group is followed by hydrolysis and reduction as previously described. Boc deprotection can be carried out with HCl/dioxane, and reductive amination can then be performed between the deprotected piperidine and cyclobutanone to afford cis and trans isomers, which were separable by HPLC. As in the previous examples, the hydroxymethyl compound can be directly deprotected, or converted to its mesylate at the SEM-protected stage and reacted with amines before deprotection as shown in Scheme X.

Scheme IX
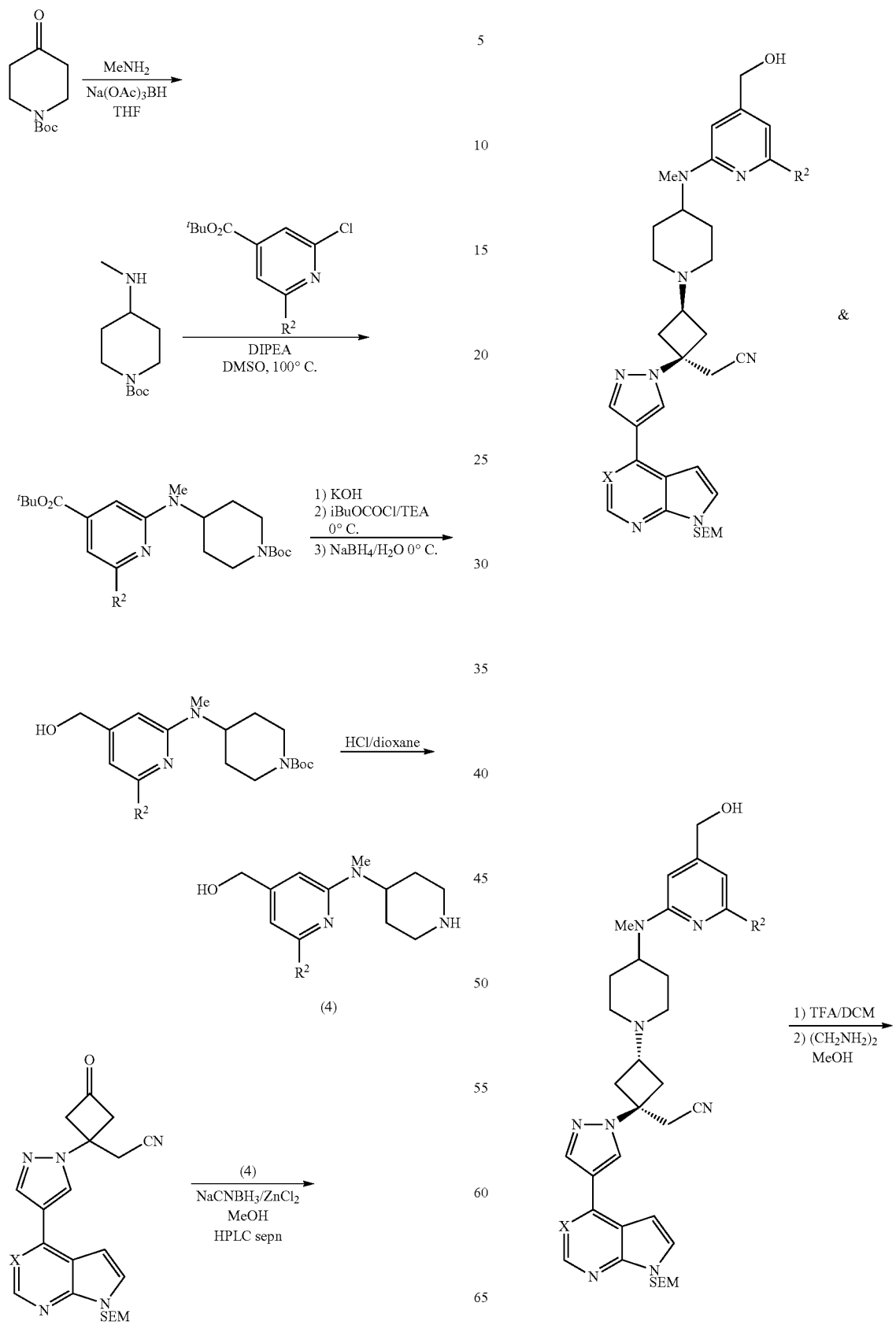

-continued

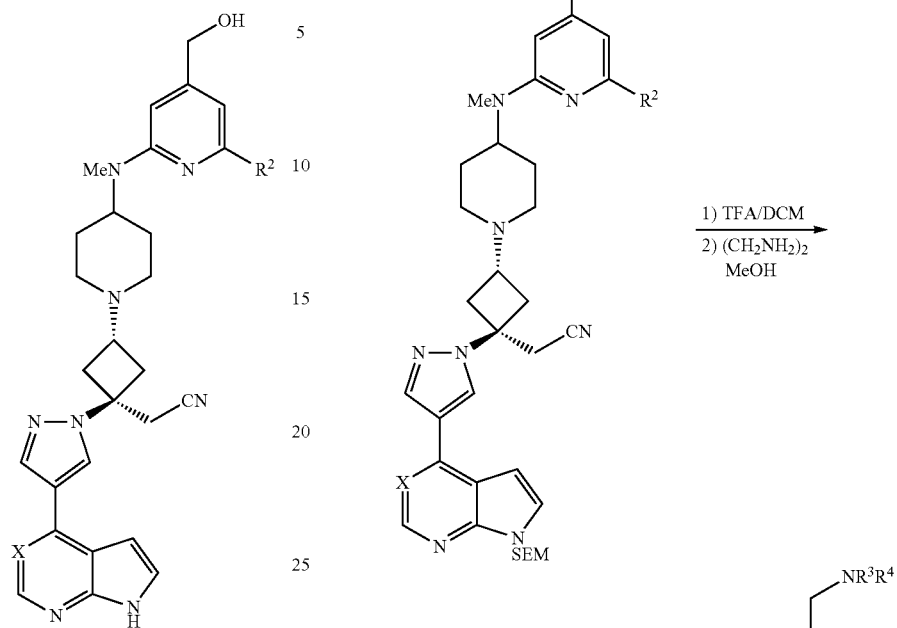

1) TFA/DCM
2) (CH$_2$NH$_2$)$_2$
MeOH

Scheme X

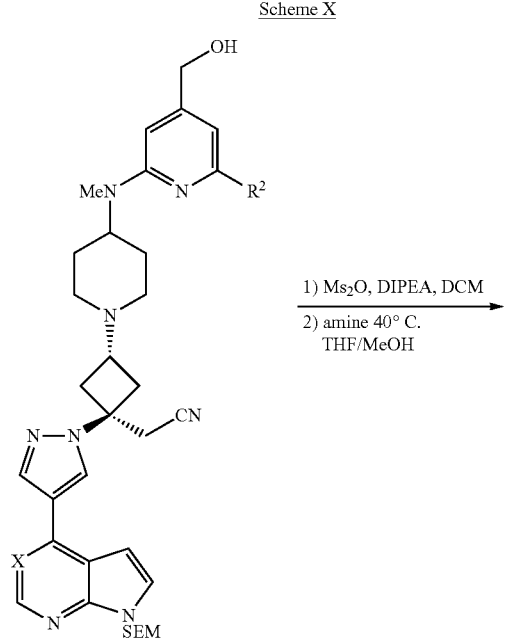

1) Ms$_2$O, DIPEA, DCM
2) amine 40° C.
THF/MeOH

Methods

Compounds of the invention are JAK inhibitors, and the majority of the compounds of the invention are JAK1 selective inhibitors. A JAK1 selective inhibitor is a compound that inhibits JAK1 activity preferentially over other Janus kinases. For example, the compounds of the invention preferentially inhibit JAK1 over one or more of JAK2, JAK3, and TYK2. In some embodiments, the compounds inhibit JAK1 preferentially over JAK2 (e.g., have a JAK1/JAK2 IC$_{50}$ ratio>1).

JAK1 plays a central role in a number of cytokine and growth factor signaling pathways that, when dysregulated, can result in or contribute to disease states. For example, IL-6 levels are elevated in rheumatoid arthritis, a disease in which it has been suggested to have detrimental effects (Fonesca, J. E. et al., Autoimmunity Reviews, 8:538-42, 2009). Because IL-6 signals, at least in part, through JAK1, antagonizing IL-6 directly or indirectly through JAK1 inhibition is expected to provide clinical benefit (Guschin, D., N., et al Embo J 14:1421, 1995; Smolen, J. S., et al. Lancet 371:987, 2008). Moreover, in some cancers JAK1 is mutated resulting in constitutive undesirable tumor cell growth and survival (Mullighan C G, Proc Natl Acad Sci USA. 106:9414-8, 2009; Flex E., et al. J Exp Med. 205:751-8, 2008). In other autoimmune diseases and cancers elevated systemic levels of inflammatory cytokines that activate JAK1 may also contribute to the disease and/or associated symptoms. Therefore, patients with such diseases may benefit from JAK1 inhibition. Selective inhibitors of JAK1 may be efficacious while avoiding unnecessary and potentially undesirable effects of inhibiting other JAK kinases.

Selective inhibitors of JAK1, relative to other JAK kinases, may have multiple therapeutic advantages over less selective inhibitors. With respect to selectivity against JAK2, a number of important cytokines and growth factors signal through JAK2 including, for example, erythropoietin (Epo) and thrombopoietin (Tpo) (Parganas E, et al. Cell. 93:385-95, 1998). Epo is a key growth factor for red blood cells production; hence a paucity of Epo-dependent signaling can result in reduced numbers of red blood cells and anemia (Kaushansky K, NEJM 354:2034-45, 2006). Tpo, another example of a JAK2-dependent growth factor, plays a central role in controlling the proliferation and maturation of megakaryocytes—the cells from which platelets are produced (Kaushansky K, NEJM 354:2034-45, 2006). As such, reduced Tpo signaling would decrease megakaryocyte numbers (megakaryocytopenia) and lower circulating platelet counts (thrombocytopenia). This can result in undesirable and/or uncontrollable bleeding. Reduced inhibition of other JAKs, such as JAK3 and Tyk2, may also be desirable as humans lacking functional version of these kinases have been shown to suffer from numerous maladies such as severe-combined immunodeficiency or hyperimmunoglobulin E syndrome (Minegishi, Y, et al. Immunity 25:745-55, 2006; Macchi P, et al. Nature. 377:65-8, 1995). Therefore a JAK1 inhibitor with reduced affinity for other JAKs would have significant advantages over a less-selective inhibitor with respect to reduced side effects involving immune suppression, anemia and thrombocytopenia.

Another aspect of the present invention pertains to methods of treating a JAK-associated disease or disorder in an individual (e.g., patient) by administering to the individual in need of such treatment a therapeutically effective amount or dose of a compound of the present invention or a pharmaceutical composition thereof. A JAK-associated disease can include any disease, disorder or condition that is directly or indirectly linked to expression or activity of the JAK, including overexpression and/or abnormal activity levels. A JAK-associated disease can also include any disease, disorder or condition that can be prevented, ameliorated, or cured by modulating JAK activity. In some embodiments, the JAK-associated disease is a JAK1-associated disease.

Examples of JAK-associated diseases include diseases involving the immune system including, for example, organ transplant rejection (e.g., allograft rejection and graft versus host disease).

Further examples of JAK-associated diseases include autoimmune diseases such as multiple sclerosis, rheumatoid arthritis, juvenile arthritis, psoriatic arthritis, type I diabetes, lupus, psoriasis, inflammatory bowel disease, ulcerative colitis, Crohn's disease, myasthenia gravis, immunoglobulin nephropathies, myocarditis, autoimmune thyroid disorders, and the like. In some embodiments, the autoimmune disease is an autoimmune bullous skin disorder such as pemphigus vulgaris (PV) or bullous pemphigoid (BP).

Further examples of JAK-associated diseases include allergic conditions such as asthma, food allergies, atopic dermatitis and rhinitis. Further examples of JAK-associated diseases include viral diseases such as Epstein Barr Virus (EBV), Hepatitis B, Hepatitis C, HIV, HTLV 1, Varicella-Zoster Virus (VZV) and Human Papilloma Virus (HPV).

Further examples of JAK-associated disease include diseases associated with cartilage turnover, for example, gouty arthritis, septic or infectious arthritis, reactive arthritis, reflex sympathetic dystrophy, algodystrophy, Tietze syndrome, costal athropathy, osteoarthritis deformans endemica, Mseleni disease, Handigodu disease, degeneration resulting from fibromyalgia, systemic lupus erythematosus, scleroderma, or ankylosing spondylitis.

Further examples of JAK-associated disease include congenital cartilage malformations, including hereditary chondrolysis, chondrodysplasias, and pseudochrondrodysplasias (e.g., microtia, enotia, and metaphyseal chrondrodysplasia).

Further examples of JAK-associated diseases or conditions include skin disorders such as psoriasis (for example, psoriasis vulgaris), atopic dermatitis, skin rash, skin irritation, skin sensitization (e.g., contact dermatitis or allergic contact dermatitis). For example, certain substances including some pharmaceuticals when topically applied can cause skin sensitization. In some embodiments, co-administration or sequential administration of at least one JAK inhibitor of the invention together with the agent causing unwanted sensitization can be helpful in treating such unwanted sensitization or dermatitis. In some embodiments, the skin disorder is treated by topical administration of at least one JAK inhibitor of the invention.

In further embodiments, the JAK-associated disease is cancer including those characterized by solid tumors (e.g., prostate cancer, renal cancer, hepatic cancer, pancreatic cancer, gastric cancer, breast cancer, lung cancer, cancers of the head and neck, thyroid cancer, glioblastoma, Kaposi's sarcoma, Castleman's disease, melanoma etc.), hematological cancers (e.g., lymphoma, leukemia such as acute lymphoblastic leukemia, acute myelogenous leukemia (AML) or multiple myeloma), and skin cancer such as cutaneous T-cell lymphoma (CTCL) and cutaneous B-cell lymphoma. Example CTCLs include Sezary syndrome and mycosis fungoides.

In some embodiments, the JAK inhibitors described herein, or in combination with other JAK inhibitors, such as those reported in U.S. Ser. No. 11/637,545, which is incorporated herein by reference in its entirety, can be used to treat inflammation-associated cancers. In some embodiments, the cancer is associated with inflammatory bowel disease. In some embodiments, the inflammatory bowel disease is ulcerative colitis. In some embodiments, the inflammatory bowel disease is Crohn's disease. In some embodiments, the inflammation-associated cancer is colitis-associated cancer. In some embodiments, the inflammation-associated cancer is colon cancer or colorectal cancer. In some embodiments, the cancer is gastric cancer, gastrointestinal carcinoid tumor, gastrointestinal stromal tumor (GIST), adenocarcinoma, small intestine cancer, or rectal cancer.

JAK-associated diseases can further include those characterized by expression of: JAK2 mutants such as those having at least one mutation in the pseudo-kinase domain (e.g., JAK2V617F); JAK2 mutants having at least one mutation outside of the pseudo-kinase domain; JAK1 mutants; JAK3 mutants; erythropoietin receptor (EPOR) mutants; or deregulated expression of CRLF2.

JAK-associated diseases can further include myeloproliferative disorders (MPDs) such as polycythemia vera (PV), essential thrombocythemia (ET), myelofibrosis with myeloid metaplasia (MMM), primary myelofibrosis (PMF), chronic myelogenous leukemia (CML), chronic myelomonocytic leukemia (CMML), hypereosinophilic syndrome (HES), systemic mast cell disease (SMCD), and the like. In some embodiments, the myeloproliferative disorder is myelofibrosis (e.g., primary myelofibrosis (PMF) or post polycythemia vera/essential thrombocythemia myelofibrosis (Post-PV/ET MF)).

The present invention further provides methods of treating psoriasis or other skin disorders by administration of a topical formulation containing a compound of the invention.

In some embodiments, JAK inhibitors described herein can be used to treat pulmonary arterial hypertension.

The present invention further provides a method of treating dermatological side effects of other pharmaceuticals by administration of the compound of the invention. For example, numerous pharmaceutical agents result in unwanted allergic reactions which can manifest as acneiform rash or related dermatitis. Example pharmaceutical agents that have such undesirable side effects include anti-cancer drugs such as gefitinib, cetuximab, erlotinib, and the like. The compounds of the invention can be administered systemically or topically (e.g., localized to the vicinity of the dermatitis) in combination with (e.g., simultaneously or sequentially) the pharmaceutical agent having the undesirable dermatological side effect. In some embodiments, the compound of the invention can be administered topically together with one or more other pharmaceuticals, where the other pharmaceuticals when topically applied in the absence of a compound of the invention cause contact dermatitis, allergic contact sensitization, or similar skin disorder. Accordingly, compositions of the invention include topical formulations containing the compound of the invention and a further pharmaceutical agent which can cause dermatitis, skin disorders, or related side effects.

Further JAK-associated diseases include inflammation and inflammatory diseases. Example inflammatory diseases include sarcoidosis, inflammatory diseases of the eye (e.g., iritis, uveitis, scleritis, conjunctivitis, or related disease), inflammatory diseases of the respiratory tract (e.g., the upper respiratory tract including the nose and sinuses such as rhinitis or sinusitis or the lower respiratory tract including bronchitis, chronic obstructive pulmonary disease, and the like), inflammatory myopathy such as myocarditis, and other inflammatory diseases.

The JAK inhibitors described herein can further be used to treat ischemia reperfusion injuries or a disease or condition related to an inflammatory ischemic event such as stroke or cardiac arrest. The JAK inhibitors described herein can further be used to treat anorexia, cachexia, or fatigue such as that resulting from or associated with cancer. The JAK inhibitors described herein can further be used to treat restenosis, sclerodermitis, or fibrosis. The JAK inhibitors described herein can further be used to treat conditions associated with hypoxia or astrogliosis such as, for example, diabetic retinopathy, cancer, or neurodegeneration. See, e.g., Dudley, A. C. et al. *Biochem. J.* 2005, 390(Pt 2):427-36 and Sriram, K. et al. *J. Biol. Chem.* 2004, 279(19):19936-47. Epub 2004 Mar. 2, both of which are incorporated herein by reference in their entirety. The JAK inhibitors described herein can be used to treat Alzheimer's disease.

The JAK inhibitors described herein can further be used to treat other inflammatory diseases such as systemic inflammatory response syndrome (SIRS) and septic shock.

The JAK inhibitors described herein can further be used to treat gout and increased prostate size due to, e.g., benign prostatic hypertrophy or benign prostatic hyperplasia.

Further JAK-associated diseases include bone resorption diseases such as osteoporosis, osteoarthritis. Bone resorption can also be associated with other conditions such as hormonal imbalance and/or hormonal therapy, autoimmune disease (e.g. osseous sarcoidosis), or cancer (e.g. myeloma). The reduction of the bone resorption due to the JAK inhibitors can be about 10%, about 20%, about 30%, about 40%, about 50%, about 60%, about 70%, about 80%, or about 90%.

In some embodiments, JAK inhibitors described herein can further be used to treat a dry eye disorder. As used herein, "dry eye disorder" is intended to encompass the disease states summarized in a recent official report of the Dry Eye Workshop (DEWS), which defined dry eye as "a multifactorial disease of the tears and ocular surface that results in symptoms of discomfort, visual disturbance, and tear film instability with potential damage to the ocular surface. It is accompanied by increased osmolarity of the tear film and inflammation of the ocular surface." Lemp, "The Definition and Classification of Dry Eye Disease: Report of the Definition and Classification Subcommittee of the International Dry Eye Workshop", *The Ocular Surface*, 5(2), 75-92 April 2007, which is incorporated herein by reference in its entirety. In some embodiments, the dry eye disorder is selected from aqueous tear-deficient dry eye (ADDE) or evaporative dry eye disorder, or appropriate combinations thereof. In some embodiments, the dry eye disorder is Sjogren syndrome dry eye (SSDE). In some embodiments, the dry eye disorder is non-Sjogren syndrome dry eye (NSSDE).

In a further aspect, the present invention provides a method of treating conjunctivitis, uveitis (including chronic uveitis), chorioditis, retinitis, cyclitis, sclieritis, episcleritis, or iritis; treating inflammation or pain related to corneal transplant, LASIK (laser assisted in situ keratomileusis), photorefractive keratectomy, or LASEK (laser assisted sub-epithelial keratomileusis); inhibiting loss of visual acuity related to corneal transplant, LASIK, photorefractive keratectomy, or LASEK; or inhibiting transplant rejection in a patient in need thereof, comprising administering to the patient a therapeutically effective amount of the compound of the invention, or a pharmaceutically acceptable salt thereof.

Additionally, the compounds of the invention, or in combination with other JAK inhibitors, such as those reported in U.S. Ser. No. 11/637,545, which is incorporated herein by reference in its entirety, can be used to treat respiratory dysfunction or failure associated with viral infection, such as influenza and SARS.

In some embodiments, the present invention provides a compound of Formula I, pharmaceutically acceptable salt thereof, as described in any of the embodiments herein, for use in a method of treating any of the diseases or disorders described herein. In some embodiments, the present invention provides the use of a compound of Formula I as described in any of the embodiments herein, for the preparation of a medicament for use in a method of treating any of the diseases or disorders described herein.

In some embodiments, the present invention provides a compound of Formula I as described herein, or a pharmaceutically acceptable salt thereof, for use in a method of modulating a JAK1. In some embodiments, the present invention also provides use of a compound of Formula I as described herein, or a pharmaceutically acceptable salt thereof, for the preparation of a medicament for use in a method of modulating a JAK1.

As used herein, the term "contacting" refers to the bringing together of indicated moieties in an in vitro system or an in vivo system. For example, "contacting" a JAK with a compound of the invention includes the administration of a compound of the present invention to an individual or patient, such as a human, having a JAK, as well as, for example, introducing a compound of the invention into a sample containing a cellular or purified preparation containing the JAK.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

As used herein, the term "treating" or "treatment" refers to one or more of (1) preventing the disease; for example, preventing a disease, condition or disorder in an individual who may be predisposed to the disease, condition or disorder but does not yet experience or display the pathology or symptomatology of the disease; (2) inhibiting the disease; for example, inhibiting a disease, condition or disorder in an individual who is experiencing or displaying the pathology or symptomatology of the disease, condition or disorder (i.e., arresting further development of the pathology and/or symptomatology); and (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

Combination Therapies

One or more additional pharmaceutical agents such as, for example, chemotherapeutics, anti-inflammatory agents, steroids, immunosuppressants, as well as Bcr-Abl, Flt-3, RAF and FAK kinase inhibitors such as, for example, those described in WO 2006/056399, which is incorporated herein by reference in its entirety, or other agents can be used in combination with the compounds described herein for treatment of JAK-associated diseases, disorders or conditions. The one or more additional pharmaceutical agents can be administered to a patient simultaneously or sequentially.

Example chemotherapeutic include proteosome inhibitors (e.g., bortezomib), thalidomide, revlimid, and DNA-damaging agents such as melphalan, doxorubicin, cyclophosphamide, vincristine, etoposide, carmustine, and the like.

Example steroids include coriticosteroids such as dexamethasone or prednisone.

Example Bcr-Abl inhibitors include the compounds, and pharmaceutically acceptable salts thereof, of the genera and species disclosed in U.S. Pat. No. 5,521,184, WO 04/005281, and U.S. Ser. No. 60/578,491, all of which are incorporated herein by reference in their entirety.

Example suitable Flt-3 inhibitors include compounds, and their pharmaceutically acceptable salts, as disclosed in WO 03/037347, WO 03/099771, and WO 04/046120, all of which are incorporated herein by reference in their entirety.

Example suitable RAF inhibitors include compounds, and their pharmaceutically acceptable salts, as disclosed in WO 00/09495 and WO 05/028444, both of which are incorporated herein by reference in their entirety.

Example suitable FAK inhibitors include compounds, and their pharmaceutically acceptable salts, as disclosed in WO 04/080980, WO 04/056786, WO 03/024967, WO 01/064655, WO 00/053595, and WO 01/014402, all of which are incorporated herein by reference in their entirety.

In some embodiments, one or more of the compounds of the invention can be used in combination with one or more other kinase inhibitors including imatinib, particularly for treating patients resistant to imatinib or other kinase inhibitors.

In some embodiments, one or more JAK inhibitors of the invention can be used in combination with a chemotherapeutic in the treatment of cancer, such as multiple myeloma, and may improve the treatment response as compared to the response to the chemotherapeutic agent alone, without exacerbation of its toxic effects. Examples of additional pharmaceutical agents used in the treatment of multiple myeloma, for example, can include, without limitation, melphalan, melphalan plus prednisone [MP], doxorubicin, dexamethasone, and Velcade (bortezomib). Further additional agents used in the treatment of multiple myeloma include Bcr-Abl, Flt-3, RAF and FAK kinase inhibitors. Additive or synergistic effects are desirable outcomes of combining a JAK inhibitor of the present invention with an additional agent. Furthermore, resistance of multiple myeloma cells to agents such as dexamethasone may be reversible upon treatment with a JAK inhibitor of the present invention. The agents can be combined with the present compounds in a single or continuous dosage form, or the agents can be administered simultaneously or sequentially as separate dosage forms.

In some embodiments, a corticosteroid such as dexamethasone is administered to a patient in combination with at least one JAK inhibitor where the dexamethasone is administered intermittently as opposed to continuously.

In some further embodiments, combinations of one or more JAK inhibitors of the invention with other therapeutic agents can be administered to a patient prior to, during, and/or after a bone marrow transplant or stem cell transplant.

In some embodiments, the additional therapeutic agent is fluocinolone acetonide (Retisert®), or rimexolone (AL-2178, Vexol, Alcon).

In some embodiments, the additional therapeutic agent is cyclosporine (Restasis®).

In some embodiments, the additional therapeutic agent is a corticosteroid. In some embodiments, the corticosteroid is triamcinolone, dexamethasone, fluocinolone, cortisone, prednisolone, or flumetholone.

In some embodiments, the additional therapeutic agent is selected from Dehydrex™ (Holles Labs), Civamide (Opko), sodium hyaluronate (Vismed, Lantibio/TRB Chemedia), cyclosporine (ST-603, Sirion Therapeutics), ARG101(T) (testosterone, Argentis), AGR1012(P) (Argentis), ecabet sodium (Senju-Ista), gefarnate (Santen), 15-(s)-hydroxyeicosatetraenoic acid (15(S)-HETE), cevilemine, doxycycline (ALTY-0501, Alacrity), minocycline, iDestrin™ (NP50301, Nascent Pharmaceuticals), cyclosporine A (Nova22007, Novagali), oxytetracycline (Duramycin, MOLI1901, Lantibio), CF101 (2S,3S,4R,5R)-3,4-dihydroxy-5-[6-[(3-iodophenyl)methylamino]purin-9-yl]-N-methyl-oxolane-2-carbamyl, Can-Fite Biopharma), voclosporin (LX212 or LX214, Lux Biosciences), ARG103 (Agentis), RX-10045 (synthetic resolvin analog, Resolvyx), DYN15 (Dyanmis Therapeutics), rivoglitazone (DE011, Daiichi Sanko), TB4 (RegeneRx), OPH-01 (Ophtalmis Monaco), PCS101 (Pericor Science), REV1-31 (Evolutec), Lacritin (Senju), rebamipide (Otsuka-Novartis), OT-551 (Othera), PAI-2 (University of Pennsylvania and Temple University), pilocarpine, tacrolimus, pimecrolimus (AMS981, Novartis), loteprednol etabonate, rituximab, diquafosol tetrasodium (INS365, Inspire), KLS-0611 (Kissei Pharmaceuticals), dehydroepiandrosterone, anakinra, efalizumab, mycophenolate sodium, etanercept (Embrel®), hydroxychloroquine, NGX267 (TorreyPines Therapeutics), or thalidomide.

In some embodiments, the additional therapeutic agent is an anti-angiogenic agent, cholinergic agonist, TRP-1 receptor modulator, a calcium channel blocker, a mucin secretagogue, MUC1 stimulant, a calcineurin inhibitor, a corticosteroid, a P2Y2 receptor agonist, a muscarinic receptor agonist, another JAK inhibitor, Bcr-Abl kinase inhibitor, Flt-3 kinase inhibitor, RAF kinase inhibitor, and FAK kinase inhibitor such as, for example, those described in WO 2006/056399, which is incorporated herein by reference in its entirety. In some embodiments, the additional therapeutic agent is a tetracycline derivative (e.g., minocycline or doxycline).

In some embodiments, the additional therapeutic agent(s) are demulcent eye drops (also known as "artificial tears"), which include, but are not limited to, compositions containing polyvinylalcohol, hydroxypropyl methylcellulose, glycerin, polyethylene glycol (e.g. PEG400), or carboxymethyl cellulose. Artificial tears can help in the treatment of dry eye by compensating for reduced moistening and lubricating capacity of the tear film. In some embodiments, the additional therapeutic agent is a mucolytic drug, such as N-acetyl-cysteine, which can interact with the mucoproteins and, therefore, to decrease the viscosity of the tear film.

In some embodiments, the additional therapeutic agent includes an antibiotic, antiviral, antifungal, anesthetic, anti-inflammatory agents including steroidal and non-steroidal anti-inflammatories, and anti-allergic agents. Examples of suitable medicaments include aminoglycosides such as amikacin, gentamycin, tobramycin, streptomycin, netilmycin, and kanamycin; fluoroquinolones such as ciprofloxacin, norfloxacin, ofloxacin, trovafloxacin, lomefloxacin, levofloxacin, and enoxacin; naphthyridine; sulfonamides; polymyxin; chloramphenicol; neomycin; paramomycin; colistimethate; bacitracin; vancomycin; tetracyclines; rifampin and its derivatives ("rifampins"); cycloserine; beta-lactams; cephalosporins; amphotericins; fluconazole; flucytosine; natamycin; miconazole; ketoconazole; corticosteroids; diclofenac; flurbiprofen; ketorolac; suprofen; cromolyn; lodoxamide; levocabastin; naphazoline; antazoline; pheniramine; or azalide antibiotic.

Pharmaceutical Formulations and Dosage Forms

When employed as pharmaceuticals, the compounds of the invention can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, the compound of the invention or a pharmaceutically acceptable salt thereof, in combination with one or more pharmaceutically acceptable carriers (excipients). In some embodiments, the composition is suitable for topical administration. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

The compounds of the invention may be milled using known milling procedures such as wet milling to obtain a particle size appropriate for tablet formation and for other formulation types. Finely divided (nanoparticulate) preparations of the compounds of the invention can be prepared by processes known in the art, e.g., see International App. No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 1,000 mg (1 g), more usually about 100 mg to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In some embodiments, the compositions of the invention contain from about 5 mg to about 50 mg of the active ingredient. One having ordinary skill in the art will appreciate that this embodies compounds or compositions containing about 5 mg to about 10 mg, about 10 mg to about 15 mg, about 15 mg to about 20 mg, about 20 mg to about 25 mg, about 25 mg to about 30 mg, about 30 mg to about 35 mg, about 35 mg to about 40 mg, about 40 mg to about 45 mg, or about 45 mg to about 50 mg of the active ingredient.

In some embodiments, the compositions of the invention contain from about 50 mg to about 500 mg of the active ingredient. One having ordinary skill in the art will appreciate that this embodies compounds or compositions containing about 50 mg to about 100 mg, about 100 mg to about 150 mg, about 150 mg to about 200 mg, about 200 mg to about 250 mg, about 250 mg to about 300 mg, about 350 mg to about 400 mg, or about 450 mg to about 500 mg of the active ingredient.

In some embodiments, the compositions of the invention contain from about 500 mg to about 1,000 mg of the active ingredient. One having ordinary skill in the art will appreciate that this embodies compounds or compositions containing about 500 mg to about 550 mg, about 550 mg to about 600 mg, about 600 mg to about 650 mg, about 650 mg to about 700 mg, about 700 mg to about 750 mg, about 750 mg to about 800 mg, about 800 mg to about 850 mg, about 850 mg to about 900 mg, about 900 mg to about 950 mg, or about 950 mg to about 1,000 mg of the active ingredient.

The active compound may be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, for example, liquid paraffin, polyoxyethylene alkyl ether, propylene glycol, white vaseline, and the like. Carrier compositions of creams can be based on water in combination with glycerol and one or more other components, e.g. glycerinemonostearate, PEG-glycerinemonostearate and cetylstearyl alcohol. Gels can be formulated using isopropyl alcohol and water, suitably in combination with other components such as, for example, glycerol, hydroxyethyl cellulose, and the like. In some embodiments, topical formulations contain at least about 0.1, at least about 0.25, at least about 0.5, at least about 1, at least about 2, or at least about 5 wt % of the compound of the invention. The topical formulations can be suitably packaged in tubes of, for example, 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of a compound of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 g/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compositions of the invention can further include one or more additional pharmaceutical agents such as a chemotherapeutic, steroid, anti-inflammatory compound, or immunosuppressant, examples of which are listed hereinabove.

In some embodiments, the compound, or pharmaceutically acceptable salt thereof, is administered as an ophthalmic composition. Accordingly, in some embodiments, the methods comprise administration of the compound, or pharmaceutically acceptable salt thereof, and an ophthalmically acceptable carrier. In some embodiments, the ophthalmic composition is a liquid composition, semi-solid composition, insert, film, microparticles or nanoparticles.

In some embodiments, the ophthalmic composition is a liquid composition. In some embodiments, the ophthalmic composition is a semi-solid composition. In some embodiments, the ophthalmic composition is an topical composition. The topical compositions include, but are not limited to liquid and semi-solid compositions. In some embodiments, the ophthalmic composition is a topical composition. In some embodiments, the topical composition comprises aqueous solution, an aqueous suspension, an ointment or a gel. In some embodiments, the ophthalmic composition is topically applied to the front of the eye, under the upper eyelid, on the lower eyelid and in the cul-de-sac. In some embodiments, the ophthalmic composition is sterilized. The sterilization can be accomplished by known techniques like sterilizing filtration of the solution or by heating of the solution in the ampoule ready for use. The ophthalmic compositions of the invention can further contain pharmaceutical excipients suitable for the preparation of ophthalmic formulations. Examples of such excipients are preserving agents, buffering agents, chelating agents, antioxidant agents and salts for regulating the osmotic pressure.

As used herein, the term "ophthalmically acceptable carrier" refers to any material that can contain and release the compound, or pharmaceutically acceptable salt thereof, and that is compatible with the eye. In some embodiments, the ophthalmically acceptable carrier is water or an aqueous solution or suspension, but also includes oils such as those used to make ointments and polymer matrices such as used in ocular inserts. In some embodiments, the composition may be an aqueous suspension comprising the compound, or pharmaceutically acceptable salt thereof. Liquid ophthalmic compositions, including both ointments and suspensions, may have a viscosity that is suited for the selected route of administration. In some embodiments, the ophthalmic composition has a viscosity in the range of from about 1,000 to about 30,000 centipoise.

In some embodiments, the ophthalmic compositions may further comprise one or more of surfactants, adjuvants, buffers, antioxidants, tonicity adjusters, preservatives (e.g., EDTA, BAK (benzalkonium chloride), sodium chlorite, sodium perborate, polyquaterium-1), thickeners or viscosity modifiers (e.g., carboxymethyl cellulose, hydroxymethyl cellulose, polyvinyl alcohol, polyethylene glycol, glycol 400, propylene glycol hydroxymethyl cellulose, hydroxpropyl-guar, hyaluronic acid, and hydroxypropyl cellulose) and the like. Additives in the formulation may include, but are not limited to, sodium chloride, sodium bicarbonate, sorbic acid, methyl paraben, propyl paraben, chlorhexidine, castor oil, and sodium perborate.

Aqueous ophthalmic compositions (solutions or suspensions) generally do not contain physiologically or ophthalmically harmful constituents. In some embodiments, purified or deionized water is used in the composition. The pH may be adjusted by adding any physiologically and ophthalmically acceptable pH adjusting acids, bases or buffers to within the range of about 5.0 to 8.5. Ophthalmically acceptable examples of acids include acetic, boric, citric, lactic, phosphoric, hydrochloric, and the like, and examples of bases include sodium hydroxide, sodium phosphate, sodium borate, sodium citrate, sodium acetate, sodium lactate, tromethamine, trishydroxymethylamino-methane, and the like. Salts and buffers include citrate/dextrose, sodium bicarbonate, ammonium chloride and mixtures of the aforementioned acids and bases.

In some embodiments, the methods involve forming or supplying a depot of the therapeutic agent in contact with the external surface of the eye. A depot refers to a source of therapeutic agent that is not rapidly removed by tears or other eye clearance mechanisms. This allows for continued, sustained high concentrations of therapeutic agent to be present in the fluid on the external surface of the eye by a single application. Without wishing to be bound by any theory, it is believed that absorption and penetration may be dependent on both the dissolved drug concentration and the contact duration of the external tissue with the drug containing fluid. As the drug is removed by clearance of the ocular fluid and/or absorption into the eye tissue, more drug is provided, e.g. dissolved, into the replenished ocular fluid from the depot. Accordingly, the use of a depot may more easily facilitate loading of the ocular tissue for more insoluble therapeutic agents. In some embodiments, the depot can remain for up to eight hours or more. In some embodiments, the ophthalmic depot forms includes, but is not limited to, aqueous polymeric suspensions, ointments, and solid inserts.

In some embodiments, the ophthalmic composition is an ointment or gel. In some embodiment, the ophthalmic composition is an oil-based delivery vehicle. In some embodiments, the composition comprises a petroleum or lanolin base to which is added the active ingredient, usually as 0.1 to 2%, and excipients. Common bases may include, but are not limited to, mineral oil, petrolatum and combinations thereof. In some embodiments, the ointment is applied as a ribbon onto the lower eyelid.

In some embodiment, the ophthalmic composition is an ophthalmic insert. In some embodiments, the ophthalmic insert is biologically inert, soft, bio-erodible, viscoelastic, stable to sterilization after exposure to therapeutic agents, resistant to infections from air borne bacteria, bio-erodible, biocompatible, and/or viscoelastic. In some embodiments, the insert comprises an ophthalmically acceptable matrix, e.g., a polymer matrix. The matrix is typically a polymer and the therapeutic agent is generally dispersed therein or bonded to the polymer matrix. In some embodiments, the therapeutic agent may be slowly released from the matrix through dissolution or hydrolysis of the covalent bond. In some embodiments, the polymer is bioerodible (soluble) and the dissolution rate thereof can control the release rate of the therapeutic agent dispersed therein. In another form, the polymer matrix is a biodegradable polymer that breaks down such as by hydrolysis to thereby release the therapeutic agent bonded thereto or dispersed therein. In further embodiments, the matrix and therapeutic agent can be surrounded with an additional polymeric coating to further control release. In some embodiments, the insert comprises a biodegradable polymer such as polycaprolactone (PCL), an ethylene/vinyl acetate copolymer (EVA), polyalkyl cyanoacrylate, polyurethane, a nylon, or poly (dl-lactide-co-glycolide) (PLGA), or a copolymer of any of these. In some embodiments, the therapeutic agent is dispersed into the matrix material or dispersed amongst the monomer composition used to make the matrix material prior to polymerization. In some embodiments, the amount of therapeutic agent is from about 0.1 to about 50%, or from about 2 to about 20%. In further embodiments, the biodegradable or bioerodible polymer matrix is used so that the spent insert does not have to be removed. As the biodegradable or bioerodible polymer is degraded or dissolved, the therapeutic agent is released.

In further embodiments, the ophthalmic insert comprises a polymer, including, but are not limited to, those described in Wagh, et al., "Polymers used in ocular dosage form and drug delivery systems", *Asian J. Pharm.*, pages 12-17 (January 2008), which is incorporated herein by reference in its entirety. In some embodiments, the insert comprises a polymer selected from polyvinylpyrrolidone (PVP), an acrylate or methacrylate polymer or copolymer (e.g., Eudragit® family of polymers from Rohm or Degussa), hydroxymethyl cellulose, polyacrylic acid, poly(amidoamine) dendrimers, poly (dimethyl siloxane), polyethylene oxide, poly(lactide-co-glycolide), poly(2-hydroxyethylmethacrylate), poly(vinyl alcohol), or poly(propylene fumarate). In some embodiments, the insert comprises Gelfoam® R. In some embodiments, the insert is a polyacrylic acid of 450 kDa-cysteine conjugate.

In some embodiments, the ophthalmic composition is a ophthalmic film. Polymers suitable for such films include, but are not limited to, those described in Wagh, et al. (ibid), In some embodiments, the film is a soft-contact lens, such as ones made from copolymers of N,N-diethylacrylamide and methacrylic acid crosslinked with ethyleneglycol dimethacrylate.

In some embodiments, the ophthalmic composition comprises microspheres or nanoparticles. In some embodiment, the microspheres comprise gelatin. In some embodiments, the microspheres are injected to the posterior segment of the eye, in the chroroidal space, in the sclera, intravitreally or sub-retinally. In some embodiments, the microspheres or nanoparticles comprises a polymer including, but not limited to, those described in Wagh, et al. (ibid), which is incorporated herein by reference in its entirety. In some embodiments, the polymer is chitosan, a polycarboxylic acid such as polyacrylic acid, albumin particles, hyaluronic acid esters, polyitaconic acid, poly(butyl)cyanoacrylate, polycaprolactone, poly(isobutyl)caprolactone, poly(lactic acid-co-glycolic acid), or poly(lactic acid). In some embodiments, the microspheres or nanoparticles comprise solid lipid particles.

In some embodiments, the ophthalmic composition comprises an ion-exchange resin. In some embodiments, the ion-exchange resin is an inorganic zeolite or synthetic organic resin. In some embodiments, the ion-exchange resin includes, but is not limited to, those described in Wagh, et al. (ibid), which is incorporated herein by reference in its entirety. In some embodiments, the ion-exchange resin is a partially neutralized polyacrylic acid.

In some embodiments, the ophthalmic composition is an aqueous polymeric suspension. In some embodiments, the therapeutic agent or a polymeric suspending agent is suspended in an aqueous medium. In some embodiments, the aqueous polymeric suspensions may be formulated so that they retain the same or substantially the same viscosity in the eye that they had prior to administration to the eye. In some embodiments, they may be formulated so that there is increased gelation upon contact with tear fluid.

Labeled Compounds and Assay Methods

Another aspect of the present invention relates to labeled compounds of the invention (radio-labeled, fluorescent-labeled, etc.) that would be useful not only in imaging techniques but also in assays, both in vitro and in vivo, for localizing and quantitating JAK in tissue samples, including human, and for identifying JAK ligands by inhibition binding of a labeled compound. Accordingly, the present invention includes JAK assays that contain such labeled compounds.

The present invention further includes isotopically-labeled compounds of the invention. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. The radionuclide that is incorporated in the instant radio-labeled compounds will depend on the specific application of that radio-labeled compound. For example, for in vitro JAK labeling and competition assays, compounds that incorporate $^3$H, $^{14}$C, $^{82}$Br, $^{125}$I, $^{131}$I, $^{35}$S or will generally be most useful. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful.

It is to be understood that a "radio-labeled" or "labeled compound" is a compound that has incorporated at least one radionuclide. In some embodiments the radionuclide is selected from the group consisting of $^3$H, $^{14}$C, $^{125}$I, $^{35}$S and $^{82}$Br. In some embodiments, the compound incorporates 1, 2, or 3 deuterium atoms.

The present invention can further include synthetic methods for incorporating radio-isotopes into compounds of the invention. Synthetic methods for incorporating radio-isotopes into organic compounds are well known in the art, and an ordinary skill in the art will readily recognize the methods applicable for the compounds of invention.

A labeled compound of the invention can be used in a screening assay to identify/evaluate compounds. For example, a newly synthesized or identified compound (i.e., test compound) which is labeled can be evaluated for its ability to bind a JAK by monitoring its concentration variation when contacting with the JAK, through tracking of the labeling. For example, a test compound (labeled) can be evaluated for its ability to reduce binding of another compound which is known to bind to a JAK (i.e., standard compound). Accordingly, the ability of a test compound to compete with the standard compound for binding to the JAK directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

Kits

The present invention also includes pharmaceutical kits useful, for example, in the treatment or prevention of JAK-associated diseases or disorders, such as cancer, which include one or more containers containing a pharmaceutical composition comprising a therapeutically effective amount of a compound of the invention. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

EXAMPLES

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples have been found to be JAK inhibitors according to at least one assay described herein. At points throughout the Examples, the stereochemistry of the cyclobutyl ring has been indicated, as currently understood.

Intermediate Example A1

{3-oxo-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile

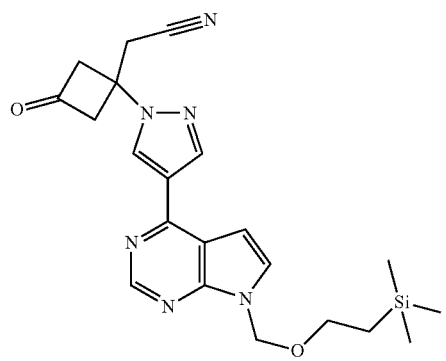 [SMILES: C[Si](C)(C)CCOCn1ccc2c(-c3cnn(C4(CC#N)CC(=O)C4)c3)ncnc21]

Step 1. [2-bromo-1-(bromomethyl)ethoxy](tert-butyl)diphenylsilane

To a solution of 1,3-dibromo-2-propanol (20.00 g, 91.79 mmol) in methylene chloride (DCM) (100 mL) cooled to 0° C. was added 1H-imidazole (6.56 g, 96.4 mmol) followed by tert-butylchlorodiphenylsilane (25.1 mL, 96.4 mmol) and 4-dimethylaminopyridine (1.12 g, 9.18 mmol). The reaction was stirred with warming to room temperature overnight. The reaction mixture was diluted with diethyl ether, washed with water, and the aqueous layer was again extracted once with ether. The combined organic extracts were washed with water, followed by brine, dried over sodium sulfate, decanted and concentrated. Flash chromatography (eluting with a gradient from 0-15% ethyl acetate/hexanes) afforded desired product (42 g, 100%). $^1$H NMR (300 MHz, CDCl$_3$): δ 7.72-7.66 (m, 4H), 7.51-7.37 (m, 6H), 4.00-3.91 (m, 1H), 3.49-3.45 (m, 4H), 1.09 (s, 9H).

Step 2. tert-butyl{[3-(methylsulfinyl)-3-(methylthio)cyclobutyl]oxy}diphenylsilane To a solution of (methylsulfinyl)(methylthio)methane (27.70 g, 223.0 mmol) in tetrahydrofuran (90 mL) at −10° C. was added dropwise, a solution of 2.5 M n-butyllithium in hexane (89.2 mL, 223 mmol). The mixture was stirred at −10° C. for 2 hours. It was then cooled to −78° C. and transferred by cannula in a slow manner to a solution of [2-bromo-1-(bromomethyl)ethoxy](tert-butyl)diphenylsilane (42 g, 93 mmol, from Step 1) in tetrahydrofuran (70 mL, 900 mmol) held at −78° C. The mixture was stirred with warming to room temperature over 2 nights. Water was added, and then the product was extracted with three portions of DCM. The combined extracts were dried over sodium sulfate, filtered and concentrated. Flash chromatography (eluting with a gradient from 0-100% ethyl acetate/hexanes) afforded desired product as a mixture of diastereomers (34.1 g, 88%). $^1$H NMR (300 MHz, CDCl$_3$), diastereomers: δ 7.74-7.58 (m, 8H), 7.48-7.31 (m, 10H), 4.52 (tt, 1H), 4.42 (tt, 1H), 3.05-1.99 (m, 8H), 2.47 (s, 3H), 2.42 (s, 3H), 2.13 (s, 3H), 2.00 (s, 3H), 1.05 (s, 9H), 1.02 (s, 9H).

Step 3. 3-{[tert-butyl(diphenyl)silyl]oxy}cyclobutanone

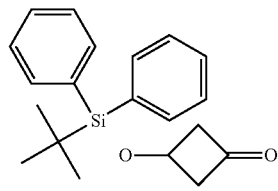

A solution of tert-butyl {[3-(methylsulfinyl)-3-(methylthio)cyclobutyl]oxy}diphenylsilane (17.05 g, 40.7 mmol, from Step 2) in ether (350 mL) cooled to 0° C. was treated with a solution of 6 M perchloric acid in water (10 mL) that was pre-diluted with water (7 mL). The bath was removed and stirred overnight. The mixture was poured into pH 7 buffer, and the product was extracted with diethyl ether. The combined extracts were dried over sodium sulfate, decanted and concentrated. The reaction was performed again on the same scale and the two batches were combined for purification. Flash chromatography, eluting with a gradient from 0-5% ethyl acetate/hexanes afforded desired product (15.7 g, 59%). $^1$H NMR (300 MHz, CDCl$_3$): δ 7.75-7.62 (m, 4H), 7.49-7.33 (m, 6H), 4.59 (tt, 1H), 3.22-3.03 (m, 4H), 1.07 (s, 9H).

Step 4. (3-{[tert-butyl(diphenyl)silyl]oxy}cyclobutylidene)acetonitrile

To a solution of 1.0 M potassium tert-butoxide in tetrahydrofuran (46.0 mL, 46.0 mmol) at 0° C. was added diethyl cyanomethylphosphonate (7.8 mL, 48 mmol). The bath was removed and the reaction mixture was allowed to warm to room temperature over 1 hour. The reaction was re-cooled to 0° C., and a solution of 3-{[tert-butyl(diphenyl)silyl]oxy}cyclobutanone (15.7 g, 48.4 mmol, from Step 3) in tetrahydrofuran (80 mL) was added. During the course of the addition, additional tetrahydrofuran (50 mL) was added into the receiving flask to facilitate stirring. Upon complete addition of the ketone, the bath was removed and the reaction allowed to reach room temperature and stirred overnight. The reaction mixture was partitioned between water and ethyl acetate and the aqueous was extracted with ethyl acetate a total of three times. The combined extracts were washed with brine, dried over sodium sulfate, decanted and concentrated. Flash chromatography, eluting with a gradient of 0-10% ethyl acetate in hexanes afforded product (16.1 g, 96%). $^1$H NMR (300 MHz, CDCl$_3$): δ 7.74-7.58 (m, 4H), 7.49-7.34 (m, 6H), 5.13 (dddd, 1H), 4.34 (tt, 1H), 3.16-2.90 (m, 4H), 1.05 (s, 9H).

Step 5. cis and trans {3-{[tert-butyl(diphenyl)silyl]oxy}-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile To a solution of (3-{[tert-butyl(diphenyl)silyl]oxy}cyclobutylidene)acetonitrile (16.1 g, 35.2 mmol, from Step 4) and 4-(1H-pyrazol-4-yl)-7-{[2-(trimethylsilyl)ethoxy]methyl}-7H-pyrrolo[2,3-d]pyrimidine (11.1 g, 35.2 mmol) (prepared as in WO2007/070514 Example 65, Step 2) in acetonitrile (100 mL) was added 1,8-diazabicyclo[5.4.0]undec-7-ene (5.3 mL, 35 mmol). The reaction was stirred over three nights. The acetonitrile was removed in vacuo. Flash chromatography, eluting with 25% ethyl acetate in hexanes until product began to elute, then 40 to 66% ethyl acetate in hexanes was used to elute desired product as a mixture of diastereomers (17.4 g, 75%). $^1$H NMR (300 MHz, CDCl$_3$), diastereomers (M=major, min=minor): δ 8.86 (s, 1H M), 8.81 (s, 1H min), 8.37 (s 1H, M), 8.30 (s, 1H M), 8.26 (s, 1H min), 8.25 (s, 1H min), 7.67-7.35 (m, 11H M & 11H min), 6.81 (d, 1H M), 6.73 (d, 1H min), 5.68 (s, 2H M), 5.66 (s, 2H min), 4.45 (tt, 1H min), 4.33 (tt, 1H M), 3.59-3.50 (m, 2H M & 2H min), 3.23 (s, 2H min), 3.11-3.00 (m, 2H min), 2.90 (s, 2H M), 2.88-2.80 (m, 4H M), 2.64-2.54 (m, 2H min), 1.08 (s, 9H min), 1.03 (s, 9H M), 0.97-0.88 (m, 2H M & 2H min), −0.06 (s, 9H M), −0.07 (s, 9H min); LCMS (M+H)$^+$: 663.3.

Step 6. cis and trans {3-hydroxy-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile To {3-{[tert-butyl(diphenyl)silyl]oxy}-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (8.7 g, 13.1 mmol, as a mixture of diastereomers from Step 5) in ethanol (355 mL) was added 5.0 M sodium hydroxide in water (90 mL, 450 mmol). The reaction was stirred for 5 hours. Additional water was added and then the ethanol was removed using rotary evaporation. The mixture was then partitioned between ethyl acetate and water. The aqueous portion was extracted with ethyl acetate a total of three times. The combined organic extracts were washed with water, then brine, dried over sodium sulfate, decanted and concentrated. The residue was azeotroped with benzene. This reaction was performed again on the same scale and the crude product of both runs was combined for purification. Flash chromatography, eluting with a gradient from 0-10% MeOH in DCM afforded product as an off-white foam (9.3 g, 83%). $^1$H NMR (300 MHz, CDCl$_3$), diastereomers (M=major, min=minor): δ 8.84 (s, 1H M & 1H min), 8.41 (s, 1H min), 8.39 (s, 1H M), 8.31 (s, 1H min), 8.30 (s, 1H M), 7.40 (d, 1H M & 1H min), 6.80 (d, 1H M & 1H min), 5.67 (s, 2H M & 2H min), 4.60-4.44 (m, 1H M & 1H min), 3.59-3.46 (m, 2H M & 2H min), 3.25 (s, 2H min), 3.25-3.16 (m, 2H min), 3.08 (s, 2H M), 3.10-3.00 (m, 2H M), 2.84-2.73 (m, 2H M), 2.64-2.51 (m, 2H min), 0.97-0.87 (m, 2H M & 2H min), −0.06 (s, 9H M & 9H min); LCMS (M+H)$^+$: 425.0.

Step 7. {3-oxo-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile To a solution of {3-hydroxy-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (9.3 g, 22 mmol, as a mixture of diastereomers from Step 6) in methylene chloride (300 mL) at 0° C. was added Dess-Martin periodinane (10.0 g, 24 mmol). After a reaction time of 2 hours, the mixture was poured into 1N NaOH and extracted with three portions of DCM. The combined extracts were washed with further 1N NaOH, dried over sodium sulfate, decanted and the solvent removed in vacuo. Flash chromatography, eluting with a gradient from 0-10% MeOH in DCM afforded product as a yellow foam. Theoretical yield assumed for use in Step 8. $^1$H NMR (300 MHz, CDCl$_3$): δ 8.85 (s, 1H), 8.50 (s, 1H), 8.35 (s, 1H), 7.42 (d, 1H), 6.80 (d, 1H), 5.68 (s, 2H), 4.11-4.00 (m, 2H), 3.74-3.61 (m, 2H), 3.59-3.50 (m, 2H), 3.31 (s, 2H), 0.96-0.88 (m, 2H), −0.06 (s, 9H); LCMS (M+H)$^+$: 423.0.

Intermediate Example A2

{cis-3-(4-{[4-(hydroxymethyl)-6-(trifluoromethyl)pyridin-2-yl]oxy}piperidin-1-yl)-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile and {trans-3-(4-{[4-(hydroxymethyl)-6-(trifluoromethyl)pyridin-2-yl]oxy}piperidin-1-yl)-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile

Step A. [2-Chloro-6-(trifluoromethyl)pyridin-4-yl]methanol

Sodium tetrahydroborate (74 mg, 2.0 mmol) was added to a solution of ethyl 2-chloro-6-(trifluoromethyl)isonicotinate (0.50 g, 2.0 mmol, Anichem) in ethanol (17 mL) at 0° C. The mixture was stirred at 0° C. for one hour, then was allowed to warm to room temperature and stir for 2 hours. The mixture was recooled in an ice bath and was quenched by the dropwise addition of 4.0 mL 1N HCl. The pH was then adjusted to 7 by the addition of saturated sodium bicarbonate solution. The reaction was further diluted with water, and then was extracted with EtOAc. The extract was washed with brine, dried over sodium sulfate, filtered and concentrated. Flash chromatography on silica gel, eluting with a gradient from 0-40% EtOAc in Hexanes afforded product as an oil (0.33 g, 79%). $^1$H NMR (300 MHz, CDCl$_3$) δ 7.61 (s, 1H), 7.56 (s, 1H), 4.84 (d, J=5.2 Hz, 2H), 2.20 (t, J=5.6 Hz, 1H); LCMS (M+H)$^+$: 212.1.

Step B. 4-({[tert-Butyl(diphenyl)silyl]oxy}methyl)-2-chloro-6-(trifluoromethyl)pyridine To a solution of [2-chloro-6-(trifluoromethyl)pyridin-4-yl]methanol (142 mg, 0.671 mmol) in methylene chloride (1.0 mL) at 0° C. was added 1H-imidazole (55 mg, 0.80 mmol) followed by tert-butylchlorodiphenylsilane (190 µL, 0.74 mmol) and 4-dimethylaminopyridine (4 mg, 0.03 mmol). The reaction was stirred with warming to room temperature for 64 hours. The reaction mixture was diluted with diethyl ether and was washed with water followed by brine, dried over sodium sulfate, decanted and concentrated. Flash chromatography on silica gel, eluting with a gradient from 0-4% EtOAc in hexanes afforded product as a white solid (0.20 g, 66%). $^1$H NMR (300 MHz, CDCl$_3$) δ 7.70-7.58 (m, 4H), 7.55-7.34 (m, 8H), 4.77 (s, 2H), 1.12 (s, 9H); $^{19}$F NMR (282 MHz, CDCl$_3$) δ −68.49 (s); LCMS (M+H)$^+$: 450.1.

Step C. tert-Butyl 4-{[4-({[tert-butyl(diphenyl)silyl]oxy}methyl)-6-(trifluoromethyl)pyridin-2-yl]oxy}piperidine-1-carboxylate To sodium hydride (36 mg, 0.89 mmol, 60% in mineral oil) in tetrahydrofuran (1.0 mL) was added tert-butyl 4-hydroxypiperidine-1-carboxylate (0.18 g, 0.89 mmol, Aldrich). After stirring for 45 minutes, 4-({[tert-butyl(diphenyl)silyl]oxy}methyl)-2-chloro-6-(trifluoromethyl)pyridine (0.20 g, 0.44 mmol, from Step B) in tetrahydrofuran (0.60 mL) was added and the mixture was stirred overnight. The reaction was quenched and diluted with water and extracted with ether. The extract was washed with water, brine, dried over sodium sulfate, filtered and concentrated. Flash chromatography on silica gel, eluting with a gradient from 0-5% EtOAc in hexanes afforded product as an oil (0.19 g, 52%). LCMS (M-tBu+H)$^+$: 559.2

Step D. 4-({[tert-Butyl(diphenyl)silyl]oxy}methyl)-2-(piperidin-4-yloxy)-6-(trifluoromethyl)pyridine To a solution of tert-butyl 4-{[4-({[tert-butyl(diphenyl)silyl]oxy}methyl)-6-(trifluoromethyl)pyridin-2-yl]oxy}piperidine-1-carboxylate (0.19 g, 0.23 mmol, from Step C) in 1,4-dioxane (2.0 mL) was added 4.0 M hydrogen chloride in dioxane (0.50 mL, 2.0 mmol). The reaction mixture was stirred for one hour. Additional 4.0 M hydrogen chloride in dioxane (0.50 mL, 2.0 mmol) was added and stirring was continued for two hours. The mixture was diluted with water, saturated sodium bicarbonate was used to adjust the pH to between 7 and 8, and then the product was extracted with two portions of DCM. The combined extracts were washed with brine, dried over sodium sulfate, filtered and concentrated. Flash chromatography on silica gel, eluting with a gradient from 0-15% MeOH in DCM afforded product as an oil (62 mg, 52%). $^1$H NMR (400 MHz, CDCl$_3$) δ 7.69-7.62 (m, 4H), 7.48-7.34 (m, 6H), 7.14-7.11 (m, 1H), 6.91 (s, 1H), 5.17 (tt, J=8.7, 4.0 Hz, 1H), 4.71 (s, 2H), 3.13 (dt, J=12.7, 4.5 Hz, 2H), 2.78 (ddd, J=12.7, 9.7, 3.0 Hz, 2H), 2.07 (dq, J=12.2, 4.1 Hz, 2H), 1.67 (dtd, J=13.0, 9.4, 3.9 Hz, 2H), 1.11 (s, 9H); LCMS (M+H)$^+$: 515.2.

Step E. {3-(4-{[4-({[tert-Butyl(diphenyl)silyl]oxy}methyl)-6-(trifluoromethyl)pyridin-2-yl]oxy}piperidin-1-yl)-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (a mixture of cis- and trans-isomers)

Sodium cyanoborohydride (8.8 mg, 0.14 mmol) and zinc dichloride (9.5 mg, 0.070 mmol) were combined in methanol (0.56 mL, 14 mmol) and stirred for 2 hours to generate the reducing solution referenced in JOC 1985, 50, 1927-1932. Subsequently, {3-oxo-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (66 mg, 0.14 mmol, from Step 7 of Example A1) and 4-({[tert-butyl(diphenyl)silyl]oxy}methyl)-2-(piperidin-4-yloxy)-6-(trifluoromethyl)pyridine (60. mg, 0.12 mmol, from Step D) were combined in methanol (2.0 mL) to dissolve, then the above generated reducing mixture was added. The reaction was stirred overnight. An additional 0.3 eq of the prestirred NaCNBH$_3$/ZnCl$_2$ mixture was added. After stirring for 3 hours, the mixture was diluted with EtOAc and was washed with saturated sodium bicarbonate solution, followed by brine, dried over sodium sulfate, filtered and concentrated. Flash chromatography on silica gel, eluting with a gradient from 0-80% EtOAc in hexanes afforded product as a mixture of cis- and trans-isomers (43 mg, 40%). LCMS (M+2H)$^{2+}$: 461.4.

Step F. {cis-3-(4-{[4-(hydroxymethyl)-6-(trifluoromethyl)pyridin-2-yl]oxy}piperidin-1-yl)-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile and {trans-3-(4-{[4-(hydroxymethyl)-6-(trifluoromethyl)pyridin-2-yl]oxy}piperidin-1-yl)-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (each diastereomer isolated)

To {3-(4-{[4-({[tert-butyl(diphenyl)silyl]oxy}methyl)-6-(trifluoromethyl)pyridin-2-yl]oxy}piperidin-1-yl)-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.35 g, 0.38 mmol, a mixture of cis- and trans-isomers from Step E) in ethanol (10. mL, 180 mmol) was added 5.0 M sodium hydroxide in water (1.5 mL, 7.6 mmol). After stirring for 3 hours, the reaction mixture was partitioned between DCM and brine. The aqueous layer was extracted with an additional portion of DCM. The combined extracts were dried over sodium sulfate, filtered and concentrated. Flash chromatography on silica gel, eluting with a gradient from 0-10% MeOH in DCM afforded a mixture of isomers (0.22 g, 76%). The isomers were separated by chiral HPLC (Phenomenex Lux-Cellulose 2 column, eluting with 45% EtOH in hexanes at 18 mL/min, ~44 mg/injection). Peak 1 retention time: 6.0 min, Peak 2 retention time: 10.2 min. Peak 1, trans isomer, 83 mg: $^1$H NMR (500 MHz, CDCl$_3$) δ 8.84 (s, 1H), 8.47 (s, 1H), 8.33 (s, 1H), 7.40 (d, J=3.7 Hz, 1H), 7.21 (s, 1H), 6.89 (s, 1H), 6.81 (d, J=3.7 Hz, 1H), 5.68 (s, 2H), 5.15 (br m, 1H), 4.73 (s, 2H), 3.61-3.45 (m, 2H), 3.22 (s, 2H), 3.08-2.97 (m, 2H), 2.97-2.84 (m, 1H), 2.67 (br m, 2H), 2.48 (br m, 2H), 2.25 (br m, 2H), 2.07 (br m, 2H), 1.84 (br m, 2H), 0.98-0.84 (m, 2H), −0.05 (s, 9H); LCMS (M+H)$^+$: 683.4. Peak 2, cis isomer, 78 mg: $^1$H NMR (500 MHz, CDCl$_3$) δ 8.83 (s, 1H), 8.39 (s, 1H), 8.29 (s, 1H), 7.39 (d, J=3.7 Hz, 1H), 7.21 (s, 1H), 6.90 (s, 1H), 6.80 (d, J=3.7 Hz, 1H), 5.67 (s, 2H), 5.20-5.06 (m, 1H), 4.73 (s, 2H), 3.64-3.46 (m, 2H), 3.14 (s, 2H), 2.90 (tt, J=7.4, 7.8 Hz, 1H), 2.84-2.76 (m, 2H), 2.75-2.52 (m, 4H), 2.28 (br m, 2H), 2.04 (br m, 2H), 1.81 (br m, 2H), 1.69 (s, 2H), 1.01-0.81 (m, 2H), −0.06 (s, 9H); LCMS (M+H)$^+$: 683.3.

Intermediate Example A3

{3-oxo-1-[4-(1-{[2-(trimethylsilyl)ethoxy]methyl}-1H-pyrrolo[2,3-b]pyridin-4-yl)-1H-pyrazol-1-yl]cyclobutyl}acetonitrile

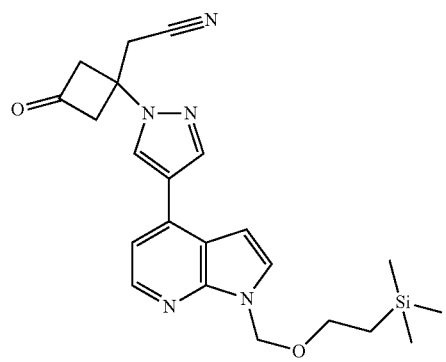 [SMILES: C[Si](C)(C)CCOCn1ccc2c(-c3cnn(C4(CC#N)CC(=O)C4)c3)ccnc21]

Step A. {3-{[tert-Butyl(diphenyl)silyl]oxy}-1-[4-(1-{[2-(trimethylsilyl)ethoxy]methyl}-1H-pyrrolo[2,3-b]pyridin-4-yl)-1H-pyrazol-1-yl]cyclobutyl}acetonitrile (a mixture of diastereomers)

To a solution of (3-{[tert-butyl(diphenyl)silyl]oxy}cyclobutylidene)acetonitrile (4.0 g, 8.7 mmol, from Step 4 of Intermediate Example A1) and 4-(1H-pyrazol-4-yl)-1-{[2-(trimethylsilyl)ethoxy]methyl}-1H-pyrrolo[2,3-b]pyridine (1.50 g, 4.77 mmol, US 20090181959) in acetonitrile (10 mL, 200 mmol) was added 1,8-diazabicyclo[5.4.0]undec-7-ene (0.68 mL, 4.6 mmol). The reaction was stirred overnight. A further portion of 1,8-diazabicyclo[5.4.0]undec-7-ene (0.7 mL, 5 mmol) was added and the reaction was allowed to continue for an additional 72 hours. Acetonitrile was removed in vacuo. Flash chromatography on silica gel, eluting with 0%-30% EtOAc/Hexanes, was used to purify product, which was obtained as a mixture of diastereomers (2 g, 60%). $^1$H NMR (300 MHz, CDCl$_3$) δ 8.33 (d, J=5.0 Hz, 1H major), 8.29 (d, J=5.0 Hz, 1H minor), 8.06 (s, 1H major), 8.03 (s, 1H major), 8.00 (s, 1H minor), 7.93 (s, 1H minor), 7.70-7.31 (m, 10H major and 10H minor), 7.19 (d, J=5.0 Hz, 1H major), 7.11 (d, J=5.0 Hz, 1H minor), 6.74 (d, J=3.6 Hz, 1H major), 6.63 (d, J=3.7 Hz, 1H minor), 5.71 (s, 2H major), 5.69 (s, 2H minor), 4.49-4.39 (m, 1H minor), 4.33 (tt, J=7.0, 7.0 Hz, 1H major), 3.67-3.45 (m, 2H major and 2H minor), 3.22 (s, 2H minor), 3.11-2.95 (m, 2H minor), 2.92-2.77 (m, 6H major), 2.65-2.50 (m, 2H minor), 1.08 (s, 9H minor), 1.03 (s, 9H major), 0.98-0.80 (m, 2H major and 2H minor), −0.06 (s, 9H major), −0.08 (s, 9H minor); LCMS (M+H)$^+$: 662.1.

Step B. {3-hydroxy-1-[4-(1-{[2-(trimethylsilyl)ethoxy]methyl}-1H-pyrrolo[2,3-b]pyridin-4-yl)-1H-pyrazol-1-yl]cyclobutyl}acetonitrile (a mixture of diastereomers)

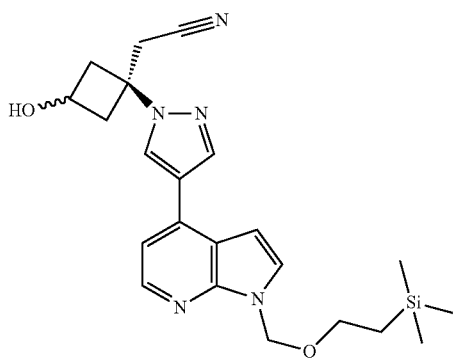

To {3-{[tert-butyl(diphenyl)silyl]oxy}-1-[4-(1-{[2-(trimethylsilyl)ethoxy]methyl}-1H-pyrrolo[2,3-b]pyridin-4-yl)-1H-pyrazol-1-yl]cyclobutyl}acetonitrile (2.0 g, 3.0 mmol, a mixture of diastereomers from Step A) ethanol (82 mL) was added 5.0 M sodium hydroxide in water (9 mL, 50 mmol). The reaction was stirred overnight. The reaction mixture was diluted with water and ethanol was removed in vacuo. The aqueous mixture was extracted with ethyl acetate (3×). The combined organic extracts were washed with water, then brine, dried over sodium sulfate, decanted and concentrated. The product, as a mixture of diastereomers, was used without further purification in Step C. LCMS (M+H)$^+$: 424.2.

Step C. {3-oxo-1-[4-(1-{[2-(trimethylsilyl)ethoxy]methyl}-1H-pyrrolo[2,3-b]pyridin-4-yl)-1H-pyrazol-1-yl]cyclobutyl}acetonitrile To a solution of {3-hydroxy-1-[4-(1-{[2-(trimethylsilyl)ethoxy]methyl}-1H-pyrrolo[2,3-b]pyridin-4-yl)-1H-pyrazol-1-yl]cyclobutyl}acetonitrile (1.3 g, 3.1 mmol, a mixture of diastereomers from Step B) in methylene chloride (40 mL) was added Dess-Martin periodinane (1.63 g, 3.84 mmol). After stirring for 1 hour and 15 minutes, the reaction mixture was poured into 1N NaOH and extracted with three portions of DCM. The combined extracts were washed with 1N NaOH, then brine, dried over sodium sulfate, decanted and solvent was removed in vacuo. Flash chromatography on silica gel, eluting with an initial gradient from 0-30% EtOAc/Hexanes, then a rapid gradient up to 100% EtOAc afforded product (1.1 g, 85%). $^1$H NMR (300 MHz, CDCl$_3$) δ 8.34 (d, J=5.0 Hz, 1H), 8.14 (s, 1H), 8.11 (s, 1H), 7.42 (d, J=3.7 Hz, 1H), 7.18 (d, J=5.0 Hz, 1H), 6.71 (d, J=3.7 Hz, 1H), 5.71 (s, 2H), 4.10-3.97 (m, 2H), 3.74-3.61 (m, 2H), 3.61-3.47 (m, 2H), 3.28 (s, 2H), 0.98-0.86 (m, 2H), −0.07 (s, 9H); LCMS (M+H)$^+$: 422.2.

Example 1

{trans-3-(4-{[4-({[(1S)-2-hydroxy-1-methylethyl]amino}methyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile

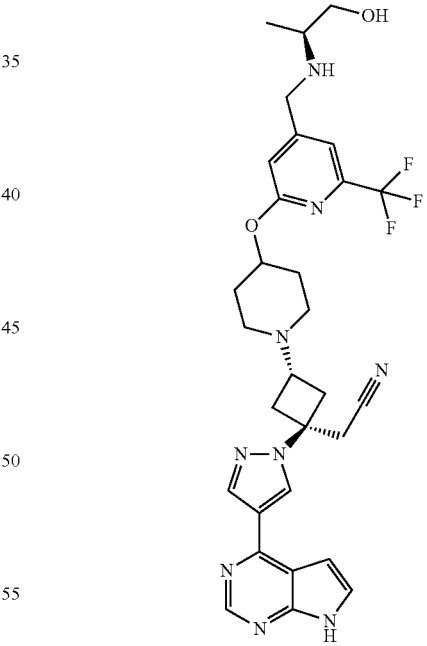

N,N-Diisopropylethylamine (9.4 μL, 0.054 mmol) and methanesulphonic anhydride (7.9 mg, 0.045 mmol) were added to a solution of {trans-3-(4-{[4-(hydroxymethyl)-6-(trifluoromethyl)pyridin-2-yl]oxy}piperidin-1-yl)-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (10.0 mg, 0.018 mmol, Peak 1 from Intermediate Example A2, Step F) in methylene chloride (0.30 mL), and the mesylate formation was stirred for 30 minutes. The solvent was removed in vacuo and the residue was redissolved in a mixture of tetrahydrofuran (0.30 mL) and methanol (0.10 mL) and (2S)-2-aminopropan-1-ol (20. µL, 0.27 mmol, Acros) was added. The reaction mixture was stirred at 40° C. overnight. Solvent was removed in vacuo and the crude product was deprotected by stirring with 1:1 TFA:DCM for one hour, then concentrated and stirred with ethylenediamine (0.10 mL) in methanol (1.0 mL) until the deprotection was complete as determined by LCMS. The product was purified using preparative HPLC-MS (C18 eluting with a gradient of MeCN/H$_2$O containing 0.15% NH$_4$OH). The eluent was frozen and lyophilized to afford the product as the free base (6.0 mg, 54%). $^1$H NMR (400 MHz, CD$_3$OD) δ 8.74 (s, 1H), 8.67 (s, 1H), 8.40 (s, 1H), 7.51 (d, J=3.6 Hz, 1H), 7.37 (s, 1H), 7.00-6.97 (m, 2H), 5.23-5.00 (m, 1H), 3.90 (d, J=14.8 Hz, 1H), 3.81 (d, J=14.8 Hz, 1H), 3.50 (dd, J=10.9, 4.9 Hz, 1H), 3.41 (dd, J=10.9, 6.9 Hz, 1H), 3.31 (s, 2H), 3.16-3.05 (m, 2H), 2.95 (p, J=7.5 Hz, 1H), 2.83-2.63 (m, 3H), 2.56-2.42 (m, 2H), 2.39-2.23 (m, 2H), 2.19-2.04 (m, 2H), 1.93-1.75 (m, 2H), 1.05 (d, J=6.4 Hz, 3H). $^{19}$F NMR (376 MHz, CD$_3$OD) δ −70.30 (s). LCMS (M+H)$^+$: 610.3

Example 2

{trans-3-(4-{[4-({[(1R)-2-hydroxy-1-methylethyl]amino}methyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile

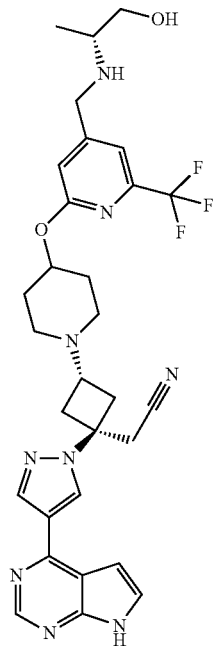

Prepared by the method of Example 1 using (R)-(−)-2-Amino-1-propanol (21 µL, 0.27 mmol, Aldrich) and heating to 60° C. for 30 additional minutes during the displacement step (3.4 mg, 31%). $^1$H NMR (400 MHz, CD$_3$OD) δ 8.74 (s, 1H), 8.67 (s, 1H), 8.40 (s, 1H), 7.51 (d, J=3.6 Hz, 1H), 7.37 (s, 1H), 7.06-6.82 (m, 2H), 5.23-5.06 (m, 1H), 3.90 (d, J=14.8 Hz, 1H), 3.82 (d, J=14.8 Hz, 1H), 3.50 (dd, J=10.9, 4.9 Hz, 1H), 3.41 (dd, J=10.9, 6.8 Hz, 1H), 3.31 (s, 2H), 3.19-3.03 (m, 2H), 2.96 (p, J=7.7 Hz, 1H), 2.80-2.62 (m, 3H), 2.55-2.43 (m, 2H), 2.39-2.22 (m, 2H), 2.20-2.01 (m, 2H), 1.98-1.74 (m, 2H), 1.05 (d, J=6.5 Hz, 3H). $^{19}$F NMR (376 MHz, CD$_3$OD) δ −70.31 (s). LCMS (M+H)$^+$: 610.3

Example 3

{trans-3-(4-{[4-{[(2-methoxyethyl)amino]methyl}-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile

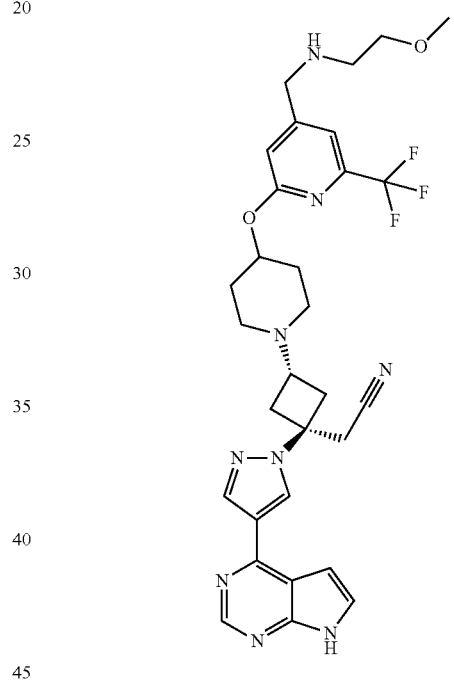

Prepared by the method of Example 1 using {trans-3-(4-{[4-(hydroxymethyl)-6-(trifluoromethyl)pyridin-2-yl]oxy}piperidin-1-yl)-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (15 mg, 0.022 mmol, Peak 1 from Intermediate Example A2, Step F), N,N-diisopropylethylamine (11 µL, 0.066 mmol) and methanesulphonic anhydride (9.6 mg, 0.055 mmol, Aldrich) and using 2-methoxyethylamine (19.1 µL, 0.220 mmol, Aldrich) at room temperature overnight for the displacement step. The product was purified in the manner of Example 1 to afford product as the free base (8.0 mg, 60%). $^1$H NMR (400 MHz, d$_6$-DMSO) δ 12.14 (br s, 1H), 8.83 (s, 1H), 8.69 (s, 1H), 8.42 (s, 1H), 7.60 (d, J=3.6 Hz, 1H), 7.42 (s, 1H), 7.08 (d, J=3.6 Hz, 1H), 7.02 (s, 1H), 5.16-4.81 (m, 1H), 3.76 (s, 2H), 3.42 (s, 2H), 3.37 (t, J=5.7 Hz, 2H), 3.22 (s, 3H), 3.07-2.97 (m, 2H), 2.81 (p, J=7.4 Hz, 1H), 2.73-2.56 (m, 4H), 2.47-2.26 (m, 3H), 2.26-2.07 (m, 2H), 2.07-1.92 (m, 2H), 1.83-1.46 (m, 2H). $^{19}$F NMR (376 MHz, d$_6$-DMSO) δ −68.11 (s). LCMS (M+H)$^+$: 610.3.

Example 4

1-{[2-[(1-{trans-3-(cyanomethyl)-3-[4-(7H-pyrrolo[2,3-d]pyrimidin-4-yl)-1H-pyrazol-1-yl]cyclobutyl}piperidin-4-yl)oxy]-6-(trifluoromethyl)pyridin-4-yl]methyl}azetidine-3-carbonitrile

Example 5

[trans-1-[4-(7H-pyrrolo[2,3-d]pyrimidin-4-yl)-1H-pyrazol-1-yl]-3-(4-{[4-[(tetrahydro-2H-pyran-4-ylamino)methyl]-6-(trifluoromethyl)pyridin-2-yl]oxy}piperidin-1-yl)cyclobutyl]acetonitrile

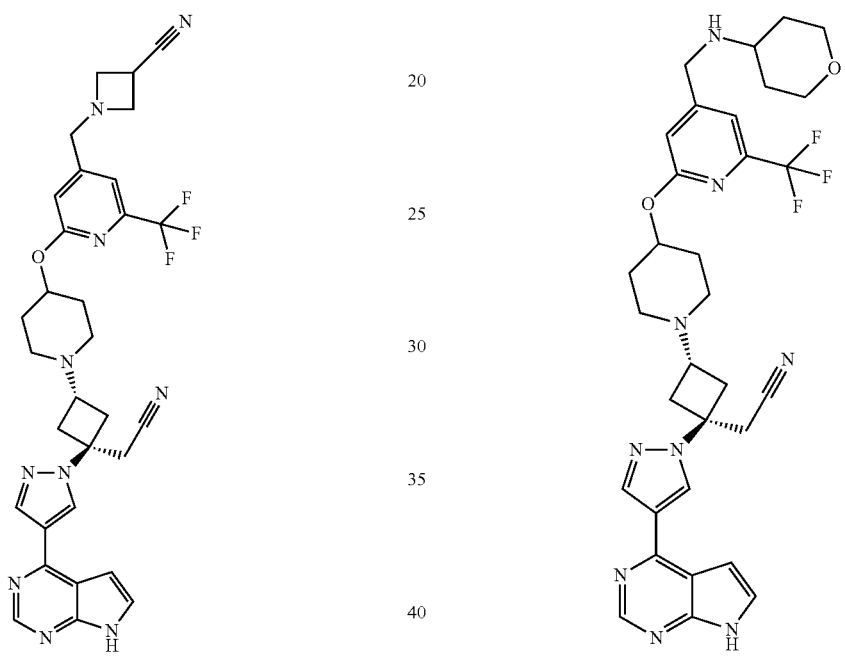

Prepared according to the method of Example 1 using azetidine-3-carbonitrile hydrochloride (13 mg, 0.11 mmol, Oakwood) and N,N-diisopropylethylamine (23 μL, 0.13 mmol) in the displacement step which was carried out at room temperature overnight, and the product was afforded as the free base (7.5 mg, 55%). $^1$H NMR (400 MHz, d$_6$-DMSO) δ 12.11 (br s, 1H), 8.83 (s, 1H), 8.69 (s, 1H), 8.42 (s, 1H), 7.60 (d, J=3.6 Hz, 1H), 7.31 (s, 1H), 7.08 (d, J=3.6 Hz, 1H), 6.96 (s, 1H), 5.28-4.71 (m, 1H), 3.66 (s, 2H), 3.56-3.46 (m, 3H), 3.42 (s, 2H), 3.38-3.24 (m, 2H), 3.09-2.95 (m, 2H), 2.81 (p, J=7.4 Hz, 1H), 2.73-2.56 (m, 2H), 2.40-2.27 (m, 2H), 2.23-2.08 (m, 2H), 2.08-1.93 (m, 2H), 1.76-1.59 (m, 2H). $^{19}$F NMR (376 MHz, d$_6$-DMSO) δ −67.38 (s). LCMS (M+H)$^+$: 617.3.

The procedure of Example 1 was followed, using tetrahydro-2H-pyran-4-amine (11 mg, 0.11 mmol, Combi-Blocks) in the displacement step at 40° C. overnight (7.9 mg, 56%). $^1$H NMR (400 MHz, d$_6$-DMSO) δ 12.08 (br s, 1H), 8.83 (s, 1H), 8.69 (s, 1H), 8.42 (s, 1H), 7.60 (d, J=3.6 Hz, 1H), 7.44 (s, 1H), 7.08 (d, J=3.6 Hz, 1H), 7.06 (s, 1H), 5.07-4.90 (m, 1H), 3.86-3.74 (m, 4H), 3.42 (s, 2H), 3.24 (td, J=11.4, 2.1 Hz, 2H), 3.10-2.95 (m, 2H), 2.81 (p, J=7.5 Hz, 1H), 2.72-2.59 (m, 2H), 2.59-2.51 (m, 1H), 2.41-2.27 (m, 2H), 2.25-2.07 (m, 2H), 2.08-1.92 (m, 2H), 1.86-1.61 (m, 4H), 1.24 (dtd, J=13.1, 11.2, 4.3 Hz, 2H). $^{19}$F NMR (376 MHz, d$_6$-DMSO) δ −67.26 (s). LCMS (M+H)$^+$: 636.3.

Example 6

{trans-3-(4-{[4-(2-oxa-6-azaspiro[3.3]hept-6-ylmethyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile

Example 7

[trans-1-[4-(7H-pyrrolo[2,3-d]pyrimidin-4-yl)-1H-pyrazol-1-yl]-3-(4-{[4-{[(3S)-tetrahydrofuran-3-ylamino]methyl}-6-(trifluoromethyl)pyridin-2-yl]oxy}piperidin-1-yl)cyclobutyl]acetonitrile

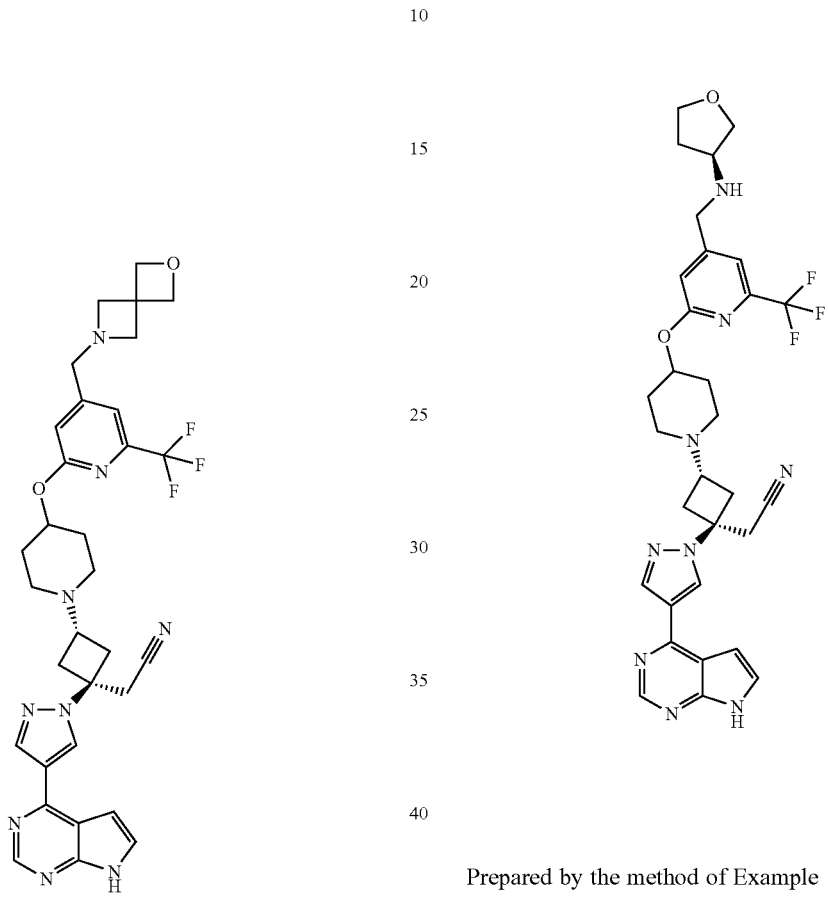

Prepared by the method of Example 1, using 2-oxa-6-azaspiro[3.3]heptane (11 mg, 0.11 mmol, J&W Pharmlab) in tetrahydrofuran (0.50 mL) and methanol (0.50 mL) at room temperature for 5.5 hours in the displacement step (7.4 mg, 53%). $^1$H NMR (400 MHz, $d_6$-DMSO) δ 12.13 (br s, 1H), 8.83 (s, 1H), 8.69 (s, 1H), 8.42 (s, 1H), 7.60 (d, J=3.6 Hz, 1H), 7.28 (s, 1H), 7.08 (d, J=3.6 Hz, 1H), 6.92 (s, 1H), 5.28-4.71 (m, 1H), 4.60 (s, 4H), 3.57 (s, 2H), 3.42 (s, 2H), 3.33 (s, 4H), 3.09-2.95 (m, 2H), 2.81 (p, J=7.6 Hz, 1H), 2.72-2.57 (m, 2H), 2.40-2.29 (m, 2H), 2.22-2.08 (m, 2H), 2.08-1.96 (m, 2H), 1.77-1.61 (m, 2H). $^{19}$F NMR (376 MHz, $d_6$-DMSO) δ −67.36 (s). LCMS (M+H)$^+$: 634.3.

Prepared by the method of Example 1 using {trans-3-(4-{[4-(hydroxymethyl)-6-(trifluoromethyl)pyridin-2-yl]oxy}piperidin-1-yl)-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (15 mg, 0.022 mmol, Peak 1 from Intermediate Example A2, Step F) and using (3S)-tetrahydrofuran-3-amine hydrochloride (14 mg, 0.11 mmol, Advanced ChemBlocks, Inc.) and N,N-diisopropylethylamine (23 µL, 0.13 mmol) in the displacement step. 0.2 mL of ethylenediamine was used in the deprotection. The product was obtained as the free base (4.5 mg, 33%). $^1$H NMR (400 MHz, $d_6$-DMSO) δ 12.13 (s, 1H), 8.83 (s, 1H), 8.69 (s, 1H), 8.42 (s, 1H), 7.60 (dd, J=3.5, 2.4 Hz, 1H), 7.43 (s, 1H), 7.08 (dd, J=3.6, 1.7 Hz, 1H), 7.05 (s, 1H), 5.23-4.71 (m, 1H), 3.82-3.70 (m, 3H), 3.72-3.57 (m, 2H), 3.48-3.37 (m, 3H), 3.27-3.17 (m, 1H), 3.09-2.95 (m, 2H), 2.81 (p, J=7.0 Hz, 1H), 2.63 (br m, 2H), 2.43-2.28 (m, 2H), 2.16 (br m, 2H), 2.00 (br m, 2H), 1.91 (dq, J=12.6, 7.2 Hz, 1H), 1.78-1.61 (m, 3H). $^{19}$F NMR (376 MHz, $d_6$-DMSO) δ −67.28 (s). LCMS (M+H)$^+$: 622.3.

Example 8

[trans-1-[4-(7H-pyrrolo[2,3-d]pyrimidin-4-yl)-1H-pyrazol-1-yl]-3-(4-{[4-{[(3R)-tetrahydrofuran-3-ylamino]methyl}-6-(trifluoromethyl)pyridin-2-yl]oxy}piperidin-1-yl)cyclobutyl]acetonitrile

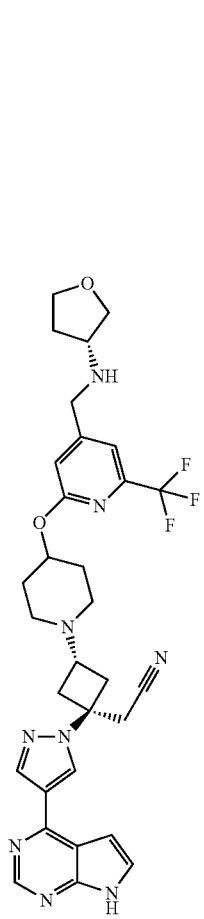 [SMILES: N#CC[C@]1(n2cc(-c3ncnc4[nH]ccc34)cn2)C[C@H](N2CCC(Oc3cc(CN[C@@H]4CCOC4)cc(C(F)(F)F)n3)CC2)C1]

Prepared by the method of Example 7 using (3R)-tetrahydrofuran-3-amine hydrochloride (14 mg, 0.11 mmol, Advanced Chem Blocks) to afford product as the free base (7.8 mg, 57%). $^1$H NMR (400 MHz, d$_6$-DMSO) δ 12.13 (s, 1H), 8.83 (s, 1H), 8.69 (s, 1H), 8.42 (s, 1H), 7.60 (dd, J=3.5, 2.4 Hz, 1H), 7.43 (s, 1H), 7.08 (dd, J=3.6, 1.6 Hz, 1H), 7.05 (s, 1H), 5.14-4.59 (m, 1H), 3.79-3.58 (m, 5H), 3.46-3.39 (m, 3H), 3.27-3.19 (m, 1H), 3.09-2.96 (m, 2H), 2.81 (p, J=7.3 Hz, 1H), 2.74-2.55 (m, 2H), 2.42-2.28 (m, 2H), 2.26-2.09 (m, 2H), 2.07-1.96 (m, 2H), 1.91 (dq, J=12.4, 7.2 Hz, 1H), 1.79-1.53 (m, 3H). $^{19}$F NMR (376 MHz, d$_6$-DMSO) δ −67.28 (s). LCMS (M+H)$^+$: 622.3.

Example 9

{trans-3-(4-{[4-{[(3-methyloxetan-3-yl)amino]methyl}-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile

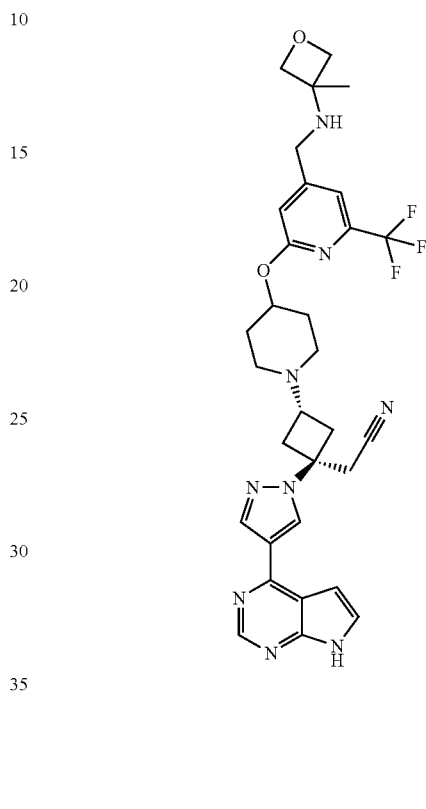

The procedure of Example 1 was followed, using {trans-3-(4-{[4-(hydroxymethyl)-6-(trifluoromethyl)pyridin-2-yl]oxy}piperidin-1-yl)-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (21 mg, 0.031 mmol, Peak 1 from Intermediate Example A2, Step F), N,N-diisopropylethylamine (11 µL, 0.062 mmol) and methanesulphonic anhydride (7.5 mg, 0.043 mmol, Aldrich) in methylene chloride (0.42 mL). However, the substitution step was carried out using 3-methyloxetan-3-amine (40 µL, 0.46 mmol, Synthonix) in tetrahydrofuran (0.42 mL) and methanol (0.20 mL) at 55° C. for 4 hours 10 followed by 50° C. overnight. Deprotection and purification carried out similarly to afford product as the free base (11 mg, 58%). $^1$H NMR (400 MHz, d$_6$-DMSO) δ 12.13 (s, 1H), 8.83 (s, 1H), 8.69 (s, 1H), 8.42 (s, 1H), 7.60 (d, J=3.6 Hz, 1H), 7.46 (s, 1H), 7.15-7.02 (m, 2H), 5.11-4.89 (m, 1H), 4.45 (d, J=5.8 Hz, 2H), 4.18 (d, J=6.0 Hz, 2H), 3.77 (d, J=7.4 Hz, 2H), 3.42 (s, 2H), 3.11-2.95 (m, 3H), 2.81 (p, J=7.4 Hz, 1H), 2.73-2.55 (m, 2H), 2.44-2.27 (m, 2H), 2.25-2.08 (m, 2H), 2.08-1.92 (m, 2H), 1.80-1.54 (m, 2H), 1.37 (s, 3H). $^{19}$F NMR (376 MHz, d$_6$-DMSO) δ −67.29 (s). LCMS (M+H)$^+$: 622.2.

0.30 (dd, J=5.8, 3.8 Hz, 2H). $^{19}$F NMR (376 MHz, d$_6$-DMSO) δ −67.28 (s). LCMS (M+H)$^+$: 606.2.

Example 10

{trans-3-(4-{[4-{[(1-methylcyclopropyl)amino]methyl}-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile Example 11

{trans-3-(4-{[4-[(oxetan-3-ylamino)methyl]-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile

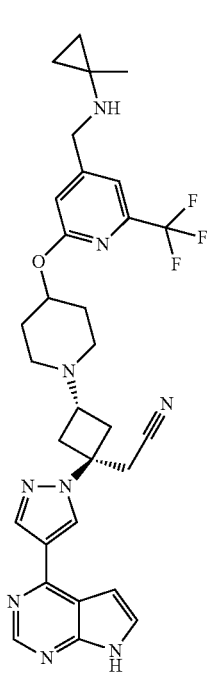 [SMILES: CC1(NCc2cc(OC3CCN([C@H]4C[C@](CC#N)(n5cc(-c6ncnc7[nH]ccc67)cn5)C4)CC3)nc(C(F)(F)F)c2)CC1]

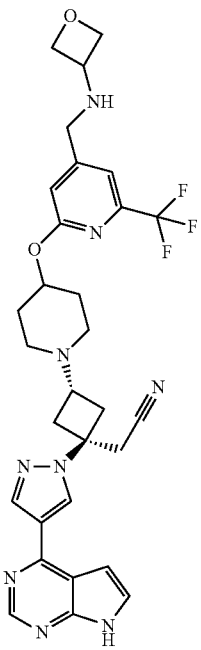 [SMILES: N#CC[C@]1(n2cc(-c3ncnc4[nH]ccc34)cn2)C[C@H](N2CCC(Oc3cc(CNC4COC4)cc(C(F)(F)F)n3)CC2)C1]

The procedure of Example 9 was followed, using 1-methylcyclopropanamine hydrochloride (33 mg, 0.31 mmol, ChemBridge Corp.) and N,N-diisopropylethylamine (64 μL, 0.37 mmol) in the substitution step, which was carried out at 55° C. for 2.5 hours. The product was obtained as the free base (6.2 mg, 33%). $^1$H NMR (400 MHz, d$_6$-DMSO) δ 12.13 (s, 1H), 8.83 (s, 1H), 8.69 (s, 1H), 8.42 (s, 1H), 7.60 (d, J=3.6 Hz, 1H), 7.39 (s, 1H), 7.08 (d, J=3.6 Hz, 1H), 7.01 (s, 1H), 4.99 (tt, J=8.4, 4.6 Hz, 1H), 3.77 (d, J=6.4 Hz, 2H), 3.42 (s, 2H), 3.10-2.94 (m, 2H), 2.81 (p, J=7.3 Hz, 1H), 2.71-2.54 (m, 3H), 2.41-2.30 (m, 2H), 2.25-2.09 (m, 2H), 2.07-1.91 (m, 2H), 1.78-1.57 (m, 2H), 1.20 (s, 3H), 0.48 (dd, J=5.7, 4.2 Hz, 2H), The procedure of Example 9 was followed, using oxetan-3-amine (34 mg, 0.46 mmol, Synthonix) in the substitution step, carried out at 55° C. for 1.5 hours. The desired product was obtained as the free base (9.7 mg, 52%). $^1$H NMR (400 MHz, d$_6$-DMSO) δ 12.13 (s, 1H), 8.83 (s, 1H), 8.69 (s, 1H), 8.42 (s, 1H), 7.60 (s, 1H), 7.42 (s, 1H), 7.08 (s, 1H), 7.03 (s, 1H), 5.10-4.88 (m, 1H), 4.56 (t, J=6.6 Hz, 2H), 4.30 (t, J=6.2 Hz, 2H), 3.94-3.77 (m, 1H), 3.68 (s, 2H), 3.42 (s, 2H), 3.28-3.09 (m, 1H), 3.09-2.91 (m, 2H), 2.91-2.73 (m, 1H), 2.74-2.54 (m, 2H), 2.42-2.26 (m, 2H), 2.25-2.07 (m, 2H), 2.07-1.89 (m, 2H), 1.83-1.60 (m, 2H). $^{19}$F NMR (376 MHz, d$_6$-DMSO) δ −67.33 (s). LCMS (M+H)$^+$: 608.3

Example 12

{trans-3-(4-{[4-{[(trans-3-hydroxycyclobutyl)amino]methyl}-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile

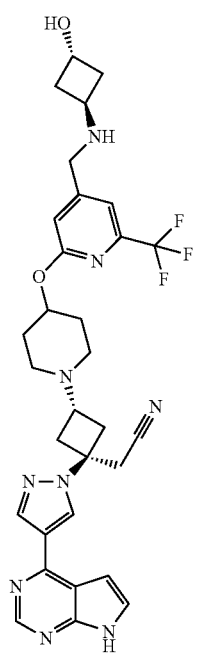 [SMILES: N#CC[C@]1(n2cc(-c3ncnc4[nH]ccc34)cn2)C[C@H](N2CCC(Oc3cc(CN[C@H]4C[C@H](O)C4)cc(C(F)(F)F)n3)CC2)C1]

The procedure of Example 9 was followed, using trans-3-aminocyclobutanol hydrochloride (38 mg, 0.31 mmol, Advanced Chem Blocks) and N,N-diisopropylethylamine (64 μL, 0.37 mmol) in the displacement step, carried out at 55° C. for 1.5 hours (yield 9.8 mg). $^1$H NMR (400 MHz, d$_6$-DMSO) δ 12.11 (s, 1H), 8.83 (s, 1H), 8.69 (s, 1H), 8.42 (s, 1H), 7.60 (d, J=3.6 Hz, 1H), 7.41 (s, 1H), 7.08 (d, J=3.6 Hz, 1H), 7.02 (s, 1H), 5.06-4.94 (m, 1H), 4.86 (d, J=5.4 Hz, 1H), 4.23 (h, J=5.9 Hz, 1H), 3.63 (s, 2H), 3.42 (s, 2H), 3.25-3.12 (m, 1H), 3.09-2.96 (m, 2H), 2.81 (p, J=7.4 Hz, 1H), 2.75-2.51 (m, 3H), 2.43-2.29 (m, 2H), 2.25-2.10 (m, 2H), 2.10-1.82 (m, 6H), 1.80-1.50 (m, 2H). $^{19}$F NMR (376 MHz, d$_6$-DMSO) δ -67.81 (s). LCMS (M+H)$^+$: 622.2.

Example 13

{trans-3-(4-{[4-[(3,3-dimethylazetidin-1-yl)methyl]-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile

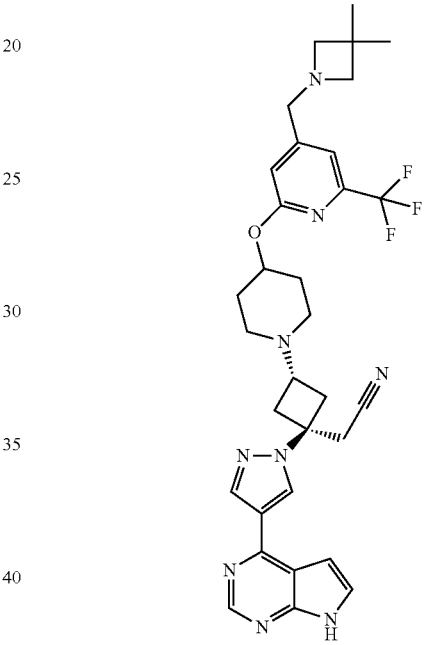

The procedure of Example 9 was followed, using 3,3-dimethylazetidine hydrochloride (22 mg, 0.18 mmol, Princeton Bio) and N,N-diisopropylethylamine (54 μL, 0.31 mmol) in the displacement step, which was carried out at room temperature overnight. (10 mg, 52%). $^1$H NMR (300 MHz, d$_6$-DMSO) δ 12.12 (s, 1H), 8.83 (s, 1H), 8.69 (s, 1H), 8.42 (s, 1H), 7.60 (d, J=3.5 Hz, 1H), 7.30 (s, 1H), 7.08 (d, J=3.6 Hz, 1H), 6.93 (s, 1H), 5.20-4.76 (m, 1H), 3.62 (s, 2H), 3.42 (s, 2H), 3.10-2.96 (m, 2H), 2.92 (s, 4H), 2.81 (p, J=7.2 Hz, 1H), 2.74-2.54 (m, 2H), 2.42-2.29 (m, 2H), 2.24-2.07 (m, 2H), 2.07-1.91 (m, 2H), 1.79-1.60 (m, 2H), 1.18 (s, 6H). $^{19}$F NMR (282 MHz, d$_6$-DMSO) δ -67.35 (s). LCMS (M+H)$^+$: 620.3

Example 14

{trans-3-(4-{[4-({[(2R)-2-hydroxypropyl]amino}methyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile

Example 15

{trans-3-(4-{[4-({[(2S)-2-hydroxypropyl]amino}methyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile

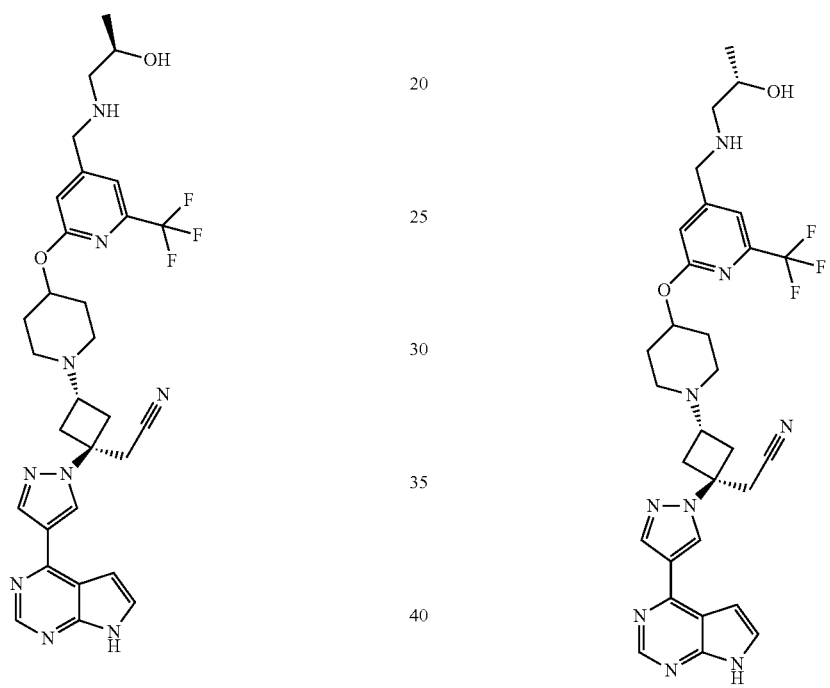

The procedure of Example 9 was followed, using (2R)-1-aminopropan-2-ol (12 µL, 0.15 mmol, Aldrich) in the displacement step, which was carried out at 50° C. for 2 hours. The product was obtained as the free base (8.7 mg, 46%). $^1$H NMR (400 MHz, d$_6$-DMSO) δ 12.13 (s, 1H), 8.83 (s, 1H), 8.69 (s, 1H), 8.42 (s, 1H), 7.60 (d, J=3.6 Hz, 1H), 7.42 (s, 1H), 7.08 (d, J=3.6 Hz, 1H), 7.04 (s, 1H), 5.11-4.90 (m, 1H), 4.49 (d, J=4.4 Hz, 1H), 3.76 (s, 2H), 3.67 (tt, J=10.3, 5.6 Hz, 1H), 3.42 (s, 2H), 3.11-2.96 (m, 2H), 2.81 (p, J=7.5 Hz, 1H), 2.74-2.56 (m, 2H), 2.46-2.25 (m, 4H), 2.24-2.09 (m, 2H), 2.09-1.90 (m, 2H), 1.81-1.51 (m, 2H), 1.03 (d, J=6.2 Hz, 3H). $^{19}$F NMR (376 MHz, d$_6$-DMSO) δ −67.29 (s). LCMS (M+H)$^+$: 610.3.

The procedure of Example 9 was followed, using (2S)-1-aminopropan-2-ol (12 µL, 0.15 mmol, Aldrich) in the displacement step, which was carried out at 50° C. for 2 hours (7.9 mg, 42%). $^1$H NMR (400 MHz, d$_6$-DMSO) δ 12.13 (s, 1H), 8.83 (s, 1H), 8.69 (s, 1H), 8.42 (s, 1H), 7.60 (d, J=3.6 Hz, 1H), 7.42 (s, 1H), 7.08 (d, J=3.6 Hz, 1H), 7.04 (s, 1H), 5.27-4.71 (m, 1H), 4.49 (d, J=4.4 Hz, 1H), 3.76 (s, 2H), 3.72-3.62 (m, 1H), 3.42 (s, 2H), 3.09-2.96 (m, 2H), 2.81 (p, J=7.4 Hz, 1H), 2.72-2.55 (m, 2H), 2.43-2.25 (m, 4H), 2.25-2.08 (m, 2H), 2.08-1.96 (m, 2H), 1.78-1.57 (m, 2H), 1.03 (d, J=6.2 Hz, 3H). $^{19}$F NMR (376 MHz, d$_6$-DMSO) δ −67.29 (s). LCMS (M+H)$^+$: 610.3.

Example 16

{trans-3-(4-{[4-{[bis(2-hydroxyethyl)amino]methyl}-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile

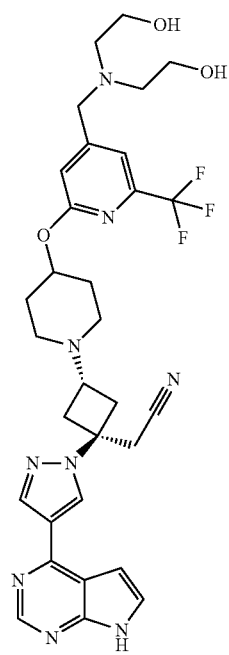 [SMILES: N#CC[C@]1(n2cc(-c3ncnc4[nH]ccc34)cn2)C[C@H](N2CCC(Oc3cc(CN(CCO)CCO)cc(C(F)(F)F)n3)CC2)C1]

The procedure of Example 9 was followed, using diethanolamine (15 µL, 0.15 mmol, Aldrich) in the displacement step, which was carried out at 40° C. overnight (7.4 mg, 38%). $^1$H NMR (400 MHz, d$_6$-DMSO) δ 12.13 (s, 1H), 8.83 (s, 1H), 8.69 (s, 1H), 8.42 (s, 1H), 7.60 (d, J=3.6 Hz, 1H), 7.45 (s, 1H), 7.10 (s, 1H), 7.08 (d, J=3.6 Hz, 1H), 5.29-4.79 (m, 1H), 4.46 (t, J=5.2 Hz, 2H), 3.73 (s, 2H), 3.51-3.38 (m, 6H), 3.09-2.96 (m, 2H), 2.81 (p, J=7.4 Hz, 1H), 2.73-2.58 (m, 2H), 2.53 (t, J=6.1 Hz, 4H), 2.40-2.31 (m, 2H), 2.21-2.09 (m, 2H), 2.08-1.96 (m, 2H), 1.75-1.61 (m, 2H). $^{19}$F NMR (376 MHz, d$_6$-DMSO) δ −67.22 (s). LCMS (M+H)$^+$: 640.1.

Example 17

{trans-3-(4-{[4-{[(2-hydroxyethyl)(methyl)amino]methyl}-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile

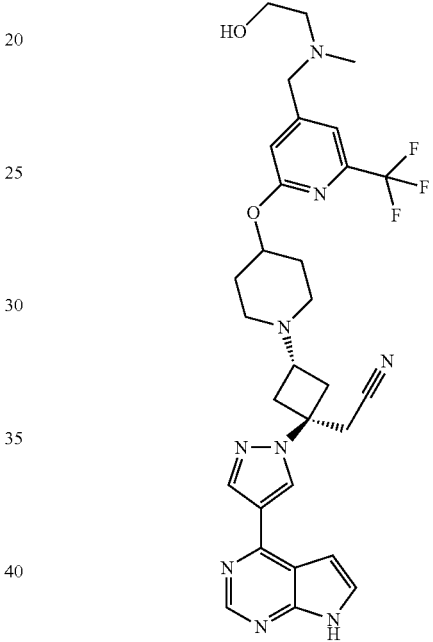

The procedure of Example 9 was followed, using 2-(methylamino)ethanol (12 µL, 0.15 mmol, Aldrich) in the displacement step, which was carried out at 40° C. overnight (8.5 mg, 45%). $^1$H NMR (400 MHz, d$_6$-DMSO) δ 12.12 (s, 1H), 8.83 (s, 1H), 8.69 (s, 1H), 8.42 (s, 1H), 7.60 (d, J=3.6 Hz, 1H), 7.40 (s, 1H), 7.08 (d, J=3.6 Hz, 1H), 7.04 (s, 1H), 4.99 (tt, J=7.6, 3.5 Hz, 1H), 4.49 (t, J=5.4 Hz, 1H), 3.58 (s, 2H), 3.50 (q, J=5.9 Hz, 2H), 3.42 (s, 2H), 3.10-2.95 (m, 2H), 2.81 (p, J=7.4 Hz, 1H), 2.73-2.55 (m, 2H), 2.43 (t, J=6.1 Hz, 2H), 2.40-2.30 (m, 2H), 2.24-2.08 (m, 5H), 2.09-1.91 (m, 2H), 1.78-1.63 (m, 2H). $^{19}$F NMR (376 MHz, d$_6$-DMSO) δ −67.28 (s). LCMS (M+H)$^+$: 610.2.

Example 18

{trans-3-(4-{[4-{[(cis-3-hydroxycyclobutyl)amino]methyl}-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile 3.6 x trifluoroacetate salt

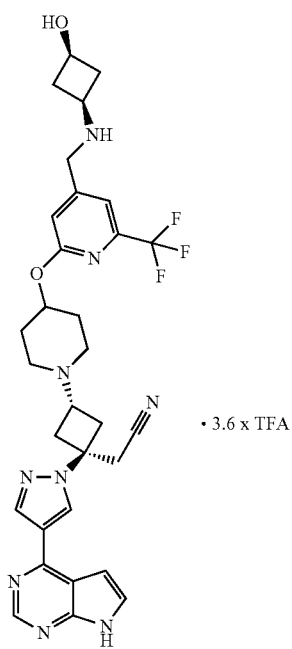 [SMILES: N#CC[C@]1(n2cc(-c3ncnc4[nH]ccc34)cn2)C[C@H](N2CCC(Oc3cc(CN[C@H]4C[C@@H](O)C4)cc(C(F)(F)F)n3)CC2)C1]

• 3.6 x TFA

{trans-3-(4-{[4-(Hydroxymethyl)-6-(trifluoromethyl)pyridin-2-yl]oxy}piperidin-1-yl)-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (71 mg, 0.010 mmol, Peak 1 from Intermediate Example A2, Step F) was dissolved in methylene chloride (2 mL) and N,N-diisopropylethylamine (54 μL, 0.31 mmol) followed by methanesulfonic anhydride (45 mg, 0.26 mmol, Aldrich) were added. The mixture was stirred for 30 minutes and the solvent was removed in vacuo. The residue was redissolved in a mixture of tetrahydrofuran (1.5 mL) and methanol (0.50 mL). Cis-3-aminocyclobutanol hydrochloride (0.064 mL, 0.52 mmol, Synthonix) and N,N-diisopropylethylamine (0.11 mL, 0.62 mmol) were added. The mixture was heated to 40° C. overnight, then at 50° C. for 3 hours. The mixture was concentrated. The residue was dissolved in 2:1 TFA:DCM and was stirred for 1.5 hours. After concentrating again, the residue was dissolved in methanol (4 mL) and ethylenediamine was added (0.7 mL). When the deprotection was complete as determined by LCMS, the product was purified via two successive preparative HPLC-MS runs (first C18 eluting with a gradient of MeCN/H$_2$O containing 0.1% TFA; then after evaporation, C18 eluting with a gradient of MeCN/H$_2$O containing 0.15% NH$_4$OH). The fractions containing product were evaporated to rid excess ammonia. The residue was redissolved in MeCN and H$_2$O containing 0.1% TFA, frozen and lyophilized to afford the product as the 3.6×TFA salt (45 mg, 42%). $^1$H NMR (500 MHz, CD$_3$OD) δ 8.94 (s, 1H), 8.81 (s, 1H), 8.51 (s, 1H), 7.70 (d, J=3.7 Hz, 1H), 7.54 (s, 1H), 7.19 (s, 1H), 7.17 (d, J=3.7 Hz, 1H), 5.42 (br m, 1H), 4.22 (s, 2H), 4.10 (p, J=7.2 Hz, 1H), 4.06-3.94 (m, 1H), 3.83-3.09 (m, 9H), 3.11-2.94 (m, 2H), 2.73 (dddd, J=12.0, 9.2, 6.2, 2.6 Hz, 2H), 2.57-2.13 (m, 4H), 2.13-2.04 (m, 2H). $^{19}$F NMR (282 MHz, CD$_3$OD) δ −70.42 (s, 3F), −77.54 (s, 10.8F). LCMS (M+H)$^+$: 622.0

Intermediate Example A4

{cis-3-(4-{[4-(2-hydroxyethyl)-6-(trifluoromethyl)pyridin-2-yl]oxy}piperidin-1-yl)-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile and {trans-3-(4-{[4-(2-hydroxyethyl)-6-(trifluoromethyl)pyridin-2-yl]oxy}piperidin-1-yl)-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile

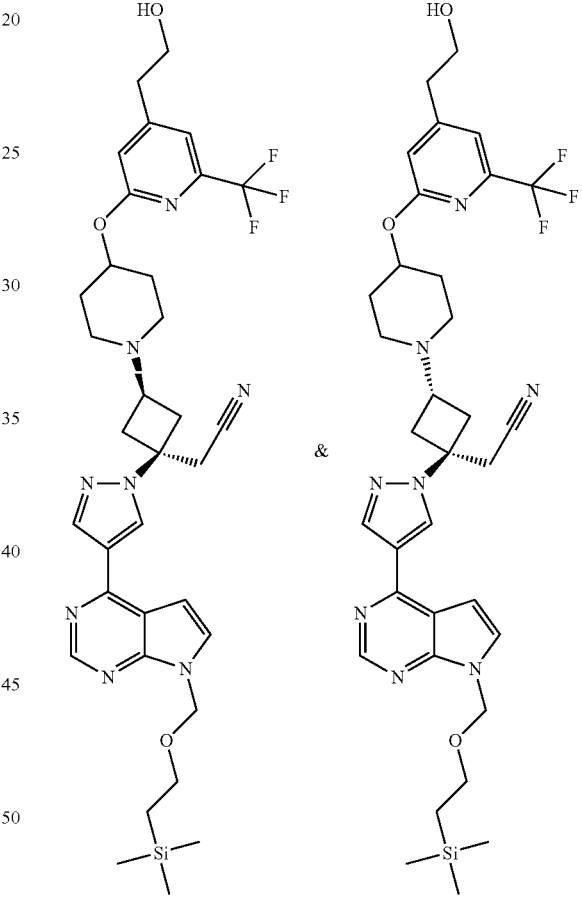

Step 1. tert-butyl 4-{[6-(trifluoromethyl)pyridin-2-yl]oxy}piperidine-1-carboxylate To a mixture of sodium hydride (0.88 g, 60% in mineral oil, 22 mmol) in tetrahydrofuran (50. mL) at 0° C. was added tert-butyl 4-hydroxypiperidine-1-carboxylate (4.4 g, 22 mmol, Aldrich). The mixture was stirred at room temperature for one hour. A solution of 2-chloro-6-(trifluoromethyl)pyridine (2.0 g, 11 mmol, Oakwood) in tetrahydrofuran (10 mL) was added. The mixture was stirred at room temperature for 2 days. The mixture was quenched by the addition of water, and the product was extracted with EtOAc. The extract was washed with water, followed by brine, was dried over sodium sulfate, filtered and concentrated. Flash chromatography on a 120 g silica gel cartridge, eluting with a gradient from 0-15% EtOAc in hexanes afforded product as a colorless oil (3.8 g, 100%). $^1$H NMR (400 MHz, CDCl$_3$) δ 7.75-7.64 (m, 1H), 7.23 (d, J=7.3 Hz, 1H), 6.88 (d, J=8.4 Hz, 1H), 5.27 (tt, J=7.7, 3.7 Hz, 1H), 3.83-3.66 (m, 2H), 3.31 (ddd, J=13.4, 8.5, 3.7 Hz, 1H), 1.99 (ddt, J=13.3, 6.9, 3.7 Hz, 2H), 1.73 (dtd, J=12.3, 8.1, 3.9 Hz, 2H), 1.47 (s, 9H). $^{19}$F NMR (376 MHz, CDCl$_3$) δ −68.94 (s). LCMS (M-tBu+H)$^+$: 291.0.

Step 2. 2-[2-(piperidin-4-yloxy)-6-(trifluoromethyl) pyridin-4-yl]ethanol 2.5 M n-Butyllithium in hexanes (1.2 mL, 2.9 mmol) was added dropwise to a solution of tert-butyl 4-{[6-(trifluoromethyl)pyridin-2-yl]oxy}piperidine-1-carboxylate (0.50 g, 1.4 mmol, from Step 1) in tetrahydrofuran (8.0 mL) at −78° C. The reaction was stirred at this temperature for 1.5 hours, and 1,3,2-dioxathiolane 2,2-dioxide (0.36 g, 2.9 mmol, Aldrich) in Tetrahydrofuran (2.0 mL) was added. The mixture was allowed to warm to room temperature and stir overnight. 12 N Hydrogen chloride in water (0.72 mL, 8.7 mmol) was added to the mixture. The mixture was stirred at room temperature for 4 hours. The mixture was then treated with saturated sodium bicarbonate to pH between 7 and 8, and brine was added. The mixture was then extracted with DCM four times. The combined extracts were dried over sodium sulfate, filtered and concentrated. Preparative HPLC-MS (C18 eluting with a gradient of MeCN/H$_2$O containing 0.15% NH4OH) was used to purify the product. It was the second peak to elute having the desired mass. $^1$H NMR (300 MHz, CD$_3$OD) δ 7.24 (s, 1H), 6.86 (s, 1H), 5.16 (tt, J=8.4, 3.9 Hz, 1H), 3.80 (t, J=6.3 Hz, 2H), 3.06 (dt, J=12.6, 4.6 Hz, 2H), 2.85 (t, J=6.3 Hz, 2H), 2.73 (ddd, J=12.7, 9.5, 3.2 Hz, 2H), 2.13-1.93 (m, 2H), 1.68 (dtd, J=13.0, 9.1, 3.9 Hz, 2H). $^{19}$F NMR (282 MHz, CD$_3$OD) δ −70.29 (s). LCMS (M+H)$^+$: 291.1

Step 3. {cis-3-(4-{[4-(2-hydroxyethyl)-6-(trifluoromethyl)pyridin-2-yl]oxy}piperidin-1-yl)-1-[4-(7-{[2-(trimethylsilyl)ethoxy]methyl}-7H-pyrrolo[2,3-d]pyrimidin-4-yl)-1H-pyrazol-1-yl] cyclobutyl}acetonitrile and {trans-3-(4-{[4-(2-hydroxyethyl)-6-(trifluoromethyl)pyridin-2-yl] oxy}piperidin-1-yl)-1-[4-(7-{[2-(trimethylsilyl) ethoxy]methyl}-7H-pyrrolo[2,3-d]pyrimidin-4-yl)-1H-pyrazol-1-yl]cyclobutyl}acetonitrile Sodium cyanoborohydride (8.2 mg, 0.13 mmol) and zinc dichloride (8.9 mg, 0.065 mmol) were combined in methanol (0.48 mL) and stirred for 2 hours. 2-[2-(piperidin-4-yloxy)-6-(trifluoromethyl)pyridin-4-yl]ethanol (27 mg, 0.093 mmol, from Step 2) and {3-oxo-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (47 mg, 0.11 mmol, from Intermediate Example A1, Step 7) were mixed in methanol (1.3 mL) and stirred briefly to dissolve, then the prestirred solution of and zinc dichloride in methanol was added. The reaction was stirred for 2.5 hours, then the products were purified via preparative HPLC-MS (C18 eluting with a gradient of MeCN/H$_2$O containing 0.15% NH$_4$OH) (waters 2525, XBridge C18, 30×100 mm, 5 μm particle size, gradient 45.1-63.1% ACN from 1.0 min to 13.0 min, peak 1: 9.6-10.3 min, peak 2: 10.5-11.2 min). Peak 1 was the cis isomer, peak 2 was the trans isomer. Peak 1, Cis-: $^1$H NMR (400 MHz, CD$_3$OD) δ 8.73 (s, 1H), 8.69 (s, 1H), 8.37 (s, 1H), 7.63 (d, J=3.7 Hz, 1H), 7.24 (s, 1H), 7.07 (d, J=3.7 Hz, 1H), 6.86 (s, 1H), 5.68 (s, 2H), 5.17-5.07 (m, 1H), 3.80 (t, J=6.3 Hz, 2H), 3.64-3.53 (m, 2H), 3.35 (s, 2H), 2.99 (p, J=7.9 Hz, 1H), 2.88-2.59 (m, 8H), 2.43-2.25 (m, 2H), 2.15-2.03 (m, 2H), 1.88-1.73 (m, 2H), 0.97-0.79 (m, 2H), −0.09 (s, 9H). $^{19}$F NMR (376 MHz, CD$_3$OD) δ −70.27 (s). LCMS (M+H): 697.2. Peak 2, Trans: $^1$H NMR (400 MHz, CD$_3$OD) δ 8.75 (s, 1H), 8.73 (s, 1H), 8.40 (s, 1H), 7.62 (d, J=3.6 Hz, 1H), 7.23 (s, 1H), 7.05 (d, J=3.6 Hz, 1H), 6.85 (s, 1H), 5.68 (s, 2H), 5.12 (br m, 1H), 3.79 (t, J=6.3 Hz, 2H), 3.58 (t, J=8.0 Hz, 2H), 3.34 (s, 2H), 3.17-3.06 (m, 2H), 2.95 (p, J=7.4 Hz, 1H), 2.84 (t, J=6.2 Hz, 2H), 2.79-2.67 (m, 2H), 2.53-2.37 (m, 2H), 2.38-2.22 (m, 2H), 2.17-2.04 (m, 2H), 1.91-1.74 (m, 2H), 0.88 (t, J=8.0 Hz, 2H), −0.09 (s, 9H). $^{19}$F NMR (376 MHz, CD$_3$OD) δ −70.26 (s). LCMS (M+H)$^+$: 697.2.

Example 20

{trans-3-(4-{[4-(2-hydroxyethyl)-6-(trifluoromethyl) pyridin-2-yl]oxy}piperidin-1-yl)-1-[4-(7H-pyrrolo[2, 3-d]pyrimidin-4-yl)-1H-pyrazol-1-yl] cyclobutyl}acetonitrile

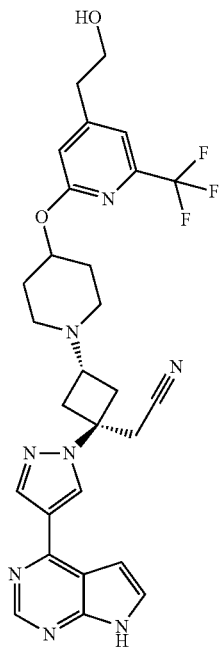 [SMILES: N#CC[C@]1(n2cc(-c3ncnc4[nH]ccc34)cn2)C[C@H](N2CCC(Oc3cc(CCO)cc(C(F)(F)F)n3)CC2)C1]

{trans-3-(4-{[4-(2-hydroxyethyl)-6-(trifluoromethyl)pyridin-2-yl]oxy}piperidin-1-yl)-1-[4-(7-{[2-(trimethylsilyl) ethoxy]methyl}-7H-pyrrolo[2,3-d]pyrimidin-4-yl)-1H-pyrazol-1-yl]cyclobutyl}acetonitrile (9.0 mg, 0.013 mmol, Peak 2 from Intermediate Example A4, Step 3) was deprotected and purified by stirred in a mixture of methylene chloride (0.50 mL) and trifluoroacetic acid (0.50 mL) for one hour. The solvents were removed in vacuo and the residue was stirred in methanol (0.1 mL) containing ethylenediamine (0.1 mL). Purification via preparative HPLC-MS (C18 eluting with a gradient of MeCN/H$_2$O containing 0.15% NH$_4$OH) afforded product as the free base (5.8 mg, 79%). $^1$H NMR (300 MHz, d$_6$-DMSO) δ 12.12 (s, 1H), 8.83 (s, 1H), 8.69 (s, 1H), 8.42 (s, 1H), 7.60 (d, J=3.6 Hz, 1H), 7.34 (s, 1H), 7.08 (d, J=3.6 Hz, 1H), 6.95 (s, 1H), 4.99 (tt, J=8.2, 4.1 Hz, 1H), 4.73 (t, J=4.9 Hz, 1H), 3.66 (q, J=5.9 Hz, 2H), 3.42 (s, 2H), 3.11-2.95 (m, 2H), 2.90-2.71 (m, 3H), 2.71-2.56 (m, 2H), 2.44-2.30 (m, 2H), 2.15 (t, J=9.2 Hz, 2H), 2.09-1.82 (m, 2H), 1.83-1.58 (m, 2H). $^{19}$F NMR (282 MHz, d$_6$-DMSO) δ −67.26 (s). LCMS (M+H): 567.2.

Example 21

{trans-3-(4-{[4-{[(2-hydroxyethyl)amino]methyl}-6-(trifluoromethyl)pyridin-2-yl]oxy}piperidin-1-yl)-1-[4-(1H-pyrrolo[2,3-b]pyridin-4-yl)-1H-pyrazol-1-yl]cyclobutyl}acetonitrile

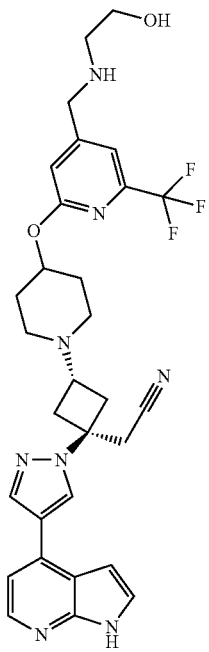 [SMILES: N#CC[C@]1(n2cc(-c3ccnc4[nH]ccc34)cn2)C[C@H](N2CCC(Oc3cc(CNCCO)cc(C(F)(F)F)n3)CC2)C1]

Step 1. tert-butyl 2-chloro-6-(trifluoromethyl)isonicotinate

2-Chloro-6-(trifluoromethyl)pyridine (20.0 g, 0.11 mol, Oakwood) was dissolved in tetrahydrofuran (397 mL) and then 1.0 M lithium chloride—chloro(2,2,6,6-tetramethylpiperidin-1-yl)magnesium (1:1) in THF (132.2 mL, 132.2 mmol, Aldrich) was added. The reaction was stirred at ambient temperature for 1 hour and was then cooled to −78° C., and then a solution of di-tert-Butyldicarbonate (48.1 g, 0.22 mol, Aldrich) in tetrahydrofuran (100 mL) was added. The reaction was stirred at −78° C. for 1 hour and then allowed to warm to room temperature overnight. The reaction was quenched with water, then ammonium chloride was added. The layers were separated and the aqueous was extracted with two portions of ethyl acetate. The combined organic extracts were washed with water, then sat'd NaCl solution, dried over Na$_2$SO$_4$, filtered and concentrated. The crude product, which was a mixture of two regioisomers, was purified by flash chromatography, eluting with 2% EtOAc in hexanes, in 3 batches, each on a 330 g silica gel cartridge. The first product to elute was the desired regioisomer, which also contained some unreacted starting material. The product crystallized on standing and the oil, which contained some unreacted starting material, was decanted away, leaving a more pure crystalline product (9.58 g, 30%). $^1$H NMR (300 MHz, CDCl$_3$) δ 8.07 (d, J=1.1 Hz, 1H), 8.02-7.99 (m, 1H), 1.62 (s, 9H). $^{19}$F NMR (282 MHz, CDCl$_3$) δ −68.43 (s). LCMS (M-tBu+H)$^+$: 225.9/227.9.

Step 2. 2-{[1-(tert-butoxycarbonyl)piperidin-4-yl]oxy}-6-(trifluoromethyl)isonicotinic acid To sodium hydride (60% in mineral oil, 0.36 g, 8.9 mmol) in tetrahydrofuran (15 mL) at 0° C. was added tert-butyl 4-hydroxypiperidine-1-carboxylate (1.8 g, 8.9 mmol, Aldrich). The reaction mixture was allowed to reach room temperature and stir for 1 hour. A solution of tert-butyl 2-chloro-6-(trifluoromethyl)isonicotinate (1.0 g, 3.6 mmol, from Step 1) in tetrahydrofuran (4.9 mL, 60. mmol) was introduced and the mixture was stirred at room temperature over five nights. The mixture was quenched by the careful addition of 1N NaOH (15 mL) and allowed to stir overnight. The reaction was diluted with additional water and the aqueous layer was washed with Et$_2$O. The aqueous layer was then acidified by the addition of c.HCl to achieve pH~3. The product was extracted with three portions of ethyl acetate. The combined EtOAc extracts were dried over sodium sulfate, filtered and concentrated. The product was used without further purification. LCMS (M-tBu+H)$^+$: 335.1.

Step 3. tert-butyl 4-{[4-(hydroxymethyl)-6-(trifluoromethyl)pyridin-2-yl]oxy}piperidine-1-carboxylate To a solution of 2-{[1-(tert-butoxycarbonyl)piperidin-4-yl]oxy}-6-(trifluoromethyl)isonicotinic acid (1.4 g, 3.6 mmol, prepared by the method of Step 2) in methanol (70. mL) at 0° C. was added 2.0 M trimethylsilyldiazomethane in ether (18 mL, 36 mmol) dropwise until TLC indicated complete reaction. Excess reagent was discharged by dropwise addition of acetic acid to the mixture cooled in an ice bath. Solvent was removed by rotary evaporation. The residue was dissolved in ethanol (28 mL), cooled to 0° C., and sodium tetrahydroborate (0.26 g, 7.0 mmol) was added. The cooling was discontinued and the reaction was allowed to stir at room temperature for 30 minutes. It was re-cooled in an ice bath and an additional portion of Sodium tetrahydroborate (0.27 g, 7.2 mmol) was added. The reaction mixture was allowed to reach room temperature and stir until the reaction was complete as determined by analytical LCMS and TLC. The reaction was quenched by the addition of saturated ammonium chloride, diluted with water, and extracted with EtOAc (2×). The combined organic extracts were washed with brine, dried over sodium sulfate, filtered and concentrated. Flash chromatography, using a 120 g silica gel cartridge and eluting with a gradient from 0-30% EtOAc in hexanes afforded product as a colorless oil (0.90 g, 67%). $^1$H NMR (400 MHz, CDCl$_3$) δ 7.22 (s, 1H), 6.90 (s, 1H), 5.27 (tt, J=7.7, 3.7 Hz, 1H), 4.74 (d, J=2.5 Hz, 2H), 3.81-3.63 (m, 2H), 3.31 (ddd, J=13.4, 8.4, 3.7 Hz, 2H), 1.98 (ddt, J=13.5, 7.0, 3.8 Hz, 2H), 1.72 (dtd, J=12.5, 8.2, 4.0 Hz, 2H), 1.47 (s, 9H). $^{19}$F NMR (376 MHz, CDCl$_3$) δ −69.21 (s). LCMS (M-tBu+H)$^+$: 321.1.

Step 4. [2-(piperidin-4-yloxy)-6-(trifluoromethyl)pyridin-4-yl]methanol 4.0 M Hydrogen chloride in dioxane (12 mL, 47 mmol) was added to a solution of tert-butyl 4-{[4-(hydroxymethyl)-6-(trifluoromethyl)pyridin-2-yl]oxy}piperidine-1-carboxylate (0.89 g, 2.4 mmol, from Step 3) in 1,4-dioxane (12 mL) and the reaction was stirred for 3 hours. The reaction was made basic by the addition of 1N NaOH to achieve a pH between 12 and 13. The product was extracted with DCM (6×) and the combined extracts were dried over sodium sulfate, filtered and concentrated to afford product as a light yellow solid (0.50 g, 75%). $^1$H NMR (300 MHz, CDCl$_3$) δ 7.22 (s, 1H), 6.91 (s, 1H), 5.23 (tt, J=7.9, 3.8 Hz, 1H), 4.74 (s, 2H), 3.26-3.06 (m, 2H), 2.88 (ddd, J=12.3, 8.6, 3.4 Hz, 2H), 2.11 (ddt, J=12.9, 6.7, 3.2 Hz, 2H), 1.92-1.56 (m, 2H). $^{19}$F NMR (282 MHz, CDCl$_3$) δ −68.89 (s). LCMS (M+H)$^+$: 277.0.

Step 5. {cis-3-(4-{[4-(hydroxymethyl)-6-(trifluoromethyl)pyridin-2-yl]oxy}piperidin-1-yl)-1-[4-(1-{[2-(trimethylsilyl)ethoxy]methyl}-1H-pyrrolo[2,3-b]pyridin-4-yl)-1H-pyrazol-1-yl]cyclobutyl}acetonitrile and {trans-3-(4-{[4-(hydroxymethyl)-6-(trifluoromethyl)pyridin-2-yl]oxy}piperidin-1-yl)-1-[4-(1-{[2-(trimethylsilyl)ethoxy]methyl}-1H-pyrrolo[2,3-b]pyridin-4-yl)-1H-pyrazol-1-yl]cyclobutyl}acetonitrile Sodium cyanoborohydride (83 mg, 1.3 mmol) and zinc dichloride (90. mg, 0.66 mmol) were pre-combined in methanol (5.0 mL) and stirred for one hour. {3-oxo-1-[4-(1-{[2-(trimethylsilyl)ethoxy]methyl}-1H-pyrrolo[2,3-b]pyridin-4-yl)-1H-pyrazol-1-yl]cyclobutyl}acetonitrile (0.40 g, 0.95 mmol, Intermediate Example A3, Step C) and [2-(piperidin-4-yloxy)-6-(trifluoromethyl)pyridin-4-yl]methanol (0.26 g, 0.95 mmol, from Step 4) were stirred briefly in methanol (13 mL) to dissolve, then the pre-stirred mixture of Sodium cyanoborohydride and zinc dichloride in methanol was added and the reaction was stirred for 16 hours. The mixture was diluted with DCM and washed with saturated sodium bicarbonate solution. The aqueous layer was extracted with a further two portions of DCM, and the combined extracts were dried over sodium sulfate, filtered and concentrated. Flash chromatography on a 120 g silica gel cartridge, eluting with a slow gradient from 0-100% EtOAc in hexanes afforded separation of the two isomers: Peak 1, cis-isomer: 0.25 g, 39%; Peak 2, trans-isomer: 0.2 g, 30%).

Step 6. {trans-3-(4-{[4-{[(2-hydroxyethyl)amino]methyl}-6-(trifluoromethyl)pyridin-2-yl]oxy}piperidin-1-yl)-1-[4-(1H-pyrrolo[2,3-b]pyridin-4-yl)-1H-pyrazol-1-yl]cyclobutyl}acetonitrile Methanesulphonic anhydride (43 mg, 0.25 mmol, Aldrich) was added to a solution of {trans-3-(4-{[4-(hydroxymethyl)-6-(trifluoromethyl)pyridin-2-yl]oxy}piperidin-1-yl)-1-[4-(1-{[2-(trimethylsilyl)ethoxy]methyl}-1H-pyrrolo[2,3-b]pyridin-4-yl)-1H-pyrazol-1-yl]cyclobutyl}acetonitrile (85 mg, 0.10 mmol, Peak 2 from Step 5) and N,N-diisopropylethylamine (52 µL, 0.30 mmol) in Methylene chloride (2.0 mL). The mixture was stirred for 30 minutes. Solvent was removed in vacuo and the residue was re-dissolved in a mixture of Tetrahydrofuran (1.0 mL) and methanol (1.0 mL). Ethanolamine (60.2 µL, 0.997 mmol, Aldrich) was added and the mixture was stirred for 5 hours and concentrated. The crude product was deprotected by stirring in a 2:1 mixture of TFA/DCM for 1.5 hours, followed by rotovapping and stirring of the residue in methanol (5 mL) containing ethylenediamine (0.4 mL) until deprotection was determined to be complete by LCMS analysis. Purification via preparative HPLC-MS (C18 eluting with a gradient of MeCN/H$_2$O containing 0.15% NH$_4$OH) afforded the desired compound as the free base (32 mg, 54%). $^1$H NMR (400 MHz, d$_6$-DMSO) δ 11.69 (s, 1H), 8.71 (s, 1H), 8.27 (s, 1H), 8.19 (d, J=5.0 Hz, 1H), 7.57-7.49 (m, 1H), 7.42 (s, 1H), 7.33 (d, J=5.0 Hz, 1H), 7.04 (s, 1H), 6.93-6.80 (m, 1H), 5.29-4.73 (m, 1H), 4.50 (t, J=5.4 Hz, 1H), 3.76 (s, 2H), 3.45 (q, J=5.7 Hz, 2H), 3.39 (s, 2H), 3.31 (s, 1H), 3.05-2.92 (m, 2H), 2.81 (p, J=7.0 Hz, 1H), 2.73-2.56 (m, 2H), 2.56-2.50 (m, 2H), 2.40-2.29 (m, 2H), 2.27-2.07 (m, 2H), 2.08-1.93 (m, 2H), 1.78-1.60 (m, 2H). $^{19}$F NMR (376 MHz, d$_6$-DMSO) δ −67.28 (s). LCMS (M+H)$^+$: 595.3.

Example 22

{trans-3-(4-{[4-(1H-imidazol-1-ylmethyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile

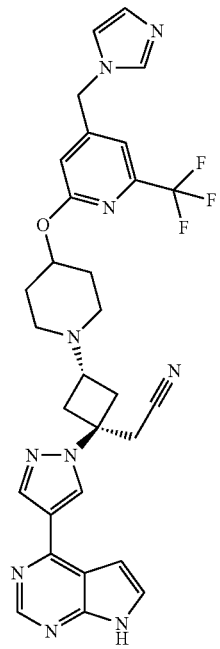 [SMILES: N#CC[C@]1(n2cc(-c3ncnc4[nH]ccc34)cn2)C[C@H](N2CCC(Oc3cc(Cn4ccnc4)cc(C(F)(F)F)n3)CC2)C1]

N,N-Diisopropylethylamine (11 µL, 0.062 mmol) and methanesulfonic anhydride (7.5 mg, 0.043 mmol) were added to a solution of {trans-3-(4-{[4-(hydroxymethyl)-6-(trifluoromethyl)pyridin-2-yl]oxy}piperidin-1-yl)-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (21 mg, 0.031 mmol, Peak 1 from Intermediate Example A2, Step F), in methylene chloride (0.42 mL). The reaction was stirred for 30 minutes and the solvent was removed in vacuo. The residue was dissolved in N,N-dimethylformamide (0.40 mL, 5.2 mmol) and 1H-imidazole (10. mg, 0.15 mmol, Aldrich) and potassium carbonate (13 mg, 0.092 mmol) were added. After stirring for 30 minutes at room temperature, the reaction mixture was heated to 40° C. for 2 hours. The mixture was then diluted with water and extracted with EtOAc. The organic layer was washed twice with water, once with brine, dried over sodium sulfate and concentrated. The crude product was deprotected by stirring in a 1:1 mixture of TFA/DCM for one hour, removing solvents, then stirring in methanol (1 mL), containing ethylenediamine (0.1 mL) until complete as determined by analytical LCMS. Purification via preparative HPLC-MS (C18 eluting with a gradient of MeCN/H$_2$O containing 0.15% NH$_4$OH) afforded the desired compound as the free base (6.4 mg, 34%). $^1$H NMR (400 MHz, d$_6$-DMSO) δ 12.12 (s, 1H), 8.82 (s, 1H), 8.69 (s, 1H), 8.42 (s, 1H), 7.80 (s, 1H), 7.60 (d, J=3.6 Hz, 1H), 7.30 (s, 1H), 7.27 (s, 1H), 7.08 (d, J=3.6 Hz, 1H), 6.96 (s, 1H), 6.72 (s, 1H), 5.31 (s, 2H), 4.98 (tt, J=7.6, 3.4 Hz, 1H), 3.41 (s, 2H), 3.07-2.91 (m, 2H), 2.80 (p, J=7.1 Hz, 1H), 2.71-2.54 (m, 2H), 2.39-2.28 (m, 2H), 2.26-2.06 (m, 2H), 2.06-1.89 (m, 2H), 1.76-1.57 (m, 2H). $^{19}$F NMR (376 MHz, d$_6$-DMSO) δ −67.51 (s). LCMS (M+H)$^+$: 603.2.

Example 23

[trans-1-[4-(7H-pyrrolo[2,3-d]pyrimidin-4-yl)-1H-pyrazol-1-yl]-3-(4-{[4-(1H-1,2,4-triazol-1-ylmethyl)-6-(trifluoromethyl)pyridin-2-yl]oxy}piperidin-1-yl)cyclobutyl]acetonitrile

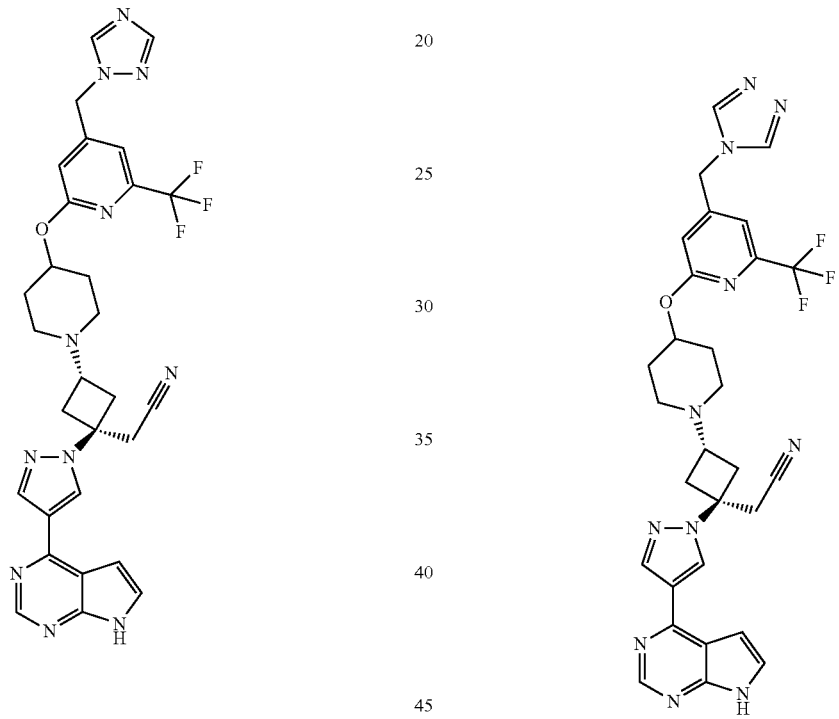

The procedure of Example 22 was followed, using 1H-1,2,4-triazole (11 mg, 0.15 mmol, Aldrich) instead of 1H-imidazole, with heating first to 40° C. for 2 hours, then to 50° C. overnight in the displacement step. Purification via preparative HPLC-MS (C18 eluting with a gradient of MeCN/H$_2$O containing 0.15% NH$_4$OH) afforded separation of the major (peak 2, compound of this Example) and minor isomer (peak 1, see Example 24). Yield: (6.2 mg, 33%). $^1$H NMR (400 MHz, CD$_3$OD) δ 8.73 (s, 1H), 8.67 (s, 1H), 8.63 (s, 1H), 8.40 (s, 1H), 8.06 (s, 1H), 7.51 (d, J=3.6 Hz, 1H), 7.21 (s, 1H), 6.99 (d, J=3.7 Hz, 1H), 6.76 (s, 1H), 5.52 (s, 2H), 5.14 (tt, J=7.8, 4.0 Hz, 1H), 3.31 (s, 2H), 3.16-3.05 (m, 2H), 2.95 (p, J=7.6 Hz, 1H), 2.82-2.63 (m, 2H), 2.55-2.42 (m, 2H), 2.40-2.21 (m, 2H), 2.17-2.02 (m, 2H), 1.92-1.76 (m, 2H). $^{19}$F NMR (376 MHz, CD$_3$OD) δ −70.50 (s). LCMS (M+H)$^+$: 604.2.

Example 24

[trans-1-[4-(7H-pyrrolo[2,3-d]pyrimidin-4-yl)-1H-pyrazol-1-yl]-3-(4-{[4-(4H-1,2,4-triazol-4-ylmethyl)-6-(trifluoromethyl)pyridin-2-yl]oxy}piperidin-1-yl)cyclobutyl]acetonitrile

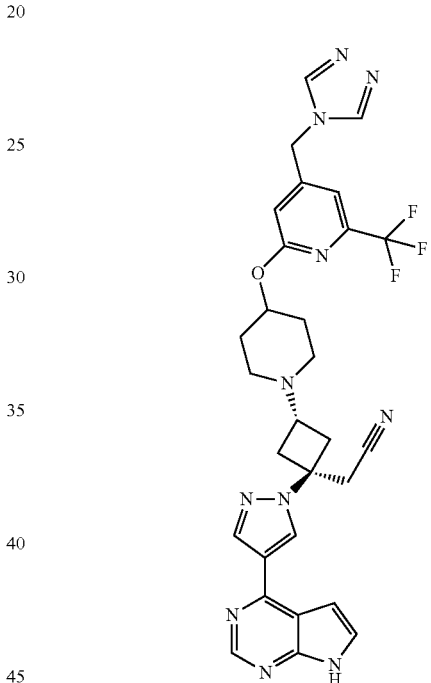

Isolated as the minor product (Peak 1) from the procedure of Example 23 (2.4 mg, 13%). $^1$H NMR (400 MHz, CD$_3$OD) δ 8.73 (s, 1H), 8.67 (s, 1H), 8.65 (s, 2H), 8.40 (s, 1H), 7.51 (d, J=3.6 Hz, 1H), 7.24 (s, 1H), 6.99 (d, J=3.6 Hz, 1H), 6.75 (s, 1H), 5.43 (s, 2H), 5.20-5.04 (m, 1H), 3.31 (s, 2H), 3.17-3.02 (m, 2H), 2.95 (p, J=7.6 Hz, 1H), 2.82-2.63 (m, 2H), 2.55-2.42 (m, 2H), 2.41-2.22 (m, 2H), 2.20-2.01 (m, 2H), 1.95-1.73 (m, 2H). $^{19}$F NMR (376 MHz, CD$_3$OD) δ −70.51 (s). LCMS (M+H)$^+$: 604.2.

Example 25

{trans-3-(4-{[4-(1H-pyrazol-1-ylmethyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile

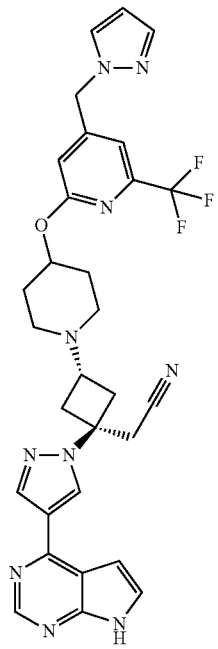 [SMILES: N#CC[C@]1(n2cc(-c3ncnc4[nH]ccc34)cn2)C[C@H](N2CCC(Oc3cc(Cn4cccn4)cc(C(F)(F)F)n3)CC2)C1]

Using 1H-pyrazole (10. mg, 0.15 mmol, Aldrich) as the heterocycle in the displacement step, the procedure of Example 24 was followed to afford the product as the free base (6.6 mg, 36%). $^1$H NMR (400 MHz, d$_6$-DMSO) δ 12.13 (s, 1H), 8.82 (s, 1H), 8.69 (s, 1H), 8.42 (s, 1H), 7.91 (d, J=2.2 Hz, 1H), 7.60 (d, J=3.6 Hz, 1H), 7.54 (d, J=1.4 Hz, 1H), 7.20 (s, 1H), 7.07 (d, J=3.6 Hz, 1H), 6.65 (s, 1H), 6.34 (t, J=2.1 Hz, 1H), 5.46 (s, 2H), 4.98 (tt, J=8.9, 4.1 Hz, 1H), 3.41 (s, 2H), 3.07-2.94 (m, 2H), 2.80 (p, J=157.5 Hz, 1H), 2.69-2.54 (m, 2H), 2.41-2.29 (m, 2H), 2.22-2.04 (m, 2H), 2.05-1.87 (m, 2H), 1.76-1.54 (m, 2H). $^{19}$F NMR (376 MHz, d$_6$-DMSO) δ −67.55 (s). LCMS (M+H)$^+$: 603.3.

Example 26

{trans-3-(4-{[4-[(3,3-dimethylazetidin-1-yl)carbonyl]-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile

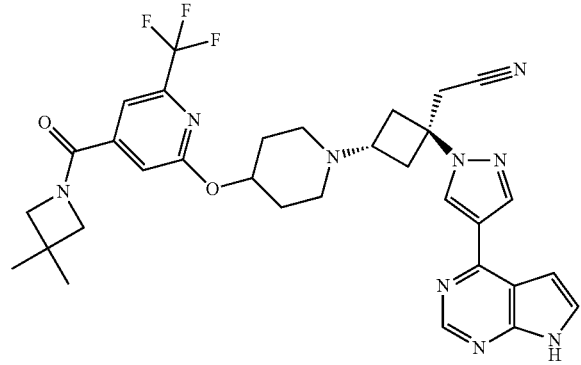 [SMILES: CC1(C)CN(C(=O)c2cc(OC3CCN([C@H]4C[C@](CC#N)(n5cc(-c6ncnc7[nH]ccc67)cn5)C4)CC3)nc(C(F)(F)F)c2)C1]

Step 1. tert-butyl 4-{[4-[(3,3-dimethylazetidin-1-yl)carbonyl)carbonyl]-6-(trifluoromethyl)pyridin-2-yl]oxy}piperidine-1-carboxylate To a solution of 2-{[1-(tert-butoxycarbonyl)piperidin-4-yl]oxy}-6-(trifluoromethyl)isonicotinic acid (0.100 g, 0.256 mmol, from Example 21, Step 2) and 3,3-dimethylazetidine hydrochloride (0.037 g, 0.30 mmol, Princeton Bio) and triethylamine (90 μL, 0.6 mmol) in methylene chloride (1 mL) was added benzotriazol-1-yloxytris(dimethylamino)phosphonium hexafluorophosphate (0.12 g, 0.28 mmol, Advanced Chem Tech). The reaction was stirred overnight. Solvent was removed in vacuo and the product was purified by flash chromatography, eluting with a gradient from 0-3% MeOH in DCM. LCMS (M+Na)$^+$: 480.1.

Step 2. 4-[(3,3-dimethylazetidin-1-yl)carbonyl)carbonyl]-2-(piperidin-4-yloxy)-6-(trifluoromethyl)pyridine tert-Butyl 4-{[4-[(3,3-dimethylazetidin-1-yl)carbonyl]-6-(trifluoromethyl)pyridin-2-yl]oxy}piperidine-1-carboxylate (0.029 g, 0.063 mmol, from Step 2) was dissolved in 1,4-dioxane (1 mL) and 4.0 M hydrogen chloride in dioxane (1 mL, 4 mmol) was added. After stirring for 4 hours, the reaction mixture was poured into saturated sodium bicarbonate and the product was extracted with three portions of ethyl acetate. The combined extracts were dried over sodium sulfate, filtered and concentrated to afford the deprotected piperidine. Theoretical yield was assumed and the product used without further purification in Step 4. LCMS (M+H): 358.2.

Step 3. {trans-3-(4-{[4-[(3,3-dimethylazetidin-1-yl)carbonyl]-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile Sodium cyanoborohydride (0.013 g, 0.21 mmol) and zinc dichloride (0.0142 g, 0.104 mmol) were stirred in methanol (0.400 mL, 9.89 mmol) for 2 hours. The piperidine from Step 3 and {3-oxo-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.027 g, 0.063 mmol, from Intermediate Example A1, Step 7) were stirred in methanol (0.5 mL, 10 mmol) for a few minutes to dissolve. One-third of the NaCNBH$_3$/ZnCl$_2$ solution was added. The reaction was stirred overnight and in the morning, an additional one-third of the reducing mixture was added and the reaction was continued for 5 hours. The resulting cis- and trans-isomers at the SEM protected stage were well separated under the following conditions: Waters mass directed fractionation system as described in (K. Blom, B. Glass, R. Sparks, A. Combs, J. Combi. Chem., 6, 874-883 (2004); Waters XBridge C18 column, 5 um particle size, 30×100 mm, Aq (0.1% NH4OH)/AcN; flow rate 60 mL/min, 49.1-67.1% B in 12 min. Retention time for peak 1 (cis-): 10.85 min, for peak 2 (trans-): 11.90 min. Each isomer was separately subjected to rotary evaporation, then stirred with 1:1 TFA:DCM for 1 hour, evaporated, and stirred with 0.2 mL ethylenediamine in methanol until deprotection was complete. The final products were purified via preparative HPLC-MS (C18, eluting with a gradient of MeCN/H$_2$O containing 0.15% NH$_4$OH) to afford product as the free base. $^1$H NMR (300 MHz, CDCl$_3$) δ 9.29 (s, 1H), 8.82 (s, 1H), 8.47 (s, 1H), 8.32 (s, 1H), 7.41 (d, J=1.0 Hz, 1H), 7.36 (dd, J=3.6, 2.2 Hz, 1H), 7.01 (s, 1H), 6.80 (dd, J=3.6, 1.7 Hz, 1H), 5.30-4.96 (m, 1H), 3.95 (s, 2H), 3.87 (s, 2H), 3.20 (s, 2H), 3.09-2.97 (m, 2H), 2.97-2.83 (m, 1H), 2.72-2.53 (m, 2H), 2.52-2.41 (m, 2H), 2.30-2.13 (m, 2H), 2.13-1.97 (m, 2H), 1.95-1.74 (m, 2H), 1.30 (s, 6H). $^{19}$F NMR (282 MHz, CDCl$_3$) δ −68.98 (s). LCMS (M+H)$^+$: 634.3.

Example 27

{trans-3-(4-{[6-(hydroxymethyl)-2-(trifluoromethyl)pyrimidin-4-yl]amino}piperidin-1-yl)-1-[4-(7H-pyrrolo[2,3-d]pyrimidin-4-yl)-1H-pyrazol-1-yl]cyclobutyl}acetonitrile

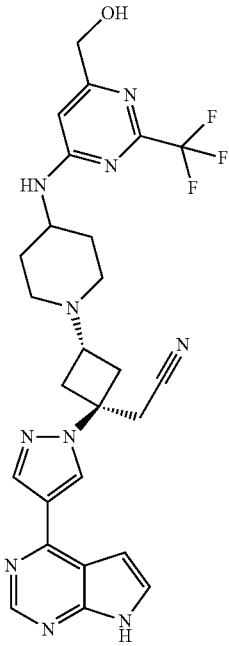

Step 1. tert-butyl 4-{[6-chloro-2-(trifluoromethyl)pyrimidin-4-yl]amino}piperidine-1-carboxylate tert-Butyl 4-aminopiperidine-1-carboxylate (1.4 g, 7.1 mmol, Aldrich) was dissolved in methylene chloride (10. mL) and to this solution was added N,N-diisopropylethylamine (2.5 mL, 14 mmol) and 4,6-dichloro-2-(trifluoromethyl)pyrimidine (1.7 g, 7.8 mmol, Synchem). The reaction was stirred overnight. The mixture was diluted with water and the product was extracted with EtOAc. The organic layer was washed twice with water, once with brine, dried over sodium sulfate, filtered and concentrated to afford product which was used without further purification in Step 2. LCMS (M+H)$^+$: 381.1.

Step 2. tert-butyl 4-{[6-[(Z)-2-ethoxyvinyl]-2-(trifluoromethyl)pyrimidin-4-yl]amino}piperidine-1-carboxylate A mixture of tert-butyl 4-{[6-chloro-2-(trifluoromethyl)pyrimidin-4-yl]amino}piperidine-1-carboxylate (1.0 g, 2.6 mmol, from Step 1), tributyl[(Z)-2-ethoxyvinyl]stannane (0.96 mL, 2.9 mmol, Synthonix Corp.) and tetrakis(triphenylphosphine)palladium(0) (0.15 g, 0.13 mmol, Strem) in toluene (3.0 mL) was degassed and then heated to 110° C. for 3 hours, then lowered to 90° C. overnight. The mixture was concentrated and flash chromatographed on a 120 g silica gel cartridge, eluting with a gradient from 0-20% EtOAc in hexanes to afford product as a white solid (0.8 g, 73%). $^1$H NMR (400 MHz, CDCl$_3$) δ 7.08 (s, 1H), 6.58 (d, J=7.1 Hz, 1H), 5.40 (d, J=7.1 Hz, 1H), 4.98 (br s, 1H), 4.18-4.00 (m, 4H), 3.82 (br s, 1H), 2.94 (t, J=11.7 Hz, 2H), 2.12-1.95 (m, 2H), 1.52-1.31 (m, 14H). $^{19}$F NMR (376 MHz, CDCl$_3$) δ −71.77 (s). LCMS (M+H): 417.2.

Step 3. tert-butyl 4-{[6-formyl-2-(trifluoromethyl)pyrimidin-4-yl]amino}piperidine-1-carboxylate tert-Butyl 4-{[6-[(Z)-2-ethoxyvinyl]-2-(trifluoromethyl)pyrimidin-4-yl]amino}piperidine-1-carboxylate (0.80 g, 1.9 mmol, from Step 2) was dissolved in 1,4-dioxane (56 mL) and water (14 mL), then sodium periodate (1.2 g, 5.8 mmol) was added followed by osmium tetraoxide (4 wt % in water, 0.424 mL, 0.0666 mmol). After stirring for 24 hours, the reaction mixture was partitioned between water and EtOAc, the phases were separated and the aqueous phase was extracted with additional EtOAc. The combined organic extracts were washed with water, then sat'd NaCl, dried over Na$_2$SO$_4$, filtered and solvent removed in vacuo. The crude product was used in the next reaction without purification. LCMS (M+H)$^+$: 375.0; (M+H$_2$O+H)$^+$: 393.0.

Step 4. tert-butyl 4-{[6-(hydroxymethyl)-2-(trifluoromethyl)pyrimidin-4-yl]amino}piperidine-1-carboxylate Sodium tetrahydroborate (73 mg, 1.9 mmol) was added to a solution of tert-butyl 4-{[6-formyl-2-(trifluoromethyl)pyrimidin-4-yl]amino}piperidine-1-carboxylate (0.90 g, 1.9 mmol, from Step 3) in Isopropyl alcohol (15 mL) at 0° C. After stirring at this temperature for 1.5 hours, the reaction was quenched by the addition of saturated ammonium chloride. The mixture was further diluted with water and extracted with EtOAc. The organic extract was washed with water and brine, dried over sodium sulfate, filtered and concentrated. Flash chromatography on a 40 g silica gel cartridge, eluting with a gradient from 0-100% EtOAc in hexanes afforded product as a white solid (0.58 g, 80% over the two steps). $^1$H NMR (400 MHz, CDCl$_3$) δ 6.50 (s, 1H), 4.66 (d, J=5.1 Hz, 2H), 4.30-3.89 (m, 2H), 2.95 (t, J=12.0 Hz, 2H), 2.73 (t, J=5.2 Hz, 1H), 2.22-1.88 (m, 2H), 1.53-1.33 (m, 11H). $^{19}$F NMR (376 MHz, CDCl$_3$) δ −71.74 (s). LCMS (M+H)$^+$: 377.1.

Step 5. [6-(piperidin-4-ylamino)-2-(trifluoromethyl)pyrimidin-4-yl]methanol 4.0 M Hydrogen chloride in dioxane (8.0 mL, 32 mmol) was added to a solution of tert-butyl 4-{[6-(hydroxymethyl)-

2-(trifluoromethyl)pyrimidin-4-yl]amino}piperidine-1-carboxylate (0.58 g, 1.5 mmol, from Step 4) in 1,4-dioxane (3.9 mL) and the mixture was stirred until deprotection was complete as determined by LCMS. The mixture was then quenched by the addition of 1N NaOH to pH 12-13 (pH needs to be high enough for better extraction), and was saturated with solid NaCl. The product was extracted with 6 portions of chloroform, and the combined extracts were dried over sodium sulfate, filtered and concentrated to afford product as a white solid (0.43 g, 91%). $^1$H NMR (400 MHz, CDCl$_3$) δ 6.48 (s, 1H), 4.65 (s, 2H), 3.13 (dt, J=11.9, 2.9 Hz, 2H), 2.81-2.66 (m, 2H), 2.04 (d, J=10.3 Hz, 2H), 1.51-1.31 (m, 2H). $^{19}$F NMR (376 MHz, CDCl$_3$) δ −71.75 (s). LCMS (M+H): 277.1.

Step 6. {cis-3-(4-{[6-(hydroxymethyl)-2-(trifluoromethyl)pyrimidin-4-yl]amino}piperidin-1-yl)-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile and {trans-3-(4-{[6-(hydroxymethyl)-2-(trifluoromethyl)pyrimidin-4-yl]amino}piperidin-1-yl)-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile Sodium cyanoborohydride (64 mg, 1.0 mmol) and zinc dichloride (69 mg, 0.51 mmol) were dissolved in methanol (3.6 mL) and stirred for 2 hours. At this time, [6-(piperidin-4-ylamino)-2-(trifluoromethyl)pyrimidin-4-yl]methanol (0.20 g, 0.72 mmol, from Step 5) and {3-oxo-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.30 g, 0.72 mmol, Intermediate Example A1, Step 7) were combined in methanol (9.1 mL) and stirred for a few minutes to dissolve. The reducing mixture prepared from combining the sodium cyanoborohydride and zinc dichloride was then added and stirred overnight. Purification via preparative HPLC-MS (C18 eluting with a gradient of MeCN/H$_2$O containing 0.15% NH$_4$OH) to give the two isomers: Peak 1, cis-isomer: (64 mg, 13%), LCMS (M+H)$^+$: 683.3; Peak 2, trans-isomer: (62 mg, 12%), LCMS (M+H)$^+$: 683.3.

Step 7. {trans-3-(4-{[6-(hydroxymethyl)-2-(trifluoromethyl)pyrimidin-4-yl]amino}piperidin-1-yl)-1-[4-(7H-pyrrolo[2,3-d]pyrimidin-4-yl)-1H-pyrazol-1-yl]cyclobutyl}acetonitrile {trans-3-(4-{[6-(Hydroxymethyl)-2-(trifluoromethyl)pyrimidin-4-yl]amino}piperidin-1-yl)-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (11 mg, 0.016 mmol, Peak 2 from Step 7) was stirred for 1 hour in a 1:1 mixture of TFA/DCM and solvents were removed in vacuo. The residue was stirred with ethylenediamine (0.1 mL) in methanol (1.0 mL) until deprotection was complete. Purification via preparative HPLC-MS (C18 eluting with a gradient of MeCN/H$_2$O containing 0.15% NH$_4$OH) afforded the desired product as the free base (5.9 mg, 66%). $^1$H NMR (400 MHz, d$_6$-DMSO, rotamers) δ 12.13 (s, 1H), 8.83 (s, 1H), 8.69 (s, 1H), 8.42 (s, 1H), 8.11-8.00 (m, 0.2H), 7.94 (d, J=7.3 Hz, 0.8H), 7.60 (d, J=3.6 Hz, 1H), 7.08 (d, J=3.6 Hz, 1H), 6.75 (s, 0.8H), 6.69 (s, 0.2H), 5.55 (s, 1H), 4.45-4.28 (m, 2H), 3.82 (s, 1H), 3.41 (s, 2H), 3.12-2.92 (m, 2H), 2.92-2.68 (m, 3H), 2.40-2.19 (m, 2H), 2.04-1.77 (m, 4H), 1.66-1.32 (m, 2H). $^{19}$F NMR (376 MHz, d$_6$-DMSO) δ −70.05 (s), −70.23 (s). LCMS (M+H)$^+$: 553.2.

Example 28

{trans-3-(4-{[6-[(ethylamino)methyl]-2-(trifluoromethyl)pyrimidin-4-yl]amino}piperidin-1-yl)-1-[4-(7H-pyrrolo[2,3-d]pyrimidin-4-yl)-1H-pyrazol-1-yl]cyclobutyl}acetonitrile

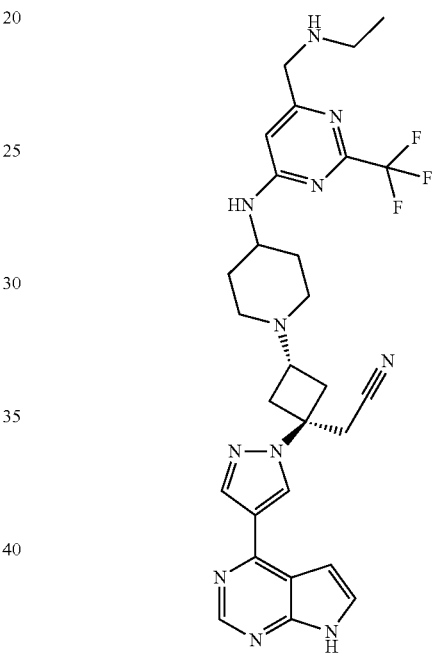

N,N-Diisopropylethylamine (14 µL, 0.082 mmol) and methanesulphonic anhydride (12 mg, 0.070 mmol, Aldrich) were added to a solution of {trans-3-(4-{[6-(hydroxymethyl)-2-(trifluoromethyl)pyrimidin-4-yl]amino}piperidin-1-yl)-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (16 mg, 0.023 mmol) (Peak 2 from Example 27, Step 6) in methylene chloride (0.32 mL). After stirring for 30 minutes, solvent was removed in vauco and replaced by Tetrahydrofuran (0.32 mL). Ethylamine (6.6 µL, 0.12 mmol, Aldrich) and methanol (0.13 mL) were added and the mixture was stirred for 2 hours at room temperature. Solvent was removed in vacuo and the crude product was deprotected first by stirring in a 1:1 mixture of TFA/DCM for 1 hour, followed by removal of solvents, then stirring with ethylenediamine (0.15 mL) in methanol (1.0 mL) until deprotection was complete as determined by LCMS. Purification via preparative HPLC-MS (C18 eluting with a gradient of MeCN/H$_2$O containing 0.15% NH$_4$OH) afforded product as the free base (4.6 mg, 34%). $^1$H NMR (400 MHz, d$_6$-DMSO, rotamers) δ 12.13 (s, 1H), 8.83 (s, 1H), 8.69 (s, 1H), 8.42 (s, 1H), 8.04-7.94 (m, 0.2H), 7.89 (d, J=7.4 Hz, 0.8H), 7.60 (d, J=3.6 Hz, 1H), 7.08 (d, J=3.6 Hz, 1H), 6.73 (s, 1H), 3.90-3.73 (m, 1H), 3.59 (s, 2H), 3.41 (s, 2H), 3.13-2.92 (m, 2H), 2.92-2.65 (m, 3H), 2.55 (q, J=7.1 Hz, 2H), 2.40-2.27 (m, 2H), 2.21 (br s, J=22.0 Hz, 1H), 2.02-1.76 (m, 4H), 1.60-1.34 (m, 2H), 1.03 (t, J=7.1 Hz, 3H). $^{19}$F NMR (376 MHz, d$_6$-DMSO) δ −70.01 (s), −70.18 (s). LCMS (M+H)$^+$: 580.3.

Example 29

{trans-3-(4-{[6-{[(2-hydroxyethyl)amino]methyl}-2-(trifluoromethyl)pyrimidin-4-yl]amino}piperidin-1-yl)-1-[4-(7H-pyrrolo[2,3-d]pyrimidin-4-yl)-1H-pyrazol-1-yl]cyclobutyl}acetonitrile

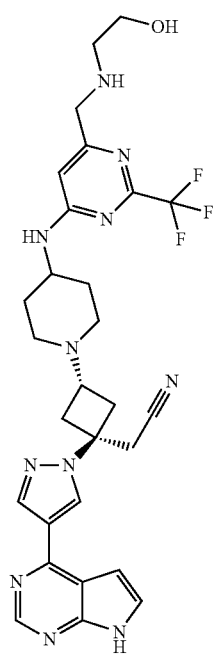 [SMILES: N#CC[C@]1(n2cc(-c3ncnc4[nH]ccc34)cn2)C[C@H](N2CCC(Nc3cc(CNCCO)nc(C(F)(F)F)n3)CC2)C1]

Prepared according to the procedure of Example 28, using ethanolamine (7.1 µL, 0.12 mmol, Aldrich) in the displacement step, which was carried out at 40° C. for 2 hours. Yield: (5.9 mg, 42%). $^1$H NMR (400 MHz, d$_6$-DMSO, rotamers) δ 12.13 (s, 1H), 8.83 (s, 1H), 8.69 (s, 1H), 8.42 (s, 1H), 7.99 (d, J=7.6 Hz, 0.2H), 7.90 (d, J=7.2 Hz, 0.8H), 7.60 (d, J=3.6 Hz, 1H), 7.08 (d, J=3.6 Hz, 1H), 6.77 (s, 0.2H), 6.72 (s, 0.8H), 4.53 (t, J=5.3 Hz, 1H), 3.81 (s, 0H), 3.62 (s, 2H), 3.47 (q, J=5.5 Hz, 2H), 3.41 (s, 2H), 3.11-2.92 (m, 2H), 2.90-2.70 (m, 3H), 2.59 (t, J=5.7 Hz, 2H), 2.40-2.12 (m, 2H), 2.03-1.76 (m, 4H), 1.63-1.34 (m, 2H). $^{19}$F NMR (376 MHz, d$_6$-DMSO) δ −70.00 (s), −70.18 (s). LCMS (M+H)$^+$: 596.3.

Example 30

{trans-3-(4-{[6-{[(trans-3-hydroxycyclobutyl)amino]methyl}-2-(trifluoromethyl)pyrimidin-4-yl]amino}piperidin-1-yl)-1-[4-(7H-pyrrolo[2,3-d]pyrimidin-4-yl)-1H-pyrazol-1-yl]cyclobutyl}acetonitrile

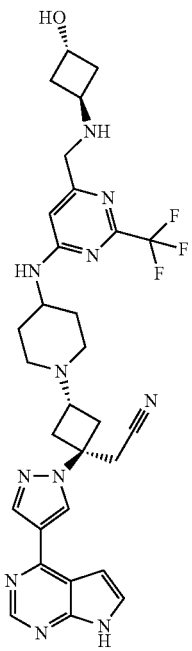 [SMILES: N#CC[C@]1(n2cc(-c3ncnc4[nH]ccc34)cn2)C[C@H](N2CCC(Nc3cc(CN[C@H]4C[C@H](O)C4)nc(C(F)(F)F)n3)CC2)C1]

Prepared according to the procedure of Example 28, using trans-3-aminocyclobutanol hydrochloride (14 mg, 0.12 mmol, Advanced Chem Blocks) and diisopropylethylamine (0.020 mL, 0.12 mmol) in the displacement step, which was carried out at 40° C. for 2 hours. Yield: (4.2 mg, 29%). $^1$H NMR (400 MHz, d$_6$-DMSO, rotamers) δ 12.13 (s, 1H), 8.83 (s, 1H), 8.69 (s, 1H), 8.42 (s, 1H), 7.98 (d, J=8.0 Hz, 0.2H), 7.90 (d, J=7.3 Hz, 0.8H), 7.60 (d, J=3.6 Hz, 1H), 7.08 (d, J=3.6 Hz, 1H), 6.73 (s, 1H), 4.88 (d, J=5.7 Hz, 1H), 4.37-4.16 (m, 1H), 3.81 (s, 1H), 3.49 (s, 2H), 3.41 (s, 2H), 3.32-3.14 (m, 1H), 3.09-2.93 (m, 2H), 2.93-2.69 (m, 3H), 2.49-2.26 (m, 3H), 2.04-1.77 (m, 8H), 1.62-1.36 (m, 2H). $^{19}$F NMR (376 MHz, d$_6$-DMSO) δ −70.00 (s), −70.17 (s). LCMS (M+H)$^+$: 622.3.

Example 31

{trans-3-(4-{[4-(hydroxymethyl)-6-(trifluoromethyl)pyridin-2-yl]amino}piperidin-1-yl)-1-[4-(7H-pyrrolo[2,3-d]pyrimidin-4-yl)-1H-pyrazol-1-yl]cyclobutyl}acetonitrile

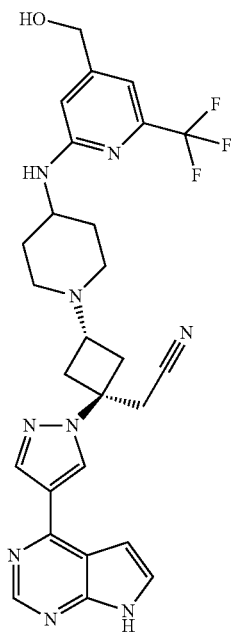 [SMILES: N#CC[C@]1(n2cc(-c3ncnc4[nH]ccc34)cn2)C[C@H](N2CCC(Nc3cc(CO)cc(C(F)(F)F)n3)CC2)C1]

Step 1. tert-butyl 2-{[1-(tert-butoxycarbonyl)piperidin-4-yl]amino}-6-(trifluoromethyl)isonicotinate A solution of tert-butyl 2-chloro-6-(trifluoromethyl)isonicotinate (3.0 g, 11 mmol, Example 21, Step 1), tert-butyl 4-aminopiperidine-1-carboxylate (4.3 g, 21 mmol, Aldrich) and N,N-diisopropylethylamine (3.7 mL, 21 mmol) in dimethyl sulfoxide (9.2 mL) was heated to 100° C. for 20 hours. The mixture was cooled to room temperature and diluted with EtOAc. The combined organic extracts were washed with water (3 times) and brine, dried over sodium sulfate, filtered and concentrated. Flash chromatography using a 120 g silica gel cartridge and eluting with a gradient from 0-15% EtOAc in hexanes afforded product as a white solid (3.4 g, 72%). LCMS (M+Na)$^+$: 468.2.

Step 2. 2-{[1-(tert-butoxycarbonyl)piperidin-4-yl]amino}-6-(trifluoromethyl)isonicotinic acid tert-Butyl 2-{[1-(tert-butoxycarbonyl)piperidin-4-yl]amino}-6-(trifluoromethyl)isonicotinate (3.4 g, 7.6 mmol, from Step 1) was treated with potassium hydroxide (3.4 g, 61 mmol) in tetrahydrofuran (50. mL). After 2 hours, the mixture was acidified to pH 2-3 by the addition of 1.0 N HCl. Brine (50 mL) was also added and the product was extracted with three 50 mL portions of chloroform. The extracts were dried over sodium sulfate, filtered and concentrated to afford product as a light yellow powder (2.8 g, 94%). LCMS (M+Na)$^+$: 412.0.

Step 3. tert-butyl 4-{[4-(hydroxymethyl)-6-(trifluoromethyl)pyridin-2-yl]amino}piperidine-1-carboxylate Isobutyl chloroformate (1.1 mL, 8.6 mmol) was added to a solution of 2-{[1-(tert-butoxycarbonyl)piperidin-4-yl]amino}-6-(trifluoromethyl)isonicotinic acid (2.8 g, 7.2 mmol, from Step 2) and triethylamine (2.0 mL, 14 mmol) in tetrahydrofuran (30. mL) at 0° C. After stirring for 30 minutes, the reaction mixture was filtered through a short pad of celite into a flask containing a mixture of sodium tetrahydroborate (0.95 g, 25 mmol) in water (15 mL) at 0° C. The celite pad was rinsed with three portions of THF (3×30 mL) into the reaction flask. The reaction was allowed to warm to room temperature and stir for 1 hour. The reaction mixture was recooled in an ice bath and was quenched by the addition of saturated ammonium chloride solution. The product was extracted with a 150 mL portion of ethyl acetate. The organic layer was washed with water and brine, was dried over sodium sulfate, filtered and concentrated. Flash chromatography, using a 120 g silica gel cartridge and eluting with a gradient from 0-80% EtOAc in hexanes afforded product as a white solid (2.7 g, 100%). $^1$H NMR (400 MHz, CDCl$_3$) δ 6.87 (s, 1H), 6.56 (s, 1H), 5.02-4.36 (m, 2H), 4.09-3.94 (m, 2H), 3.81 (dtt, J=14.2, 8.0, 3.9 Hz, 1H), 3.03-2.85 (m, 2H), 2.07-1.97 (m, 2H), 1.46 (s, 9H), 1.37 (qd, J=12.2, 3.8 Hz, 2H). $^{19}$F NMR (376 MHz, CDCl$_3$) δ −69.21 (s). LCMS (M+Na)$^+$: 398.0.

Step 4. [2-(piperidin-4-ylamino)-6-(trifluoromethyl)pyridin-4-yl]methanol 4.0 M Hydrogen chloride in dioxane (36 mL, 140 mmol) was added to a solution of tert-butyl 4-{[4-(hydroxymethyl)-6-(trifluoromethyl)pyridin-2-yl]amino}piperidine-1-carboxylate (2.7 g, 7.2 mmol, from Step 3) in 1,4-dioxane (18 mL). After stirring for 30 minutes, the mixture was then basified to pH 12-13 by the addition of 1.0 N NaOH. The product was extracted with DCM (6×). The combined organic extracts were dried over sodium sulfate, filtered and concentrated to afford the product as a white powder (1.64 g, 83%). $^1$H NMR (400 MHz, d$_6$-DMSO) δ 6.94 (d, J=7.6 Hz, 1H), 6.77 (s, 1H), 6.67 (s, 1H), 5.39 (t, J=5.8 Hz, 1H), 4.42 (d, J=5.5 Hz, 2H), 3.76-3.60 (m, 1H), 2.92 (dt, J=12.4, 3.3 Hz, 2H), 2.57-2.43 (m, 2H), 1.87-1.77 (m, 2H), 1.25 (qd, J=11.8, 3.8 Hz, 2H). $^{19}$F NMR (376 MHz, d$_6$-DMSO) δ −67.68 (s). LCMS (M+H)$^+$: 276.1.

Step 5. {cis-3-(4-{[4-(hydroxymethyl)-6-(trifluoromethyl)pyridin-2-yl]amino}piperidin-1-yl)-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile and {trans-3-(4-{[4-(hydroxymethyl)-6-(trifluoromethyl)pyridin-2-yl]amino}piperidin-1-yl)-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile A reducing mixture was generated by combining sodium cyanoborohydride (0.27 g, 4.4 mmol) and zinc dichloride (0.30 g, 2.2 mmol) in methanol (25 mL) and stirring for 2 hours). {3-oxo-1-[4-{7-{[2-(trimethylsilyl)ethoxy]methyl}-7H-pyrrolo[2,3-d]pyrimidin-4-yl)-1H-pyrazol-1-yl]cyclobutyl}acetonitrile (1.5 g, 3.5 mmol, Intermediate Example A1, Step 7) and [2-(piperidin-4-ylamino)-6-(trifluoromethyl)pyridin-4-yl]methanol (1.0 g, 2.9 mmol, from Step 4) were combined in methanol (52 mL) and stirred for a few minutes just to dissolve. The reducing mixture was then added and the reaction was continued for 1 hour. Additional {3-oxo-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.24 g, 0.58 mmol) was then added and the reaction continued for 3 additional hours. Saturated sodium bicarbonate was added to the mixture and then the mixture was diluted with additional water. The product was then extracted with a mixture of EtOAc/DCM. The combined organic extracts were washed twice with water, once with brine, dried over sodium sulfate, filtered and concentrated. Flash chromatography using a 120 g silica gel cartridge and eluting with a slow gradient from 0-10% MeOH in EtOAc afforded separation of the diastereomers (Peak 1, cis-: 0.59 g 30%; Peak 2 trans-0.54 g, 27%). Peak 1, Cis-isomer: LCMS (M+H)+: 682.1. Peak 2, Trans-isomer: LCMS (M+H)+: 682.2. Alternatively, the isomers could be separated using preparative HPLC-MS (C18 eluting with a gradient of MeCN and H$_2$O containing 0.15% NH$_4$OH) to afford Peak 1, cis-isomer and Peak 2, trans-isomer.

Step 6. {trans-3-(4-{[4-(hydroxymethyl)-6-(trifluoromethyl)pyridin-2-yl]amino}piperidin-1-yl)-1-[4-(7H-pyrrolo[2,3-d]pyrimidin-4-yl)-1H-pyrazol-1-yl]cyclobutyl}acetonitrile Each isomer from Step 5 was deprotected separately by stirring in a solution of 1:1 TFA/DCM for one hour, evaporation of solvents, and stirring with ethylenediamine (0.1 mL) in MeOH (1.0 mL) until the deprotection was complete. Purification of the final deprotected products using preparative HPLC-MS (C18 eluting with a gradient of MeCN and H$_2$O containing 0.15% NH$_4$OH) afforded the desired products as the free base. Cis: $^1$H NMR (400 MHz, d$_6$-DMSO) δ 12.11 (br s, 1H), 8.68 (s, 1H), 8.67 (s, 1H), 8.38 (s, 1H), 7.59 (d, J=3.5 Hz, 1H), 7.05 (d, J=3.5 Hz, 1H), 6.96 (d, J=7.4 Hz, 1H), 6.77 (s, 1H), 6.66 (s, 1H), 5.38 (br, 1H), 4.41 (s, 2H), 3.64 (br, 1H), 3.45 (s, 2H), 2.87 (p, J=7.6 Hz, 1H), 2.82-2.68 (m, 2H), 2.62-2.52 (m, 4H), 2.02-1.71 (m, 4H), 1.46-1.29 (m, 2H). $^{19}$F NMR (376 MHz, d$_6$-DMSO) δ −67.67 (s). LCMS (M+H)+: 552.2. Trans: $^1$H NMR (400 MHz, d$_6$-DMSO) δ 12.11 (br s, 1H), 8.83 (s, 1H), 8.69 (s, 1H), 8.42 (s, 1H), 7.60 (d, J=3.6 Hz, 1H), 7.08 (d, J=3.6 Hz, 1H), 6.98 (d, J=7.5 Hz, 1H), 6.79 (s, 1H), 6.68 (s, 1H), 5.40 (br s, 1H), 4.43 (s, 2H), 3.65 (br s, 1H), 3.41 (s, 2H), 3.05-2.96 (m, 2H), 2.89-2.70 (m, 3H), 2.41-2.27 (m, 2H), 1.98-1.82 (m, 4H), 1.51-1.35 (m, 2H). $^{19}$F NMR (376 MHz, d$_6$-DMSO) δ −67.68 (s). LCMS (M+H)+: 552.2.

Example 32

{trans-3-(4-{[4-[(ethylamino)methyl]-6-(trifluoromethyl)pyridin-2-yl]amino}piperidin-1-yl)-1-[4-(7H-pyrrolo[2,3-d]pyrimidin-4-yl)-1H-pyrazol-1-yl]cyclobutyl}acetonitrile

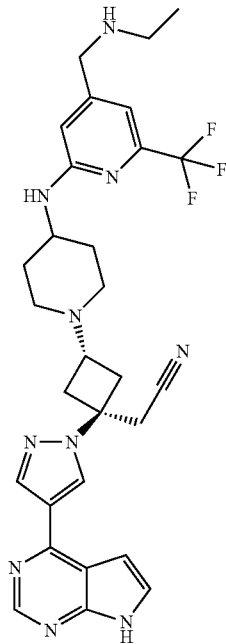 [SMILES: CCNCc1cc(NC2CCN([C@H]3C[C@](CC#N)(n4cc(-c5ncnc6[nH]ccc56)cn4)C3)CC2)nc(C(F)(F)F)c1]

Methanesulphonic anhydride (12 mg, 0.070 mmol, Aldrich) and N,N-diisopropylethylamine (14 μL, 0.082 mmol) were added to a solution of {trans-3-(4-{[4-(hydroxymethyl)-6-(trifluoromethyl)pyridin-2-yl]amino}piperidin-1-yl)-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (16 mg, 0.023 mmol, Peak 2 from Example 31, Step 5) in methylene chloride (0.32 mL). After stirring for 30 minutes, solvent was removed in vacuo and replaced with tetrahydrofuran (0.32 mL) and methanol (0.13 mL) and ethylamine (6.6 μL, 0.12 mmol, Aldrich) was added. The mixture was stirred at room temperature for 1.5 hours. Solvent was again removed in vacuo and the crude product was deprotected by stirring in a 1:1 mixture of TFA/DCM for one hour, followed by evaporation and stirring with ethylenediamine (0.2 mL) in methanol (1.0 mL) until deprotection was complete as determined by analytical LCMS. Purification via preparative HPLC-MS (C18 eluting with a gradient of MeCN and H$_2$O containing 0.15% NH$_4$OH) afforded the product as the free base (8.4 mg, 62%). $^1$H NMR (300 MHz, d$_6$-DMSO) δ 12.11 (br s, 1H), 8.83 (s, 1H), 8.69 (s, 1H), 8.42 (s, 1H), 7.60 (d, J=3.5 Hz, 1H), 7.08 (d, J=3.6 Hz, 1H), 6.93 (d, J=7.5 Hz, 1H), 6.85 (s, 1H), 6.67 (s, 1H), 3.76-3.52 (m, 3H), 3.41 (s, 2H), 3.09-2.91 (m, 2H), 2.90-2.67 (m, 3H), 2.46 (q, J=7.1 Hz, 2H), 2.41-2.22 (m, 2H), 2.01-1.75 (m, 4H), 1.54-1.27 (m, 2H), 1.01 (t, J=7.1 Hz, 3H). $^{19}$F NMR (282 MHz, d$_6$-DMSO) δ −67.58 (s). LCMS (M+H)+: 579.3.

101
Example 33

{trans-3-(4-{[4-{[(2-hydroxyethyl)amino]methyl}-6-(trifluoromethyl)pyridin-2-yl]amino}piperidin-1-yl)-1-[4-(7H-pyrrolo[2,3-d]pyrimidin-4-yl)-1H-pyrazol-1-yl]cyclobutyl}acetonitrile

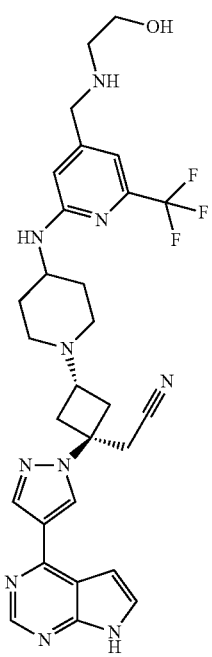

Prepared according to the procedure of Example 32 using ethanolamine (7.1 µL, 0.12 mmol, Aldrich) in the displacement step, which was carried out at 40° C. for 1.5 hours. Yield: (6.7 mg, 48%). $^1$H NMR (300 MHz, $d_6$-DMSO) δ 12.07 (br s, 1H), 8.83 (s, 1H), 8.69 (s, 1H), 8.42 (s, 1H), 7.60 (d, J=3.6 Hz, 1H), 7.08 (d, J=3.6 Hz, 1H), 6.93 (d, J=7.4 Hz, 1H), 6.85 (s, 1H), 6.68 (s, 1H), 4.49 (t, J=5.3 Hz, 1H), 3.63 (s, 2H), 3.45 (q, J=5.6 Hz, 2H), 3.41 (s, 2H), 3.11-2.91 (m, 2H), 2.90-2.63 (m, 3H), 2.52 (q, J=5.9 Hz, 2H), 2.41-2.26 (m, 2H), 2.02-1.77 (m, 4H), 1.43 (q, J=10.3 Hz, 2H). $^{19}$F NMR (282 MHz, $d_6$-DMSO) δ −67.58 (s). LCMS (M+H)$^+$: 595.3.

102
Example 34

{trans-3-(4-{[4-{[(trans-3-hydroxycyclobutyl)amino]methyl}-6-(trifluoromethyl)pyridin-2-yl]amino}piperidin-1-yl)-1-[4-(7H-pyrrolo[2,3-d]pyrimidin-4-yl)-1H-pyrazol-1-yl]cyclobutyl}acetonitrile

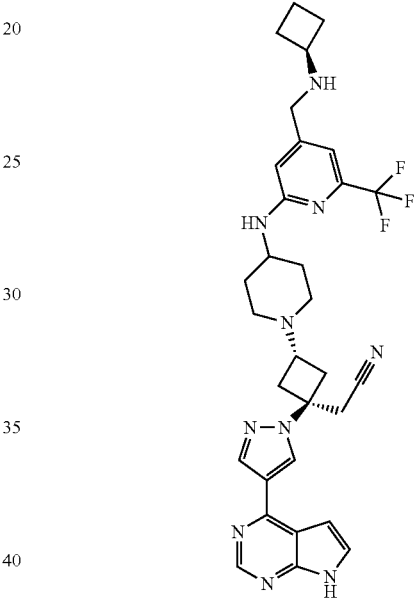

Prepared according to the procedure of Example 32 using trans-3-aminocyclobutanol hydrochloride (28 mg, 0.24 mmol, Advanced Chem Blocks) and diisopropylethylamine (0.04 mL, 0.24 mmol) in the displacement step, which was carried out at 40° C. overnight. Yield: (4.2 mg, 29%). $^1$H NMR (300 MHz, $d_6$-DMSO) δ 8.83 (s, 1H), 8.69 (s, 1H), 8.42 (s, 1H), 7.60 (d, J=3.6 Hz, 1H), 7.08 (d, J=3.6 Hz, 1H), 6.93 (d, J=7.5 Hz, 1H), 6.83 (s, 1H), 6.66 (s, 1H), 4.85 (d, J=5.1 Hz, 1H), 4.24 (h, J=6.3, 5.8 Hz, 1H), 3.76-3.55 (m, 1H), 3.49 (s, 2H), 3.41 (s, 2H), 3.20 (tt, J=7.7, 4.3 Hz, 1H), 3.07-2.91 (m, 2H), 2.91-2.69 (m, 3H), 2.40-2.27 (m, 2H), 2.08-1.81 (m, 8H), 1.43 (q, J=10.4, 10.0 Hz, 2H). $^{19}$F NMR (282 MHz, $d_6$-DMSO) δ −67.57 (s). LCMS (M+H)$^+$: 621.3.

Example 35

{trans-3-(4-{[4-[(3,3-dimethylazetidin-1-yl)methyl]-6-(trifluoromethyl)pyridin-2-yl]amino}piperidin-1-yl)-1-[4-(7H-pyrrolo[2,3-d]pyrimidin-4-yl)-1H-pyrazol-1-yl]cyclobutyl}acetonitrile

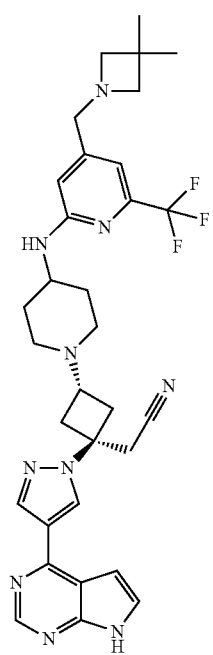 [SMILES: CC1(C)CN(Cc2cc(NC3CCN([C@H]4C[C@](CC#N)(n5cc(-c6ncnc7[nH]ccc67)cn5)C4)CC3)nc(C(F)(F)F)c2)C1]

N,N-diisopropylethylamine (15 µL, 0.088 mmol) and methanesulphonic anhydride (13 mg, 0.073 mmol, Aldrich) were added to a solution of {trans-3-(4-{[4-(hydroxymethyl)-6-(trifluoromethyl)pyridin-2-yl]amino}piperidin-1-yl)-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (20. mg, 0.029 mmol, Peak 2 from Example 31, Step 5) in methylene chloride (0.40 mL). After stirring for 30 minutes, solvent was removed in vacuo and replaced with tetrahydrofuran (0.19 mL) and methanol (0.19 mL). N,N-diisopropylethylamine (51 µL, 0.29 mmol) and 3,3-dimethylazetidine hydrochloride (18 mg, 0.15 mmol, Princeton Bio) were added and the reaction was heated to 40° C. for 1 hour. The mixture was then concentrated on the rotovap. The crude product was deprotected by stirring in 1:1 TFA/DCM for one hour, concentrating and then stirring in methanol (2.0 mL) with ethylenediamine (0.40 mL). Purification via preparative HPLC-MS (C18 eluting with a gradient of MeCN and $H_2O$ containing 0.15% $NH_4OH$) afforded the product as the free base (7.3 mg, 40%). $^1$H NMR (400 MHz, $d_6$-DMSO) δ 12.13 (br s, 1H), 8.83 (s, 1H), 8.69 (s, 1H), 8.42 (s, 1H), 7.60 (d, J=3.6 Hz, 1H), 7.08 (d, J=3.6 Hz, 1H), 6.98 (d, J=7.3 Hz, 1H), 6.72 (s, 1H), 6.62 (s, 1H), 3.71-3.57 (m, 1H), 3.48 (s, 2H), 3.41 (s, 2H), 3.07-2.95 (m, 2H), 2.90 (s, 4H), 2.85-2.70 (m, 3H), 2.40-2.26 (m, 2H), 2.01-1.80 (m, 4H), 1.42 (q, J=10.3 Hz, 2H), 1.18 (s, 6H). $^{19}$F NMR (376 MHz, $d_6$-DMSO) δ −67.67 (s). LCMS (M+H)$^+$: 619.4.

Example 36

{trans-3-(4-{[4-[(3,3-difluoropyrrolidin-1-yl)methyl]-6-(trifluoromethyl)pyridin-2-yl]amino}piperidin-1-yl)-1-[4-(7H-pyrrolo[2,3-d]pyrimidin-4-yl)-1H-pyrazol-1-yl]cyclobutyl}acetonitrile

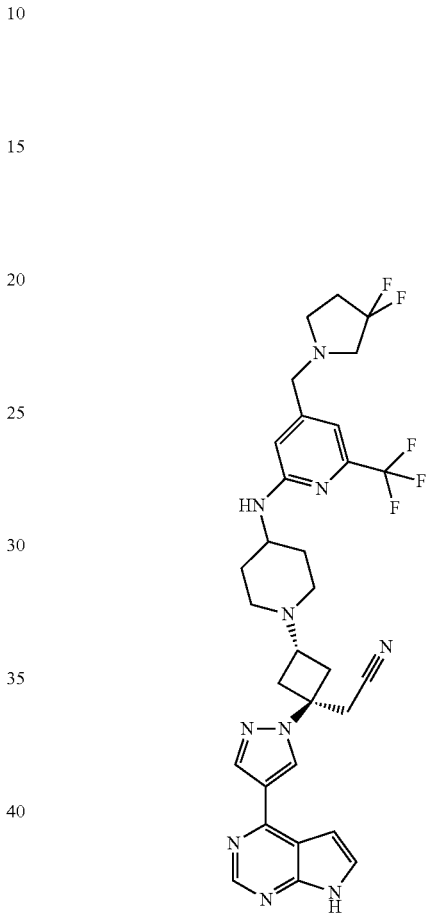

Prepared by the method of Example 35, using 3,3-difluoropyrrolidine hydrochloride (21 mg, 0.15 mmol, Matrix) and N,N-diisopropylethylamine (51 µL, 0.29 mmol) in the displacement step. Yield: (8.8 mg, 47%). $^1$H NMR (400 MHz, $d_6$-DMSO) δ 12.10 (br s, 1H), 8.83 (s, 1H), 8.69 (s, 1H), 8.42 (s, 1H), 7.60 (d, J=3.6 Hz, 1H), 7.08 (d, J=3.6 Hz, 1H), 7.04 (d, J=7.3 Hz, 1H), 6.79 (s, 1H), 6.67 (s, 1H), 3.66 (br s, 1H), 3.56 (s, 2H), 3.41 (s, 2H), 3.10-2.95 (m, 2H), 2.89 (t, J=13.3 Hz, 2H), 2.84-2.74 (m, 3H), 2.71 (t, J=7.0 Hz, 2H), 2.38-2.19 (m, 4H), 2.05-1.62 (m, 4H), 1.43 (q, J=10.4 Hz, 2H). $^{19}$F NMR (376 MHz, $d_6$-DMSO) δ −67.69 (s), −91.33 (p, J=15.2, 14.7 Hz). LCMS (M+H)$^+$: 641.3.

Example 37

{trans-3-(4-{[4-{[cyclopropyl(methyl)amino]methyl}-6-(trifluoromethyl)pyridin-2-yl]amino}piperidin-1-yl)-1-[4-(7H-pyrrolo[2,3-d]pyrimidin-4-yl)-1H-pyrazol-1-yl]cyclobutyl}acetonitrile

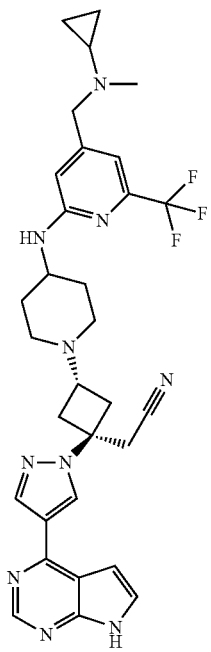 [SMILES: CN(Cc1cc(NC2CCN([C@H]3C[C@](CC#N)(n4cc(-c5ncnc6[nH]ccc56)cn4)C3)CC2)nc(C(F)(F)F)c1)C1CC1]

Prepared by the method of Example 35, using N-methylcyclopropanamine hydrochloride (16 mg, 0.15 mmol, Accela ChemBio) and N,N-diisopropylethylamine (51 µL, 0.29 mmol) in the displacement step. Yield: (7.8 mg, yield 44%). $^{1}$H NMR (400 MHz, d$_{6}$-DMSO) δ 12.10 (br s, 1H), 8.83 (s, 1H), 8.69 (s, 1H), 8.42 (s, 1H), 7.60 (d, J=3.6 Hz, 1H), 7.08 (d, J=3.6 Hz, 1H), 6.98 (d, J=7.4 Hz, 1H), 6.73 (s, 1H), 6.61 (s, 1H), 3.72-3.59 (m, 1H), 3.54 (s, 2H), 3.41 (s, 2H), 3.09-2.92 (m, 2H), 2.86-2.70 (m, 3H), 2.39-2.27 (m, 2H), 2.16 (s, 3H), 2.01-1.81 (m, 4H), 1.76 (tt, J=6.6, 3.6 Hz, 1H), 1.42 (q, J=10.6 Hz, 2H), 0.50-0.42 (m, 2H), 0.37-0.31 (m, 2H). $^{19}$F NMR (376 MHz, d$_{6}$-DMSO) δ –67.62 (s). LCMS (M+H)$^{+}$: 605.3.

Example 38

{cis-3-(4-{[4-(2-hydroxyethyl)-6-(trifluoromethyl)pyridin-2-yl]amino}piperidin-1-yl)-1-[4-(7H-pyrrolo[2,3-d]pyrimidin-4-yl)-1H-pyrazol-1-yl]cyclobutyl}acetonitrile and {trans-3-(4-{[4-(2-hydroxyethyl)-6-(trifluoromethyl)pyridin-2-yl]amino}piperidin-1-yl)-1-[4-(7H-pyrrolo[2,3-d]pyrimidin-4-yl)-1H-pyrazol-1-yl]cyclobutyl}acetonitrile

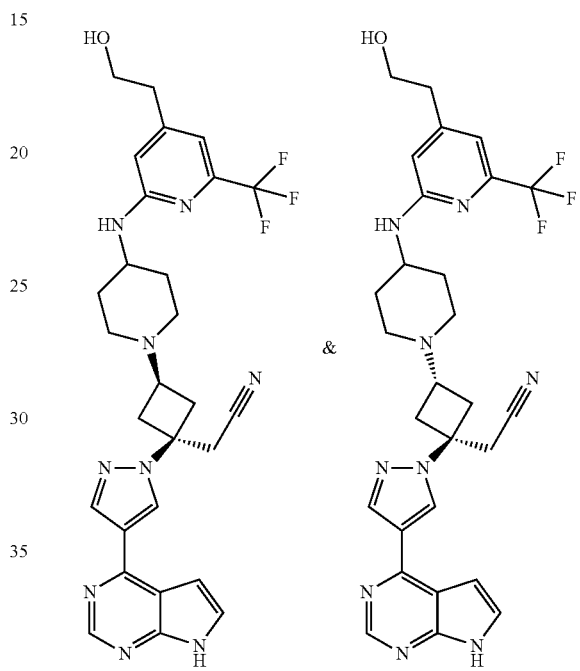

Step 1. 2-[2-chloro-6-(trifluoromethyl)pyridin-4-yl]ethanol

2-Chloro-4-iodo-6-(trifluoromethyl)pyridine (0.50 g, 1.6 mmol, *European Journal of Organic Chemistry*, (18), 3793-3798, 2004) was dissolved in tetrahydrofuran (9.0 mL) and cooled to –78° C. 2.5 M n-Butyllithium in hexanes (0.98 mL, 2.4 mmol) was added dropwise. The reaction was stirred at –78° C. for 45 minutes, at which time 1,3,2-dioxathiolane 2,2-dioxide (0.24 g, 2.0 mmol, Aldrich) in Tetrahydrofuran (2.2 mL) was added. The mixture was then allowed to warm to ambient temperature and stir over 1.5 hours. 12.0 M hydrogen chloride in water (0.81 mL, 9.8 mmol) was added to the mixture and the reaction was stirred overnight. 1N NaOH was then added to achieve a pH between 8 and 9, and brine was also added. The product was extracted with EtOAc, and the organic layer was dried over sodium sulfate, filtered and concentrated. Flash chromatography using a 40 g silica gel cartridge, eluting with a gradient from 0-40% EtOAc in hexanes afforded product as a mixture of isomers, which contained about 50% of the desired isomer (0.09 g, 24%). LCMS (M+H)$^{+}$: 226.0/228.1.

Step 2. 2-[2-(piperidin-4-ylamino)-6-(trifluoromethyl)pyridin-4-yl]ethanol

A mixture of 2-[2-chloro-6-(trifluoromethyl)pyridin-4-yl]ethanol (0.085 g, 0.38 mmol, from Step 1), tert-butyl 4-aminopiperidine-1-carboxylate (0.30 g, 1.5 mmol) and N,N-diisopropylethylamine (0.16 mL, 0.94 mmol) in dimethyl sulfoxide (0.86 mL) was heated in the microwave to 100° C. for one hour, then to 140° C. for 140 minutes. The reaction mixture was concentrated. The residue was dissolved in 1,4-dioxane (2.8 mL) and was treated with 4.0 M hydrogen chloride in dioxane (2.8 mL, 11 mmol). After stirring overnight, solvent was removed in vacuo. Purification via preparative HPLC-MS (C18 eluting with a gradient of MeCN and H$_2$O containing 0.15% NH$_4$OH) afforded two major fractions, the desired product was the first eluting of the peaks having the desired mass (16 mg, 15%). LCMS (M+H)$^+$: 290.1.

Step 3. {cis-3-(4-{[4-(2-hydroxyethyl)-6-(trifluoromethyl)pyridin-2-yl]amino}piperidin-1-yl)-1-[4-(7H-pyrrolo[2,3-d]pyrimidin-4-yl)-1H-pyrazol-1-yl]cyclobutyl}acetonitrile and {trans-3-(4-{[4-(2-hydroxyethyl)-6-(trifluoromethyl)pyridin-2-yl]amino}piperidin-1-yl)-1-[4-(7H-pyrrolo[2,3-d]pyrimidin-4-yl)-1H-pyrazol-1-yl]cyclobutyl}acetonitrile Sodium cyanoborohydride (7.3 mg, 0.12 mmol) and zinc dichloride (8.1 mg, 0.060 mmol) were combined in methanol (0.45 mL) and stirred for 2 hours to generate the reducing solution. {3-oxo-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (36 mg, 0.086 mmol, Intermediate Example A1, Step 7) and 2-[2-(piperidin-4-ylamino)-6-(trifluoromethyl)pyridin-4-yl]ethanol (15 mg, 0.052 mmol, from Step 2) were dissolved in methanol (0.93 mL) and the reducing solution generated above was added. After a reaction time of 80 minutes, preparative HPLC-MS (C18 eluting with a gradient of MeCN and H$_2$O containing 0.15% NH$_4$OH) was used to separate and purify the cis- and trans-isomers. The two isomers were then deprotected separately according to the following procedure: first the compound was stirred with 1:1 TFA/DCM for one hour, then solvents were removed in vacuo and the residue was stirred with ethylenediamine (0.10 mL) in methanol (1 mL) until the deprotection was complete. Preparative HPLC-MS (C18 eluting with a gradient of MeCN and H$_2$O containing 0.15% NH$_4$OH) was used to purify the final compounds, which were obtained as the free base. (Peak 1 yield: 2.3 mg, 8%. Peak 2 yield: 2.1 mg, 7%). Peak 1: LCMS (M+H)$^+$: 566.0. Peak 2: LCMS (M+H)$^+$: 566.1.

Example 39

{trans-3-(4-{[4-(azetidin-1-ylmethyl)-6-(trifluoromethyl)pyridin-2-yl]amino}piperidin-1-yl)-1-[4-(7H-pyrrolo[2,3-d]pyrimidin-4-yl)-1H-pyrazol-1-yl]cyclobutyl}acetonitrile

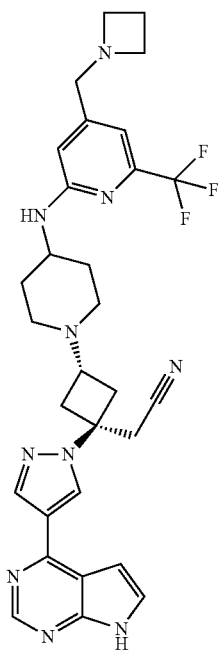 [SMILES: N#CC[C@]1(n2cc(-c3ncnc4[nH]ccc34)cn2)C[C@H](N2CCC(Nc3cc(CN4CCC4)cc(C(F)(F)F)n3)CC2)C1]

Methanesulphonic anhydride (9.6 mg, 0.055 mmol, Aldrich) was added to a solution of {trans-3-(4-{[4-(hydroxymethyl)-6-(trifluoromethyl)pyridin-2-yl]amino}piperidin-1-yl)-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (15 mg, 0.022 mmol, Peak 2 of Example 31, Step 5) and N,N-diisopropylethylamine (11 μL, 0.066 mmol) in methylene chloride (0.30 mL). After 30 minutes, solvent was removed in vacuo and replaced with tetrahydrofuran (0.30 mL). Azetidine (0.008 mL, 0.1 mmol, Aldrich) and methanol (0.12 mL, 3.0 mmol) were added and the reaction was stirred overnight. Solvent was again removed and the crude product was deprotected by stirring with 1:1 TFA/DCM for 1 hour, evaporating, and stirring with ethylenediamine (0.15 mL) in methanol (1.0 mL). Purification via preparative HPLC-MS (C18 eluting with a gradient of MeCN and H$_2$O containing 0.15% NH$_4$OH) afforded product as the free base. Purification on pH10 prep-LCMS gave the desired products. Yield: (3.3 mg, 25%). $^1$H NMR (400 MHz, d$_6$-DMSO) δ 12.13 (br s, 1H), 8.83 (s, 1H), 8.69 (s, 1H), 8.42 (s, 1H), 7.60 (d, J=3.6 Hz, 1H), 7.08 (d, J=3.6 Hz, 1H), 6.97 (d, J=7.5 Hz, 1H), 6.73 (s, 1H), 6.62 (s, 1H), 3.73-3.53 (m, 1H), 3.45 (s, 2H), 3.41 (s, 2H), 3.14 (t, J=7.0 Hz, 4H), 3.07-2.92 (m, 2H), 2.85-2.69 (m, 3H), 2.41-2.25 (m, 2H), 1.99 (p, J=6.9 Hz, 2H), 1.94-1.81 (m, 4H), 1.53-1.29 (m, 2H). $^{19}$F NMR (376 MHz, d$_6$-DMSO) δ −67.68 (s). LCMS (M+H)$^+$: 591.2.

Example 40

{trans-3-(4-{[4-(morpholin-4-ylmethyl)-6-(trifluoromethyl)pyridin-2-yl]amino}piperidin-1-yl)-1-[4-(7H-pyrrolo[2,3-d]pyrimidin-4-yl)-1H-pyrazol-1-yl]cyclobutyl}acetonitrile

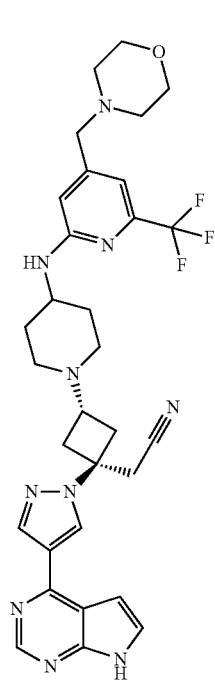 [SMILES: N#CC[C@]1(n2cc(-c3ncnc4[nH]ccc34)cn2)C[C@H](N2CCC(Nc3cc(CN4CCOCC4)cc(C(F)(F)F)n3)CC2)C1]

Prepared according to the method of Example 39, using morpholine (0.010 mL, 0.1 mmol, Aldrich) in the displacement step, which was carried out at 40° C. overnight. Yield: (5.1 mg, 37%). $^1$H NMR (400 MHz, d$_6$-DMSO) δ 12.12 (br s, 1H), 8.83 (s, 1H), 8.69 (s, 1H), 8.42 (s, 1H), 7.60 (d, J=3.6 Hz, 1H), 7.08 (d, J=3.6 Hz, 1H), 7.01 (d, J=7.4 Hz, 1H), 6.81 (s, 1H), 6.68 (s, 1H), 3.76-3.61 (m, 1H), 3.61-3.50 (m, 4H), 3.41 (s, 2H), 3.39 (s, 2H), 3.07-2.94 (m, 2H), 2.86-2.70 (m, 3H), 2.43-2.25 (m, 6H), 2.01-1.81 (m, 4H), 1.43 (q, J=10.1 Hz, 2H). $^{19}$F NMR (376 MHz, d$_6$-DMSO) δ −67.65 (s). LCMS (M+H)$^+$: 621.1.

Example 41

{trans-3-(4-{[4-[(3-hydroxyazetidin-1-yl)methyl]-6-(trifluoromethyl)pyridin-2-yl]amino}piperidin-1-yl)-1-[4-(7H-pyrrolo[2,3-d]pyrimidin-4-yl)-1H-pyrazol-1-yl]cyclobutyl}acetonitrile

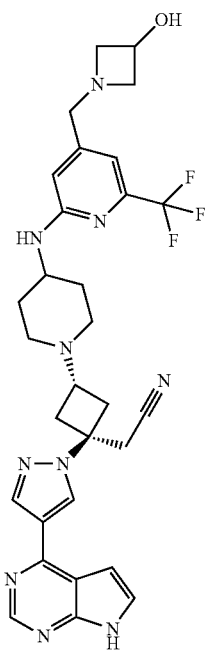 [SMILES: N#CC[C@]1(n2cc(-c3ncnc4[nH]ccc34)cn2)C[C@H](N2CCC(Nc3cc(CN4CC(O)C4)cc(C(F)(F)F)n3)CC2)C1]

Prepared according to the method of Example 39, using azetidin-3-ol hydrochloride (12 mg, 0.11 mmol, Oakwood) and N,N-diisopropylethylamine (0.019 mL, 0.11 mmol) in the displacement step. Yield: (4.7 mg, 35%). $^1$H NMR (400 MHz, d$_6$-DMSO) δ 12.12 (br s, 1H), 8.83 (s, 1H), 8.69 (s, 1H), 8.42 (s, 1H), 7.60 (d, J=3.6 Hz, 1H), 7.08 (d, J=3.6 Hz, 1H), 6.97 (d, J=7.4 Hz, 1H), 6.73 (s, 1H), 6.61 (s, 1H), 5.34 (d, J=6.4 Hz, 1H), 4.20 (h, J=6.0 Hz, 1H), 3.72-3.56 (m, 1H), 3.52 (td, J=6.1, 1.9 Hz, 2H), 3.48 (s, 2H), 3.41 (s, 2H), 3.06-2.95 (m, 2H), 2.87-2.69 (m, 5H), 2.41-2.21 (m, 2H), 2.01-1.79 (m, 4H), 1.42 (q, J=10.9 Hz, 2H). ¹⁹F NMR (376 MHz, d₆-DMSO) δ −67.67 (s). LCMS (M+H)⁺: 607.2.

Example 42

{trans-3-(4-{[4-{[(2-hydroxyethyl)(methyl)amino]methyl}-6-(trifluoromethyl)pyridin-2-yl]amino}piperidin-1-yl)-1-[4-(7H-pyrrolo[2,3-d]pyrimidin-4-yl)-1H-pyrazol-1-yl]cyclobutyl}acetonitrile

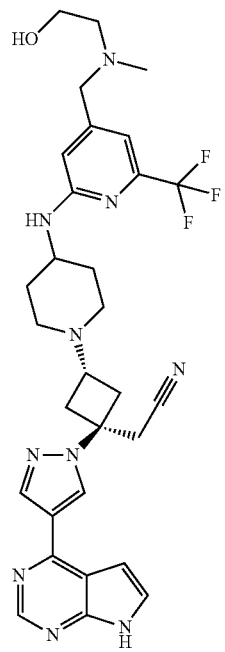 [SMILES: CN(CCO)Cc1cc(NC2CCN([C@H]3C[C@](CC#N)(n4cc(-c5ncnc6[nH]ccc56)cn4)C3)CC2)nc(C(F)(F)F)c1]

Prepared according to the method of Example 39, using 2-(methylamino)ethanol (0.009 mL, 0.1 mmol, Aldrich) in the displacement step, which was carried out at 40° C. overnight. Yield: (5.4 mg, 40%). ¹H NMR (400 MHz, d₆-DMSO) δ 12.12 (br s, 1H), 8.83 (s, 1H), 8.69 (s, 1H), 8.42 (s, 1H), 7.60 (d, J=3.6 Hz, 1H), 7.08 (d, J=3.6 Hz, 1H), 6.97 (d, J=7.4 Hz, 1H), 6.83 (s, 1H), 6.67 (s, 1H), 4.45 (t, J=5.4 Hz, 1H), 3.73-3.57 (m, 1H), 3.50 (q, J=6.2 Hz, 2H), 3.43 (s, 2H), 3.41 (s, 2H), 3.01 (ddd, J=10.0, 7.2, 1.9 Hz, 2H), 2.86-2.72 (m, 3H), 2.42 (t, J=6.3 Hz, 2H), 2.39-2.28 (m, 2H), 2.16 (s, 3H), 2.00-1.81 (m, 4H), 1.43 (q, J=10.4 Hz, 2H). ¹⁹F NMR (376 MHz, d₆-DMSO) δ −67.60 (s). LCMS (M+H): 609.3.

Example 43

{trans-3-(4-{[4-{[(3S)-3-hydroxypyrrolidin-1-yl]methyl}-6-(trifluoromethyl)pyridin-2-yl]amino}piperidin-1-yl)-1-[4-(7H-pyrrolo[2,3-d]pyrimidin-4-yl)-1H-pyrazol-1-yl]cyclobutyl}acetonitrile

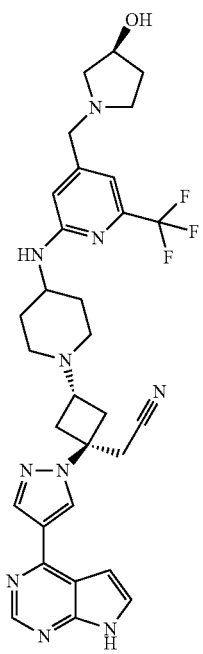 [SMILES: N#CC[C@]1(n2cc(-c3ncnc4[nH]ccc34)cn2)C[C@H](N2CCC(Nc3cc(CN4CC[C@H](O)C4)cc(C(F)(F)F)n3)CC2)C1]

Prepared according to the method of Example 39, using (3S)-pyrrolidin-3-ol (0.009 mL, 0.1 mmol, Acros) in the displacement step. Yield: (5.3 mg, 39%). ¹H NMR (400 MHz, d₆-DMSO) δ 3.65 (s, 0H), 3.56-3.43 (m, 7H), 3.41 (s, 6H), 3.01 (ddd, J=10.1, 7.2, 1.9 Hz, 10H), 2.78 (t, J=7.4 Hz, 15H), 2.67 (dd, J=9.6, 6.2 Hz, 4H), 2.57 (q, J=7.8 Hz, 5H), 2.41 (td, J=8.1, 5.7 Hz, 5H), 2.37-2.23 (m, 11H), 2.07-1.77 (m, 11H), 1.62-1.50 (m, 5H), 1.43 (q, J=10.4, 9.8 Hz, 5H). ¹⁹F NMR (376 MHz, d₆-DMSO) δ −67.62 (s). LCMS (M+H)⁺: 621.3.

Example 44

{trans-3-(4-{[4-{[(3R)-3-hydroxypyrrolidin-1-yl]methyl}-6-(trifluoromethyl)pyridin-2-yl]amino}piperidin-1-yl)-1-[4-(7H-pyrrolo[2,3-d]pyrimidin-4-yl)-1H-pyrazol-1-yl]cyclobutyl}acetonitrile

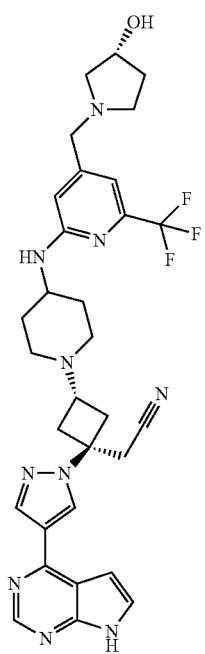 [SMILES: N#CC[C@]1(n2cc(-c3ncnc4[nH]ccc34)cn2)C[C@H](N2CCC(Nc3cc(CN4CC[C@@H](O)C4)cc(C(F)(F)F)n3)CC2)C1]

Prepared according to the method of Example 39, using (3R)-pyrrolidin-3-ol (0.009 mL, 0.1 mmol, Acros) in the displacement step. Yield: (6.4 mg, 47%). ¹H NMR (400 MHz, d₆-DMSO) δ 12.14 (br s, 1H), 8.83 (s, 1H), 8.70 (s, 1H), 8.43 (s, 1H), 7.61 (d, J=3.6 Hz, 1H), 7.09 (d, J=3.6 Hz, 1H), 6.98 (d, J=7.4 Hz, 1H), 6.80 (s, 1H), 6.67 (s, 1H), 4.73 (d, J=4.3 Hz, 1H), 4.20 (tt, J=7.7, 3.8 Hz, 1H), 3.79-3.59 (m, 1H), 3.56-3.44 (m, 2H), 3.42 (s, 2H), 3.09-2.93 (m, 2H), 2.87-2.72 (m, 3H), 2.68 (dd, J=9.6, 6.2 Hz, 1H), 2.58 (q, J=7.8 Hz, 1H), 2.42 (td, J=8.1, 5.6 Hz, 1H), 2.38-2.26 (m, 3H), 2.08-1.79 (m, 5H), 1.55 (dddd, J=13.1, 8.0, 5.5, 3.5 Hz, 1H), 1.43 (q, J=10.9, 10.4 Hz, 2H). ¹⁹F NMR (376 MHz, d₆-DMSO) δ −67.62 (s). LCMS (M+H): 621.2.

Example 45

{trans-3-(4-{[4-(methoxymethyl)-6-(trifluoromethyl)pyridin-2-yl]amino}piperidin-1-yl)-1-[4-(7H-pyrrolo[2,3-d]pyrimidin-4-yl)-1H-pyrazol-1-yl]cyclobutyl}acetonitrile

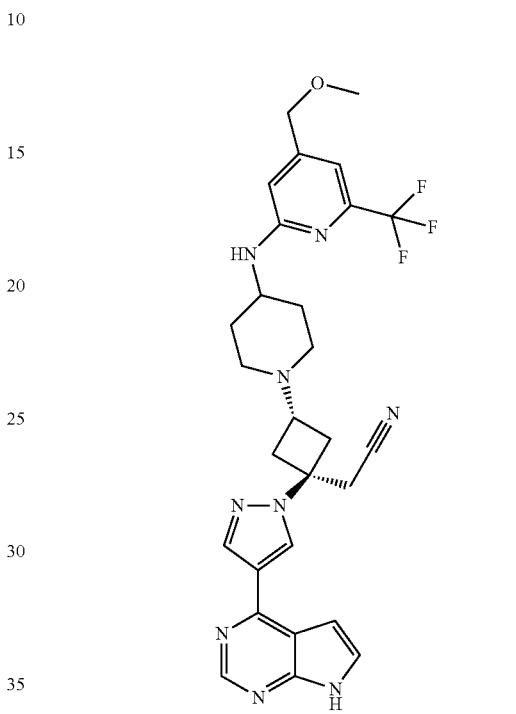

Methanesulphonic anhydride (13 mg, 0.073 mmol, Aldrich) was added to a solution of {trans-3-(4-{[4-(hydroxymethyl)-6-(trifluoromethyl)pyridin-2-yl]amino}piperidin-1-yl)-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (20. mg, 0.029 mmol, Peak 2 of Example 31, Step 5) and N,N-diisopropylethylamine (15 μL, 0.088 mmol) in methylene chloride (1.0 mL). After stirring for 30 minutes, solvent was removed in vacuo and replaced with methanol (1.0 mL). The mixture was heated in a sealed vial to 80° C. for 30 minutes, then to 85° C. for 3.5 hours. The methanol was removed in vacuo and the crude product was deprotected by stirring with 1:1 mixture of TFA/DCM for one hour, followed by evaporation of solvents and stirring with ethylenediamine (0.1 mL) in methanol (1.0 mL) for 10 minutes. Purification via preparative HPLC-MS (C18 eluting with a gradient of MeCN and H₂O containing 0.15% NH₄OH) afforded product as the free base (8.0 mg, 48%). ¹H NMR (400 MHz, d₆-DMSO) δ 12.13 (br s, 1H), 8.83 (s, 1H), 8.69 (s, 1H), 8.42 (s, 1H), 7.60 (d, J=3.6 Hz, 1H), 7.08 (d, J=3.6 Hz, 1H), 7.04 (d, J=7.5 Hz, 1H), 6.77 (s, 1H), 6.66 (s, 1H), 4.37 (s, 2H), 3.72-3.58 (m, 1H), 3.41 (s, 2H), 3.32 (s, 3H), 3.07-2.94 (m, 2H), 2.86-2.69 (m, 3H), 2.41-2.26 (m, 2H), 2.01-1.76 (m, 4H), 1.43 (q, J=10.6 Hz, 2H). ¹⁹F NMR (376 MHz, d₆-DMSO) δ −67.76 (s). LCMS (M+H)⁺: 566.0.

Example 46

{trans-3-(4-{[4-(2-oxa-6-azaspiro[3.3]hept-6-ylmethyl)-6-(trifluoromethyl)pyridin-2-yl]amino}piperidin-1-yl)-1-[4-(7H-pyrrolo[2,3-d]pyrimidin-4-yl)-1H-pyrazol-1-yl]cyclobutyl}acetonitrile

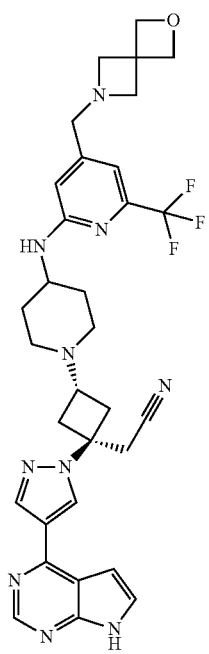

Prepared according to the method of Example 39, using 2-oxa-6-azaspiro[3.3]heptane (11 mg, 0.11 mmol, J&W Pharmlab) in a mixture of THF (0.5 mL) and methanol (0.5 mL) in the displacement step, which was carried out at room temperature for 2 hours. Yield: (6.4 mg, 46%). $^1$H NMR (400 MHz, CD$_3$OD) δ 8.74 (s, 1H), 8.67 (s, 1H), 8.41 (s, 1H), 7.51 (d, J=3.6 Hz, 1H), 7.00 (d, J=3.7 Hz, 1H), 6.76 (s, 1H), 6.53 (s, 1H), 4.73 (s, 4H), 3.92-3.72 (m, 1H), 3.50 (s, 2H), 3.45 (s, 4H), 3.18-3.04 (m, 2H), 3.02-2.80 (m, 3H), 2.55-2.41 (m, 2H), 2.27-1.95 (m, 4H), 1.70-1.36 (m, 2H). $^{19}$F NMR (376 MHz, CD$_3$OD) δ −70.74 (s). LCMS (M+H)$^+$: 633.3.

Example 47

{trans-3-{4-[[4-(hydroxymethyl)-6-(trifluoromethyl)pyridin-2-yl](methyl)amino]piperidin-1-yl}-1-[4-(7H-pyrrolo[2,3-d]pyrimidin-4-yl)-1H-pyrazol-1-yl]cyclobutyl}acetonitrile

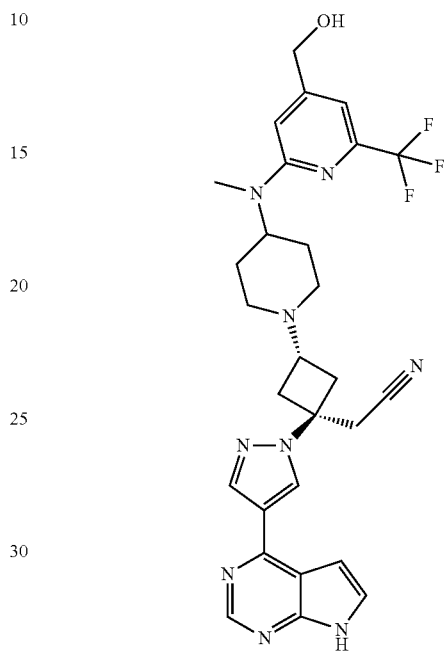

Step 1. tert-butyl 4-(methylamino)piperidine-1-carboxylate

To a solution of tert-butyl 4-oxo-1-piperidinecarboxylate (0.50 g, 2.5 mmol, Aldrich) and 2.0 M methylamine in Tetrahydrofuran (10. mL, 20. mmol, Aldrich) was added sodium triacetoxyborohydride (1.3 g, 6.3 mmol). After stirring of the suspension overnight, the reaction was quenched with water and stirred for 1 hour. Brine was added and the product was extracted with two portions of DCM. The combined organic extracts were dried over sodium sulfate, filtered and concentrated. The product was used without further purification in Step 2. LCMS (M+H)$^+$: 215.2.

Step 2. tert-butyl 2-[[1-(tert-butoxycarbonyl)piperidin-4-yl](methyl)amino]-6-(trifluoromethyl)isonicotinate A mixture of tert-butyl 2-chloro-6-(trifluoromethyl)isonicotinate (0.47 g, 1.7 mmol, from Example 21, Step 1), tert-butyl 4-(methylamino)piperidine-1-carboxylate (0.54 g, 2.5 mmol, from Step 1) and N,N-diisopropylethylamine (0.58 mL, 3.4 mmol) in dimethyl sulfoxide (1.4 mL) was heated in an oil bath held at 100° C. for 26 hours. The mixture was cooled to room temperature and diluted with EtOAc. The organic solution was washed with three portions of water, one portion of brine, was dried over sodium sulfate, filtered and concentrated. Flash chromatography using a 40 g silica gel cartridge and eluting with a gradient from 0-20% EtOAc in hexanes afforded product as a white solid (0.30 g, 39%).

¹H NMR (400 MHz, CDCl₃) δ 7.31 (d, J=0.8 Hz, 1H), 7.22 (s, 1H), 4.80-4.52 (m, 1H), 4.23 (br m, 2H), 2.94 (s, 3H), 2.81 (br m, J=28.1 Hz, 2H), 1.73-1.61 (m, 4H), 1.60 (s, 9H), 1.48 (s, 9H). ¹⁹F NMR (376 MHz, CDCl₃) δ −69.15 (s). LCMS (M−tBu+H)⁺: 404.0.

Step 3. tert-butyl 4-[[4-(hydroxymethyl)-6-(trifluoromethyl)pyridin-2-yl](methyl)amino]piperidine-1-carboxylate Potassium hydroxide (0.29 g, 5.2 mmol) was added to a solution of tert-butyl 2-[[1-(tert-butoxycarbonyl)piperidin-4-yl](methyl)amino]-6-(trifluoromethyl)isonicotinate (0.30 g, 0.65 mmol, from Step 2) in tetrahydrofuran (4.3 mL). After stirring for 1 hour, the mixture was treated with 1.0 N HCl to achieve a pH between 2 and 3. Brine was added (10 mL) and the product was extracted with three portions of CHCl₃ (10 mL each). The combined extracts were dried over sodium sulfate, filtered and concentrated to afford product as a light yellow powder (0.38 g). The carboxylic acid was dissolved in tetrahydrofuran (3.0 mL) and cooled in an ice bath. Triethylamine (0.18 mL, 1.3 mmol) followed by Isobutyl chloroformate (0.10 mL, 0.78 mmol) were introduced. After stirring for 30 minutes, the reaction was filtered through a short pad of celite into a flask containing ice-cold Sodium tetrahydroborate (86 mg, 2.3 mmol) in Water (1.4 mL). THF (10 mL) was used to rinse through the celite pad, into the reaction flask. The reaction was allowed to warm to room temperature and stir for 1 hour. Saturated ammonium chloride solution was introduced to quench the reaction. The product was extracted into ethyl acetate. The organic solution was washed with brine, dried over sodium sulfate, filtered and concentrated. Flash chromatography, using a 40 g silica gel cartridge and eluting with a gradient from 0-50% EtOAc in hexanes afforded product as a white solid (50 mg, 20%). ¹H NMR (400 MHz, CDCl₃) δ 6.85 (s, 1H), 6.67 (s, 1H), 4.74-4.62 (m, 1H), 4.69 (s, 2H), 4.15 (br m, J=57.8 Hz, 2H), 2.95-2.73 (br m, 2H), 2.89 (s, 3H), 1.74-1.52 (m, 4H), 1.47 (s, 9H). LCMS (M−tBu+H)⁺: 334.0.

Step 4. {cis-3-{4-[[4-(hydroxymethyl)-6-(trifluoromethyl)pyridin-2-yl](methyl)amino]piperidin-1-yl}-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile and {trans-3-{4-[[4-(hydroxymethyl)-6-(trifluoromethyl)pyridin-2-yl](methyl)amino]piperidin-1-yl}-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile A solution of tert-butyl 4-[[4-(hydroxymethyl)-6-(trifluoromethyl)pyridin-2-yl](methyl)amino]piperidine-1-carboxylate (43 mg, 0.11 mmol, from Step 3) in 1,4-dioxane (1.0 mL) was treated with 4.0 M hydrogen chloride in dioxane (0.55 mL, 2.2 mmol) and stirred for 1.5 hours. The mixture was treated with 1.0 N NaOH to achieve pH~12, then was saturated with NaCl and extracted with six portions of chloroform. The combined organic extracts were dried over sodium sulfate, filtered and concentrated. A reducing mixture was prepared by combining sodium cyanoborohydride (16 mg, 0.25 mmol) and zinc dichloride (17 mg, 0.13 mmol) in methanol (0.95 mL) and stirring for 2 hours. After the Boc-deprotection and extraction, the piperidine was mixed with {3-oxo-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (78 mg, 0.18 mmol, Intermediate Example A1, Step 7) in methanol (2.0 mL) and the reducing mixture generated by combining NaCNBH₃ and ZnCl₂ was added. The reaction was stirred until determined complete by analytical LCMS. Purification via preparative HPLC-MS (C18 eluting with a gradient of MeCN and H₂O containing 0.15% NH₄OH) afforded separated products (Peak 1, cis-isomer: 7.0 mg, 9%, Peak 2, trans-isomer: 10.1 mg, 13%). Cis-isomer: ¹H NMR (400 MHz, CDCl₃) δ 8.85 (s, 1H), 8.39 (s, 1H), 8.30 (s, 1H), 7.40 (d, J=3.7 Hz, 1H), 6.84 (s, 1H), 6.80 (d, J=3.7 Hz, 1H), 6.66 (s, 1H), 5.68 (s, 2H), 4.69 (s, 2H), 4.61-4.39 (m, 1H), 3.64-3.36 (m, 2H), 3.14 (s, 2H), 3.02-2.76 (m, 5H), 2.91 (s, 3H), 2.76-2.65 (m, 2H), 2.09-1.94 (m, 2H), 1.85-1.67 (m, 4H), 1.02-0.74 (m, 2H), −0.05 (s, 9H). LCMS (M+H)⁺: 696.0. Trans-isomer: ¹H NMR (400 MHz, CDCl₃) δ 8.86 (s, 1H), 8.48 (s, 1H), 8.34 (s, 1H), 7.41 (d, J=3.7 Hz, 1H), 6.84 (s, 1H), 6.82 (d, J=3.7 Hz, 1H), 6.67 (s, 1H), 5.68 (s, 2H), 4.69 (s, 2H), 4.57-4.45 (m, 1H), 3.61-3.47 (m, 2H), 3.22 (s, 2H), 3.09-2.98 (m, 4H), 2.97-2.88 (m, 1H), 2.95 (s, 3H), 2.52-2.39 (m, 2H), 1.96 (td, J=11.4, 2.0 Hz, 2H), 1.88-1.63 (m, 4H), 0.98-0.86 (m, 2H), −0.06 (s, 9H). LCMS (M+H)⁺: 696.0.

Step 5. {trans-3-{4-[[4-(hydroxymethyl)-6-(trifluoromethyl)pyridin-2-yl](methyl)amino]piperidin-1-yl}-1-[4-(7H-pyrrolo[2,3-d]pyrimidin-4-yl)-1H-pyrazol-1-yl]cyclobutyl}acetonitrile {trans-3-{4-[[4-(Hydroxymethyl)-6-(trifluoromethyl)pyridin-2-yl](methyl)amino]piperidin-1-yl}-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (5.0 mg, 0.0072 mmol, Peak 2 from Step 4) was dissolved in a 1:1 mixture of TFA/DCM and stirred for one hour, then solvents were removed in vacuo. The residue was then stirred in methanol (1.0 mL) containing ethylenediamine (0.1 mL) for 10 minutes. Purification via preparative HPLC-MS (C18 eluting with a gradient of MeCN and H₂O containing 0.15% NH₄OH) afforded product as the free base (2.0 mg, 49%). ¹H NMR (400 MHz, CD₃OD) δ 8.75 (s, 1H), 8.67 (s, 1H), 8.41 (s, 1H), 7.52 (d, J=3.6 Hz, 1H), 7.00 (d, J=3.6 Hz, 1H), 6.89 (s, 1H), 6.81 (s, 1H), 4.60 (s, 2H), 3.32 (s, 2H), 3.18-3.05 (m, 4H), 3.03-2.92 (m, 1H), 2.97 (s, 3H), 2.57-2.41 (m, 2H), 2.04 (t, J=11.1 Hz, 2H), 1.89 (qd, J=12.2, 11.7, 3.5 Hz, 2H), 1.80-1.63 (m, 2H). ¹⁹F NMR (376 MHz, CD₃OD) δ −70.65 (s). LCMS (M+H)⁺: 566.1.

Example 48

{trans-3-{4-[[4-[(ethylamino)methyl]-6-(trifluoromethyl)pyridin-2-yl](methyl)amino]piperidin-1-yl}-1-[4-(7H-pyrrolo[2,3-d]pyrimidin-4-yl)-1H-pyrazol-1-yl]cyclobutyl}acetonitrile

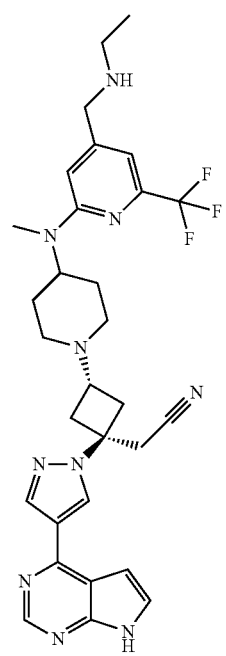 [SMILES: CCNCc1cc(N(C)C2CCN([C@H]3C[C@](CC#N)(n4cc(-c5ncnc6[nH]ccc56)cn4)C3)CC2)nc(C(F)(F)F)c1]

Methanesulphonic anhydride (3.8 mg, 0.022 mmol, Aldrich) was added to a solution of {trans-3-{4-[[4-(hydroxymethyl)-6-(trifluoromethyl)pyridin-2-yl](methyl)amino]piperidin-1-yl}-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (5.0 mg, 0.0072 mmol, Peak 2 from Example 47, Step 4) and N,N-diisopropylethylamine (6.2 µL, 0.036 mmol) in methylene chloride (0.20 mL) and the reaction was stirred for 30 minutes. Solvent was removed in vacuo and replaced by tetrahydrofuran (0.20 mL). Ethylamine (16 µL, 0.29 mmol, Aldrich) was added, followed by methanol (0.10 mL). The mixture was heated to 40° C. for 30 minutes. The crude product was deprotected by stirring in 1:1 TFA/DCM for 1 hour, removal of solvents, then stirring with ethylenediamine (0.1 mL) in methanol (1.0 mL) until deprotection was complete. Purification via preparative HPLC-MS (C18 eluting with a gradient of MeCN and $H_2O$ containing 0.15% $NH_4OH$) afforded product as the free base (1.7 mg, 40%). $^1H$ NMR (400 MHz, $CD_3OD$) δ 8.75 (s, 1H), 8.67 (s, 1H), 8.41 (s, 1H), 7.52 (d, J=3.6 Hz, 1H), 7.00 (d, J=3.6 Hz, 1H), 6.93 (s, 1H), 6.81 (s, 1H), 4.68-4.50 (m, 1H), 3.74 (s, 2H), 3.32 (s, 2H), 3.17-3.06 (m, 4H), 3.02-2.90 (m, 1H), 2.97 (s, 3H), 2.64 (q, J=7.2 Hz, 2H), 2.54-2.44 (m, 2H), 2.04 (t, J=11.1 Hz, 2H), 1.89 (qd, J=12.4, 3.5 Hz, 2H), 1.79-1.68 (m, 2H), 1.15 (t, J=7.2 Hz, 3H). $^{19}F$ NMR (376 MHz, $CD_3OD$) δ -70.62 (s). LCMS (M+H)$^+$: 593.1.

Example 49

{trans-3-(4-{[4-(3-hydroxyoxetan-3-yl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile

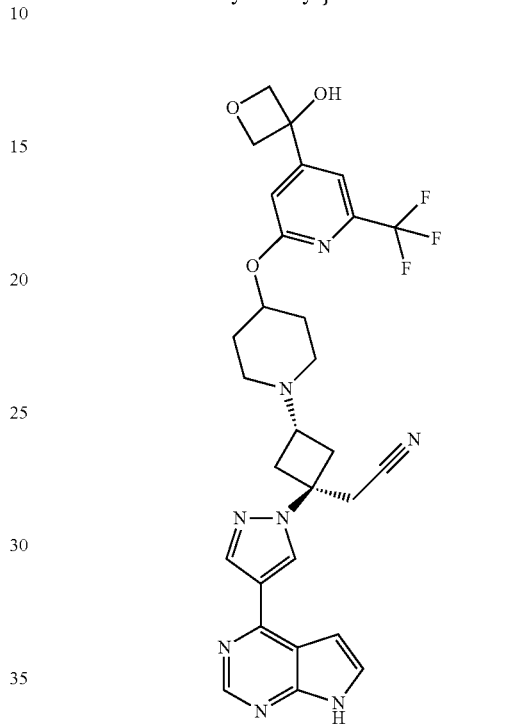

Step 1. 3-[2-chloro-6-(trifluoromethyl)pyridin-4-yl]oxetan-3-ol

To a solution of 2-chloro-4-iodo-6-(trifluoromethyl)pyridine (1.00 g, 3.25 mmol, *European Journal of Organic Chemistry*, (18), 3793-3798, 2004) in tetrahydrofuran (20 mL) at 0° C. was added dropwise 2.0 M isopropylmagnesium chloride in diethyl ether (1.95 mL, 3.90 mmol, Aldrich). After stirring for 30 minutes at 0° C., a solution of oxetan-3-one (0.281 g, 3.90 mmol, Synthonix) in Tetrahydrofuran (5 mL) was added. After stirring for 1 hour, the reaction was quenched by the addition of water and ammonium chloride. The product was extracted with two portions of ethyl acetate. The combined organic extracts were dried over sodium sulfate, filtered and concentrated. Flash chromatography, eluting with a gradient from 0-40% EtOAc in hexanes on a 40 g silica gel cartridge afforded purified product (0.31 g, 38%). LCMS (M+H)$^+$: 254.1.

Step 2. tert-butyl 4-{[4-(3-hydroxyoxetan-3-yl)-6-(trifluoromethyl)pyridin-2-yl]oxy}piperidine-1-carboxylate To sodium hydride (60% in mineral oil, 0.20 g, 4.9 mmol) in a dry flask was added tetrahydrofuran (20 mL), followed by tert-butyl 4-hydroxypiperidine-1-carboxylate (0.98 g, 4.9 mmol, Aldrich). After stirring for 1 hour at room temperature, a solution of 3-[2-chloro-6-(trifluoromethyl)pyridin-4-yl]oxetan-3-ol (0.31 g, 1.2 mmol, from Step 1) in tetrahydrofuran (11 mL) was introduced. The reaction was stirred at ambient temperature for 2 hours, followed by heating to 65° C. overnight. The reaction was cooled to room temperature and water was added, followed by saturated ammonium chloride to adjust the pH to between 7 and 8. The product was extracted with two portions of DCM. The combined organic extracts were dried over sodium sulfate, decanted and concentrated. The product was purified by flash chromatography, eluting with a gradient from 0-20% EtOAc in hexanes, on a 40 g silica gel column to afford 0.17 g of desired product (yield 30%). $^1$H NMR (400 MHz, CDCl$_3$) δ 7.58 (d, J=1.3 Hz, 1H), 7.22-7.15 (m, 1H), 5.28 (tt, J=7.6, 3.7 Hz, 1H), 4.91 (d, J=7.6 Hz, 2H), 4.77 (d, J=6.9 Hz, 2H), 3.72 (ddd, J=12.5, 6.6, 3.9 Hz, 2H), 3.32 (ddd, J=13.8, 8.0, 3.7 Hz, 2H), 1.98 (ddt, J=13.6, 7.1, 3.6 Hz, 2H), 1.73 (ddt, J=16.5, 8.1, 3.9 Hz, 2H), 1.46 (s, 9H). $^{19}$F NMR (376 MHz, CDCl$_3$) δ −68.78 (s). LCMS (M+Na)$^+$: 441.1.

Step 3. 3-[2-(piperidin-4-yloxy)-6-(trifluoromethyl)pyridin-4-yl]oxetan-3-ol

A solution of tert-butyl 4-{[4-(3-hydroxyoxetan-3-yl)-6-(trifluoromethyl)pyridin-2-yl]oxy}piperidine-1-carboxylate (0.080 g, 0.17 mmol, from Step 2) in 1,4-dioxane (1.0 mL) was treated with a few drops of water and six drops of concentrated H$_2$SO$_4$ and was stirred overnight. The mixture was made basic with 10 mL of saturated sodium bicarbonate solution and the product was extracted with three portions of DCM. The combined extracts were dried over sodium sulfate, filtered and concentrated to afford crude product, which was used directly in the next step (44 mg, 81%). $^1$H NMR (300 MHz, CDCl$_3$) δ 7.58 (d, J=1.2 Hz, 1H), 7.18 (s, 1H), 5.22 (tt, J=8.2, 3.9 Hz, 1H), 4.91 (d, J=7.4 Hz, 2H), 4.78 (d, J=7.4 Hz, 2H), 3.10 (dt, J=11.9, 4.3 Hz, 2H), 2.79 (ddd, J=12.5, 9.1, 3.1 Hz, 2H), 2.16-1.98 (m, 2H), 1.70 (dtd, J=12.7, 8.8, 3.8 Hz, 2H). $^{19}$F NMR (282 MHz, CDCl$_3$) δ −68.76 (s). LCMS (M+H)$^+$: 319.1.

Step 4. {cis-3-(4-{[4-(3-hydroxyoxetan-3-yl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile and {trans-3-(4-{[4-(3-hydroxyoxetan-3-yl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile A reducing mixture was prepared by combining sodium cyanoborohydride (11 mg, 0.17 mmol) and zinc dichloride (12 mg, 0.087 mmol) in methanol (0.65 mL) and stirring for 2 hours. Then, 3-[2-(piperidin-4-yloxy)-6-(trifluoromethyl)pyridin-4-yl]oxetan-3-ol (44 mg, 0.12 mmol, from Step 3) and {3-oxo-1-[4-(7H-pyrrolo[2,3-d]pyrimidin-4-yl)-1H-pyrazol-1-yl]cyclobutyl}acetonitrile (44 mg, 0.15 mmol) (prepared by stirring the product of Intermediate Example A1, Step 7 in 1:1 TFA/DCM for an hour, then evaporating solvent and stirring with ammonium hydroxide/Methanol until deprotection complete, followed by purification via preparative HPLC-MS (C18, eluting with a gradient of MeCN/H$_2$O containing 0.15% NH4OH)) were mixed in methanol (1.8 mL) and stirred just enough time to dissolve, then the reducing mixture generated above was added. After stirring overnight, the mixture was purified via preparative HPLC-MS (C18, eluting with a gradient of MeCN/H$_2$O containing 0.15% NH$_4$OH) to afford a mixture of two diastereomers. (15.7 mg. yield 21%). The two diastereomers were separated using a chiral HPLC column (Phenomenex Lux Cellulose-2, eluting with 45% EtOH in Hexanes at 18 ml/min, using a loading of ~6 mg/injection). Retention time for Peak 1: 7.25 min, trans-isomer, 4.2 mg, 5.6% yield. Retention time for Peak 2: 9.84 min, cis-isomer, 4.5 mg, 6% yield. Peak 1, Trans-isomer: $^1$H NMR (400 MHz, d$_6$-DMSO) δ 12.13 (s, 1H), 8.83 (s, 1H), 8.43 (s, 1H), 7.67-7.50 (m, 2H), 7.22 (s, 1H), 7.08 (dd, J=3.5, 1.7 Hz, 1H), 6.79 (s, 1H), 5.04 (br s, 1H), 4.77 (d, J=6.9 Hz, 2H), 4.67 (d, J=6.8 Hz, 2H), 3.42 (s, 2H), 3.09-2.94 (m, 2H), 2.94-2.74 (m, 1H), 2.74-2.57 (m, 2H), 2.43-2.28 (m, 2H), 2.28-2.11 (m, 2H), 2.11-1.90 (m, 2H), 1.84-1.59 (m, 2H). $^{19}$F NMR (376 MHz, d$_6$-DMSO) δ −67.38 (s). LCMS (M+H)$^+$: 595.3. Peak 2, Cis-isomer: $^1$H NMR (400 MHz, d6-DMSO) δ 12.13 (s, 1H), 8.70 (s, 1H), 8.68 (s, 1H), 8.40 (s, 1H), 7.60 (d, J=3.9 Hz, 1H), 7.22 (s, 1H), 7.07 (d, J=3.6 Hz, 1H), 6.80 (s, 1H), 5.04 (tt, J=8.3, 4.0 Hz, 1H), 4.77 (d, J=7.1 Hz, 2H), 4.67 (d, J=7.1 Hz, 2H), 3.47 (s, 2H), 2.94 (p, J=7.6 Hz, 1H), 2.72-2.54 (m, 6H), 2.28-2.10 (m, 2H), 2.07-1.90 (m, 2H), 1.76-1.62 (m, 2H). $^{19}$F NMR (376 MHz, d$_6$-DMSO) δ −67.38 (s). LCMS (M+H)$^+$: 595.2

Example 50

{trans-3-(4-{[4-(3-aminooxetan-3-yl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile

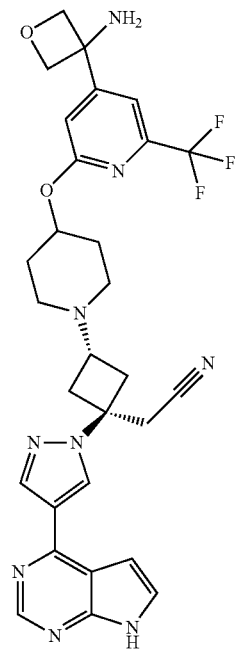 [SMILES: N#CC[C@]1(n2cc(-c3ncnc4[nH]ccc34)cn2)C[C@H](N2CCC(Oc3cc(C4(N)COC4)cc(C(F)(F)F)n3)CC2)C1]

Step 1. tert-butyl 4-{[4-{3-[(methylsulfonyl)oxy]oxetan-3-yl}-6-(trifluoromethyl)pyridin-2-yl]oxy}piperidine-1-carboxylate Methanesulfonyl chloride (50. μL, 0.64 mmol) was added to a solution of tert-butyl 4-{[4-(3-hydroxyoxetan-3-yl)-6-(trifluoromethyl)pyridin-2-yl]oxy}piperidine-1-carboxylate (0.20 g, 0.43 mmol, from Example 49, Step 2) and triethylamine (120 μL, 0.86 mmol) in methylene chloride (5.0 mL) at 0° C. The mixture was allowed to warm to room temperature and stir for 1 hour, then the reaction was further diluted with DCM and water, and the mixture was neutralized by the addition of saturated sodium bicarbonate. The organic layer was separated and washed with water and brine, was dried over sodium sulfate, filtered and concentrated to afford 0.22 g of a light yellow oil. The oil was dissolved in dimethyl sulfoxide (2.0 mL) and sodium azide (0.17 g, 2.6 mmol) was added. The reaction was stirred at room temperature for 50 minutes and then was heated to 40° C. overnight, followed by 70° C. for 3 hours. The mixture was then cooled to room temperature and was diluted with EtOAc. The organic solution was washed with water (3×), brine (1×), dried over sodium sulfate, filtered and concentrated to afford 0.14 g crude product, yield 66%. $^1$H NMR (300 MHz, CDCl$_3$) δ 7.45 (d, J=1.3 Hz, 1H), 7.12-7.02 (m, 1H), 5.29 (tt, J=7.9, 3.9 Hz, 1H), 5.06 (d, J=7.5 Hz, 2H), 4.86 (d, J=7.5 Hz, 2H), 3.75 (ddd, J=12.1, 6.2, 3.7 Hz, 2H), 3.33 (ddd, J=13.3, 8.3, 3.6 Hz, 2H), 1.99 (ddt, J=10.3, 7.0, 3.6 Hz, 2H), 1.75 (dtd, J=12.7, 8.3, 4.1 Hz, 2H), 1.47 (s, 9H). $^{19}$F NMR (282 MHz, CDCl$_3$) δ −68.86 (s). LCMS (M+Na)$^+$: 466.1.

Step 2. tert-butyl 4-{[4-(3-aminooxetan-3-yl)-6-(trifluoromethyl)pyridin-2-yl]oxy}piperidine-1-carboxylate To a solution of tert-butyl 4-{[4-(3-azidooxetan-3-yl)-6-(trifluoromethyl)pyridin-2-yl]oxy}piperidine-1-carboxylate (0.14 g, 0.28 mmol, from Step 1) in tetrahydrofuran (6.3 mL) and water (2 mL) was added dropwise a solution of 1.0 M trimethylphosphine in THF (0.34 mL, 0.34 mmol, Aldrich). After 20 minutes, the mixture was partitioned between water and DCM, and the aqueous layer was extracted with one additional portion of DCM. The combined organic extracts were dried over sodium sulfate, filtered and concentrated. Purification using flash chromatography on a 12 g silica gel column, eluting with a gradient of 0-5% MeOH in DCM afforded product as an oil (0.10 g, 86%). $^1$H NMR (300 MHz, CDCl$_3$) δ 7.53 (br s, 2H), 7.34 (d, J=1.0 Hz, 1H), 6.99-6.85 (m, 1H), 5.36-5.19 (m, 1H), 5.12 (d, J=6.6 Hz, 2H), 4.87 (d, J=6.6 Hz, 2H), 3.82-3.66 (m, 2H), 3.32 (ddd, J=13.2, 8.3, 3.6 Hz, 2H), 1.99 (ddt, J=13.9, 7.0, 3.6 Hz, 2H), 1.85-1.62 (m, 2H), 1.47 (s, 9H). $^{19}$F NMR (282 MHz, CDCl$_3$) δ −68.80 (s). LCMS (M+Na)$^+$: 440.1.

Step 3. {cis-3-(4-{[4-(3-aminooxetan-3-yl)-6-(trifluoromethyl)pyridin-2-yl]oxy}piperidin-S-yl)-1-[4-(7H-pyrrolo[2,3-d]pyrimidin-4-yl)-1H-pyrazol-1-yl]cyclobutyl}acetonitrile and {trans-3-(4-{[4-(3-aminooxetan-3-yl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile tert-Butyl 4-{[4-(3-aminooxetan-3-yl)-6-(trifluoromethyl)pyridin-2-yl]oxy}piperidine-1-carboxylate (95 mg, 0.23 mmol, from Step 2) was Boc-deprotected by stirring in 1,4-dioxane (1.3 mL) containing a few drops of water and a few drops of c.H$_2$SO$_4$ overnight. The mixture was basified by the addition of 15 mL saturated sodium bicarbonate solution and the product was extracted with chloroform (4×). The combined organic extracts were dried over sodium sulfate, filtered and concentrated to afford the crude product, LCMS (M+H)$^+$: 318.1. This product was dissolved along with {3-oxo-1-[4-(7H-pyrrolo[2,3-d]pyrimidin-4-yl)-1H-pyrazol-1-yl]cyclobutyl}acetonitrile (66 mg, 0.23 mmol, prepared as described in Example 49, Step 4) in methanol (5.0 mL). Then a pre-generated solution of sodium cyanoborohydride (20. mg, 0.32 mmol) and Zinc dichloride (22 mg, 0.16 mmol) in methanol (1.0 mL) (which had been stirred for 2 hours) was added. The reductive amination step was carried on for 4 hours. Purification via preparative HPLC-MS (C18 eluting with a gradient of MeCN/H$_2$O containing 0.15% NH$_4$OH) afforded the product as a mixture of cis- and trans-diastereomers (33 mg, 24%). The isomers were separated by chiral HPLC: Phenomenex Lux Cellulose-1, 21.2×250 mm, 5 μm, 2.5 mg/inj, eluting with 20% ethanol in hexanes at 18 ml/min. Retention time of Peak 1, cis-isomer: 12.22 min, (yield: 11 mg, 8%). Retention time of Peak 2, trans-isomer: 16.25 min, (yield: 12 mg, 9%). Peak 1, Cis-isomer: $^1$H NMR (400 MHz, d$_6$-DMSO) δ 12.13 (s, 1H), 8.70 (s, 1H), 8.69 (s, 1H), 8.40 (s, 1H), 7.65 (s, 1H), 7.60 (dd, J=3.3, 2.4 Hz, 1H), 7.24 (s, 1H), 7.07 (dd, J=3.4, 1.6 Hz, 1H), 5.09-4.98 (m, 1H), 4.64 (s, 4H), 3.47 (s, 2H), 3.06-2.54 (m, 7H), 2.29-2.13 (m, 2H), 2.07-1.88 (m, 2H), 1.76-1.61 (m, 2H). $^{19}$F NMR (376 MHz, d$_6$-DMSO) δ −67.27 (s). LCMS (M+H)$^+$: 594.2. Peak 2, Trans-isomer: $^1$H NMR (400 MHz, d$_6$-DMSO) δ 12.13 (s, 1H), 8.83 (s, 1H), 8.69 (s, 1H), 8.42 (s, 1H), 7.64 (d, J=0.9 Hz, 1H), 7.61 (d, J=2.5 Hz, 1H), 7.23 (s, 1H), 7.08 (d, J=3.4 Hz, 1H), 5.04 (tt, J=8.7, 4.1 Hz, 1H), 4.63 (s, 4H), 3.42 (s, 2H), 3.11-2.94 (m, 2H), 2.92-2.56 (m, 5H), 2.41-2.27 (m, 2H), 2.27-2.09 (m, 2H), 2.02 (s, 2H), 1.78-1.64 (m, 2H). $^{19}$F NMR (376 MHz, d$_6$-DMSO) δ −67.27 (s). LCMS (M+H)$^+$: 594.2.

Example A

In Vitro JAK Kinase Assay

Compounds herein were tested for inhibitory activity of JAK targets according to the following in vitro assay described in Park et al., *Analytical Biochemistry* 1999, 269, 94-104. The catalytic domains of human JAK1 (a.a. 837-1142) and JAK2 (a.a. 828-1132) with an N-terminal His tag were expressed using baculovirus in insect cells and purified. The catalytic activity of JAK1 and JAK2 was assayed by measuring the phosphorylation of a biotinylated peptide. The phosphorylated peptide was detected by homogenous time resolved fluorescence (HTRF). IC$_{50}$s of compounds were measured for each kinase in the 40 microL reactions that contain the enzyme, ATP and 500 nM peptide in 50 mM Tris (pH 7.8) buffer with 100 mM NaCl, 5 mM DTT, and 0.1 mg/mL (0.01%) BSA. For the 1 mM IC$_{50}$ measurements, ATP concentration in the reactions was 1 mM. Reactions were carried out at room temperature for 1 hour and then stopped with 20 μL 45 mM EDTA, 300 nM SA-APC, 6 nM Eu-Py20 in assay buffer (Perkin Elmer, Boston, Mass.). Binding to the Europium labeled antibody took place for 40 minutes and HTRF signal was measured on a Fusion plate reader (Perkin Elmer, Boston, Mass.). See Table A for data related to compounds of the Examples (at 1 mM). Data is indicated as ranges: <20 nM (+), 20 to <150 nM (++), 150 to 500 nM (+++).

TABLE A

| Example | JAK1 IC$_{50}$ (nM) at 1 mM ATP | JAK2 IC$_{50}$ (nM) at 1 mM ATP | JAK2/JAK1 |
|---------|-----|-----|-----|
| 1 | + | ++ | >10 |
| 2 | + | ++ | >10 |
| 3 | + | ++ | >10 |
| 4 | + | ++ | >10 |
| 5 | + | ++ | >10 |
| 6 | + | ++ | >10 |
| 7 | + | ++ | >10 |
| 8 | + | ++ | >10 |
| 9 | + | ++ | >10 |
| 10 | + | ++ | >10 |
| 11 | + | ++ | >10 |
| 12 | + | ++ | >10 |
| 13 | + | ++ | >10 |
| 14 | + | ++ | >10 |

TABLE A-continued

| Example | JAK1 IC$_{50}$ (nM) at 1 mM ATP | JAK2 IC$_{50}$ (nM) at 1 mM ATP | JAK2/JAK1 |
|---|---|---|---|
| 15 | + | ++ | >10 |
| 16 | + | ++ | >10 |
| 17 | + | ++ | >10 |
| 18 | + | ++ | >10 |
| 20 | + | ++ | >10 |
| 21 | + | +++ | >10 |
| 22 | + | ++ | >10 |
| 23 | + | ++ | >10 |
| 24 | + | ++ | >10 |
| 25 | + | +++ | >10 |
| 26 | + | +++ | >10 |
| 27 | + | ++ | >10 |
| 28 | + | ++ | >10 |
| 29 | + | ++ | >10 |
| 30 | + | ++ | >10 |
| 31 | + | ++ | >10 |
| 32 | + | ++ | >10 |
| 33 | + | ++ | >10 |
| 34 | + | ++ | >10 |
| 35 | + | ++ | >10 |
| 36 | + | +++ | >10 |
| 37 | + | +++ | >10 |
| 38 | + | ++ | >10 |
| 39 | + | ++ | >10 |
| 40 | + | ++ | >10 |
| 41 | + | ++ | >10 |
| 42 | + | ++ | >10 |
| 43 | + | ++ | >10 |
| 44 | + | ++ | >10 |
| 45 | + | ++ | >10 |
| 46 | + | ++ | >10 |
| 47 | + | +++ | >10 |
| 48 | + | ++ | >10 |
| 49 | + | ++ | >10 |
| 50 | + | ++ | >10 |

Example B

Cellular Assays

Cancer cell lines dependent on cytokines and hence JAK/STAT signal transduction, for growth, can be plated at 6000 cells per well (96 well plate format) in RPMI 1640, 10% FBS, and 1 nG/mL of appropriate cytokine. Compounds can be added to the cells in DMSO/media (final concentration 0.2% DMSO) and incubated for 72 hours at 37° C., 5% CO$_2$. The effect of compound on cell viability is assessed using the CellTiter-Glo Luminescent Cell Viability Assay (Promega) followed by TopCount (Perkin Elmer, Boston, Mass.) quantitation. Potential off-target effects of compounds are measured in parallel using a non-JAK driven cell line with the same assay readout. All experiments are typically performed in duplicate.

The above cell lines can also be used to examine the effects of compounds on phosphorylation of JAK kinases or potential downstream substrates such as STAT proteins, Akt, Shp2, or Erk. These experiments can be performed following an overnight cytokine starvation, followed by a brief preincubation with compound (2 hours or less) and cytokine stimulation of approximately 1 hour or less. Proteins are then extracted from cells and analyzed by techniques familiar to those schooled in the art including Western blotting or ELISAs using antibodies that can differentiate between phosphorylated and total protein. These experiments can utilize normal or cancer cells to investigate the activity of compounds on tumor cell survival biology or on mediators of inflammatory disease. For example, with regards to the latter, cytokines such as IL-6, IL-12, IL-23, or IFN can be used to stimulate JAK activation resulting in phosphorylation of STAT protein(s) and potentially in transcriptional profiles (assessed by array or qPCR technology) or production and/or secretion of proteins, such as IL-17. The ability of compounds to inhibit these cytokine mediated effects can be measured using techniques common to those schooled in the art.

Compounds herein can also be tested in cellular models designed to evaluate their potency and activity against mutant JAKs, for example, the JAK2V617F mutation found in myeloid proliferative disorders. These experiments often utilize cytokine dependent cells of hematological lineage (e.g. BaF/3) into which the wild-type or mutant JAK kinases are ectopically expressed (James, C., et al. Nature 434:1144-1148; Staerk, J., et al. JBC 280:41893-41899). Endpoints include the effects of compounds on cell survival, proliferation, and phosphorylated JAK, STAT, Akt, or Erk proteins.

Certain compounds herein can be evaluated for their activity inhibiting T-cell proliferation. Such as assay can be considered a second cytokine (i.e. JAK) driven proliferation assay and also a simplistic assay of immune suppression or inhibition of immune activation. The following is a brief outline of how such experiments can be performed. Peripheral blood mononuclear cells (PBMCs) are prepared from human whole blood samples using Ficoll Hypaque separation method and T-cells (fraction 2000) can be obtained from PBMCs by elutriation. Freshly isolated human T-cells can be maintained in culture medium (RPMI 1640 supplemented with 10% fetal bovine serum, 100 U/ml penicillin, 100 g/ml streptomycin) at a density of 2×10$^6$ cells/ml at 37° C. for up to 2 days. For IL-2 stimulated cell proliferation analysis, T-cells are first treated with Phytohemagglutinin (PHA) at a final concentration of 10 g/mL for 72 h. After washing once with PBS, 6000 cells/well are plated in 96-well plates and treated with compounds at different concentrations in the culture medium in the presence of 100 U/mL human IL-2 (ProSpec-Tany TechnoGene; Rehovot, Israel). The plates are incubated at 37° C. for 72 h and the proliferation index is assessed using CellTiter-Glo Luminescent reagents following the manufactory suggested protocol (Promega; Madison, Wis.).

Example C

In Vivo Anti-Tumor Efficacy

Compounds herein can be evaluated in human tumor xenograft models in immune compromised mice. For example, a tumorigenic variant of the INA-6 plasmacytoma cell line can be used to inoculate SCID mice subcutaneously (Burger, R., et al. Hematol J. 2:42-53, 2001). Tumor bearing animals can then be randomized into drug or vehicle treatment groups and different doses of compounds can be administered by any number of the usual routes including oral, i.p., or continuous infusion using implantable pumps. Tumor growth is followed over time using calipers. Further, tumor samples can be harvested at any time after the initiation of treatment for analysis as described above (Example B) to evaluate compound effects on JAK activity and downstream signaling pathways. In addition, selectivity of the compound(s) can be assessed using xenograft tumor models that are driven by other know kinases (e.g. Bcr-Abl) such as the K562 tumor model.

Example D

Murine Skin Contact Delayed Hypersensitivity Response Test

Compounds herein can also be tested for their efficacies (of inhibiting JAK targets) in the T-cell driven murine delayed hypersensitivity test model. The murine skin contact delayed-type hypersensitivity (DTH) response is considered to be a valid model of clinical contact dermatitis, and other T-lymphocyte mediated immune disorders of the skin, such as psoriasis (*Immunol Today.* 1998 January; 19(1):37-44). Murine DTH shares multiple characteristics with psoriasis, including the immune infiltrate, the accompanying increase in inflammatory cytokines, and keratinocyte hyperproliferation. Furthermore, many classes of agents that are efficacious in treating psoriasis in the clinic are also effective inhibitors of the DTH response in mice (Agents Actions. 1993 January; 38(1-2): 116-21).

On Day 0 and 1, Balb/c mice are sensitized with a topical application, to their shaved abdomen with the antigen 2,4, dinitro-fluorobenzene (DNFB). On day 5, ears are measured for thickness using an engineer's micrometer. This measurement is recorded and used as a baseline. Both of the animals' ears are then challenged by a topical application of DNFB in a total of 20 μL (10 μL on the internal pinna and 10 μL on the external pinna) at a concentration of 0.2%. Twenty-four to seventy-two hours after the challenge, ears are measured again. Treatment with the test compounds is given throughout the sensitization and challenge phases (day −1 to day 7) or prior to and throughout the challenge phase (usually afternoon of day 4 to day 7). Treatment of the test compounds (in different concentration) is administered either systemically or topically (topical application of the treatment to the ears). Efficacies of the test compounds are indicated by a reduction in ear swelling comparing to the situation without the treatment. Compounds causing a reduction of 20% or more were considered efficacious. In some experiments, the mice are challenged but not sensitized (negative control).

The inhibitive effect (inhibiting activation of the JAK-STAT pathways) of the test compounds can be confirmed by immunohistochemical analysis. Activation of the JAK-STAT pathway(s) results in the formation and translocation of functional transcription factors. Further, the influx of immune cells and the increased proliferation of keratinocytes should also provide unique expression profile changes in the ear that can be investigated and quantified. Formalin fixed and paraffin embedded ear sections (harvested after the challenge phase in the DTH model) are subjected to immunohistochemical analysis using an antibody that specifically interacts with phosphorylated STAT3 (clone 58E12, Cell Signaling Technologies). The mouse ears are treated with test compounds, vehicle, or dexamethasone (a clinically efficacious treatment for psoriasis), or without any treatment, in the DTH model for comparisons. Test compounds and the dexamethasone can produce similar transcriptional changes both qualitatively and quantitatively, and both the test compounds and dexamethasone can reduce the number of infiltrating cells. Both systemically and topical administration of the test compounds can produce inhibitive effects, i.e., reduction in the number of infiltrating cells and inhibition of the transcriptional changes.

Example E

In Vivo Anti-Inflammatory Activity

Compounds herein can be evaluated in rodent or non-rodent models designed to replicate a single or complex inflammation response. For instance, rodent models of arthritis can be used to evaluate the therapeutic potential of compounds dosed preventatively or therapeutically. These models include but are not limited to mouse or rat collagen-induced arthritis, rat adjuvant-induced arthritis, and collagen antibody-induced arthritis. Autoimmune diseases including, but not limited to, multiple sclerosis, type I-diabetes mellitus, uveoretinitis, thyroditis, myasthenia gravis, immunoglobulin nephropathies, myocarditis, airway sensitization (asthma), lupus, or colitis may also be used to evaluate the therapeutic potential of compounds herein. These models are well established in the research community and are familiar to those schooled in the art (Current Protocols in Immunology, Vol 3, Coligan, J. E. et al, Wiley Press; *Methods in Molecular Biology* Vol. 225, Inflammation Protocols, Winyard, P. G. and Willoughby, D. A., Humana Press, 2003.).

Example F

Animal Models for the Treatment of Dry Eye, Uveitis, and Conjunctivitis

Agents may be evaluated in one or more preclinical models of dry eye known to those schooled in the art including, but not limited to, the rabbit concanavalin A (ConA) lacrimal gland model, the scopolamine mouse model (subcutaneous or transdermal), the Botulinumn mouse lacrimal gland model, or any of a number of spontaneous rodent autoimmune models that result in ocular gland dysfunction (e.g. NOD-SCID, MRL/lpr, or NZB/NZW) (Barabino et al., Experimental Eye Research 2004, 79, 613-621 and Schrader et al., Developmental Opthalmology, Karger 2008, 41, 298-312, each of which is incorporated herein by reference in its entirety). Endpoints in these models may include histopathology of the ocular glands and eye (cornea, etc.) and possibly the classic Schirmer test or modified versions thereof (Barabino et al.) which measure tear production. Activity may be assessed by dosing via multiple routes of administration (e.g. systemic or topical) which may begin prior to or after measurable disease exists.

Agents may be evaluated in one or more preclinical models of uveitis known to those schooled in the art. These include, but are not limited to, models of experimental autoimmune uveitis (EAU) and endotoxin induced uveitis (EIU). EAU experiments may be performed in the rabbit, rat, or mouse and may involve passive or activate immunization. For instance, any of a number or retinal antigens may be used to sensitize animals to a relevant immunogen after which animals may be challenged ocuarly with the same antigen. The EIU model is more acute and involves local or systemic administration of lipopolysaccaride at sublethal doses. Endpoints for both the EIU and EAU models may include fundoscopic exam, histopathology amongst others. These models are reviewed by Smith et al. (Immunology and Cell Biology 1998, 76, 497-512, which is incorporated herein by reference in its entirety). Activity is assessed by dosing via multiple routes of administration (e.g. systemic or topical) which may begin prior to or after measurable disease exists. Some models listed above may also develop scleritis/episcleritis, chorioditis, cyclitis, or iritis and are therefore useful in investigating the potential activity of compounds for the therapeutic treatment of these diseases.

Agents may also be evaluated in one or more preclinical models of conjunctivitis known those schooled in the art. These include, but are not limited to, rodent models utilizing guinea-pig, rat, or mouse. The guinea-pig models include those utilizing active or passive immunization and/or immune challenge protocols with antigens such as ovalbumin or ragweed (reviewed in Groneberg, D. A., et al., Allergy 2003, 58, 1101-1113, which is incorporated herein by reference in its entirety). Rat and mouse models are similar in general design to those in the guinea-pig (also reviewed by Groneberg). Activity may be assessed by dosing via multiple routes of administration (e.g. systemic or topical) which may begin prior to or after measurable disease exists. Endpoints for such studies may include, for example, histological, immunological, biochemical, or molecular analysis of ocular tissues such as the conjunctiva.

Example G

In Vivo Protection of Bone

Compounds may be evaluated in various preclinical models of osteopenia, osteoporosis, or bone resorption known to those schooled in the art. For example, ovariectomized rodents may be used to evaluate the ability of compounds to affect signs and markers of bone remodeling and/or density (W. S. S. Jee and W. Yao, J Musculoskel. Nueron. Interact., 2001, 1(3), 193-207, which is incorporated herein by reference in its entirety). Alternatively, bone density and architecture may be evaluated in control or compound treated rodents in models of therapy (e.g. glucocorticoid) induced osteopenia (Yao, et al. Arthritis and Rheumatism, 2008, 58(6), 3485-3497; and id. 58(11), 1674-1686, both of which are incorporated herein by reference in its entirety). In addition, the effects of compounds on bone resorption and density may be evaluable in the rodent models of arthritis discussed above (Example E). Endpoints for all these models may vary but often include histological and radiological assessments as well as immunohisotology and appropriate biochemical markers of bone remodeling.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:
1. A compound of Formula I:

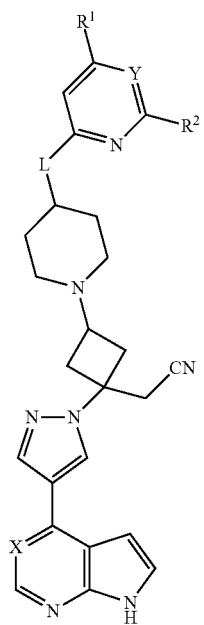

I or a pharmaceutically acceptable salt thereof; wherein:
X is N or CH;
L is O or $NR^{2a}$;
(a) wherein when L is O, then:
Y is CH;
$R^1$ is —C(=O)$NR^3R^4$, —$CH_2CH_2OH$, —$CH_2NR^3R^4$, or an oxetane ring, wherein the oxetane ring is optionally substituted with $R^5$;
$R^2$ is $CF_3$;
$R^3$ is —[CH($R^{6a}$)]$_n$—$OR^{6b}$, cyclopropyl, cyclobutyl, tetrahydro-2H-pyran ring, tetrahydrofuran ring, or oxetane ring, wherein said cyclopropyl, cyclobutyl, tetrahydro-2H-pyran ring, tetrahydrofuran ring, and oxetane ring are each optionally substituted with 1 or 2 groups independently selected from CN, OH, methyl, ethyl, n-propyl, isopropyl, methoxy, ethoxy, and propoxy;
$R^4$ is H, $CH_3$, or —[CH($R^{6a}$)]$_n$—$OR^{6b}$;
or alternatively, $R^3$ and $R^4$, taken together with the nitrogen atom to which they are attached, form an azetidinyl, 1H-pyrazolyl, a 1H-imidazolyl, or a 1H-triazolyl group, wherein said azetidinyl group is optionally substituted with 1 or 2 independently selected $R^{3a}$ groups;
each $R^{3a}$ is independently CN, OH, methyl, ethyl, n-propyl, isopropyl, methoxy, ethoxy, propoxy, or —$CH_2$—OH;
or alternatively, two $R^{3a}$ groups, taken together with the carbon atom to which they are both attached, form an oxetane ring;
$R^5$ is OH or $NH_2$;
$R^{6a}$ and $R^{6b}$ are each independently H or $CH_3$; and
each n is independently 2 or 3;
provided that when X is N, then $NR^3R^4$ is not $NHCH_2CH_2$—OH, $NHCH_2CH_2CH_2$—OH,

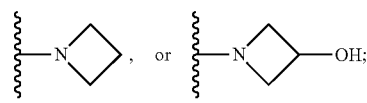 [SMILES: *N1CCC1 ; *N1CC(O)C1]

or alternatively,
(b) wherein when L is $NR^{2a}$, then:
Y is CH or N;
$R^1$ is halo, cyano, nitro, $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, $C_{1-10}$ heteroaryl-$C_{1-4}$-alkyl, —$OR^a$, —$SR^a$, —$S(=O)R^b$, —$S(=O)_2R^b$, —$S(=O)_2NR^eR^f$, —$C(=O)R^b$, —$C(=O)OR^a$, —$C(=O)NR^eR^f$, —$OC(=O)R^b$, —$OC(=O)NR^eR^f$, —$NR^eR^f$, —$NR^cC(=O)R^d$, —$NR^cC(=O)OR^d$, —$NR^cS(=O)_2R^d$, or —$NR^cS(=O)_2NR^eR^f$; wherein said $C_{1-6}$ alkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, and $C_{1-10}$ heteroaryl-$C_{1-4}$-alkyl are each optionally substituted by 1, 2, 3, or 4 independently selected $R^g$ groups;
$R^2$ is H, halo, cyano, nitro, $C_{1-4}$ alkyl, or $C_{1-4}$ haloalkyl;
$R^{2a}$ is H or $CH_3$;
each $R^a$, $R^c$, $R^d$, $R^e$, and $R^f$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, and $C_{1-10}$ heteroaryl-$C_{1-4}$-alkyl; wherein said $C_{1-6}$ alkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, and $C_{1-10}$ heteroaryl-$C_{1-4}$-alkyl are each optionally substituted by 1, 2, 3, or 4 independently selected $R^g$ groups;

each $R^b$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, and $C_{1-10}$ heteroaryl-$C_{1-4}$-alkyl; wherein said $C_{1-6}$ alkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, and $C_{1-10}$ heteroaryl-$C_{1-4}$-alkyl are each optionally substituted by 1, 2, 3, or 4 independently selected $R^g$ groups;

each $R^g$ is independently selected from halo, cyano, nitro, $C_{1-6}$ alkyl, $C_{1-6}$ haloalkyl, $C_{2-6}$ alkenyl, $C_{2-6}$ alkynyl, $C_{3-7}$ cycloalkyl, $C_{3-7}$ cycloalkyl-$C_{1-3}$-alkyl, $C_{2-7}$ heterocycloalkyl, $C_{2-7}$ heterocycloalkyl-$C_{1-3}$-alkyl, phenyl, phenyl-$C_{1-3}$-alkyl, $C_{1-7}$ heteroaryl, $C_{1-7}$ heteroaryl-$C_{1-3}$-alkyl, —$OR^{a1}$, —$SR^{a1}$, —$S(=O)R^{b1}$, —$S(=O)_2R^{b1}$, —$S(=O)_2NR^{e1}R^{f1}$, —$C(=O)R^{b1}$, —$C(=O)OR^{a1}$, —$C(=O)NR^{e1}R^{f1}$, —$OC(=O)R^{b1}$, —$OC(=O)NR^{e1}R^{f1}$, —$NR^{e1}R^{f1}$, —$NR^{c1}C(=O)R^{d1}$, —$NR^{c1}C(=O)OR^{d1}$, —$NR^{c1}S(=O)_2R^{d1}$, and —$NR^{c1}S(=O)_2NR^{e1}R^{f1}$; wherein said $C_{1-6}$ alkyl, $C_{2-6}$ alkenyl, $C_{2-6}$ alkynyl, $C_{3-7}$ cycloalkyl, $C_{3-7}$ cycloalkyl-$C_{1-3}$-alkyl, $C_{2-7}$ heterocycloalkyl, $C_{2-7}$ heterocycloalkyl-$C_{1-3}$-alkyl, phenyl, phenyl-$C_{1-3}$-alkyl, $C_{1-7}$ heteroaryl, and $C_{1-7}$ heteroaryl-$C_{1-3}$-alkyl are each optionally substituted with 1, 2, 3, or 4 independently selected $R^h$ groups;

each $R^{a1}$, $R^{c1}$, $R^{d1}$, $R^{e1}$, and $R^{f1}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, $C_{3-7}$ cycloalkyl-$C_{1-3}$-alkyl, $C_{2-7}$ heterocycloalkyl, $C_{2-7}$ heterocycloalkyl-$C_{1-3}$-alkyl, phenyl, phenyl-$C_{1-3}$-alkyl, $C_{1-7}$ heteroaryl, and $C_{1-7}$ heteroaryl-$C_{1-3}$-alkyl; wherein said $C_{1-6}$ alkyl, $C_{2-6}$ alkenyl, $C_{2-6}$ alkynyl, $C_{3-7}$ cycloalkyl, $C_{3-7}$ cycloalkyl-$C_{1-3}$-alkyl, $C_{2-7}$ heterocycloalkyl, $C_{2-7}$ heterocycloalkyl-$C_{1-3}$-alkyl, phenyl, phenyl-$C_{1-3}$-alkyl, $C_{1-7}$ heteroaryl, and $C_{1-7}$ heteroaryl-$C_{1-3}$-alkyl are each optionally substituted by 1, 2, 3, or 4 independently selected $R^h$ groups;

each $R^{b1}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, $C_{3-7}$ cycloalkyl-$C_{1-3}$-alkyl, $C_{2-7}$ heterocycloalkyl, $C_{2-7}$ heterocycloalkyl-$C_{1-3}$-alkyl, phenyl, phenyl-$C_{1-3}$-alkyl, $C_{1-7}$ heteroaryl, and $C_{1-7}$ heteroaryl-$C_{1-3}$-alkyl; wherein said $C_{1-6}$ alkyl, $C_{2-6}$ alkenyl, $C_{2-6}$ alkynyl, $C_{3-7}$ cycloalkyl, $C_{3-7}$ cycloalkyl-$C_{1-3}$-alkyl, $C_{2-7}$ heterocycloalkyl, $C_{2-7}$ heterocycloalkyl-$C_{1-3}$-alkyl, phenyl, phenyl-$C_{1-3}$-alkyl, $C_{1-7}$ heteroaryl, and $C_{1-7}$ heteroaryl-$C_{1-3}$-alkyl are each optionally substituted by 1, 2, 3, or 4 independently selected $R^h$ groups; and each $R^h$ is independently selected from cyano, halo, hydroxy, $C_{1-4}$ alkyl, $C_{1-4}$ haloalkyl, $C_{1-4}$ alkoxy, $C_{1-4}$ haloalkoxy, amino, $C_{1-4}$ alkylamino, di-$C_{1-4}$-alkylamino, hydroxy-$C_{1-4}$ alkyl, $C_{1-4}$ alkoxy-$C_{1-4}$ alkyl, cyano-$C_{1-4}$ alkyl, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

2. A compound of claim 1, having Formula II:

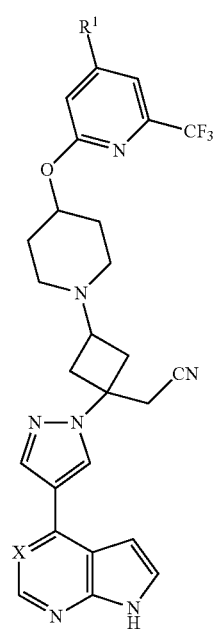

or a pharmaceutically acceptable salt thereof.

3. A compound of claim 2, or a pharmaceutically acceptable salt thereof, wherein:

$R^1$ is —$C(=O)NR^3R^4$, —$CH_2CH_2OH$, —$CH_2NR^3R^4$, or an oxetane ring, wherein the oxetane ring is optionally substituted with $R^5$;

$R^3$ is —$CH_2CH_2$—$OR^{6b}$, —$CH(CH_3)CH_2$—$OR^{6b}$, —$CH_2CH(CH_3)$—$OR^{6b}$, cyclopropyl, cyclobutyl, tetrahydro-2H-pyran ring, tetrahydrofuran ring, or oxetane ring, wherein said cyclopropyl, cyclobutyl, tetrahydro-2H-pyran ring, tetrahydrofuran ring, and oxetane ring are each optionally substituted with 1 or 2 groups independently selected from $CH_3$, CN, OH, and $OCH_3$;

$R^4$ is H, $CH_3$, —$CH_2CH_2$—$OR^{6b}$, —$CH(CH_3)CH_2$—$OR^{6b}$, or —$CH_2CH(CH_3)$—$OR^{6b}$;

or alternatively, $R^3$ and $R^4$, taken together with the nitrogen atom to which they are attached, form an azetidinyl, 1H-pyrazolyl, a 1H-imidazolyl, a 1H-1,3,4-triazolyl, or a 1H-1,2,4-triazolyl group, wherein said azetidinyl group is optionally substituted with 1 or 2 independently selected $R^{3a}$ groups;

each $R^{3a}$ is independently CN, OH, methyl, ethyl, n-propyl, isopropyl, methoxy, ethoxy, propoxy, or —$CH_2$—OH;

or alternatively, two $R^{3a}$ groups, taken together with the carbon atom to which they are both attached, form an oxetane ring;

$R^5$ is OH or $NH_2$; and $R^{6b}$ is independently H or $CH_3$.

4. A compound of claim 2, or a pharmaceutically acceptable salt thereof, wherein each $R^{3a}$ is independently $CH_3$, CN, OH, $OCH_3$, or —$CH_2$—OH; or alternatively, two $R^{3a}$ groups, taken together with the carbon atom to which they are both attached, form an oxetane ring.

5. A compound of claim 1, or a pharmaceutically acceptable salt thereof, wherein:

L is O;

X is N or CH;

$R^1$ is an oxetane ring, wherein the oxetane ring is optionally substituted with $R^5$;

$R^2$ is $CF_3$; and
$R^5$ is OH or $NH_2$.

6. A compound of claim 2, having Formula IIa:

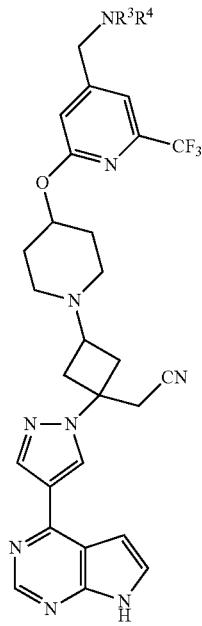

IIa or a pharmaceutically acceptable salt thereof.

7. A compound of claim 2, having Formula IIa,

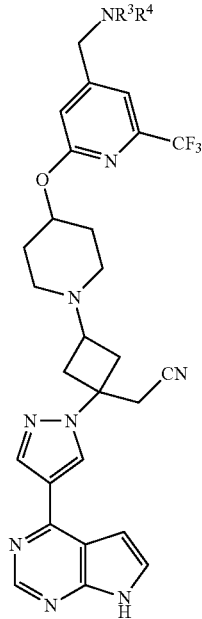

IIa or a pharmaceutically acceptable salt thereof, wherein:
$R^3$ is —$CH_2CH_2$—$OR^{6b}$, —$CH(CH_3)CH_2$—$OR^{6b}$, —$CH_2CH(CH_3)$—$OR^{6b}$, cyclopropyl, cyclobutyl, tetrahydro-2H-pyran ring, tetrahydrofuran ring, or oxetane ring, wherein said cyclopropyl, cyclobutyl, tetrahydro-2H-pyran ring, tetrahydrofuran ring, and oxetane ring are each optionally substituted with 1 or 2 groups independently selected from $CH_3$, CN, OH, and $OCH_3$;

$R^4$ is H, $CH_3$, —$CH_2CH_2$—$OR^{6b}$, —$CH(CH_3)CH_2$—$OR^{6b}$, or —$CH_2CH(CH_3)$—$OR^{6b}$;

or alternatively, $R^3$ and $R^4$, taken together with the nitrogen atom to which they are attached, form an azetidinyl, 1H-pyrazolyl, a 1H-imidazolyl, a 1H-1,3,4-triazolyl, or a 1H-1,2,4-triazolyl group, wherein said azetidinyl group is optionally substituted with 1 or 2 independently selected $R^{3a}$ groups;

each $R^{3a}$ is independently $CH_3$, CN, OH, $OCH_3$, or —$CH_2$—OH;

or alternatively, two $R^{3a}$ groups, taken together with the carbon atom to which they are both attached, form a oxetane ring;

$R^5$ is OH or $NH_2$; and $R^{6b}$ is independently H or $CH_3$;

provided that $NR^3R^4$ is not $NHCH_2CH_2$—OH,

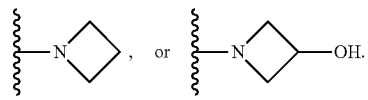 [SMILES: *N1CCC1 ; *N1CC(O)C1]

8. A compound of claim 2, having Formula IIa,

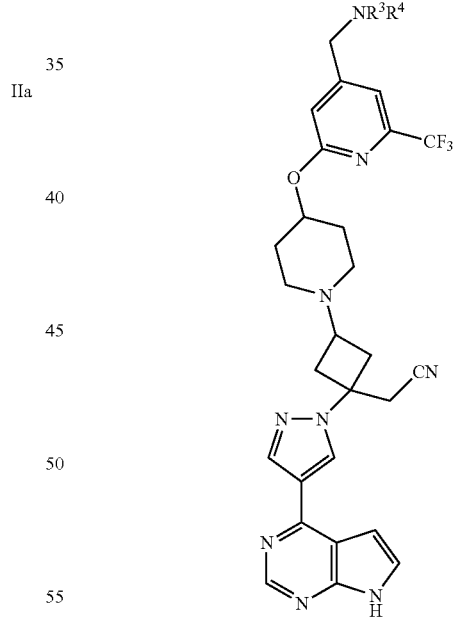

IIa or a pharmaceutically acceptable salt thereof, wherein:
$R^3$ is —$CH_2CH_2$—$OR^{6b}$, —$CH(CH_3)CH_2$—$OR^{6b}$, or —$CH_2CH(CH_3)$—$OR^{6b}$;

$R^4$ is H, $CH_3$, —$CH_2CH_2$—$OR^{6b}$, —$CH(CH_3)CH_2$—$OR^{6b}$, or —$CH_2CH(CH_3)$—$OR^{6b}$; and $R^{6b}$ is independently H or $CH_3$;

provided that $NR^3R^4$ is not $NHCH_2CH_2$—OH.

9. A compound of claim 2 having Formula IIa,

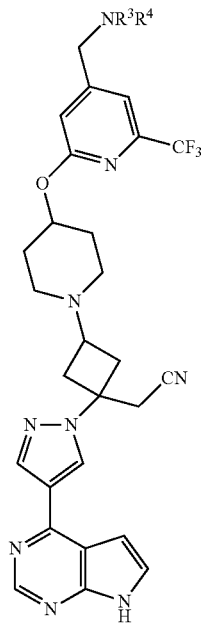

or a pharmaceutically acceptable salt thereof, wherein:
R³ is cyclopropyl, cyclobutyl, tetrahydro-2H-pyran ring, tetrahydrofuran ring, or oxetane ring, wherein said cyclopropyl, cyclobutyl, tetrahydro-2H-pyran ring, tetrahydrofuran ring, and oxetane ring are each optionally substituted with 1 or 2 groups independently selected from CH₃, CN, OH, and OCH₃; and
R⁴ is H.

10. A compound of claim 2 having Formula IIa,

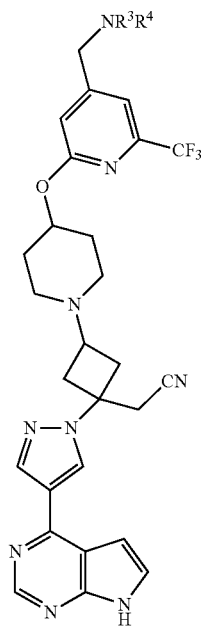

or a pharmaceutically acceptable salt thereof, wherein:
R³ and R⁴, taken together with the nitrogen atom to which they are attached, form an azetidinyl group, which is optionally substituted with 1 or 2 independently selected R³ᵃ groups;
each R³ᵃ is independently CH₃, CN, OH, OCH₃, or —CH₂—OH;
or alternatively, two R³ᵃ groups, taken together with the carbon atom to which they are both attached, form a oxetane ring; and
provided that NR³R⁴ is not

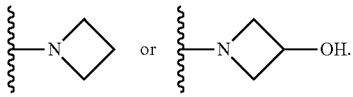 [SMILES: *N1CCC1 ; *N1CC(O)C1]

11. A compound of claim 2 having Formula IIa,

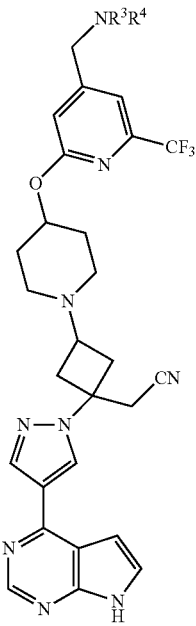

or a pharmaceutically acceptable salt thereof, wherein:
R³ and R⁴, taken together with the nitrogen atom to which they are attached, form a 1H-pyrazolyl, a 1H-imidazolyl, a 1H-1,3,4-triazolyl, or a 1H-1,2,4-triazolyl group.

12. A compound of claim 1, having Formula III:

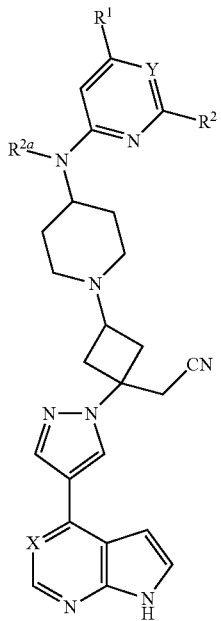

or a pharmaceutically acceptable salt thereof.

13. A compound of claim 12, or a pharmaceutically acceptable salt thereof, wherein:
   $R^1$ is $C_{1-3}$ alkyl substituted by —$OR^{a1}$, —$NR^{e1}R^{f1}$, or $C_{2-7}$ heterocycloalkyl;
   $R^{a1}$ is H or $C_{1-4}$ alkyl;
   $R^{e1}$ is H or $C_{1-4}$ alkyl; wherein $C_{1-4}$ alkyl is substituted by 1 or 2 independently selected $R^h$ groups;
   $R^{f1}$ is H, $C_{1-4}$ alkyl, cyclopropyl, cyclobutyl, or cyclohexyl; wherein $C_{1-4}$ alkyl, cyclopropyl, cyclobutyl, or cyclohexyl are each substituted by 1 or 2 independently selected $R^h$ groups; and
   each $R^h$ is independently selected from hydroxy, halo, cyano, $C_{1-4}$ alkyl, and $C_{1-4}$ alkoxy.

14. A compound of claim 12, or a pharmaceutically acceptable salt thereof, wherein $R^2$ is $CF_3$.

15. A compound of claim 12, or a pharmaceutically acceptable salt thereof, wherein Y is N.

16. A compound of claim 12, or a pharmaceutically acceptable salt thereof, wherein Y is CH.

17. A compound of claim 12, or a pharmaceutically acceptable salt thereof, wherein X is N.

18. A compound of claim 1, or a pharmaceutically acceptable salt thereof; wherein:
   X is N or CH;
   L is $NR^{2a}$;
   Y is CH or N;
   $R^1$ is $C_{1-3}$ alkyl substituted by —$OR^{a1}$, —$NR^{e1}R^{f1}$, or $C_{2-7}$ heterocycloalkyl;
   $R^2$ is $CF_3$;
   $R^{2a}$ is H or $CH_3$;
   $R^{a1}$ is H or $C_{1-4}$ alkyl;
   $R^{e1}$ is H or $C_{1-4}$ alkyl; wherein $C_{1-4}$ alkyl is substituted by 1 or 2 independently selected $R^h$ groups;
   $R^{f1}$ is H, $C_{1-4}$ alkyl, cyclopropyl, cyclobutyl, or cyclohexyl; wherein $C_{1-4}$ alkyl, cyclopropyl, cyclobutyl, or cyclohexyl are each substituted by 1 or 2 independently selected $R^h$ groups; and
   each $R^h$ is independently selected from hydroxy, halo, cyano, $C_{1-4}$ alkyl, and $C_{1-4}$ alkoxy.

19. The compound of claim 1, selected from:
   {trans-3-(4-{[4-({[(1S)-2-hydroxy-1-methylethyl]amino}methyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile;
   {trans-3-(4-{[4-({[(1R)-2-hydroxy-1-methylethyl]amino}methyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile;
   {trans-3-(4-{[4-{[(2-methoxyethyl)amino]methyl}-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile;
   1-{[2-[(1-{trans-3-(cyanomethyl)-3-[4-(7H-pyrrolo[2,3-d]pyrimidin-4-yl)-1H-pyrazol-1-yl]cyclobutyl}piperidin-4-yl)oxy]-6-(trifluoromethyl)pyridin-4-yl]methyl}azetidine-3-carbonitrile;
   [trans-1-[4-(7H-pyrrolo[2,3-d]pyrimidin-4-yl)-1H-pyrazol-1-yl]-3-(4-{[4-[(tetrahydro-2H-pyran-4-ylamino)methyl]-6-(trifluoromethyl)pyridin-2-yl]oxy}piperidin-1-yl)cyclobutyl]acetonitrile;
   {trans-3-(4-{[4-(2-oxa-6-azaspiro[3.3]hept-6-ylmethyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile;
   [trans-1-[4-(7H-pyrrolo[2,3-d]pyrimidin-4-yl)-1H-pyrazol-1-yl]-3-(4-{[4-{[(3S)-tetrahydrofuran-3-ylamino]methyl}-6-(trifluoromethyl)pyridin-2-yl]oxy}piperidin-1-yl)cyclobutyl]acetonitrile;
   [trans-1-[4-(7H-pyrrolo[2,3-d]pyrimidin-4-yl)-1H-pyrazol-1-yl]-3-(4-{[4-{[(3R)-tetrahydrofuran-3-ylamino]methyl}-6-(trifluoromethyl)pyridin-2-yl]oxy}piperidin-1-yl)cyclobutyl]acetonitrile;
   {trans-3-(4-{[4-{[(3-methyloxetan-3-yl)amino]methyl}-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile;
   {trans-3-(4-{[4-{[(1-methylcyclopropyl)amino]methyl}-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile;
   {trans-3-(4-{[4-[(oxetan-3-ylamino)methyl]-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile;
   {trans-3-(4-{[4-{[(trans-3-hydroxycyclobutyl)amino]methyl}-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile;
   {trans-3-(4-{[4-[(3,3-dimethylazetidin-1-yl)methyl]-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile;
   {trans-3-(4-{[4-({[(2R)-2-hydroxypropyl]amino}methyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile;
   {trans-3-(4-{[4-({[(2S)-2-hydroxypropyl]amino}methyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile;
   {trans-3-(4-{[4-{[bis(2-hydroxyethyl)amino]methyl}-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile;

{trans-3-(4-{[4-{[(2-hydroxyethyl)(methyl)amino]methyl}-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile;

{trans-3-(4-{[4-{[(cis-3-hydroxycyclobutyl)amino]methyl}-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile;

{trans-3-(4-{[4-(2-hydroxyethyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile;

{trans-3-(4-{[4-{[(2-hydroxyethyl)amino]methyl}-6-(trifluoromethyl)pyridin-2-yl]oxy}piperidin-1-yl)-1-[4-(1H-pyrrolo[2,3-b]pyridin-4-yl)-1H-pyrazol-1-yl]cyclobutyl}acetonitrile;

{trans-3-(4-{[4-(1H-imidazol-1-ylmethyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile;

[trans-1-[4-(7H-pyrrolo[2,3-d]pyrimidin-4-yl)-1H-pyrazol-1-yl]-3-(4-{[4-(1H-1,2,4-triazol-1-ylmethyl)-6-(trifluoromethyl)pyridin-2-yl]oxy}piperidin-1-yl)cyclobutyl]acetonitrile;

[trans-1-[4-(7H-pyrrolo[2,3-d]pyrimidin-4-yl)-1H-pyrazol-1-yl]-3-(4-{[4-(4H-1,2,4-triazol-4-ylmethyl)-6-(trifluoromethyl)pyridin-2-yl]oxy}piperidin-1-yl)cyclobutyl]acetonitrile;

{trans-3-(4-{[4-(1H-pyrazol-1-ylmethyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile;

{trans-3-(4-{[4-[(3,3-dimethylazetidin-1-yl)carbonyl]-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile;

{trans-3-(4-{[6-(hydroxymethyl)-2-(trifluoromethyl)pyrimidin-4-yl]amino}piperidin-1-yl)-1-[4-(7H-pyrrolo[2,3-d]pyrimidin-4-yl)-1H-pyrazol-1-yl]cyclobutyl}acetonitrile;

{trans-3-(4-{[6-[(ethylamino)methyl]-2-(trifluoromethyl)pyrimidin-4-yl]amino}piperidin-1-yl)-1-[4-(7H-pyrrolo[2,3-d]pyrimidin-4-yl)-1H-pyrazol-1-yl]cyclobutyl}acetonitrile;

{trans-3-(4-{[6-{[(2-hydroxyethyl)amino]methyl}-2-(trifluoromethyl)pyrimidin-4-yl]amino}piperidin-1-yl)-1-[4-(7H-pyrrolo[2,3-d]pyrimidin-4-yl)-1H-pyrazol-1-yl]cyclobutyl}acetonitrile;

{trans-3-(4-{[6-{[(trans-3-hydroxycyclobutyl)amino]methyl}-2-(trifluoromethyl)pyrimidin-4-yl]amino}piperidin-1-yl)-1-[4-(7H-pyrrolo[2,3-d]pyrimidin-4-yl)-1H-pyrazol-1-yl]cyclobutyl}acetonitrile;

{trans-3-(4-{[4-(hydroxymethyl)-6-(trifluoromethyl)pyridin-2-yl]amino}piperidin-1-yl)-1-[4-(7H-pyrrolo[2,3-d]pyrimidin-4-yl)-1H-pyrazol-1-yl]cyclobutyl}acetonitrile;

{trans-3-(4-{[4-[(ethylamino)methyl]-6-(trifluoromethyl)pyridin-2-yl]amino}piperidin-1-yl)-1-[4-(7H-pyrrolo[2,3-d]pyrimidin-4-yl)-1H-pyrazol-1-yl]cyclobutyl}acetonitrile;

{trans-3-(4-{[4-{[(2-hydroxyethyl)amino]methyl}-6-(trifluoromethyl)pyridin-2-yl]amino}piperidin-1-yl)-1-[4-(7H-pyrrolo[2,3-d]pyrimidin-4-yl)-1H-pyrazol-1-yl]cyclobutyl}acetonitrile;

{trans-3-(4-{[4-{[(trans-3-hydroxycyclobutyl)amino]methyl}-6-(trifluoromethyl)pyridin-2-yl]amino}piperidin-1-yl)-1-[4-(7H-pyrrolo[2,3-d]pyrimidin-4-yl)-1H-pyrazol-1-yl]cyclobutyl}acetonitrile;

{trans-3-(4-{[4-[(3,3-dimethylazetidin-1-yl)methyl]-6-(trifluoromethyl)pyridin-2-yl]amino}piperidin-1-yl)-1-[4-(7H-pyrrolo[2,3-d]pyrimidin-4-yl)-1H-pyrazol-1-yl]cyclobutyl}acetonitrile;

{trans-3-(4-{[4-[(3,3-difluoropyrrolidin-1-yl)methyl]-6-(trifluoromethyl)pyridin-2-yl]amino}piperidin-1-yl)-1-[4-(7H-pyrrolo[2,3-d]pyrimidin-4-yl)-1H-pyrazol-1-yl]cyclobutyl}acetonitrile;

{trans-3-(4-{[4-{[cyclopropyl(methyl)amino]methyl}-6-(trifluoromethyl)pyridin-2-yl]amino}piperidin-1-yl)-1-[4-(7H-pyrrolo[2,3-d]pyrimidin-4-yl)-1H-pyrazol-1-yl]cyclobutyl}acetonitrile;

{cis-3-(4-{[4-(2-hydroxyethyl)-6-(trifluoromethyl)pyridin-2-yl]amino}piperidin-1-yl)-1-[4-(7H-pyrrolo[2,3-d]pyrimidin-4-yl)-1H-pyrazol-1-yl]cyclobutyl}acetonitrile and {trans-3-(4-{[4-(2-hydroxyethyl)-6-(trifluoromethyl)pyridin-2-yl]amino}piperidin-1-yl)-1-[4-(7H-pyrrolo[2,3-d]pyrimidin-4-yl)-1H-pyrazol-1-yl]cyclobutyl}acetonitrile;

{trans-3-(4-{[4-(azetidin-1-ylmethyl)-6-(trifluoromethyl)pyridin-2-yl]amino}piperidin-1-yl)-1-[4-(7H-pyrrolo[2,3-d]pyrimidin-4-yl)-1H-pyrazol-1-yl]cyclobutyl}acetonitrile;

{trans-3-(4-{[4-(morpholin-4-ylmethyl)-6-(trifluoromethyl)pyridin-2-yl]amino}piperidin-1-yl)-1-[4-(7H-pyrrolo[2,3-d]pyrimidin-4-yl)-1H-pyrazol-1-yl]cyclobutyl}acetonitrile;

{trans-3-(4-{[4-[(3-hydroxyazetidin-1-yl)methyl]-6-(trifluoromethyl)pyridin-2-yl]amino}piperidin-1-yl)-1-[4-(7H-pyrrolo[2,3-d]pyrimidin-4-yl)-1H-pyrazol-1-yl]cyclobutyl}acetonitrile;

{trans-3-(4-{[4-{[(2-hydroxyethyl)(methyl)amino]methyl}-6-(trifluoromethyl)pyridin-2-yl]amino}piperidin-1-yl)-1-[4-(7H-pyrrolo[2,3-d]pyrimidin-4-yl)-1H-pyrazol-1-yl]cyclobutyl}acetonitrile;

{trans-3-(4-{[4-{[(3S)-3-hydroxypyrrolidin-1-yl]methyl}-6-(trifluoromethyl)pyridin-2-yl]amino}piperidin-1-yl)-1-[4-(7H-pyrrolo[2,3-d]pyrimidin-4-yl)-1H-pyrazol-1-yl]cyclobutyl}acetonitrile;

{trans-3-(4-{[4-{[(3R)-3-hydroxypyrrolidin-1-yl]methyl}-6-(trifluoromethyl)pyridin-2-yl]amino}piperidin-1-yl)-1-[4-(7H-pyrrolo[2,3-d]pyrimidin-4-yl)-1H-pyrazol-1-yl]cyclobutyl}acetonitrile;

{trans-3-(4-{[4-(methoxymethyl)-6-(trifluoromethyl)pyridin-2-yl]amino}piperidin-1-yl)-1-[4-(7H-pyrrolo[2,3-d]pyrimidin-4-yl)-1H-pyrazol-1-yl]cyclobutyl}acetonitrile;

{trans-3-(4-{[4-(2-oxa-6-azaspiro[3.3]hept-6-ylmethyl)-6-(trifluoromethyl)pyridin-2-yl]amino}piperidin-1-yl)-1-[4-(7H-pyrrolo[2,3-d]pyrimidin-4-yl)-1H-pyrazol-1-yl]cyclobutyl}acetonitrile;

{trans-3-{4-[[4-(hydroxymethyl)-6-(trifluoromethyl)pyridin-2-yl](methyl)amino]piperidin-1-yl}-1-[4-(7H-pyrrolo[2,3-d]pyrimidin-4-yl)-1H-pyrazol-1-yl]cyclobutyl}acetonitrile;

{trans-3-{4-[[4-[(ethylamino)methyl]-6-(trifluoromethyl)pyridin-2-yl](methyl)amino]piperidin-1-yl}-1-[4-(7H-pyrrolo[2,3-d]pyrimidin-4-yl)-1H-pyrazol-1-yl]cyclobutyl}acetonitrile;

{trans-3-(4-{[4-(3-hydroxyoxetan-3-yl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile; and {trans-3-(4-{[4-(3-aminooxetan-3-yl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile;
or a pharmaceutically acceptable salt of any of the aforementioned.

20. A compound of claim 1, which is trans-3-(4-{[4-({[(1S)-2-hydroxy-1-methylethyl]amino}methyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile, or a pharmaceutically acceptable salt thereof.

21. A compound of claim 1, which is {trans-3-(4-{[4-({[(2R)-2-hydroxypropyl]amino}methyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile, or a pharmaceutically acceptable salt thereof.

22. A compound of claim 1, which is {trans-3-(4-{[4-({[(2S)-2-hydroxypropyl]amino}methyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile, or a pharmaceutically acceptable salt thereof.

23. A compound of claim 1, which is {trans-3-(4-{[4-(2-hydroxyethyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile, or a pharmaceutically acceptable salt thereof.

24. A composition comprising a compound according to claim 1, or a pharmaceutically acceptable salt thereof, and at least one pharmaceutically acceptable carrier.

25. A method of inhibiting an activity of JAK1 comprising contacting JAK1 with a compound according to claim 1, or a pharmaceutically acceptable salt thereof.

26. A method according to claim 25, wherein said compound, or pharmaceutically acceptable salt thereof, is selective for JAK1 over JAK2.

27. A method of treating a disease selected from myelofibrosis, polycythemia vera (PV), essential thrombocythemia (ET), post polycythemia vera myelofibrosis (Post-PV MF), post polycythemia vera myelofibrosis (Post-ET MF), multiple myeloma, pancreatic cancer, breast cancer, lung cancer, colorectal cancer, rheumatoid arthritis, psoriasis, lymphoma, leukemia, acute myelogenous leukemia, acute lymphoblastic leukemia, chronic myelogenous leukemia (CML), chronic myelomonocytic leukemia (CMML), cachexia, and Castleman's disease in a patient in need thereof, comprising administering to said patient a therapeutically effective amount of a compound of claim 1, or a pharmaceutically acceptable salt thereof.

28. A method according to claim 27, wherein said disease is rheumatoid arthritis.

29. A method according to claim 27, wherein said disease is myelofibrosis.

30. A method according to claim 29 wherein said myelofibrosis is primary myelofibrosis (PMF).

31. A method according to claim 27, wherein said disease is post polycythemia vera myelofibrosis (Post-PV MF).

32. A method according to claim 27, wherein said disease is post polycythemia vera myelofibrosis (Post-ET MF).

33. A method according to claim 27, wherein said disease is polycythemia vera (PV).

34. A method according to claim 27, wherein said disease is essential thrombocythemia (ET).

35. A method according to claim 27, wherein said disease is multiple myeloma.

36. A method according to claim 27, wherein said disease is pancreatic cancer.

37. A method according to claim 27, wherein said disease is breast cancer.

38. A method according to claim 27, wherein said disease is lung cancer.

39. A method according to claim 27, wherein said disease is colorectal cancer.

40. A method according to claim 27, wherein said disease is psoriasis.

41. A method according to claim 27, wherein said disease is lymphoma.

42. A method according to claim 27, wherein said disease is leukemia.

43. A method according to claim 27, wherein said disease is acute myelogenous leukemia.

44. A method according to claim 27, wherein said disease is acute lymphoblastic leukemia.

45. A method according to claim 27, wherein said disease is chronic myelogenous leukemia (CML).

46. A method according to claim 27, wherein said disease is chronic myelomonocytic leukemia (CMML).

47. A method according to claim 27, wherein said disease is Castleman's disease.

48. A method according to claim 27, wherein said disease is cachexia, wherein said cachexia results from or is associated with cancer.

* * * * *